US010709118B2

(12) United States Patent
Srikumaran et al.

(10) Patent No.: US 10,709,118 B2
(45) Date of Patent: *Jul. 14, 2020

(54) **COMPOSITIONS AND METHODS FOR TREATING OR PREVENTING CONDITIONS AND DISEASES ASSOCIATED WITH *MANNHEIMIA HAEMOLYTICA***

(71) Applicants: Subramaniam Srikumaran, Pullman, WA (US); Sudarvili Shanthalingam, Pullman, WA (US)

(72) Inventors: Subramaniam Srikumaran, Pullman, WA (US); Sudarvili Shanthalingam, Pullman, WA (US)

(73) Assignee: Washington State University, Pullman, WA (US)

( * ) Notice: Subject to any disclaimer, the term of this patent is extended or adjusted under 35 U.S.C. 154(b) by 339 days.

This patent is subject to a terminal disclaimer.

(21) Appl. No.: 14/815,240

(22) Filed: Jul. 31, 2015

(65) Prior Publication Data
US 2015/0327522 A1    Nov. 19, 2015

Related U.S. Application Data

(63) Continuation of application No. 13/147,578, filed as application No. PCT/US2010/022932 on Feb. 2, 2010, now Pat. No. 9,102,925.

(60) Provisional application No. 61/149,278, filed on Feb. 2, 2009.

(51) Int. Cl.
| | | |
|---|---|---|
| *A01K 67/00* | (2006.01) | |
| *A01K 67/027* | (2006.01) | |
| *C12N 5/16* | (2006.01) | |
| *C07K 14/705* | (2006.01) | |
| *A61K 38/00* | (2006.01) | |
| *C07K 16/28* | (2006.01) | |

(52) U.S. Cl.
CPC .... *A01K 67/0275* (2013.01); *C07K 14/70553* (2013.01); *C12N 5/16* (2013.01); *A01K 2227/101* (2013.01); *A61K 38/00* (2013.01); *C07K 16/2845* (2013.01); *C07K 2317/34* (2013.01)

(58) Field of Classification Search
CPC .................. A01K 67/0275; C07K 14/70553
See application file for complete search history.

(56) References Cited

PUBLICATIONS

Dolatshad et al. Mamm Genome 26:598-208, 2015.*
Kong et al. PLoS ONE 4(8):1-10, 2009.*
Twyman and Whitelaw. Gene Expression in Recombinant Animal Cells and Transgenic Animals. Encyclopedia of Industrial Biotechnology: Bioprocess, Bioseparation, and Cell Technology. MC Flickinger (ed.). John Wiley&Sons, Inc. Published 2013. pp. 1-75.*
Kuroiwa et al. Nature Genetics 36(7):775-780, 2004.*
Liu et al. Nature Communications Oct. 14, 2013, pp. 1-11.*
Carlson et al. PNAS 109:17382-17387, 2012.*
Laible et al. Biotechnology Journal 10:109-120, 2015.*
Gao et al. Genome Biology 18:1-15, 2017.*
Twyman and Whitelaw. Gene expression in Recombinant Animal Cells and Transgenic Animals. Encyclopedia of Industrial Biotechnology: Bioprocess, Bioseparation, and Cell Technology. MC Flickinger (ed.) John Wiley & Sons, Inc. Published 2013. pp. 1-75.7.
Printout from http://www.ncbi.nlm.nih.gov/protein/?term=bovine+CD18, pp. 1-2, Dec. 9, 2014.
Chen et al. Molecular Therapy 16(3):548-556, Mar. 2008.
Naito et al. Journal of Reproduction and Fertility 113, 137-143.

* cited by examiner

*Primary Examiner* — Marcia S Noble
(74) *Attorney, Agent, or Firm* — W&C IP

(57) ABSTRACT

Particular aspects show that the signal peptide remains intact on the mature CD18 molecule on ruminant leukocytes rendering these cells susceptible to cytolysis by Lkt. Comparative amino acid sequence analysis of the signal peptide of CD18 of eight ruminants and five non-ruminants revealed that the ruminant CD18 signal peptides contain 'cleavage-inhibiting' glutamine (Q), compared to 'cleavage-conducive' glycine in non-ruminants, at position −5 relative to the cleavage site. Mutagenesis of Q at position −5 of the bovine CD18 signal peptide to G resulted in the abrogation of Lkt-mediated cytolysis of transfectants expressing bovine CD18 carrying the Q(−5)G mutation. Provided is novel technology to clone cattle and other ruminants expressing CD18 without the signal peptide on their leukocytes, providing ruminants that are less susceptible to *M. haemolytica*. Methods for treating conditions and/or diseases associated with *M. haemolytica* (e.g., pneumonic pasteurellosis), comprising administration of polypeptides comprising CD18 signal peptide sequences are also provided.

6 Claims, 14 Drawing Sheets

Specification includes a Sequence Listing.

A

B

COMPOSITIONS AND METHODS FOR TREATING OR PREVENTING CONDITIONS AND DISEASES ASSOCIATED WITH *MANNHEIMIA HAEMOLYTICA*

CROSS-REFERENCE TO RELATED APPLICATIONS

This application claims the benefit of priority to U.S. Provisional Patent Application Ser. No. 61/149,278 filed 2 Feb. 2009 and entitled COMPOSITIONS AND METHODS FOR TREATING OR PREVENTING CONDITIONS AND DISEASES ASSOCIATED WITH *MANNHEIMIA HAEMOLYTICA*, which is incorporated by reference herein in its entirety.

FIELD OF THE INVENTION

Aspects of the present invention relate generally to conditions and/or diseases associated with *M. haemolytica* in ruminants, and more particularly to novel and efficacious compositions and methods for treating or preventing conditions and/or diseases associated with *M. haemolytica* in ruminants.

BACKGROUND

*Mannheimia haemolytica* (*M. haemolytica*) is the most significant bacterial pathogen of respiratory disease in cattle, sheep, goats and other ruminants, and causes extensive economic losses world-wide[8]. *M. haemolytica* is commonly found in the nasopharynx of healthy ruminants. In conjunction with active viral infection and stress factors, *M. haemolytica* migrates to the lungs, where it multiplies rapidly, and causes a fibrinonecrotic pleuropneumonia. *M. haemolytica* produces several virulence factors[8]. Based on the observation that leukotoxin-deletion mutants (Lkt-deletion mutants) of *M. haemolytica* cause reduced mortality and much milder lung lesions than the wild-type organisms, Lkt is considered as the most important virulence factor of this organism[9-13]. Lkt belongs to the family of RTX (repeats in toxins) toxins, and shares extensive homology with the exotoxins produced by other gram-negative bacteria such as *Escherichia coli*[14], *Actinobacillus pleuropneumoniae*[15], and *Actinobacillus actinomycetemcomitans*[16]. Cytolytic activity of *M. haemolytica* Lkt is specific for ruminant leukocytes[17-18]. Although all the subsets of leukocytes are susceptible to the cytolytic effects of Lkt, PMNs are the most susceptible subset[19]. PMN-depletion mitigates the lung injury in calves caused by *M. haemolytica* infection[20]. Therefore, Lkt-induced PMN lysis and degranulation are the primary causes of acute inflammation and lung injury characteristic of pneumonic pasteurellosis[8,13,20].

There is, therefore a pronounced need in the art for novel and efficacious compositions and methods for treating or preventing conditions and/or diseases associated with *M. haemolytica* (e.g., in mammals, ruminants).

SUMMARY OF EXEMPLARY ASPECTS OF THE INVENTION

In particular aspects of the present invention, studies aimed at mapping the *Mannheimia* (*Pasteurella*) *haemolytica* leukotoxin (Lkt) binding site on its receptor CD18 have unexpectedly shown, as disclosed herein, that the signal peptide of ruminant CD18 remains intact on the mature CD18 molecule on the leukocytes of ruminants and renders these cells susceptible to cytolysis by Lkt.

In additional aspects, comparative analysis of the amino acid (aa) sequence of the signal peptide of CD18 of eight ruminants and five non-ruminants revealed that the signal peptide of CD18 of ruminants contain 'cleavage-inhibiting' glutamine (Q), whereas that of non-ruminants contain 'cleavage-conducive' glycine (G) at position −5 relative to the cleavage site.

In further aspects, site-directed mutagenesis of Q at position −5 of the signal peptide of bovine CD18 to G resulted in the abrogation of cytolysis of transfectants expressing bovine CD18 carrying the Q(−5)G mutation.

Particular aspects, therefore provide a hitherto unavailable technology to clone cattle and other ruminants expressing CD18 without the signal peptide on their leukocytes, providing ruminants that are less susceptible to pneumonic pasteurellosis that costs millions of dollars world-wide annually.

Particular preferred aspects provide a purified or recombinant ruminant CD18 polypeptide, comprising a ruminant CD18 polypeptide, or portion thereof, having a cleavable signal peptide with a helix-breaking amino acid residue at amino acid position 18 (−5 with respect to signal peptide cleavage site). In certain aspects, the amino acid residue at amino acid position 18 is selected from the group consisting of glycine, proline, arginine, and tyrosine. In further preferred aspects, the ruminant is selected from the group consisting of cattle, bison, buffalo, goat, domestic sheep, big horn sheep, deer, elk, giraffes, yaks, camels, alpacas, llamas, wildebeest, antelope, pronghorn and nilgai. Yet further aspects provide, that the recombinant ruminant CD18 polypeptide is one Q(−5)G CD18 mutant selected from the group consisting of SEQ ID NOS:57, 58, 60, 62, 64, 66, 68, 70 and CD18 signal peptide-comprising portions thereof.

Additional aspects provide an isolated nucleic acid comprising a sequence that encodes the polypeptide of CD18 having a cleavable signal peptide with a helix breaking amino acid residue at amino acid position 18.

Further preferred aspects provide for a recombinant expression vector, comprising a nucleic acid comprising a sequence that encodes a polypeptide comprising a ruminant CD18 polypeptide, or portion thereof, having a cleavable signal peptide with a helix-breaking amino acid residue at amino acid position 18 (−5 with respect to signal peptide cleavage site).

Yet further preferred aspects provide for a recombinant or cloned ruminant cell or ruminant animal, comprising a ruminant cell capable of expressing a polypeptide comprising a ruminant CD18 polypeptide, or portion thereof, having a cleavable signal peptide with a helix-breaking amino acid residue at amino acid position 18 (−5 with respect to signal peptide cleavage site). Additional aspects provide that expression of a polypeptide comprises a ruminant CD18 polypeptide having a cleavable signal peptide comprises expressing from a genomic locus, or from a recombinant expression vector. Further aspects provide that the cell or animal is less susceptible to, or resistant to the effects of *M. haemolytica*, relative to wild-type control cells.

Additional aspects provide that the cell or animal is that of a ruminant selected from the group consisting of cattle, bison, buffalo, goat, domestic sheep, big horn sheep, deer, elk, giraffes, yaks, camels, alpacas, llamas, wildebeest, antelope, pronghorn and nilgai. Further preferred aspects provide that the cell capable of expressing a polypeptide comprising a ruminant CD18 polypeptide, or portion thereof, having a cleavable signal peptide, there is reduced or no expression of the endogenous wild-type CD18 polypeptide having a non-cleavable signal peptide.

Further preferred aspects provide for a method of providing a recombinant or cloned ruminant cell, comprising introduction into, or engineering within the ruminant cell, a nucleic acid comprising a sequence that encodes a polypeptide comprising a ruminant CD18 polypeptide, or portion thereof, having a cleavable signal peptide with a helix-breaking amino acid residue at amino acid position 18 (−5 with respect to signal peptide cleavage site), wherein the cell is less susceptible to, or resistant to the effects of *M. haemolytica*, relative to wild-type control cells. Yet further aspects provide for the amino acid residue at amino acid position 18 is selected from the group consisting of glycine, proline, arginine, and tyrosine.

Additional preferred aspects provide for a method where the ruminant is selected from the group consisting of cattle, bison, buffalo, goat, domestic sheep, big horn sheep, deer, elk, giraffes, yaks, camels, alpacas, llamas, wildebeest, antelope, pronghorn and nilgai. Further preferred aspects provide for the recombinant ruminant CD18 polypeptide is one Q(−5)G CD18 mutant selected from the group consisting of SEQ ID NOS:57, 58, 60, 62, 64, 66, 68, 70 and CD18 signal peptide-comprising portions thereof.

Further preferred aspects provide a method of providing a recombinant or cloned ruminant animal, comprising introduction into, or engineering within one or more cells of a ruminant animal, a nucleic acid comprising a sequence that encodes a polypeptide comprising a ruminant CD18 polypeptide, or portion thereof, having a cleavable signal peptide with a helix-breaking amino acid residue at amino acid position 18 (−5 with respect to signal peptide cleavage site), wherein the recombinant or cloned ruminant animal is less susceptible to, or resistant to the effects of *M. haemolytica*, relative to wild-type control cells. Yet further aspects provide for the use of ruminant stem cells or enucleated ruminant cells.

Additional preferred aspects provide a method where the amino acid residue at amino acid position 18 is selected from the group consisting of glycine, proline, arginine, and tyrosine. Further preferred aspects provide a method where the ruminant is selected from the group consisting of cattle, bison, buffalo, goat, domestic sheep, big horn sheep, deer, elk, giraffes, yaks, camels, alpacas, llamas, wildebeest, antelope, pronghorn and nilgai.

Further preferred aspects provide a method where the recombinant ruminant CD18 polypeptide is one Q(−5)G CD18 mutant selected from the group consisting of SEQ ID NOS:57, 58, 60, 62, 64, 66, 68, 70 and CD18 signal peptide-comprising portions thereof.

Yet further preferred aspects provide a method of treating or preventing conditions and diseases associated with *M. haemolytica* in ruminants, comprising administering to a ruminant subject in need thereof, an amount of a polypeptide comprising a CD18 signal peptide, or portion thereof, suitable to treat, prevent or otherwise ameliorate a condition or diseases associated with *M. haemolytica* in the ruminant.

Additional aspects provide a method of treating whereby the polypeptide comprising a CD18 signal peptide, or portion thereof, is a polypeptide comprising from about 13 to about 24 contiguous amino acid residues of the first 24 amino acids of the N-terminus of the native (full-length nascent) CD18 sequence, wherein the polypeptide is suitable to provide for at least one of binding to *M. haemolytica* leukotoxin (Lkt) and abrogation of Lkt-induced cytolysis. Further aspects provide a method whereby the polypeptide comprises a contiguous portion of the CD18 signal polypeptide beginning at amino acid residue 5. Yet further aspects provide a method whereby the polypeptide comprises residues 5 to 17 of the CD18 signal polypeptide.

Further preferred aspects provide a method whereby the CD18 sequence is selected from the group consisting of cattle, bison, buffalo, goat, domestic sheep, big horn sheep, deer, elk, giraffes, yaks, camels, alpacas, llamas, wildebeest, antelope, pronghorn, nilgai, human, chimp, mouse, rat and pig. Additional preferred aspects provide a method whereby the CD18 sequence is selected from the group consisting of SEQ ID NOS:2, 4, 6, 8, 10, 12, 14, 16, 18, 20, 22, 21, 26, 57, 58, 60, 62, 64, 66, 68 and 70.

Certain preferred aspects provide a method whereby the CD18 signal peptide sequence is selected from the group consisting of cattle, bison, buffalo, goat, domestic sheep, big horn sheep, deer, elk, giraffes, yaks, camels, alpacas, llamas, wildebeest, antelope, pronghorn and nilgai, human, chimp, mouse, rat and pig. Additional preferred aspects provide a method whereby the CD18 signal peptide sequence is selected from the group consisting of SEQ ID NOS:28, 30, 32, 34, 36, 40, 42, 44, 46, 48, 50, 52 and 54.

Certain aspects further comprise administration of an anti-leukotoxin antibody reagent or epitope-binding portion thereof.

In particular aspects, administering the amount of the polypeptide comprising a CD18 signal peptide, or portion thereof, comprises administration to a ruminant previously vaccinated against *M. haemolytica*. In certain embodiments, vaccination against *M. haemolytica* comprises administration of *M. haemolytica* leukotoxin (Lkt) or a portion thereof.

Additional aspects provide an antibody specific for a CD18 signal peptide, or portion thereof comprising from about 13 to about 24 contiguous amino acid residues of the first 24 amino acids of the N-terminus of the native (full-length nascent) ruminant CD18 sequence, wherein the polypeptide is suitable to provide for at least one of binding to *M. haemolytica* leukotoxin (Lkt) and abrogation of Lkt-induced cytolysis. In certain embodiments, the polypeptide comprises a contiguous portion of the CD18 signal polypeptide beginning at amino acid residue 5. In certain aspects, the polypeptide comprises residues 5 to 17 of the CD18 signal polypeptide. In particular embodiments, the CD18 sequence is selected from the group consisting of cattle, bison, buffalo, goat, domestic sheep, big horn sheep, deer, elk, giraffes, yaks, camels, alpacas, llamas, wildebeest, antelope, pronghorn, nilgai, human, chimp, mouse, rat and pig. In certain embodiments, the CD18 sequence is selected from the group consisting of SEQ ID NOS:2, 4, 6, 8, 10, 12, 14, 16, 18, 20, 22, 21, 26, 57, 58, 60, 62, 64, 66, 68 and 70.

Yet further aspects provide a method of treating for treating or preventing conditions and diseases associated with *M. haemolytica* in ruminants, comprising administering to a ruminant subject in need thereof, an amount of an antibody specific for a CD18 signal peptide, or portion thereof comprising from about 13 to about 24 contiguous amino acid residues of the first 24 amino acids of the N-terminus of the native (full-length nascent) ruminant CD18 sequence, wherein the polypeptide is suitable to provide for at least one of binding to *M. haemolytica* leukotoxin (Lkt) and abrogation of Lkt-induced cytolysis, wherein a method of treating for treating or preventing conditions and diseases associated with *M. haemolytica* in ruminants is provided. In certain aspects, the antibody is according to those anti-ruminant CD18 signal peptide antibodies described herein.

DETAILED DESCRIPTION OF EXEMPLARY ASPECTS OF THE INVENTION

Figures 1A, 1B:
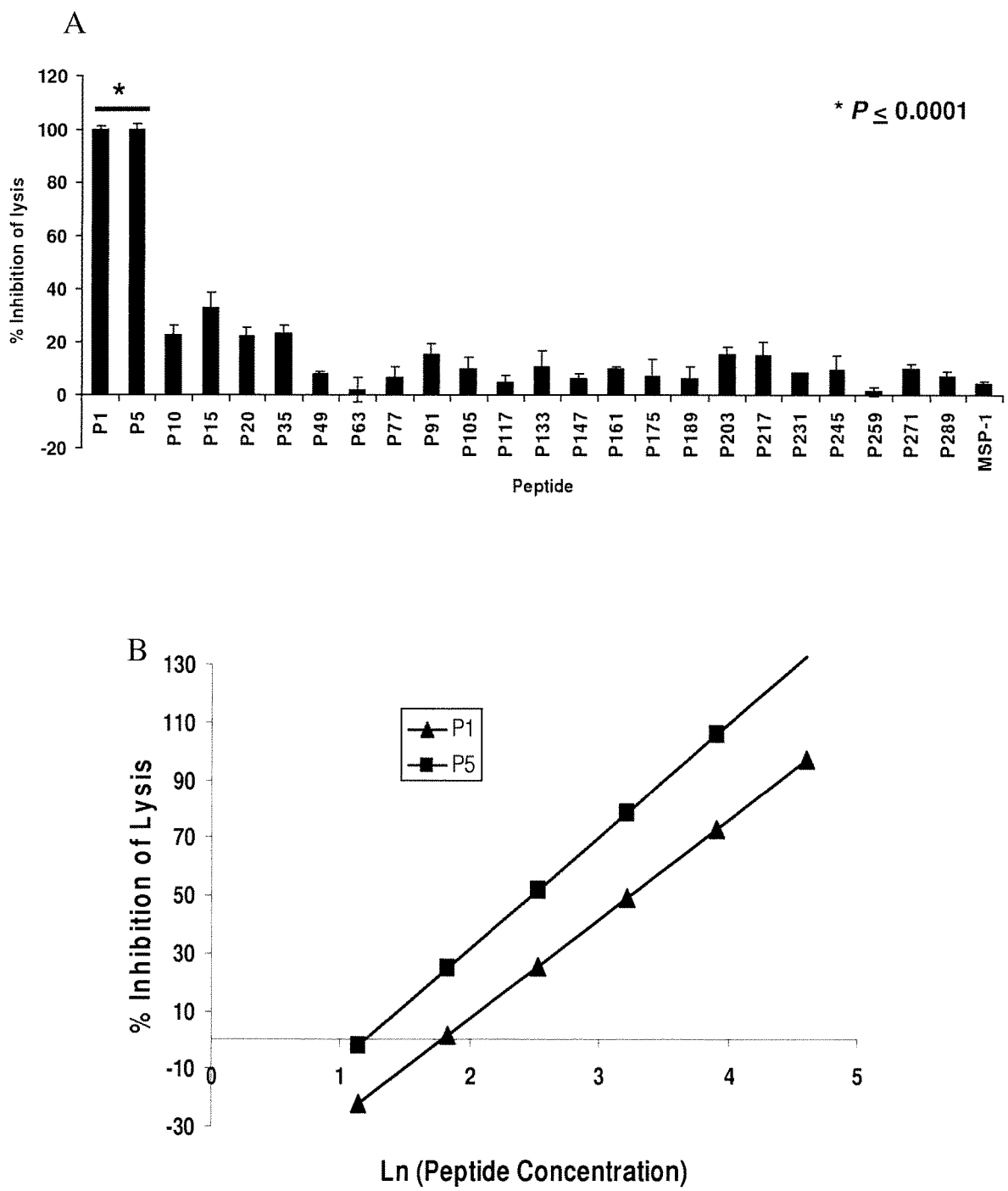
FIGS. 1A-1C show, according to particular exemplary aspects, that the CD18 signal peptide analog P5 (aa 5-24) inhibits Lkt-induced cytolysis of bovine PMNs. See working EXAMPLE 2 for details.

Generally, a nascent membrane protein contains a signal sequence that directs the protein/ribosome to the endoplasmic reticulum (ER) membrane[1-3]. The signal peptide binds to the signal recognition particle (SRP) which in turn binds to the SRP receptor on the ER membrane and helps in the translocation of the protein into the lumen of the ER. The signal peptide is cleaved from the protein by the ER-resident signal peptidase while it is still growing on the ribosome. Thus the signal peptide is not present on the mature protein that reaches the plasma membrane following post-translational modifications.

As disclosed herein, however, Applicants' mapping the *Mannheimia* (*Pasteurella*) *haemolytica* leukotoxin (Lkt) binding site on its receptor CD18 have led to the unexpected finding that the signal peptide of ruminant CD18 remains intact on the mature CD18 molecule on the leukocytes of ruminants and renders these cells susceptible to cytolysis by Lkt.

Therefore, the signal peptide of ruminant CD18, the β subunit of leukocyte-specific β2-integrins, is an exception to general phenomenon that signal peptides are not present on the mature protein that reaches the plasma membrane. Intriguingly, as disclosed herein, the intact signal peptide of CD18 is responsible for the susceptibility of ruminant leukocytes to *Mannheimia* (*Pasteurella*) *haemolytica* leukotoxin, and the resultant susceptibility of ruminants to severe pneumonia caused by this organism.

Previously, Applicants identified CD18 as the receptor for Lkt on bovine[4] and ovine[5,6] leukocytes, and mapped the Lkt-binding site to lie between amino acids 1-291[7]. As disclosed herein, under working EXAMPLE 2, inhibition of Lkt-induced cytolysis of ruminant leukocytes by CD18 peptide analogs revealed that the Lkt-binding site is formed by aa 5-17 of CD18 which, surprisingly, comprise a part of the signal peptide.

As shown herein under working EXAMPLE 3, flow cytometric analysis of ruminant leukocytes with an anti-signal peptide serum indicated the presence of the signal peptide on the mature CD18 molecules expressed on the cell surface.

As shown herein under working EXAMPLE 4, analysis of the transfectants expressing CD18 containing the 'FLAG' epitope at the putative cleavage site confirmed that the signal peptide of CD18 is not cleaved.

Working EXAMPLE 5 below, discloses a comparative analysis of the amino acid (aa) sequence of the signal peptide of CD18 of eight ruminants and five non-ruminants, and revealed that the signal peptide of CD18 of ruminants contain 'cleavage-inhibiting' glutamine (Q), whereas that of non-ruminants contain 'cleavage-conducive' glycine (G) at position −5 relative to the cleavage site.

Working EXAMPLE 6 below, discloses that site-directed mutagenesis of Q at position −5 of the signal peptide of bovine CD18 to G resulted in the abrogation of cytolysis of transfectants expressing bovine CD18 carrying the Q(−5)G mutation. According to particular aspects, replacement of 'cleavage-inhibiting' Q at −5 position with 'cleavage-conducive' G resulted in the cleavage of the signal peptide and the resultant loss of susceptibility of the transfectants to Lkt-induced cytolysis. According to additional aspects, it is possible that abrogation of cytolysis is not due to cleavage of signal peptide, but due to conformational changes caused by the replacement of Q with G. Irrespective of the molecular basis underlying the abrogation of cytolysis, however, the exemplary Q(−5)G mutation presents an exemplary embodiment of a hitherto unavailable technology to, among other things, clone cattle and other ruminants expressing CD18 without the signal peptide on their leukocytes, and thus provide animals that are substantially less susceptible to pneumonic pasteurellosis.

Definitions: "Functional variants" as used herein refers to at least one protein selected from the group consisting of SEQ ID NOS:2, 4, 6, 8, 10, 12 14, 16, 18, 20, 22, 24, 26, 28, 30, 32, 34, 36, 38, 40, 42, 44, 46, 48, 50, 52, 54, 57, 58, 60, 62, 64, 66, 68, and 70 sequences having at least 60%, 65%, 70%, 75%, 80%, 85%, 90%, 95%, 96%, 97%, 98% or 99% sequence identity thereto, and biologically active variants thereof, where functional or biologically active variants are those proteins that display one or more of the biological activities of at least one protein selected from the group consisting of SEQ ID NOS: 2, 4, 6, 8, 10, 12 14, 16, 18, 20, 22, 24, 26, 28, 30, 32, 34, 36, 38, 40, 42, 44, 46, 48, 50, 52, 54, 57, 58, 60, 62, 64, 66, 68, and 70, sequences having at least 60%, 65%, 70%, 75%, 80%, 85%, 90%, 95%, 96%, 97%, 98% or 99% sequence identity thereto, including but not limited to the activities disclosed herein (e.g., binding to the bacterial toxin Lkt; producing proteins resistant to binding by Lkt)

As used herein, a pharmaceutical or therapeutic effect refers to an effect observed upon administration of an agent intended for the prevention or treatment of a disease or disorder or for amelioration of the symptoms thereof.

As used herein, treatment means any manner in which the symptoms of a condition, disorder or disease or other indication, are ameliorated or otherwise beneficially altered.

As used herein therapeutic effect means an effect resulting from treatment of a subject that alters, typically improves or ameliorates the symptoms of a disease or condition or that cures a disease or condition. A therapeutically effective amount refers to the amount of a composition, molecule or compound which results in a therapeutic effect following administration to a subject.

As used herein, the term "subject" refers to ruminant animals, including mammals, such as cattle.

As used herein, the phrase "associated with" refers to certain biological aspects such as expression of a receptor or signaling by a receptor that occurs in the context of a disease or condition. Such biological aspect may or may not be causative or integral to the disease or condition but merely an aspect of the disease or condition.

As used herein, a biological activity refers to a function of a polypeptide including but not limited to complexation, dimerization, multimerization, receptor-associated kinase activity, receptor-associated protease activity, phosphorylation, dephosphorylation, autophosphorylation, ability to form complexes with other molecules, ligand binding, catalytic or enzymatic activity, activation including auto-activation and activation of other polypeptides, inhibition or modulation of another molecule's function, stimulation or inhibition of signal transduction and/or cellular responses such as cell proliferation, migration, differentiation, and growth, degradation, membrane localization, membrane binding, and oncogenesis. A biological activity can be assessed by assays described herein and by any suitable assays known to those of skill in the art, including, but not limited to in vitro assays, including cell-based assays, in vivo assays, including assays in animal models for particular diseases.

Table 1 contains a brief description and sequence listing including some but not all (e.g., exemplary) of the peptides and polypeptides within the scope of this invention. Therapeutic peptides to be used in the prevention and/or treatment of an infection of M. haemolytica may be a portion of CD18 from ruminants containing the signal sequence. In preferred aspects, the therapeutic contains the amino acid residues of CD18 from ruminants from amino acids 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, and 1 to 10. Additionally, the therapeutic contains the amino acid residues of CD18 from ruminants from amino acids 2 to 25, 2 to 24, 2 to 23, 2 to 22, 2 to 21, 2 to 20, 2 to 19, 2 to 18, 2 to 17, 2 to 16, 2 to 15, 2 to 14, 2 to 13, 2 to 12, 2 to 11, and 2 to 10. In further preferred embodiments, the therapeutic contains the amino acid residues of CD18 from ruminants from amino acids 3 to 25, 3 to 24, 3 to 23, 3 to 22, 3 to 21, 3 to 20, 3 to 19, 3 to 18, 3 to 17, 3 to 16, 3 to 15, and 3 to 14, 3 to 13, 3 to 12, 3 to 11, and 3 to 10. In yet further preferred embodiments, the therapeutic contains the amino acid residues of CD18 from ruminants from amino acids 4 to 25, 4 to 24, 4 to 23, 4 to 22, 4 to 21, 4 to 20, 4 to 19, 4 to 18, 4 to 17, 4 to 16, 4 to 15, and 4 to 14, 4 to 13, 4 to 12, 4 to 11, and 4 to 10. In additional, preferred embodiments, the therapeutic contains the amino acid residues of CD18 from ruminants from amino acids 5 to 25, 5 to 24, 5 to 23, 5 to 22, 5 to 21, 5 to 20, 5 to 19, 5 to 18, 5 to 17, 5 to 16, 5 to 15, and 5 to 14, 5 to 13, 5 to 12, 5 to 11, and 5 to 10.

TABLE 1

Summary of exemplary SEQ ID NOS and brief descriptions thereof.

| BRIEF DESCRIPTION | SEQ ID NO | |
|---|---|---|
| | Nucleic Acid | Protein |
| Full Length CD18 Protein | | |
| Cattle | SEQ ID NO: 1 | SEQ ID NO: 2 |
| Bison | SEQ ID NO: 3 | SEQ ID NO: 4 |
| Buffalo | SEQ ID NO: 5 | SEQ ID NO: 6 |
| Goat | SEQ ID NO: 7 | SEQ ID NO: 8 |
| Domestic Sheep | SEQ ID NO: 9 | SEQ ID NO: 10 |
| Wild Sheep | SEQ ID NO: 11 | SEQ ID NO: 12 |
| Deer | SEQ ID NO: 13 | SEQ ID NO: 14 |
| Elk | SEQ ID NO: 15 | SEQ ID NO: 16 |
| Human | SEQ ID NO: 17 | SEQ ID NO: 18 |
| Mouse | SEQ ID NO: 19 | SEQ ID NO: 20 |
| Rat | SEQ ID NO: 21 | SEQ ID NO: 22 |
| Pig | SEQ ID NO: 23 | SEQ ID NO: 24 |
| Chimp | SEQ ID NO: 25 | SEQ ID NO: 26 |
| Exemplary Mutated CD18 | | |
| Cattle | SEQ ID NO: 55 | SEQ ID NO: 58 |
| Bison | SEQ ID NO: 59 | SEQ ID NO: 60 |
| Buffalo | SEQ ID NO: 56 | SEQ ID NO: 57 |
| Goat | SEQ ID NO: 61 | SEQ ID NO: 62 |
| Domestic Sheep | SEQ ID NO: 63 | SEQ ID NO: 64 |
| Wild Sheep | SEQ ID NO: 65 | SEQ ID NO: 66 |
| Deer | SEQ ID NO: 67 | SEQ ID NO: 68 |
| Elk | SEQ ID NO: 69 | SEQ ID NO: 70 |
| Peptide from CD18 Signal Sequence | | |
| Cattle | SEQ ID NO: 27 | SEQ ID NO: 28 |
| Bison | SEQ ID NO: 27 | SEQ ID NO: 28 |
| Buffalo | SEQ ID NO: 29 | SEQ ID NO: 30 |
| Goat | SEQ ID NO: 31 | SEQ ID NO: 32 |
| Domestic Sheep | SEQ ID NO: 33 | SEQ ID NO: 34 |
| Wild Sheep | SEQ ID NO: 33 | SEQ ID NO: 34 |
| Deer | SEQ ID NO: 35 | SEQ ID NO: 36 |
| Elk | SEQ ID NO: 37 | SEQ ID NO: 38 |
| Human | SEQ ID NO: 39 | SEQ ID NO: 40 |
| Chimp | SEQ ID NO: 39 | SEQ ID NO: 40 |
| Mouse | SEQ ID NO: 41 | SEQ ID NO: 42 |
| Rat | SEQ ID NO: 43 | SEQ ID NO: 44 |
| Pig | SEQ ID NO: 45 | SEQ ID NO: 46 |
| Exemplary Mutated Peptide from CD18 Signal Sequence | | |
| Human | SEQ ID NO: 47 | SEQ ID NO: 48 |
| Chimp | SEQ ID NO: 47 | SEQ ID NO: 48 |
| Mouse | SEQ ID NO: 49 | SEQ ID NO: 50 |
| Rat | SEQ ID NO: 51 | SEQ ID NO: 52 |
| Pig | SEQ ID NO: 53 | SEQ ID NO: 54 |

Variants of at least one protein selected from the group consisting of SEQ ID NOS:2, 4, 6, 8, 10, 12 14, 16, 18, 20, 22, 24, 26, 28, 30, 32, 34, 36, 38, 40, 42, 44, 46, 48, 50, 52, 54, 57, 58, 60, 62, 64, 66, 68, and 70, sequences having at least 60%, 65%, 70%, 75%, 80%, 85%, 90%, 95%, 96%, 97%, 98% or 99% sequence identity thereto have utility for aspects of the present invention. Variants can be naturally or non-naturally occurring. Naturally occurring variants (e.g., polymorphisms) are found in humans or other species and comprise amino acid sequences which are substantially identical to the amino acid sequences disclosed herein. Species homologs of the protein can be obtained using subgenomic polynucleotides of the invention, as described below, to make suitable probes or primers for screening cDNA expression libraries from other species, such as mice, monkeys, yeast, or bacteria, identifying cDNAs which encode homologs of the protein, and expressing the cDNAs as is known in the art.

Non-naturally occurring variants which retain substantially the same biological activities as naturally occurring protein variants. Preferably, naturally or non-naturally occurring variants have amino acid sequences which are at least 60%, 65%, 70%, 75%, 80%, 85%, 90%, 95%, 96%, 97%, 98% or 99% identical to the amino acid sequenced disclosed herein. More preferably, the molecules are at least 98% or 99% identical. Percent identity is determined using any method known in the art. A non-limiting example is the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* 2:482-489, 1981.

As used herein, "amino acid residue" refers to an amino acid formed upon chemical digestion (hydrolysis) of a polypeptide at its peptide linkages. The amino acid residues described herein are generally in the "L" isomeric form. Residues in the "D" isomeric form can be substituted for any L-amino acid residue, as long as the desired functional property is retained by the polypeptide. NH2 refers to the free amino group present at the amino terminus of a polypeptide. COOH refers to the free carboxy group present at the carboxyl terminus of a polypeptide. In keeping with standard polypeptide nomenclature described in J. Biol. Chem., 243:3552-59 (1969) and adopted at 37 C.F.R. §§ 1.821-1.822, abbreviations for amino acid residues are shown in Table 2:

TABLE 2

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Praline |
| K | Lys | Lysine |
| H | His | Histidine |
| Q | Gln | Glutamine |
| E | Glu | glutamic acid |
| Z | Glx | Glu and/or Gln |
| W | Trp | Tryptophan |
| R | Arg | Arginine |
| D | Asp | aspartic acid |
| N | Asn | Asparagines |
| B | Asx | Asn and/or Asp |
| C | Cys | Cysteine |
| X | Xaa | Unknown or other |

It should be noted that all amino acid residue sequences represented herein by a formula have a left to right orientation in the conventional direction of amino-terminus to carboxyl-terminus. In addition, the phrase "amino acid residue" is defined to include the amino acids listed in the Table of Correspondence and modified and unusual amino acids, such as those referred to in 37 C.F.R. §§ 1.821-1.822, and incorporated herein by reference. Furthermore, it should be noted that a dash at the beginning or end of an amino acid residue sequence indicates a peptide bond to a further sequence of one or more amino acid residues or to an amino-terminal group such as NH) or to a carboxyl-terminal group such as COOH.

Guidance in determining which amino acid residues can be substituted, inserted, or deleted without abolishing biological or immunological activity can be found using computer programs well known in the art, such as DNASTAR software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting variant.

Variants of the at least one protein selected from the group consisting of SEQ ID NOS: 2, 4, 6, 8, 10, 12 14, 16, 18, 20, 22, 24, 26, 28, 30, 32, 34, 36, 38, 40, 42, 44, 46, 48, 50, 52, 54, 57, 58, 60, 62, 64, 66, 68, and 70, sequences having at least 60%, 65%, 70%, 75%, 80%, 85%, 90%, 95%, 96%, 97%, 98% or 99% sequence identity thereto disclosed herein include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

A subset of mutants, called muteins, is a group of polypeptides in which neutral amino acids, such as serines, are substituted for cysteine residues which do not participate in disulfide bonds. These mutants may be stable over a broader temperature range than native secreted proteins (see, e.g., Mark et al., U.S. Pat. No. 4,959,314).

Preferably, amino acid changes in the variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting secreted protein or polypeptide variant. Properties and functions of the variants are of the same type as a protein comprising the amino acid sequence encoded by the nucleotide sequence shown in SEQ ID NOS: 2, 4, 6, 8, 10, 12 14, 16, 18, 20, 22, 24, 26, 28, 30, 32, 34, 36, 38, 40, 42, 44, 46, 48, 50, 52, 54, 57, 58, 60, 62, 64, 66, 68, and 70, and sequences having at least 60%, 65%, 70%, 75%, 80%, 85%, 90%, 95%, 96%, 97%, 98% or 99% sequence identity thereto, although the properties and functions of variants can differ in degree.

Variants of at least one protein selected from the group consisting of SEQ ID NOS: 2, 4, 6, 8, 10, 12 14, 16, 18, 20, 22, 24, 26, 28, 30, 32, 34, 36, 38, 40, 42, 44, 46, 48, 50, 52, 54, 57, 58, 60, 62, 64, 66, 68, and 70, sequences having at least 60%, 65%, 70%, 75%, 80%, 85%, 90%, 95%, 96%, 97%, 98% or 99% sequence identity thereto include glycosylated forms, aggregative conjugates with other molecules, and covalent conjugates with unrelated chemical moieties (e.g., pegylated molecules). The variants also include allelic variants, species variants, and muteins. Truncations or deletions of regions which do not affect functional activity of the proteins are also variants. Covalent variants can be prepared by linking functionalities to groups which are found in the amino acid chain or at the N- or C-terminal residue, as is known in the art.

It will be recognized in the art that some amino acid sequences of the polypeptides of the invention can be varied without significant effect on the structure or function of the protein. If such differences in sequence are contemplated, it should be remembered that there are critical areas on the protein which determine activity. In general, it is possible to replace residues that form the tertiary structure, provided that residues performing a similar function are used. In other instances, the type of residue may be completely unimportant if the alteration occurs at a non-critical region of the protein. The replacement of amino acids can also change the selectivity of binding to cell surface receptors (Ostade et al., *Nature* 361:266-268, 1993). Thus, the polypeptides of the present invention may include one or more amino acid substitutions, deletions or additions, either from natural mutations or human manipulation.

Of particular interest are substitutions of charged amino acids with another charged amino acid and with neutral or negatively charged amino acids. The latter results in proteins with reduced positive charge to improve the characteristics of the disclosed protein. The prevention of aggregation is highly desirable. Aggregation of proteins not only results in a loss of activity but can also be problematic when preparing pharmaceutical formulations, because they can be immunogenic (see, e.g., Pinckard et al., *Clin. Exp. Immunol.* 2:331-340 (1967); Robbins et al., *Diabetes* 36:838-845 (1987); and Cleland et al., *Crit. Rev. Therapeutic Drug Carrier Systems* 10:307-377 (1993)).

Amino acids in polypeptides of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as binding to a natural or synthetic binding partner. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

As indicated, changes are preferably of a minor nature, such as conservative amino acid substitutions that do not significantly affect the folding or activity of the protein. Of course, the number of amino acid substitutions a skilled artisan would make depends on many factors, including those described above. Generally speaking, the number of substitutions for any given polypeptide will not be more than 50, 40, 30, 25, 20, 15, 10, 5 or 3.

In addition, pegylation of the inventive polypeptides and/or muteins is expected to provide such improved properties as increased half-life, solubility, and protease resistance. Pegylation is well known in the art.

Fusion Proteins

Fusion proteins comprising proteins or polypeptide fragments of at least one protein selected from the group consisting of SEQ ID NOS: 2, 4, 6, 8, 10, 12 14, 16, 18, 20, 22, 24, 26, 28, 30, 32, 34, 36, 38, 40, 42, 44, 46, 48, 50, 52, 54, 57, 58, 60, 62, 64, 66, 68, and 70, sequences having at least 60%, 65%, 70%, 75%, 80%, 85%, 90%, 95%, 96%, 97%, 98% or 99% sequence identity thereto can also be constructed. Fusion proteins are useful for generating antibodies against amino acid sequences and for use in various targeting and assay systems. For example, fusion proteins can be used to identify proteins which interact with a polypeptide of the invention or which interfere with its biological function. Physical methods, such as protein affinity chromatography, or library-based assays for protein-protein interactions, such as the yeast two-hybrid or phage display systems, can also be used for this purpose. Such methods are well known in the art and can also be used as drug screens. Fusion proteins comprising a signal sequence can be used.

A fusion protein comprises two protein segments fused together by means of a peptide bond. Amino acid sequences for use in fusion proteins of the invention can be utilize the amino acid sequence shown in SEQ ID NOS: 2, 4, 6, 8, 10, 12 14, 16, 18, 20, 22, 24, 26, 28, 30, 32, 34, 36, 38, 40, 42, 44, 46, 48, 50, 52, 54, 57, 58, 60, 62, 64, 66, 68, and 70, and sequences having at least 60%, 65%, 70%, 75%, 80%, 85%, 90%, 95%, 96%, 97%, 98% or 99% sequence identity thereto, or can be prepared from biologically active variants such as those described above. The first protein segment can include of a full-length polypeptide selected from the group consisting of SEQ ID NOS: 2, 4, 6, 8, 10, 12 14, 16, 18, 20, 22, 24, 26, 28, 30, 32, 34, 36, 38, 40, 42, 44, 46, 48, 50, 52, 54, 57, 58, 60, 62, 64, 66, 68, and 70, sequences having at least 60%, 65%, 70%, 75%, 80%, 85%, 90%, 95%, 96%, 97%, 98% or 99% sequence identity thereto.

Other first protein segments can consist of biologically active portions of SEQ ID NOS: 2, 4, 6, 8, 10, 12 14, 16, 18, 20, 22, 24, 26, 28, 30, 32, 34, 36, 38, 40, 42, 44, 46, 48, 50, 52, 54, 57, 58, 60, 62, 64, 66, 68, and 70, sequences having at least 60%, 65%, 70%, 75%, 80%, 85%, 90%, 95%, 96%, 97%, 98% or 99% sequence identity thereto.

The second protein segment can be a full-length protein or a polypeptide fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions.

These fusions can be made, for example, by covalently linking two protein segments or by standard procedures in the art of molecular biology. Recombinant DNA methods can be used to prepare fusion proteins, for example, by making a DNA construct which comprises a coding region for the protein sequence of SEQ ID NOS: 2, 4, 6, 8, 10, 12 14, 16, 18, 20, 22, 24, 26, 28, 30, 32, 34, 36, 38, 40, 42, 44, 46, 48, 50, 52, 54, 57, 58, 60, 62, 64, 66, 68, and 70, sequences having at least 60%, 65%, 70%, 75%, 80%, 85%, 90%, 95%, 96%, 97%, 98% or 99% sequence identity thereto in proper reading frame with a nucleotide encoding the second protein segment and expressing the DNA construct in a host cell, as is known in the art. Many kits for constructing fusion proteins are available from companies that supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Pharmaceutical Compositions and Therapeutic Uses

Pharmaceutical compositions of the invention can comprise CD18 signal peptide (or a portion thereof)—comprising polypeptides of SEQ ID NOS: 2, 4, 6, 8, 10, 12 14, 16, 18, 20, 22, 24, 26, 28, 30, 32, 34, 36, 38, 40, 42, 44, 46, 48, 50, 52, 54, 57, 58, 60, 62, 64, 66, 68, and 70, and sequences having at least 60%, 65%, 70%, 75%, 80%, 85%, 90%, 95%, 96%, 97%, 98% or 99% sequence identity thereto polypeptide-based agents of the claimed invention in a therapeutically effective amount. The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation is determined by routine experimentation and is within the judgment of the clinician. For purposes of the present invention, an effective dose will generally be from about 0.01 mg/kg to 50 mg/kg or 0.05 mg/kg to about 10 mg/kg of the SEQ ID NOS: 2, 4, 6, 8, 10, 12 14, 16, 18, 20, 22, 24, 26, 28, 30, 32, 34, 36, 38, 40, 42, 44, 46, 48, 50, 52, 54, 57, 58, 60, 62, 64, 66, 68, and 70, sequences having at least 60%, 65%, 70%, 75%, 80%, 85%, 90%, 95%, 96%, 97%, 98% or 99% sequence identity thereto polypeptide constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the subject receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles. Typically, the therapeutic compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in *Remington's Pharmaceutical Sciences* (Mack Pub. Co., New Jersey, 1991).

Delivery Methods.

Once formulated, the compositions of the invention can be administered directly to the subject or delivered ex vivo, to cells derived from the subject (e.g., as in ex vivo gene therapy). Direct delivery of the compositions will generally be accomplished by parenteral injection, e.g., subcutaneously, intraperitoneally, intravenously or intramuscularly, myocardial, intratumoral, peritumoral, or to the interstitial space of a tissue. Other modes of administration include oral and pulmonary administration, suppositories, implants, and transdermal applications, needles, and gene guns or hyposprays. Specific oral treatment includes, but is not limited to, the inclusion of the therapeutic in the animal feed. Dosage treatment can be a single dose schedule or a multiple dose schedule.

Methods for the ex vivo delivery and reimplantation of transformed cells into a subject are known in the art and described in e.g., International Publication No. WO 93/14778. Examples of cells useful in ex vivo applications include, for example, stem cells, particularly hematopoetic, lymph cells, macrophages, dendritic cells, APCs, or tumor cells. Generally, delivery of nucleic acids for both ex vivo and in vitro applications can be accomplished by, for example, dextran-mediated transfection, calcium phosphate precipitation, polybrene mediated transfection, protoplast fusion, electroporation, encapsulation of the polynucleotide(s) in liposomes, direct microinjection of the DNA into nuclei, and viral-mediated, such as adenovirus or alphavirus, all well known in the art.

In a preferred embodiments, disorders can be amenable to treatment by administration of a therapeutic agent based on the provided polynucleotide or corresponding polypeptide. The therapeutic agent can be administered in conjunction with one or more other agents including, but not limited to, receptor-specific antibodies and/or chemotherapeutic (e.g., anti-neoplastic agents). Administered "in conjunction" includes administration at the same time, or within 1 day, 12 hours, 6 hours, one hour, or less than one hour, as the other therapeutic agent(s). The compositions may be mixed for co-administration, or may be administered separately by the same or different routes.

The dose and the means of administration of the inventive pharmaceutical compositions are determined based on the specific qualities of the therapeutic composition, the condition, age, and weight of the patient, the progression of the disease, and other relevant factors. For example, administration of polynucleotide therapeutic compositions agents of the invention includes local or systemic administration, including injection, oral administration, particle gun or catheterized administration, and topical administration. The therapeutic polynucleotide composition can contain an expression construct comprising a promoter operably linked to a polynucleotide encoding, for example, SEQ ID NOS: 2, 4, 6, 8, 10, 12 14, 16, 18, 20, 22, 24, 26, 28, 30, 32, 34, 36, 38, 40, 42, 44, 46, 48, 50, 52, 54, 57, 58, 60, 62, 64, 66, 68, and 70, and sequences having at least 60%, 65%, 70%, 75%, 80%, 85%, 90%, 95%, 96%, 97%, 98% or 99% sequence identity thereto. Various methods can be used to administer the therapeutic composition directly to a specific site in the body. For example, a target tissue is located and the therapeutic composition injected several times in several different locations within the target tissue. Alternatively, arteries which serve a target tissue are identified, and the therapeutic composition injected into such an artery, in order to deliver the composition directly into the target tissue. X-ray imaging is used to assist in certain of the above delivery methods.

Inventive polypeptide-mediated targeted delivery of therapeutic agents to specific tissues can also be used. Receptor-mediated DNA delivery techniques are described in, for example, Findeis et al., *Trends Biotechnol.* (1993) 11:202; Chiou et al., *Gene Therapeutics: Methods And Applications Of Direct Gene Transfer* (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci.* (USA) (1990) 87:3655; Wu et al., *J. Biol. Chem.* (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 mg to about 2 mg, about 5 mg to about 500 mg, and about 20 mg to about 100 mg of DNA can also be used during a gene therapy protocol. Factors such as method of action (e.g., for enhancing or inhibiting levels of the encoded gene product) and efficacy of transformation and expression are considerations which will affect the dosage required for ultimate efficacy of the subgenomic polynucleotides. Where greater expression is desired over a larger area of tissue, larger amounts of subgenomic polynucleotides or the same amounts readministered in a successive protocol of administrations, or several administrations to different adjacent or close tissue portions of, for example, a tumor site, may be required to affect a positive therapeutic outcome. In all cases, routine experimentation in clinical trials will determine specific ranges for optimal therapeutic effect.

The therapeutic polynucleotides and polypeptides of the present invention can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., WO 90/07936; WO 94/03622; WO 93/25698; WO 93/25234; U.S. Pat. No. 5,219,740; WO 93/11230; WO 93/10218; U.S. Pat. No. 4,777,127; GB Patent No. 2,200,651; EP 0 345 242; and WO 91/02805), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532), and adeno-associated virus (AAV) vectors (see, e.g., WO 94/12649, WO 93/03769; WO 93/19191; WO 94/28938; WO 95/11984 and WO 95/00655). Administration of DNA linked to killed adenovirus as described in Curiel, *Hum. Gene Ther.* (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther.* (1992) 3:147); ligand-linked DNA (see, e.g., Wu, *J. Biol. Chem.* 264:16985 (1989)); eukaryotic cell delivery vehicles cells (see, e.g., U.S. Pat. No. 5,814,482; WO 95/07994; WO 96/17072; WO 95/30763; and WO 97/42338) and nucleic charge neutralization or fusion with cell membranes. Naked DNA can also be employed. Exemplary naked DNA introduction methods are described in WO 90/11092 and U.S. Pat. No. 5,580,859. Liposomes that can act as gene delivery vehicles are described in U.S. Pat. No. 5,422,120; WO 95/13796; WO 94/23697; WO 91/14445; and EP 0524968. Additional approaches are described in Philip, *Mol. Cell Biol.* 14:2411 (1994), and in Woffendin, *Proc. Natl. Acad. Sci.* (1994) 91:11581-11585.

Further non-viral delivery suitable for use includes mechanical delivery systems such as the approach described in Woffendin et al., *Proc. Natl. Acad. Sci. USA* 91(24):11581 (1994). Moreover, the coding sequence and the product of expression of such can be delivered through deposition of photopolymerized hydrogel materials or use of ionizing radiation (see, e.g., U.S. Pat. No. 5,206,152 and WO 92/11033). Other conventional methods for gene delivery that can be used for delivery of the coding sequence include, for example, use of hand-held gene transfer particle gun (see, e.g., U.S. Pat. No. 5,149,655); use of ionizing radiation for activating transferred gene (see, e.g., U.S. Pat. No. 5,206,152 and WO 92/11033).)

Recombinant and Cloned Ruminant Animals:

Inventive CD18-related aspects (e.g. polypeptide-mediated treatment, etc) include producing animals that are naturally resistant to the effects of Lkt. This is accomplished by, for example, universally altering the genotype of an animal, wherein, the native CD18 molecule, which binds to the toxin Lkt, is replaced with the mutant CD18, which has limited Lkt binding. Universally altering the genotype of animal includes cloning of a given animal having the modified genotype. Additionally, the invention encompasses transgenic animals. Transgenic animals are those that carry a non-native gene that were introduced into the animal using similar techniques as described herein and those well known in the art. Transgenic animals can subsequently be cloned.

Cloned Ruminants:

Cloned fetuses and calves are produced using the chromatin transfer procedure, as described in Kuroiwa et al., (2004) hereby incorporated by reference specifically for its teaching of cloning of cattle. The method consists of sequential application of gene targeting by homologous recombination and rejuvenation of cell lines by production of cloned fetuses. For example, to generate cattle containing a CD18 molecule that had a Q(−5)G mutation (an exemplary mutation which results in limited binding of Lkt to CD18 signal sequence), a male Holstein primary fetal fibroblast line 6594 is transfected with vectors containing the mutated signal sequence to replace the native CD18 coding region. This fetal cell line containing the mutated CD18 are established at 40-60 days of gestation. Certain fetal cell lines that look promising are recloned to produce calves. To verify that each calf produced contains the mutated CD18 genotype, applicants collect ear biopsies and establish fibroblast cell lines for genotyping (Richt et al., 2007, hereby incorporated by reference to teach analysis of cells and animals post cloning). Genotyping is done by genomic PCR specific to each gene targeting event, followed by sequence analysis. Additionally, applicants verify the calf phenotype by collecting blood samples and isolating PMNs and ensuring that anti-signal peptide serum cannot bind to membrane CD18 of PMNs, as described in FIG. 4 and Example 3.

Gene replacement techniques used in the practice of applicant's invention includes, but is not limited to, the gene replacement techniques described in Kuroiwa et al., (2004) hereby incorporated by reference specifically for its teaching of gene replacement techniques and sequential application of those techniques. For example, the wildtype CD18 molecule is replaced by the exemplary Q(−5)G mutation in the signal sequence of CD18 that produces a CD18 molecule with a cleavable signal sequence. More specifically two different vectors, each containing specific selection cassettes (e.g., cassettes conferring resistance to neomycin or puromycin) are constructed containing the mutated CD18 molecule Q(−5)G. The mutated CD18 coding sequence is flanked on both the 5' and 3' ends with between 1 and 10 kb of native sequences, i.e. sequences that flank the CD18 gene in vivo in cattle. These vectors are then transfected into male Holstein primary fetal fibroblast line 6594.

Additionally, using techniques known in the art, practicing this invention includes gene therapy. Gene therapy or gene introduction encompasses treating an animal in need thereof with a vector that contains a gene sequence encoding the therapeutic to be produced and provided to the animal via the animal's own protein producing mechanisms. According to certain aspects the invention includes expressing nucleic acids sequences encoding CD18 polypeptides (e.g., SEQ ID NOS:2, 4, 6, 8, 10, 12 14, 16, 18, 20, 22, 24, 26, 28, 30, 32, 34, 36, 38, 40, 42, 44, 46, 48, 50, 52, 54, 57, 58, 60, 62, 64, 66, 68, and 70, sequences having at least 60%, 65%, 70%, 75%, 80%, 85%, 90%, 95%, 96%, 97%, 98% or 99% sequence identity thereto include glycosylated forms) by the cell's own machinery.

Antibodies or Antibody Fragments

Agents of the present invention include antibodies and/or antibody fragments, and in particular aspects, they are specific for (directed against): (1) *M. haemolytica* leukotoxin (Lkt); (2) against Lkt or antigen or portion thereof that is suitable for binding the signal peptide, and optionally wherein the anti-Lkt antibody can also bind Lkt complexed with ruminant CD18 signal peptide; (3) or against a CD18 signal peptide, or portion thereof comprising from about 13 to about 24 contiguous amino acid residues of the first 24 amino acids of the N-terminus of the native (full-length nascent) ruminant CD18 sequence, wherein the polypeptide is suitable to provide for at least one of binding to *M. haemolytica* leukotoxin (Lkt) and abrogation of Lkt-induced cytolysis; and (4) against signal peptide and able to bind Lkt complexed with ruminant CD18 signal peptide.

Suitable antibodies may be monoclonal, polyclonal or monoclonal antibodies tailored to a specific ruminant species (in analogy with humanized antibodies). Antibodies may be derived by conventional hybridoma based methodology, from antisera isolated from validated protein inoculated animals or through recombinant DNA technology. Alternatively, inventive antibodies or antibody fragments may be identified in vitro by use of one or more of the readily available phage display libraries. Exemplary methods are disclosed herein.

In one exemplary embodiment of the present invention, antibody agents are monoclonal antibodies that may be produced as follows. Target proteins in a baculovirus based system. By this method, target protein cDNAs or epitope-bearing fragments thereof are ligated into a suitable plasmid vector that is subsequently used to transfect Sf9 cells to facilitate protein production. In addition, it may be advantageous to incorporate an epitope tag or other moiety to facilitate affinity purification of the target protein. Clones of Sf9 cells expressing a particular protein are identified, e.g., by enzyme-linked immunosorbant assay (ELISA), lysates are prepared and the target protein purified by affinity chromatography. The purified target protein is, for example, injected intraperitoneally, into BALB/c mice to induce antibody production. It may be advantageous to add an adjuvant, such as Freund's adjuvant, to increase the resulting immune response.

Serum is tested for the production of specific antibodies, and spleen cells from animals having a positive specific antibody titer are used for cell fusions with myeloma cells to generate hybridoma clones. Supernatants derived from hybridoma clones are tested for the presence of monoclonal antibodies having specificity against a particular validated protein or fragments thereof. For a general description of monoclonal antibody methodology, See, e.g., Harlow and Lane, *Antibodies: A Laboratory Manual*, Cold Spring Harbor Laboratory (1988).

In addition to the baculovirus expression system, other suitable bacterial or yeast expression systems may be employed for the expression of a particular target protein or polypeptides thereof. As with the baculovirus system, it may be advantageous to utilize one of the commercially available affinity tags to facilitate purification prior to inoculation of the animals. Thus, the target protein cDNA or fragment thereof may be isolated by, e.g., agarose gel purification and ligated in frame with a suitable tag protein such as 6-His, glutathione-S-transferase (GST) or other such readily available affinity tag. See, e.g., Molecular Biotechnology: Principles and Applications of Recombinant DNA, ASM Press pp. 160-161 (ed. Glick, B. R. and Pasternak, J. J. 1998).

In additional embodiments of the present invention, antibody agents are ruminantized anti-target protein monoclonal antibodies. The phrase "ruminantized antibody" refers to an antibody derived from a non-ruminant antibody—typically a mouse monoclonal antibody. Alternatively, a ruminantized antibody may be derived from a chimeric antibody that retains or substantially retains the antigen-binding properties of the parental, non-ruminant, antibody but which exhibits diminished immunogenicity as compared to the parental antibody when administered to ruminant. The phrase "chimeric antibody," as used herein, refers to an antibody containing sequence derived from two different antibodies (see, e.g., U.S. Pat. No. 4,816,567) which typically originate from different species. Most typically, chimeric antibodies comprise human and murine antibody fragments, generally bovine constant and mouse variable regions.

Because ruminantized antibodies are far less immunogenic in ruminant than the parental mouse monoclonal antibodies, they can be used for the treatment of ruminant with far less risk of anaphylaxis. Thus, these antibodies may be preferred in therapeutic applications that involve in vivo administration to a ruminant such as, e.g., use as radiation sensitizers for the treatment of neoplastic disease or use in methods to reduce the side effects of, e.g., cancer therapy.

Ruminantized antibodies may be achieved by a variety of methods including, for example: (1) grafting the non-ruminant complementarity determining regions (CDRs) onto a ruminant framework and constant region (a process referred to in the art as "humanizing"), or, alternatively, (2) transplanting the entire non-ruminant variable domains, but "cloaking" them with a ruminant-like surface by replacement of surface residues (a process referred to in the art as "veneering"). In the present invention, ruminantized antibodies will include both "ruminantized" and "veneered" antibodies. These methods, in the context of humanized antibodies, are disclosed in, e.g., Jones et al., *Nature* (1986) 321:522-525; Morrison et al., *Proc. Natl. Acad. Sci.*, U.S.A., (1984) 81:6851-6855; Morrison and Oi, *Adv. Immunol.* (1988) 44:65-92; Verhoeyer et al., *Science* (1988) 239:1534-1536; Padlan, *Molec. Immun.* (1991) 28:489-498; Padlan, *Molec. Immunol.* (1994) 31(3):169-217; and Kettleborough, C. A. et al., *Protein Eng.* (1991) 4:773-83 each of which is incorporated herein by reference.

The phrase "complementarity determining region" refers to amino acid sequences which together define the binding affinity and specificity of the natural Fv region of a native immunoglobulin binding site. See, e.g., Chothia et al., *J. Mol. Biol.* (1987) 196:901-917; Kabat et al., U.S. Dept. of Health and Human Services NIH Publication No. 91-3242 (1991). The phrase "constant region" refers to the portion of the antibody molecule that confers effector functions. In the present invention, mouse constant regions are substituted by human constant regions. The constant regions of the subject humanized antibodies are derived from human immunoglobulins. The heavy chain constant region can be selected from any of the five isotypes: alpha, delta, epsilon, gamma or mu.

One method of ruminantized antibodies comprises aligning the non-ruminant heavy and light chain sequences to ruminant heavy and light chain sequences, selecting and replacing the non-ruminant framework with a ruminant framework based on such alignment, molecular modeling to predict the conformation of the ruminantized sequence and comparing to the conformation of the parent antibody. This process is followed by repeated back mutation of residues in the CDR region which disturb the structure of the CDRs until the predicted conformation of the ruminantized sequence model closely approximates the conformation of the non-ruminant CDRs of the parent non-ruminant antibody. Such ruminantized antibodies may be further derivatized to facilitate uptake and clearance, e.g., via recpetors in analogy with the use of Ashwell receptors (see, e.g., U.S. Pat. Nos. 5,530,101 and 5,585,089, both incorporated herein by reference.

Ruminantized antibodies to a particular target protein can also be produced using transgenic animals that are engineered to contain ruminant immunoglobulin loci. In analogy with humanized antibodies for example, WO 98/24893 discloses transgenic animals having a human Ig locus wherein the animals do not produce functional endogenous immunoglobulins due to the inactivation of endogenous heavy and light chain loci. WO 91/10741 also discloses transgenic non-primate mammalian hosts capable of mounting an immune response to an immunogen, wherein the antibodies have primate constant and/or variable regions, and wherein the endogenous immunoglobulin-encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy claims, and express an exogenous immunoglobulin locus comprising one or more xenogeneic constant regions.

Using a transgenic animal described above, an immune response can be produced to a selected antigenic molecule (e.g., target protein or fragment thereof), and antibody-producing cells can be removed from the animal and used to produce hybridomas that secrete ruminant monoclonal antibodies. Immunization protocols, adjuvants, and the like are known in the art, and are used in immunization of, for example, a transgenic mouse as described in WO 96/33735. This publication discloses monoclonal antibodies against a variety of antigenic molecules including IL-6, IL-8, TNFα, human CD4, L-selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8-induced functions of neutrophils. Human monoclonal antibodies with specificity for the antigen used to immunize transgenic animals are also disclosed in WO 96/34096.

For purposes of the present invention, target polypeptides and variants thereof are used to immunize an animal or transgenic animal as described above. Monoclonal antibodies are made using methods known in the art, and the specificity of the antibodies is tested using isolated target polypeptides. The suitability of the antibodies for clinical use is tested by, for example, exposing HCMV-infected cells to the antibodies and measuring cell growth and/or phenotypic changes. Ruminant monoclonal antibodies specific for a particular validated protein, or for a variant or fragment thereof can be tested for their ability to inhibit, for example, cell migration. Such antibodies would be suitable for preclinical and clinical trials as pharmaceutical agents for preventing or controlling virus or bacterial-mediated effects, conditions or diseases.

It will be appreciated that alternative target protein inhibitor antibodies may be readily obtained by other methods commonly known in the art. One exemplary methodology for identifying antibodies having a high specificity for a particular validated protein is the phage display technology.

Phage display libraries for the production of high-affinity antibodies are described in, for example, Hoogenboom, H. R. et al., *Immunotechnology* (1998) 4(1):1-20; Hoogenboom, H. R., *Trends Biotechnol.* (1997) 15:62-70 and McGuinness, B. et al., *Nature Bio. Technol.* (1996) 14:1149-1154 each of which is incorporated herein by reference. Among the advantages of the phage display technology is the ability to isolate antibodies of ruminant origin that cannot otherwise be easily isolated by conventional hybridoma technology. Furthermore, phage display antibodies may be isolated in vitro without relying on an animal's immune system.

Antibody phage display libraries may be accomplished, for example, by the method of McCafferty et al., *Nature* (1990) 348:552-554 which is incorporated herein by reference. In short, the coding sequence of the antibody variable region is fused to the amino terminus of a phage minor coat protein (pIII). Expression of the antibody variable region-pIII fusion construct results in the antibody's "display" on the phage surface with the corresponding genetic material encompassed within the phage particle.

A target protein, or fragment thereof suitable for screening a phage library may be obtained by, for example, expression in baculovirus Sf9 cells as described, supra. Alternatively, the target protein coding region may be PCR amplified using primers specific to the desired region of the validated protein. As discussed above, the target protein may be expressed in E. coli or yeast as a fusion with one of the commercially available affinity tags.

The resulting fusion protein may then be adsorbed to a solid matrix, e.g., a tissue culture plate or bead. Phage expressing antibodies having the desired anti-target protein binding properties may subsequently be isolated by successive panning, in the case of a solid matrix, or by affinity adsorption to a validated protein antigen column. Phage having the desired target protein inhibitory activities may be reintroduced into bacteria by infection and propagated by standard methods known to those skilled in the art. See Hoogenboom, H. R., Trends Biotechnol., supra for a review of methods for screening for positive antibody-pIII phage.

Vaccination of Ruminants

Agents of the present invention include compositions that elicit a specific immune response in a ruminant in need thereof. According to certain embodiments, the elicitation of the specific immune response treats, reduces the likelihood, and/or limits a M. haemolytica infection and/or the symptoms thereof. In particular aspects, these compositions that elicit a specific immune response are: (1) M. haemolytica leukotoxin (Lkt); (2) Lkt or antigen or portion thereof that is suitable for binding the signal peptide, and optionally wherein the immune response elicited can also recognize Lkt complexed with ruminant CD18 signal peptide; (3) a CD18 signal peptide, or portion thereof comprising from about 13 to about 24 contiguous amino acid residues of the first 24 amino acids of the N-terminus of the native (full-length nascent) ruminant CD18 sequence; and/or (4) signal peptide, wherein the elicited immune response is capable of binding to Lkt complexed with ruminant CD18 signal peptide.

According to certain embodiments, a composition that elicits a specific immune response is a vaccine. The terms "vaccine" "vaccination" and "vaccinating" mean the inoculation of a substance or composition (a vaccine) into the body of the subject for the purpose of producing immunity against a disease that is for the purpose of treating or preventing a disease. Accordingly, vaccination may be therapeutic or prophylactic. By therapeutic vaccination is meant the administration of a vaccine to a subject already suffering from a M. haemolytica infection, typically for the purpose of heightening or broadening the immune response to thereby halt, impede or reverse the progression of the disease.

Vaccination in accordance with the invention may provide protective immunity against a M. haemolytica infection to the subject being vaccinated. That is, the component(s) of the vaccine may elicit a protective immune response in the subject, for example by inducing the production of autoantibodies, innate immunity or adaptive immunity against the component(s). As used herein, the term "protective immunity" refers to the ability of a molecule or composition administered to a subject to elicit an appropriate immune response in the subject and thereby provide protection to the subject from the development or progression of a M. haemolytica infection.

The efficacy of compositions that elicit a specific immune response for use in accordance with the invention may be enhanced by the use of one or more adjuvants. Adjuvants capable of enhancing the delivery or protective or therapeutic efficacy of vaccines (for example by boosting the immune response produced) are well known to those skilled in the art.

Compositions that elicit a specific immune response may be prepared according to methods which are known to those of ordinary skill in the art and accordingly may include a pharmaceutically acceptable carrier, diluent and/or adjuvant. For administration in accordance with the present invention, a suitable vaccine may be formulated in a pharmaceutically acceptable carrier according to the mode and route of administration to be used. The carriers, diluents and adjuvants must be "acceptable" in terms of being compatible with the other ingredients of the composition, and not deleterious to the recipient thereof. Typically a sterile water or isotonic formulation is employed. For example, a suitable isotonic solution is phosphate buffered saline or Ringer's solution.

Those skilled in the art will appreciate that the methods and vaccinations contemplated by the present invention may be carried out in conjunction with other therapies or preventative measures for the treatment or prevention of M. haemolytica infections or symptoms associated with such diseases. For such combination therapies, each component of the combination therapy may be administered at the same time, or sequentially in any order, or at different times, so as to provide the desired effect. Alternatively, the components may be formulated together in a single dosage unit as a combination product.

EXAMPLE 1

Materials and Methods

Inhibition of Lkt Binding to, and Cytolysis of Target Cells by the Peptide Analogs of CD18.

Flow cytometric analysis of Lkt binding to target cells, and MTT dye-reduction cytotoxicity assay for detection of Lkt-induced cytolysis have been previously described by Applicants[4,7]. Detection of inhibition of Lkt binding to, and Lkt-induced cytolysis of, target cells by peptides in the disclosed studies were performed essentially as described, with the obvious exception that Lkt was pre-incubated with the peptides before incubation with the target cells.

Peptides.

The nested set of 20-mer peptides spanning aa 1-291 of bovine CD18, and the N- and C-terminally truncated versions of the Lkt-binding minimal peptide were synthesized at Sigma-Genosys. An irrelevant peptide (20-mer) derived from major surface protein 1 (MSP1) of Anaplasma marginale was used as the negative control.

Cloning and Expression of Bovine CD18 Carrying the Mutation Q to G.

The bovine cDNA for CD18[28] was previously subcloned into the mammalian expression vector pCI-neo to yield pMD1[4]. To produce the Q(−5)G mutation in bovine CD18, site-directed mutagenesis was performed using the GeneTailor™ site-directed mutagenesis system (Invitrogen). CD18 sequence after the point mutation was checked by DNA sequencing. Transfection of P815 cells with Lipofectamine™ 2000 was carried out according to the supplier's recommendations.

Cloning and expression of bovine CD18 carrying the 'FLAG' epitope at the cleavage site. The GeneTailor™ site-directed mutagenesis system (Invitrogen) was used to insert the 'FLAG' epitope (DYKDDDDK; SEQ ID NO:75) into the vector pMD1 carrying bovine CD18 cDNA, at the signal peptide cleavage site (between aa 22 and 23). The insertion was carried out in two steps (12 bp at a time) according to the manufacturer's instructions. The insertion of 'FLAG' epitope into CD18 was confirmed by DNA sequencing. The vector carrying the 'FLAG'-tagged CD18 was transfected into P815 cells with Lipofectamine™ 2000 according to the manufacturer's protocol.

Statistical Analysis.

One-way ANOVA was employed to determine whether the differences in % inhibition caused by the different peptides are statistically significant.

Preparation of Lkt.

Production of Lkt from *M. haemolytica* A1 has been previously described by Applicants[29]. The undiluted toxin preparation contained 640 Units of toxin per ml. All experiments were performed with the same batch of toxin aliquoted and frozen at −20° C.

Cell Lines and Antibodies.

The cell lines P815 (murine mastocytoma), and BL3 (bovine lymphoma3), were propagated in complete Dulbecco's minimum Eagle's medium or RPMI 1640, respectively, supplemented with 10% fetal bovine serum, 2 mM L-glutamine, and 20 ug/ml of gentamicin (complete medium). The transfectant 2B2, expressing full-length bovine CD18 on the cell surface, was previously developed in Applicants' laboratory by transfecting P815 with cDNA for bovine CD18[4]. The transfectants were selected and propagated in the complete DMEM together with 500 ug/ml of Geneticin (Invitrogen). PMNs were isolated from peripheral blood by density gradient centrifugation using Ficoll-Paque (Amersham Pharmacia Biotech.), followed by hypotonic lysis of the erythrocyte pellet, as previously described[30]. Anti-bovine CD18 monoclonal antibody (mAb) BAQ30A was obtained from Washington State University Monoclonal Antibody Center. The Lkt-non-neutralizing mAb MM605 (IgG2a) was previously developed in Applicants' laboratory[29]. FITC-conjugated MM-605 was used in flow cytometry to detect Lkt-binding[7].

Peptides.

A nested set of 20-mer peptides spanning aa 1-291 of bovine CD18 was synthesized with either 6 or 15 aa overlap. Once the peptide which inhibits Lkt-induced cytotoxicity was identified, another set of peptides were synthesized with N-terminal truncation by dropping one aa at a time while keeping the C-terminal aa constant. Once the N-terminal aa of the minimal peptide was identified, another set of peptides were synthesized with C-terminal truncation by dropping one aa at a time while keeping the N-terminal aa constant. Peptides were purchased from Sigma Genosys. All the peptides were referred to by the sequence number of their first amino acid. An irrelevant peptide (20-mer) derived from major surface protein 1 (MSP1) of *Anaplasma marginate* was used as the negative control. All the peptides were resuspended in dimethysulfoxide (ATCC) at a concentration of 1 mg/ml, aliquoted and stored at −20° C.

Detection of Inhibition of Lkt-Induced Cytolysis of Target Cells by the Peptide Analogs of CD18.

The MTT [3-(4,5-dimethylthiazoyl-2-YI]-2,5-diphenyl tetrazolium bromide; Sigma] dye reduction cytotoxicity assay for detection of Lkt-induced cytolysis of target cells has been previously described by Applicants[30]. This assay measures the ability of the endoplasmic reticulum-resident enzymes in viable cells to convert a tetrazolium dye into a purple formazan precipitate, which is later dissolved in acid isopropanol. The optical density (OD) of the end product, representing the intensity of the purple color which developed, is directly proportional to the viability of the cells. The percent cytotoxicity was calculated as follows:

$$\%\ \text{cytotoxicity}=[1-(\text{OD of toxin-treated cells}/\text{OD of toxin-untreated cells})]\times 100.$$

Inhibition of Lkt-induced cytolysis of target cells by the peptide analogs was detected by the MTT assay with the obvious exception that Lkt was pre-incubated with the peptides before incubation with the target cells. Lkt was used at the dilution that causes 50% cytolysis of target cells. The percent inhibition of cytolysis was calculated as follows:

$$\%\ \text{Inhibition of cytolysis}=[(1-\%\ \text{cytolysis in the presence of peptide})/\%\ \text{cytolysis in the absence of peptide}]\times 100.$$

Flow Cytometric Analysis of Inhibition of Lkt Binding to Target Cells.

Flow cytometric analysis of Lkt binding to target cells has been previously described by Applicants. Inhibition of Lkt binding to target cells by the peptides in the presently disclosed studies was performed essentially as previously described by Applicants with the obvious exception that Lkt was pre-incubated with the peptides before incubation with the target cells.

Flow Cytometric Analysis of the Cell Surface Expression of CD18 on Transfectant.

Transfectants were examined for the cell surface expression of CD18 using anti-CD18 MAb by flow cytometry, as previously described[4].

EXAMPLE 2

Peptide Analogs of Bovine CD18 Inhibited Lkt Binding to, and Cytolysis of, Ruminant PMNs Applicants previously mapped the Lkt binding site on bovine CD18 to lie between amino acids (aa)1-291[7]. In this EXAMPLE, inhibition of Lkt-induced cytolysis of target cells by a nested set of 20-mer peptides spanning aa 1-291 of bovine CD18 was used to determine the Lkt binding site on bovine CD18. Lkt-induced cytolysis of bovine PMNs was strongly inhibited by two peptides, P1 and P5, containing aa 1-20 and 5-24, respectively, at a concentration of 5 ug/50 ul (FIG. 1*a*).

Specifically FIG. 1*a* shows, according to particular exemplary aspects, that the CD18 signal peptide analog P5 (aa 5-24) inhibits Lkt-induced cytolysis of bovine PMNs. Inhibition of Lkt-induced cytolysis of bovine PMNs by a nested set of peptides (20-mers) spanning the aa 1-291 was tested by the MTT dye-reduction cytotoxicity assay. All data are expressed as mean±s.d. (n=3). a. Inhibition of cytolysis of bovine PMNs by Lkt. The peptides are designated by the sequence number of their first amino acid. Since the most pronounced aa sequence difference in the CD18 of ruminants and non-ruminants was observed in the N-terminal region, the point of origin of first 5 peptides was staggered by 5 aa, and the rest of the peptides were staggered by 14 aa. A 20-mer peptide derived from major surface protein 1 of *Anaplasma marginale* (MSP-1) was used as the negative control. The peptides were used at a concentration of 5 μg/50 μl. % Inhibition was calculated as described in the Methods. b. Determination of the concentration of P1 and P5 that gives 50% inhibition of Lkt-induced cytolysis of bovine PMNs. The peptides P1 and P5 were used in the inhibition assay at concentrations ranging from 3.1 ug/ml to 100 ug/ml. c. Specificity of inhibition of Lkt-induced cytolysis of bovine PMNs by the peptide P5. Two peptides containing the same aa as the peptide P5, but in a randomly scrambled sequence, were used in the cytotoxicity assay along with P5.

Figure 1C:
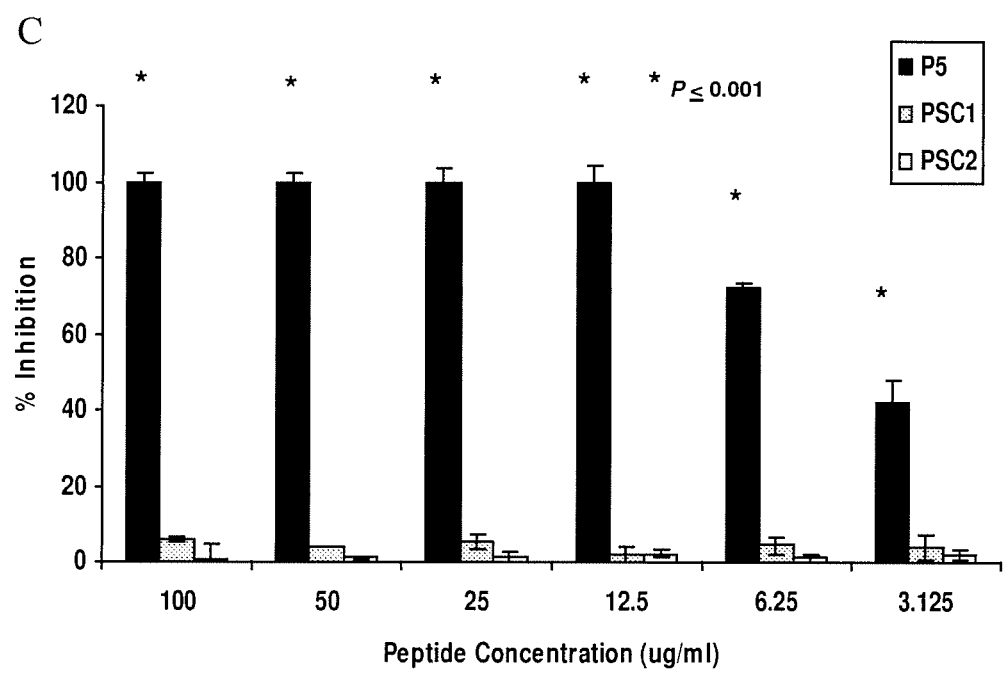

Comparison of the concentration of peptides P1 and P5 which causes 50% inhibition of Lkt-induced cytolysis of bovine PMNs revealed the potency of peptide P5 to be higher than that of peptide P1 (12 ug/ml versus 26 ug/ml; FIG. 1b). Similar results were obtained with PMNs of other ruminants (goats, domestic sheep, wild sheep, and deer) as well (data not shown). Two other peptides containing the same as P5, but in a randomly scrambled sequence, failed to inhibit Lkt-induced cytolysis of target cells indicating that the inhibition of Lkt-induced cytolysis of bovine PMNs by the peptide P5 is specific (FIG. 1c).

Figures 2A, 2B:
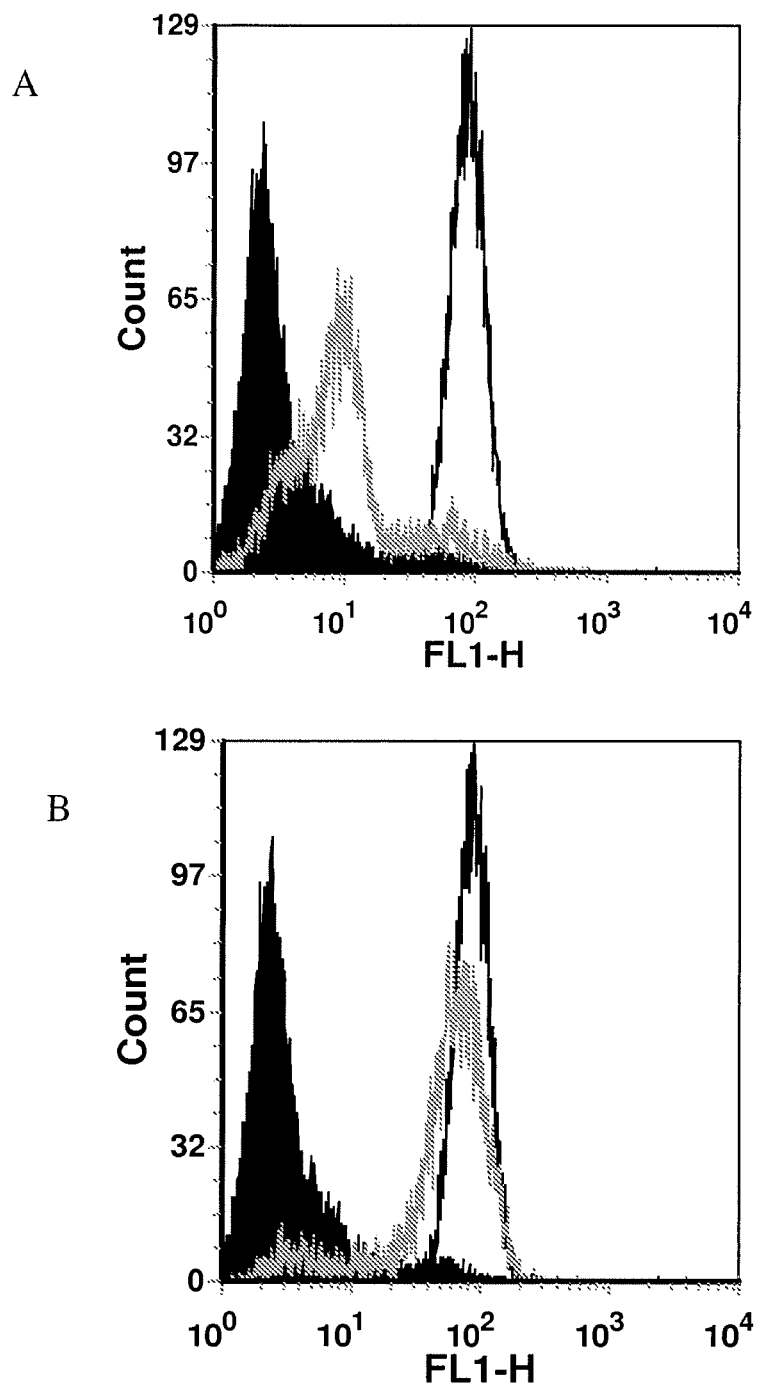
FIGS. 2A and 2B show, according to particular exemplary aspects, that peptide P5 inhibits Lkt binding to bovine PMNs. See working EXAMPLE 2 for details.

Flow cytometric analysis confirmed the inhibition of Lkt binding to bovine PMNs by peptide P5 (FIG. 2).

Specifically, FIG. 2 shows, according to particular exemplary aspects, that peptide P5 inhibits Lkt binding to bovine PMNs. Binding of Lkt to bovine PMNs was tested by flow cytometry, in the absence of any peptide (a & b; black histogram), or in the presence of peptide P5 (a; gray histogram), or an irrelevant peptide (b; gray histogram) by flow cytometry. Shaded histogram represents the background fluorescence given by the cells. The x and y axis show the fluorescence intensity and the number of cells, respectively. Results of one representative experiment out of three are shown.

Inhibition of Lkt-induced cytolysis of target cells by shorter versions of peptides derived from P5 by N- and C-terminal truncations identified aa 5-17 of ruminant CD18 as the sequence that serves as the receptor for Lkt. Hence the peptide made up of aa 5-17 is the minimal peptide analog of ruminant CD18 that effectively inhibits Lkt-induced cytolysis of ruminant PMNs and other leukocyte subsets (FIG. 3).

Figure 3A:
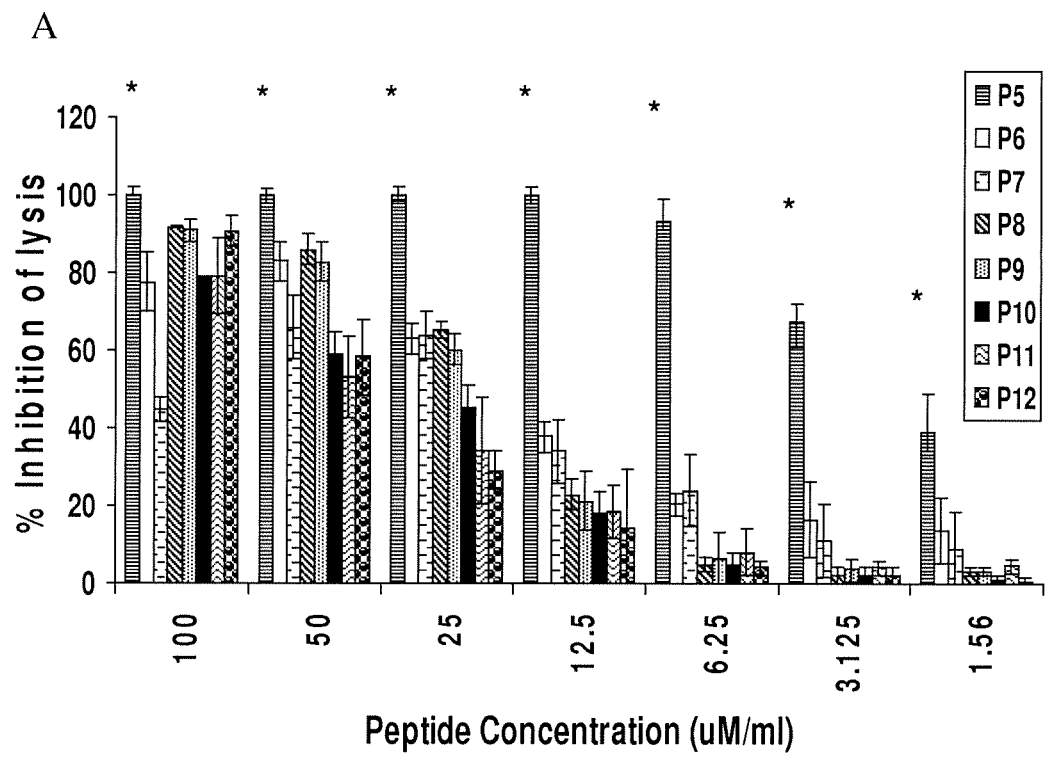
FIGS. 3A-3C show, according to particular exemplary aspects, that N- and C-terminal truncations of peptide P5 identifies the minimal peptide sequence of bovine CD18 bound by Lkt as aa 5-17. See working EXAMPLE 2 for details.
Figure 3B:
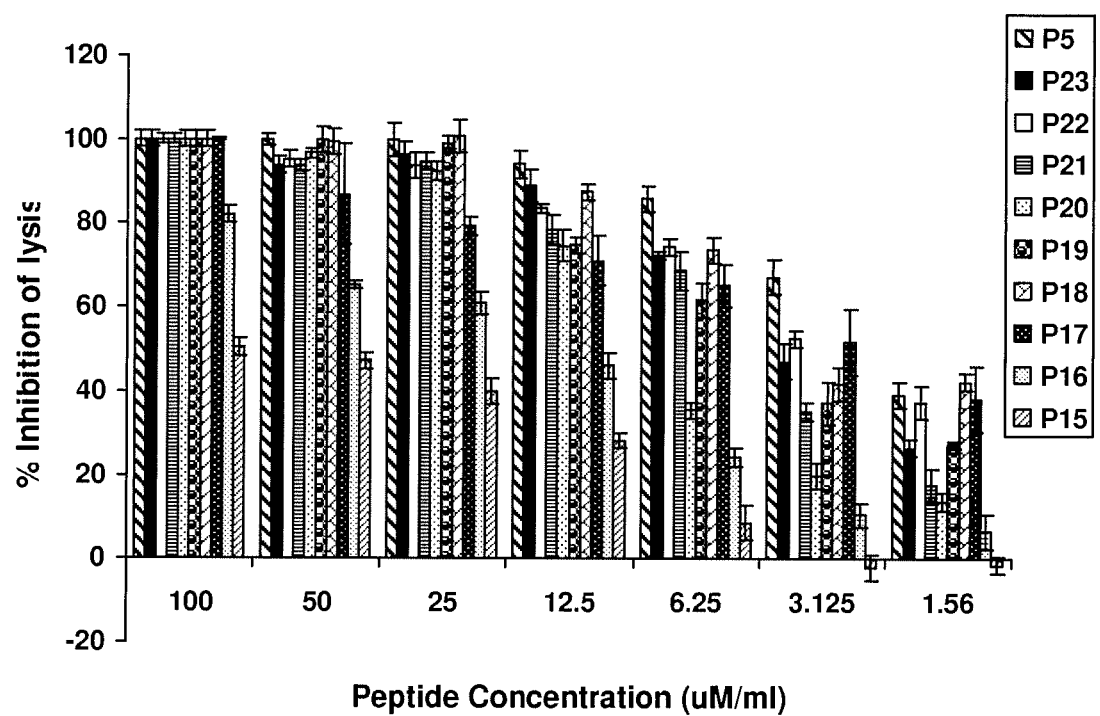
Figure 3C:
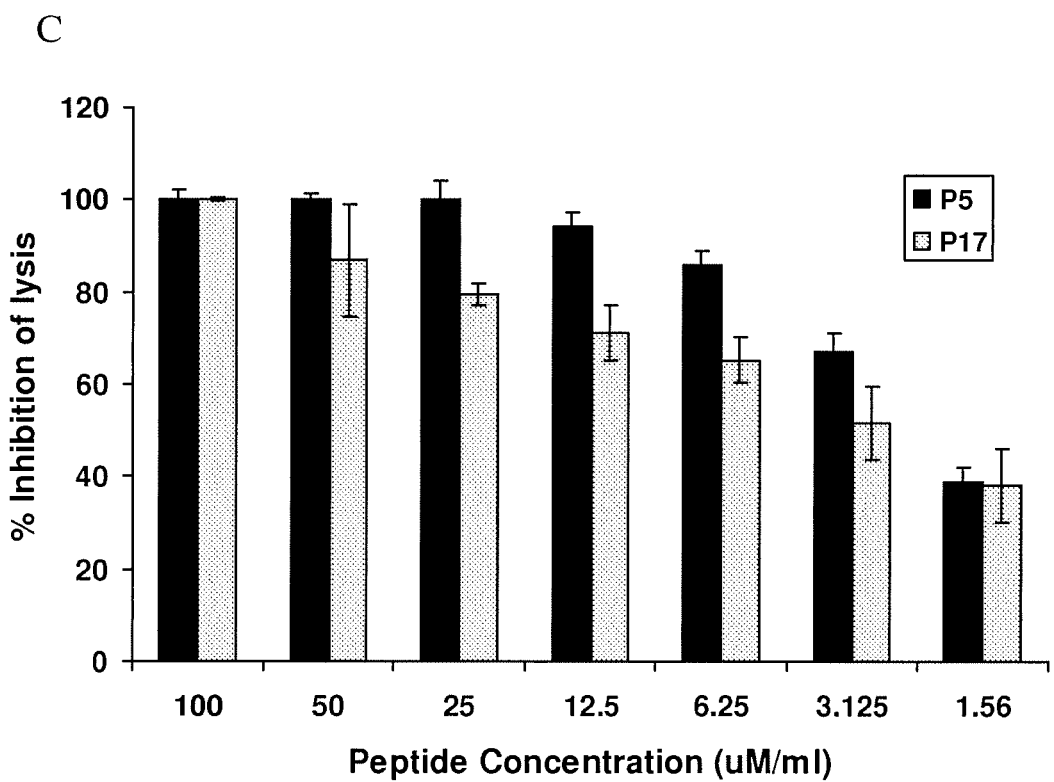

Specifically, FIG. 3 shows, according to particular exemplary aspects, that N- and C-terminal truncations of peptide P5 identifies the minimal peptide sequence of bovine CD18 bound by Lkt as aa 5-17. Inhibition of Lkt-induced cytolysis of BL-3 cells by N-terminally truncated or C-terminally truncated versions of peptide P5 were determined by the MTT dye-reduction cytotoxicity assay. Peptides were used at concentrations ranging from 1.56 to 100 um/ml. All data are expressed as mean±s.d. (n=3). a. Inhibition of Lkt-induced cytolysis of BL-3 cells by peptides with N-terminal truncation. The peptides used were: P5 (aa 5-24); P6 (aa 6-24); P7 (aa 7-24); P8 (aa 8-24); P9 (aa 9-24); P10 (aa 10-24); P11 (aa 11-24); P12 (aa 12-24); P6 (aa 6-24); P6 (aa 6-24). b. Inhibition of Lkt-induced cytolysis of BL-3 cells by peptides with C-terminal truncation. Results of the inhibition assay in a above, identified the N-terminal aa of the minimal peptide sequence as aa #5. Therefore, the C-terminally truncated versions of peptide P5 were synthesized with aa #5 as the N-terminal aa. The peptides used were: P24 (aa 5-24); P23 (aa 5-23); P22 (aa 5-22); P21 (aa 5-21); P20 (aa 5-20); P19 (aa 5-19); P18 (aa 5-18); P17 (aa 5-17); P16 (aa 5-16). Results of the inhibition assay in a and b above, identified the minimal peptide sequence of bovine CD18 bound by leukotoxin as aa 5-17. c. Comparison of inhibition given by the peptide P5 (aa 5-24) and the minimal peptide P17 (aa 5-17).

EXAMPLE 3

The Amino Acid Sequence of the Bovine CD18 Peptide Analog that Inhibits Lkt-Induced Cytolysis was Shown to be from the Signal Sequence of CD18

The amino acids 5-17 constitute the bulk of the predicted signal sequence (amino acids 1-22) of CD18. As appreciated in the relevant art, paradigm dictates that signal peptides of plasma membrane proteins are cleaved by the signal peptidase in the ER[1-3]. Therefore Applicants checked for the presence of the signal peptide on mature cell surface CD18.

Figures 4A, 4B, 4C, 4D, 4E, 4F, 4G, 4H:
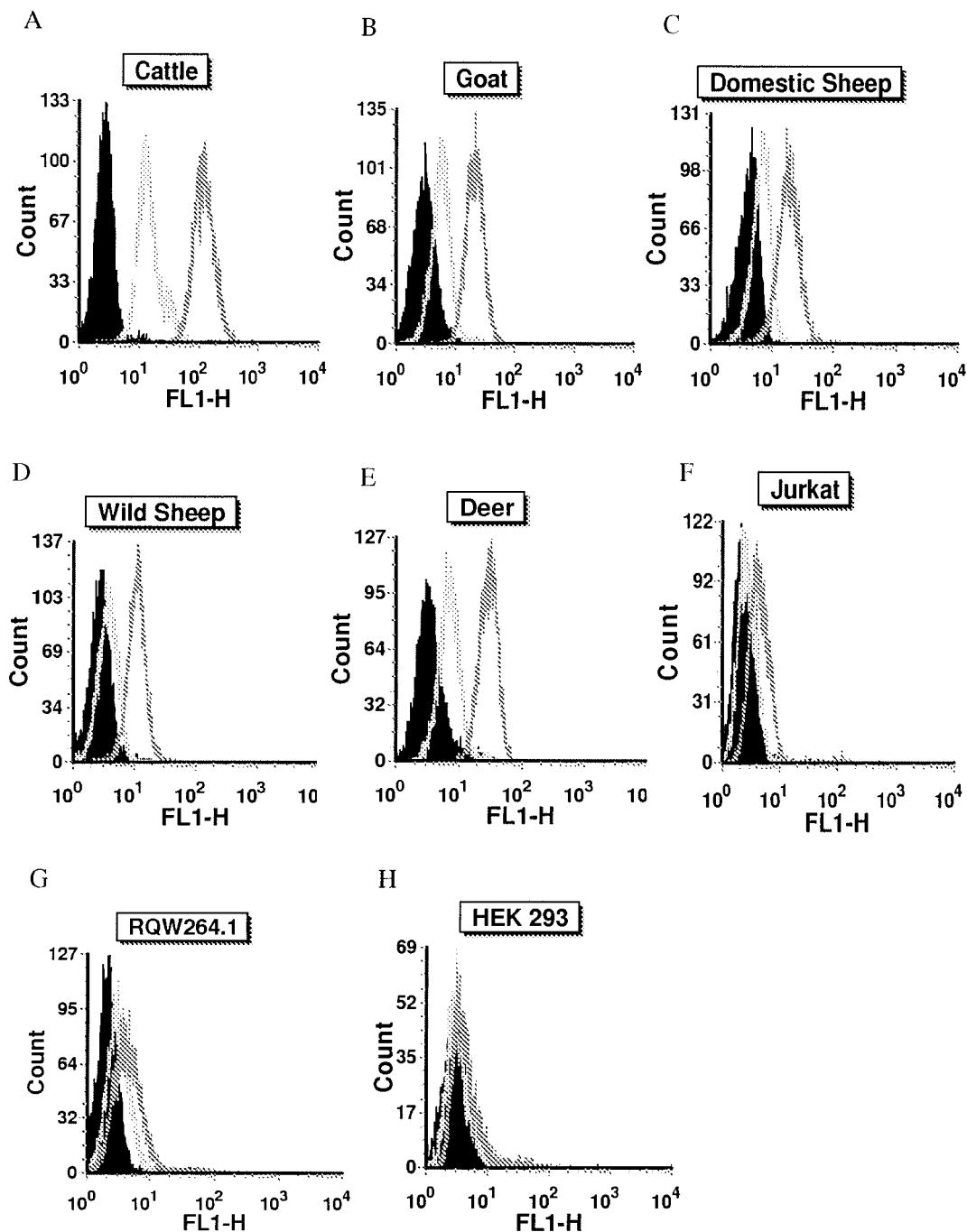
FIG. 4A-4H show, according to particular exemplary aspects, that anti-signal peptide serum binds to membrane CD18 of PMNs of all ruminants tested. See working EXAMPLE 3 for details.

As shown in FIG. 4, flow cytometric analysis with an anti-serum specific for the signal peptide of bovine CD18 indicated that the CD18 molecules are on the surface of ruminant PMNs and, indeed, have the signal peptide intact.

Specifically, FIG. 4 shows, according to particular exemplary aspects, that anti-signal peptide serum binds to membrane CD18 of PMNs of all ruminants tested. PMNs from the indicated animals were tested by flow cytometry for the binding of a chicken anti-serum (1/1000 dilution) developed against a synthetic peptide spanning aa 5-19 of bovine CD18 signal peptide. Serum from un-immunized chicken, and MDBK cells, were used as the negative controls for the serum and cells, respectively. The different panels show the results of flow cytometry with PMNs of (a) cattle; (b) goats; (c) domestic sheep; (d) wild sheep; (e) deer; (f) Jurkat cells (human T-lymphoma); (g) RAW264.A cells (mouse macrophage); (h) HEK-293 (human embryonic kidney). Shaded histogram: cells only; silver histogram: cells treated with serum from un-immunized chicken; gray histogram: cells treated with anti-serum against signal peptide of bovine CD18. Results of one representative experiment out of three are shown.

EXAMPLE 4

The Signal Peptide of Ruminant CD18 was Shown not to be Cleaved from the Mature Protein To confirm the fact that the signal peptide of bovine CD18 is not cleaved, Applicants introduced a minigene encoding the 'FLAG' epitope[21] at the putative signal peptide cleavage site (between aa 22 and 23). Transfectants stably expressing bovine CD18 containing the 'FLAG' epitope between aa 22 and 23 were tested with two monoclonal antibodies (MAbs), M1 and M2, specific for the 'FLAG' epitope. M1 recognizes the free N-terminal end of 'FLAG', while M2 recognizes 'FLAG' irrespective of its sequence context[21].

Figures 5A, 5B, 5C, 5D:
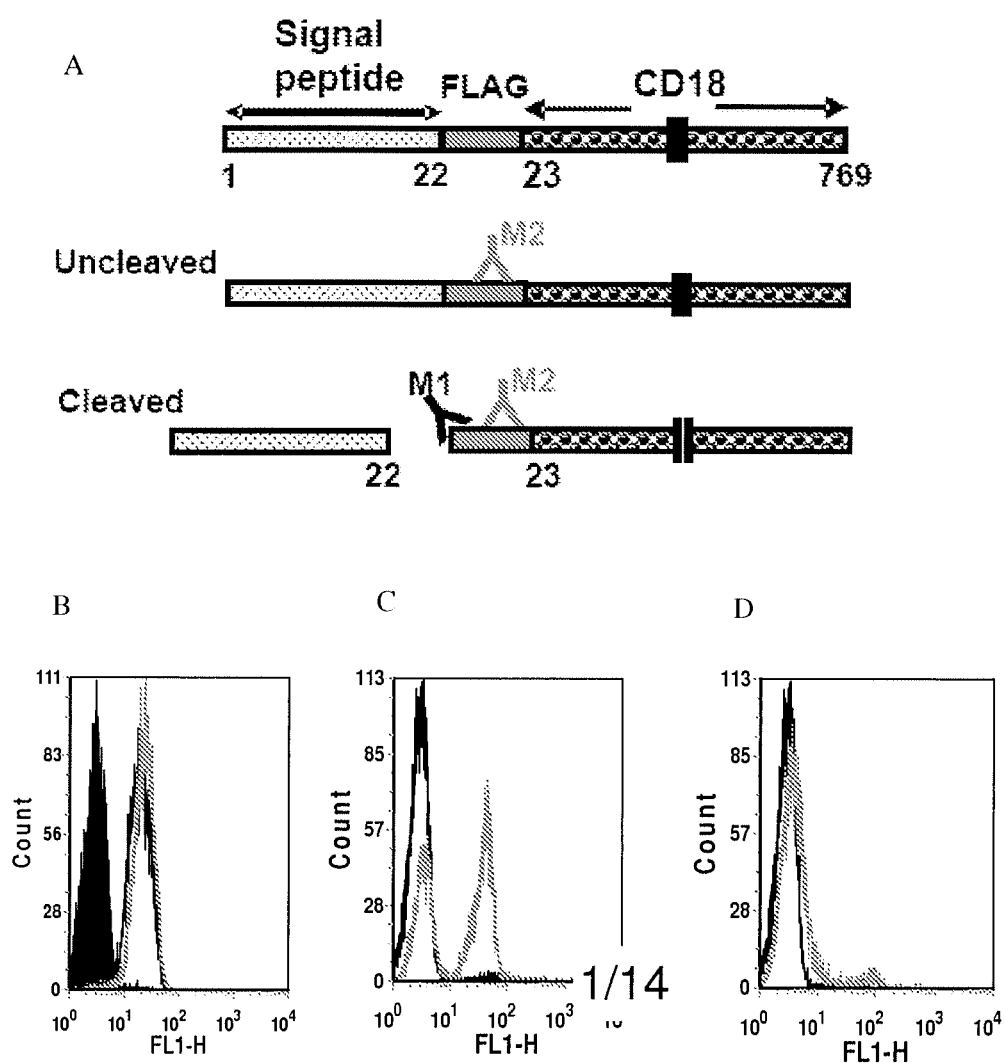
FIGS. 5A-5D show, according to particular exemplary aspects, that the signal peptide of bovine CD18 is not cleaved. See working EXAMPLE 4 for details.

As shown in FIG. 5, the MAb M2, but not M1, bound to the transfectants expressing 'FLAG'-containing CD18 confirming that the signal peptide of bovine CD18 is indeed not cleaved.

Specifically, FIG. 5 shows, according to particular exemplary aspects, that the signal peptide of bovine CD18 is not cleaved. a. Introduction of the 'FLAG' epitope at the signal peptide cleavage site and its detection by two monoclonal antibodies. The 'FLAG' epitope (DYKDDDDK) introduced at the signal peptide cleavage site (between aa 22 and 23) can be detected by two anti-'FLAG' epitope antibodies M1 and M2. M1 recognizes the free N-terminal end of 'FLAG' (if cleavage occurs), while M2 recognizes 'FLAG' irrespective of its sequence context. b. Flow cytometric analysis of bovine CD18 expression. The untransfected parent cells P815 (shaded histogram), or P815 cells transfected with either bovine CD18 (2B2; black histogram) or bovine CD18 containing the 'FLAG' epitope at the cleavage site (BFL; gray histogram), were tested for expression of bovine CD18 by flow cytometric analysis with an anti-bovine CD18 monoclonal antibody. C.-d. Flow cytometric analysis of expression of the 'FLAG' epitope. The transfectants 2B2 and BFL were tested for the expression of the 'FLAG' epitope with the monoclonal antibody M2 (c.) and M1 (d.). Results of one representative experiment out of three are shown.

EXAMPLE 5

The Signal Peptide of CD18 of Non-Ruminants was Shown to Contain 'Cleavage-Conducive' Glycine, Whereas that of Ruminants was Shown to Contain 'Cleavage-Inhibiting' Glutamine at Position −5 Relative to the Cleavage Site Applicants' finding that a sequence (aa 5-17) within the signal peptide of ruminant CD18 serve as the receptor for *M. haemolytica* Lkt, and the fact that the cytolytic activity of Lkt is absolutely specific for ruminant leukocytes, prompted examination of the signal peptide of CD18 of ruminants and non-ruminants. The amino acid sequences of CD18 of eight ruminants and five non-ruminants were compared (FIG. 6).

Figures 6A, 6B:
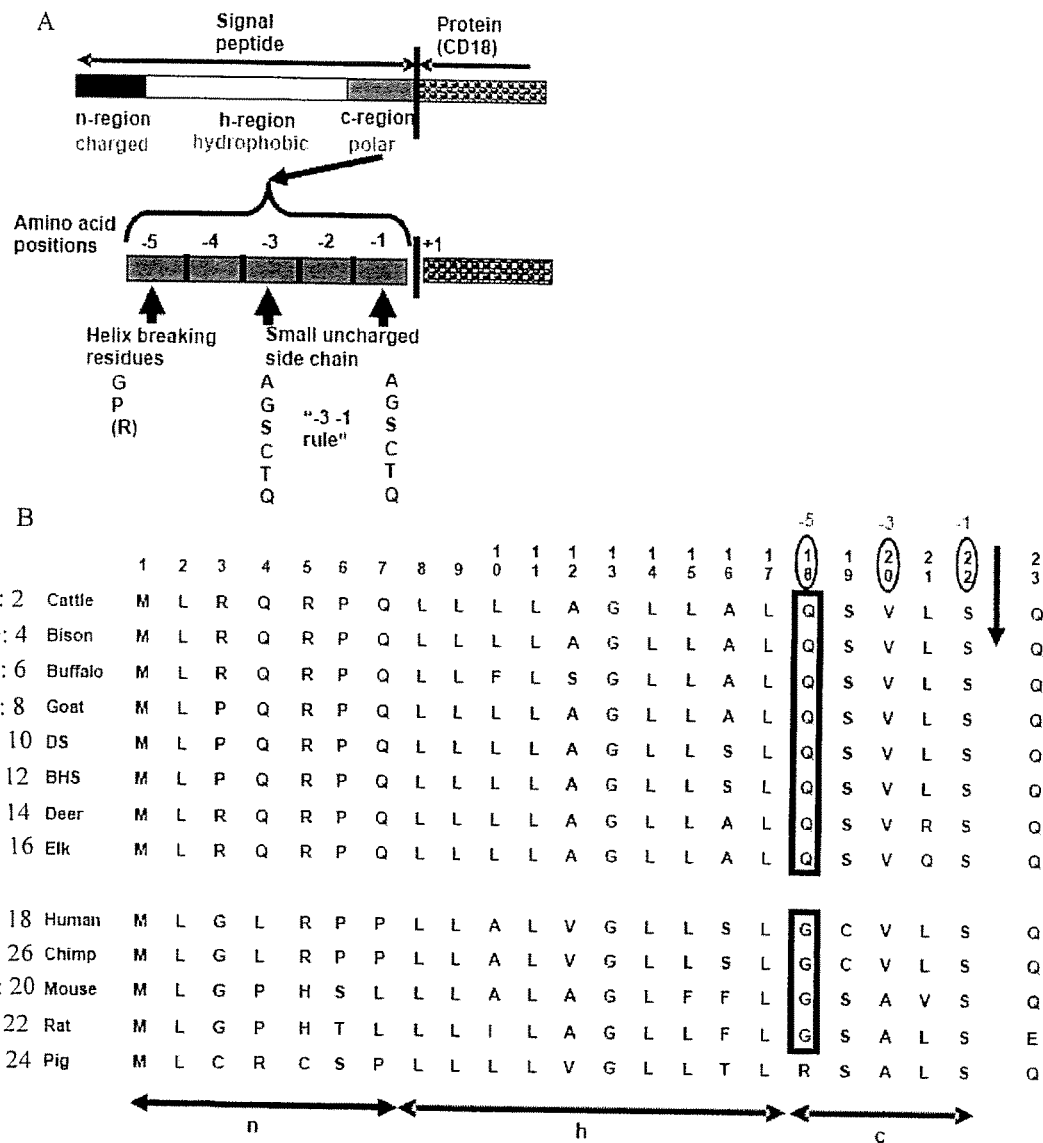
FIGS. 6A-6B show, according to particular exemplary aspects, Signal peptide of CD18 of ruminants contain glutamine at aa position −5 relative to the cleavage site, whereas that of non-ruminants contain glycine. See working EXAMPLE 5 for details.

Specifically, FIG. 6 shows, according to particular exemplary aspects, that the signal peptide of CD18 of ruminants contain glutamine at aa position −5 relative to the cleavage site, whereas that of non-ruminants contain glycine. a. The "−3,−1, rule" for cleavage of signal peptides (Von Hejne[22]). b. Comparison of signal peptide sequences of ruminants and non-ruminants (GenBank Accession #: cattle: M81233; bison: EU553919; buffalo: AY842449; goat: AY452481; domestic sheep: DQ470837; wild sheep: DQ104444; deer: EU623794; elk: EU553918; human: NM0002211; chimpanzee: NM001034122; mouse: X14951; rat: NM001037780; pig: U13941). DS, BHS and chimp denote domestic sheep, wild sheep (bighorn sheep) and chimpanzee, respectively. Arrow indicates the signal peptide cleavage site.

The predicted signal sequence of both the ruminant and non-ruminant CD18 contains 22 aa. The "−3-1 rule" of Von Hejne[22] for signal peptide cleavage calls for the presence of amino acids with small uncharged amino acids at position −1 and −3 relative to the cleavage site. Both ruminant and non-ruminant CD18 signal peptides conform to this rule. The amino acid residue at position −5 could also determine whether the signal peptide gets cleaved or not[23]. Helix-breaking residues glycine and proline are conducive for signal peptide) cleavage[23]. Arginine is also conducive to signal peptide cleavage[22,23]. Glutamine on the other hand has been shown to inhibit cleavage of signal peptide[23]. Astonishingly, CD18 of all five non-ruminants examined contained the 'cleavage-conducive' glycine (humans, mice, rats, and chimpanzees) or arginine (pigs), while CD18 of all eight ruminants examined contained 'cleavage-inhibiting' glutamine.

EXAMPLE 6

Transfectants Expressing Bovine CD18 Containing the Mutation of Glutamine at −5 Position to Glycine were Shown to be not Susceptible to *M. haemolytica* Lkt-Induced Cytolysis The observation that the signal peptide of CD18 of ruminants (Lkt-susceptible) contains Q at −5 position whereas that of non-ruminants (Lkt-non-susceptible) contains G raised the question as to whether site-directed mutagenesis of Q to G [Q(−5)G] would result in the abrogation of Lkt-induced cytolysis of transfectants expressing Q(−5)G mutation in the signal peptide of CD18. Indeed, as disclosed herein, that is precisely what was found. The Q(−5)G mutation in the signal peptide of bovine CD18 abrogated Lkt-induced cytolysis of the transfectants expressing the mutated CD18 (FIG. 7).

Figure 7:
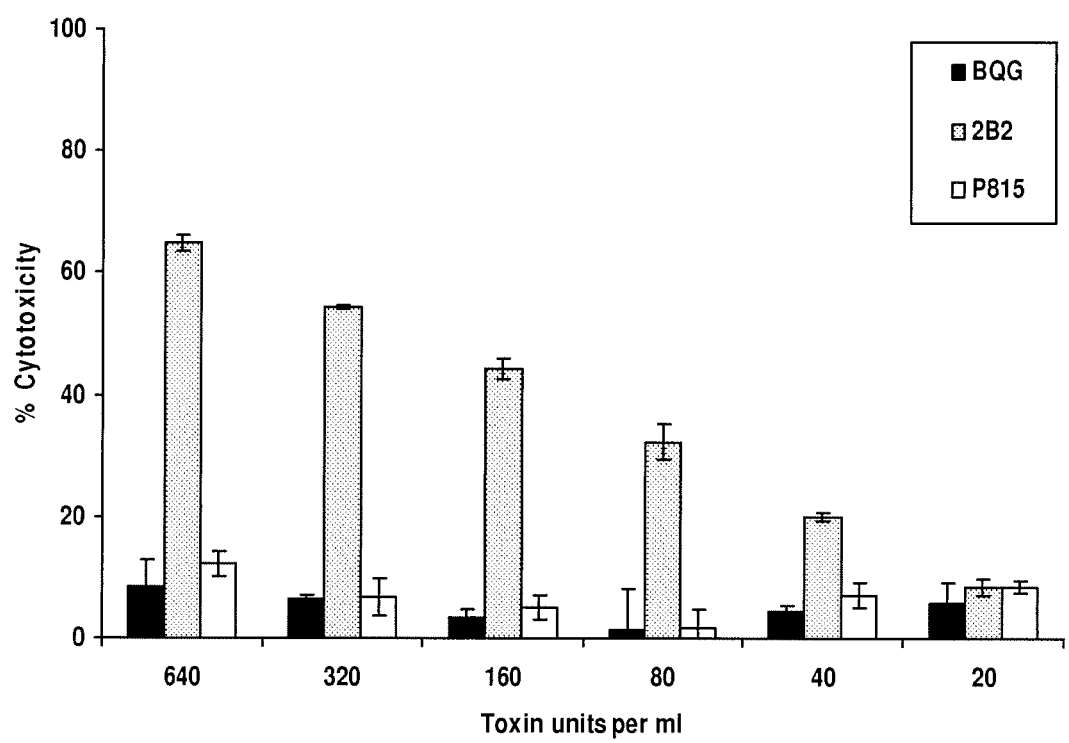
FIG. 7 shows, according to particular exemplary aspects, that mutation of glutamine at position −5 of the signal peptide of bovine CD18 to glycine abrogates Lkt-induced cytolysis of transfectants expressing CD18 with Q(−5)G mutation. See working EXAMPLE 6 for details.

Specifically, FIG. 7 shows, according to particular exemplary aspects, that mutation of glutamine at position −5 of the signal peptide of bovine CD18 to glycine abrogates Lkt-induced cytolysis of transfectants expressing CD18 with Q(−5)G mutation. Transfectants expressing bovine CD18 (2B2), those expressing bovine CD18 containing the Q(−5)G mutation (BQG), and the parent cells (P815) were tested for susceptibility to Lkt-induced cytolysis by the MTT dye-reduction cytotoxicity assay. All data are expressed as mean±s.d. (n=3).

In summary, particular aspects disclosed herein demonstrate for the first time that the aa 5-17 within the signal peptide of ruminant CD18 serve as the receptor for *M. haemolytica* Lkt, and that the failure of the signal peptide to be cleaved from mature CD18 molecules renders the ruminant leukocytes susceptible to Lkt.

Dileepan et al.[24,25] has previously reported that Lkt binding site lies within aa 500-600, more precisely between aa 541-581 of bovine CD18. The present results indicate that this conclusion is erroneous for various reasons.

Figures 8A, 8B, 8C:
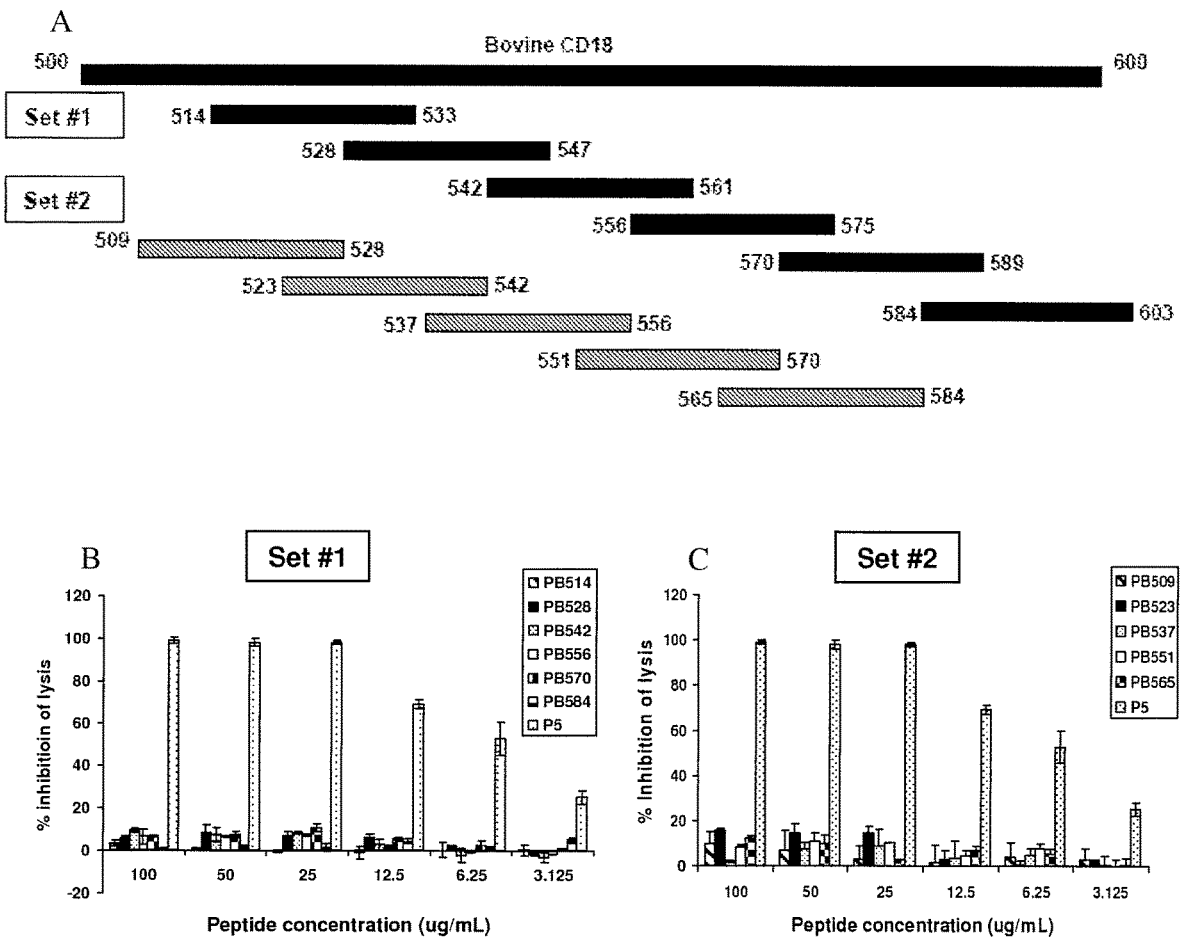
FIGS. 8A-8C shows, according to particular exemplary aspects, that peptides spanning aa 500-600 of bovine CD18 fail to inhibit Lkt-induced cytolysis of bovine PMNs. See working EXAMPLE 6 for details.

First, two different sets of synthetic peptides spanning aa 500-600 failed to inhibit Lkt-induced cytolysis of bovine PMNs (FIG. 8). Specifically, FIG. 8 shows, according to particular exemplary aspects, that peptides spanning aa 500-600 of bovine CD18 fail to inhibit Lkt-induced cytolysis of bovine PMNs. a. Nested sets of peptides spanning aa 500-600. One set (#1) of peptides (20-mer) spanning aa 500-600 were synthesized and tested in the inhibition assay. Since none of the peptides inhibited Lkt-induced cytolysis of bovine PMNs, another set (#2) of peptides with points of origin different from that of the first set were synthesized. b & c. Inhibition of Lkt-induced cytolysis of bovine PMNs by the nested set of peptides was tested by the MTT dye-reduction cytotoxicity assay. All data are expressed as mean±s.d. (n=3).

Second, synthetic peptides containing the signal sequence aa 5-17 completely inhibited Lkt-induced cytolysis of PMNs of bovine (FIG. 1) and other ruminants. If Lkt bound to CD18 between aa 541 and 581, one would expect to see cytolysis of target cells when Lkt is incubated with a synthetic peptide representing the signal sequence (aa 5-17).

Third, Applicants; transfectants expressing CD18 containing the Q(−5)G mutation in the signal peptide are not lysed by Lkt although the aa 500 to 600 are intact in the CD18. According to particular aspects, the failure of Dileepan et al[24,25] to identify aa 5-17 in the signal peptide as the Lkt binding region was likely due to the fact that their transductants were developed with K562 cells. According to further aspects, K562 cells transfected with bovine CD18 do not express CD18 with intact signal peptide (Applicants' unpublished observations). Therefore, according to additional aspects, K562 cells likely carry a signal peptidase that cleaves the signal peptide in spite of the presence of Q at position −5. K562 is a poorly characterized cell-line, and conflicting reports regarding the lineage of this cell-line can be found in the literature[26,27]. Applicants' studies indicate that the findings of Dileepan et al.[24,25] are unique to bovine CD18 transductants developed with K562 cells, and do not reflect the molecular events occurring in ruminant leukocytes.

According to particular aspects, the replacement of 'cleavage-inhibiting' Q at −5 position with 'cleavage-conducive' G likely results in the cleavage of the signal peptide and the resultant loss of susceptibility of the transfectants to Lkt-induced cytolysis. According to additional aspects, abrogation of cytolysis is not due to cleavage of signal peptide, but rather due to conformational changes caused by the replacement of Q with G. According to further aspects, both effects are involved. Irrespective of the molecular basis or mechanism underlying the abrogation of cytolysis, the exemplary Q(-5)G mutation embodiment provides for a hitherto unavailable technology to, among other things, clone cattle and other ruminants expressing CD18 without the signal peptide on their leukocytes, and hence provide animals less susceptible to pneumonic pasteurellosis, and which will save millions of dollars annually with worldwide benefit.

EXAMPLE 7

Endobronchial Inoculation of a Peptide Analog of CD18 was an Effective Inhibitor of *M. haemolytica*-Caused Pneumonia in a Calf Challenge Model Overview.

In this Example, a study was conducted that confirmed the ability of the peptide spanning amino acids 5-17 of bovine CD18 to inhibit or mitigate the disease caused by *M. haemolytica*, in a calf challenge model.

Leukotoxin (Lkt) produced by *Mannheimia haemolytica* is the major virulence factor of this organism. Lkt-induced cytolysis and degranulation of alveolar macrophages and polymorphonuclear leukocytes is responsible for the acute inflammation and lung injury characteristic of pneumonia caused by *M. haemolytica*. Applicants identified a peptide analog of CD18 (P17, spanning amino acids 5-17) that effectively inhibited Lkt-induced cytolysis of ruminant leukocytes in in vitro cytotoxicity assays (Shanthalingam and Srikumaran, 2009). The objective of this study was to determine the ability of this peptide to inhibit or mitigate lung lesions in a calf challenge model of *M. haemolytica*. Three groups of four calves each were endobronchially inoculated with logarithmic phase cultures of *M. haemolytica* ($5 \times 10^9$ CFU per 10 ml of culture medium) alone (Group I), or along with a control peptide (Group II), or with the CD18 peptide analog P17 (Group III). Animals were observed for clinical signs at different time points, euthanized at 90 hours post-inoculation, and necropsied. The total clinical disease scores for Group III calves were lower than those for group I and II at all time points except 48 hours. This difference was statistically significant ($P<0.05$) at 24 hours post-inoculation. All the calves presented gross pulmonary lesions consistent with fibrinonecrotic pneumonia characteristic of *M. haemolytica* infection. The difference in percent volume of lungs exhibiting gross pneumonic lesions among the three groups was not statistically significant ($P=0.9$). However, *M. haemolytica* isolated from the lungs of Group III calves was 100- to 1000-fold less than those isolated from the calves in Group I and Group II. This difference, expressed as CFU of *M. haemolytica* per g of lung tissue, was statistically significant ($P<0.001$) indicating that the CD18 peptide analog reduced leukotoxic activity in the lungs enabling more effective bacterial clearance by the phagocytes.

In particular aspects, prolonging the presence and activity of the CD18 peptide analog in the lungs using a nanoparticle delivery system such as crystallized dextran microspheres enhances its protective ability.

Materials and Methods.

Preparation of *M. haemolytica* Inoculum for Endobronchial Challenge.

*M. haemolytica* serotype-1 strain SH789, isolated from the pneumonic lung of a calf, was streaked on blood agar plate and incubated overnight at 37° C. The following day few colonies were transferred to 3 ml of pre-warmed brain heart infusion (BHI) broth and incubated for 3 hours at 37° C. with constant shaking (200 cycles/minute). Two BHI agar plates were 'lawned' with this bacterial culture using sterile cotton swabs and incubated overnight at 37° C. The following day (day of inoculation) *M. haemolytica* was harvested from the BHI agar plates and transferred to 40 ml of pre-warmed BHI broth in a 250 ml flask, and incubated for 2.5 hours at 37° C. with constant shaking to obtain cultures in the logarithmic phase of growth. The culture was centrifuged at 6000×g at 20° C. for 30 minutes and the pellet was washed once with RPMI 1640 (without phenol red) medium. The bacterial pellet was re-suspended in 4 ml of RPMI 1640 (without phenol red), and 1 ml of this culture was added to 50 ml of pre-warmed RPMI 1640 (without phenol red) containing L-glutamine (1 ml L-glutamine/100 ml RPMI) in a 250 ml flask. Bacteria were incubated for 3 hours at 37° C. with constant shaking to obtain logarithmic phase culture and the optical density (OD) was measured. The culture was appropriately diluted to obtain a concentration of $1 \times 10^9$ CFU of *M. haemolytica* per ml. Five ml of this preparation per calf was used for endobronchial challenge. The bacterial concentration was confirmed the following day by culturing diluted aliquots of the inoculum on BHI agar and counting the resulting colonies.

Peptides.

The peptide (P17) containing amino acids 5-17 of bovine CD18 (NH$_2$-RPQLLLLAGLLAL-OH) (SEQ ID NO.:71), and the peptide (PSC) containing the same amino acids as peptide P17 but in a randomly scrambled sequence (NH$_2$-LRALLPLQLLAGL-OH) (SEQ ID NO.:72), were synthesized at Neopeptide (Cambridge, Mass.). Both peptides were re-suspended in dimethysulfoxide (ATCC) at a concentration of 20 mg/ml and stored at −20° C. until used. Based on the results of in vitro neutralization of Lkt by peptide P17, each calf was endobronchially inoculated with 2 mg of peptide in 5 ml of RPMI mixed with $5 \times 10^9$ CFU of *M. haemolytica* in 5 ml of RPMI.

In Vitro Neutralization of Lkt.

Five ml aliquots of *M. haemolytica* containing $1 \times 10^9$ CFU/ml of RPMI 1640 were mixed with 5 ml aliquots of the peptide (P17 or PSC) at a concentration of 5, 4, or 2 mg per 5 ml of RPMI 1640 (without phenol red), and incubated for 4-5 hours at 37° C. with constant shaking. The bacteria were removed from the culture by centrifugation (13, 500×g for 20 min at 4° C.), and the supernatant fluid was filter-sterilized and stored at −20° C. until tested by the cytotoxicity assay for leukotoxic activity.

Detection of Lkt-Induced Cytolysis of Target Cells.

The MTT [3-(4,5-dimethylthiazoyl-2-YI)-2,5-diphenyl tetrazolium bromide; Sigma] dye reduction cytotoxicity assay for detection of Lkt-induced cytolysis of target cells has been previously described by us (Gentry and Srikumaran, 1991). This assay measures the ability of the ER-resident enzymes in viable cells to convert a tetrazolium dye into a purple formazan precipitate, which is later dissolved in acid isopropanol. The optical density (OD) of the end product, representing the intensity of the purple color developed, is directly proportional to the viability of the cells. Briefly, the target cells were re-suspended in colorless RPMI 1640 (without phenol red) at a concentration of $5 \times 10^6$ cells ml$^{-1}$, and seeded into 96 well round bottom microtiter plates (50 ul/well) containing the serially diluted Lkt in duplicates and incubated at 37° C. for 1 hour. Cells were centrifuged at 600×g for 5 min following incubation, and the supernatant fluid was discarded. The cell pellets were re-suspended in 100 ul of colorless RPMI 1640 and 20 ul of 0.5% MTT dye were added to each well. After 1 hour of incubation at 37° C., the plates were centrifuged at 600×g for 5 min and the supernatant fluid was removed. The formazan precipitate was thoroughly dissolved in 100 ul acid isopropanol and the OD of the samples was measured using an ELISA reader at 540 nm. The percent cytotoxicity was calculated as follows: % cytotoxicity=[1−(OD of toxin-treated cells/OD of toxin-untreated cells)]×100.

Detection of Inhibition of Lkt-Induced Cytolysis of Target Cells by the Lkt-Neutralizing Abs in Serum.

For Lkt neutralization, 50 ul of toxin preparation at a 50% toxicity end point titer of 40 Units/ml was incubated with 50 ul of serum (2 fold dilutions starting at 1:20) at 4° C. for 1 hour. Bovine lymphoma cells (BL3; 5×10$^6$/ml) were added, and the MTT assay was performed as described above. The percent inhibition of cytolysis was calculated as follows: % Inhibition of cytolysis=[1−(% cytolysis in the presence of serum/% cytolysis in the absence of serum)]×100.

Animal Inoculation.

All experimental protocols were approved by the Institutional Animal Care and Use Committee (IACUC) at Washington State University before the onset of the study. Twelve Holstein calves were randomly assigned to three experimental groups. Calves were matched for age when assigned into three groups. Prior to inoculation, serum samples and pharyngeal and nasal swabs were collected from all the calves. Group I calves received endobronchial injections of 5×10$^9$ CFU of M. haemolytica in 10 ml of RPMI. Group II calves received 5×10$^9$ CFU of M. haemolytica and 2 mg of peptide PSC in 10 ml of RPMI. Group III calves received 5×10$^9$ CFU of M. haemolytica and 2 mg of peptide P17 in 10 ml of RPMI. The inoculum was flushed down with an additional 10 ml of RPMI in all calves. Clinical disease in each calf was scored at different time points post-inoculation. Calves were humanely euthanized 90 hours post-inoculation, and the percent volume of lungs exhibiting gross pulmonary pathology was calculated using morphometric methods.

Scoring of Clinical Disease.

Physical examination of each calf was performed immediately prior to experimental infection and at 6, 18, 24, 42, 48, 66, 72, and 90 hours post-inoculation. Signs of clinical disease were allocated points according to the scoring system followed by Malazdrewich et al (2003; Table 3).

TABLE 3

Evaluation and scoring of clinical signs

| Clinical signs | Clinical score |
|---|---|
| Body temperature > 103.5° F. | 2 |
| Inappetance | 1 |
| Lethargy/depression | 1 |
| Marked weakness/recumbency | 2 |
| Moribund state | 3 |
| Cough | 1 |
| Nasal discharge | 1 |
| Respiratory rate > 60 breaths/min | 1 |
| Dyspnea | 2 |
| Abnormal breath sounds on auscultation | 1 |

Serotyping.

M. haemolytica isolated from pharyngeal and nasal swabs prior to inoculation and from lung tissue at necropsy, were typed using anti-serotype A1 serum (kindly provided by Dr. Robert Briggs, National Animal Disease Center, Ames, Iowa). One milliliter of fresh culture was centrifuged at 6800×g for 3 minutes and the pellet was re-suspended in 100 μl of Hanks' balanced salt solution (HBSS) medium containing 0.25% of bovine serum albumin (BSA). Twenty-five μl of culture was then placed on the agglutination plate. Anti-A1 specific serum was diluted in HBSS medium containing 0.25% of BSA and 25 μl of the diluted serum at 1/16 dilution was added to the bacteria and mixed by gentle rocking of the plate. The reference A1 strain and culture media were used as the positive and negative controls, respectively.

Quantitation of Gross Pulmonary Pathology.

On necropsy lungs were removed and gross pneumonic lesion development in each lobe of lung was observed. The entire lung from each animal was sliced at 1 cm thickness and the total and pneumonic lesion areas were traced onto transparent acetate sheets. The traced portions were scanned into ImgaeJ, NIH Image (National Institute of Health; Nethesda, Md.), which was used to measure areas representing both the total serial section and the gross pneumonic lesions within it. Measured areas for each serial section were used to calculate the volume of each lung and the grossly pneumonic regions within it using Simpson's rule: $V=(\frac{1}{3}) h [(A_0+A_n)+4(A_1+A_3+ \ldots +A_{n-1})+2 (A_2+A_4+ \ldots +A_{n-2})]$ where V is the total or pneumonic lung volume, h is the thickness of each slice in centimeters, and A, $A_0$, $A_1$, $A_2$, $A_n$ represent measured lung or pneumonic lesion areas for lung slices 0, 1, 2, n. These values were then used to calculate the percent volume of the lung exhibiting gross pulmonary pathology in each calf.

Lung tissues from representative gross lesions in each calf were collected for histopathological evaluation. Tissue samples were fixed in 10% neutral buffered formalin and embedded in paraffin using standard techniques. After routine processing, 5 μm tissue sections were stained with hematoxylin and eosin and used for subjective, non-quantitative histopathological examination.

Re-Isolation of M. haemolytica from Pneumonic Lungs.

Using aseptic techniques, fresh lung samples and pharyngeal and nasal swabs were obtained for isolation and characterization of bacteria including M. haemolytica and other Pasteurella species. Serotyping of M. haemolytica isolates were performed using anti-serotype A1 specific sera.

Bacteriological Examination.

Small samples of tissue (1 g) were obtained from affected regions from the same lobe. The samples were homogenized into 3 mls of RPMI 1640 and diluted 10-fold ($1\times10^{-1}$ to $1\times10^{-6}$). Ten μl aliquots of each dilution were applied to BHI agar plates on 5 spots and incubated at 37° C. overnight and viable counts were determined. Representative colonies were checked for M. haemolytica by colony PCR. Primers used were as follows: forward 5'-AGAGGCCAATCTG-CAAACCTC-3' (SEQ ID NO.:73) and reverse 5'-GTTCG-TATTGCCCAACGCCG-3' (SEQ ID NO.:74). Counts were expressed as CFU of M. haemolytica/g of lung tissue.

Statistical Analysis.

Clinical scores and the percent volume of the lung exhibiting gross pneumonic lesions were expressed as the mean±SEM. Clinical scores between the groups were compared using one-way analysis of variance tests (ANOVA). Pneumonic lung scores and the quantity of M. haemolytica/g of lung tissue of all three groups were also compared using one-way ANOVA. Differences were considered significant at a value of P<0.05.

Results

Co-Incubation of Peptide P17 with In Vitro Cultures of *M. haemolytica* Abrogates Leukotoxic Activity.

Figure 9:
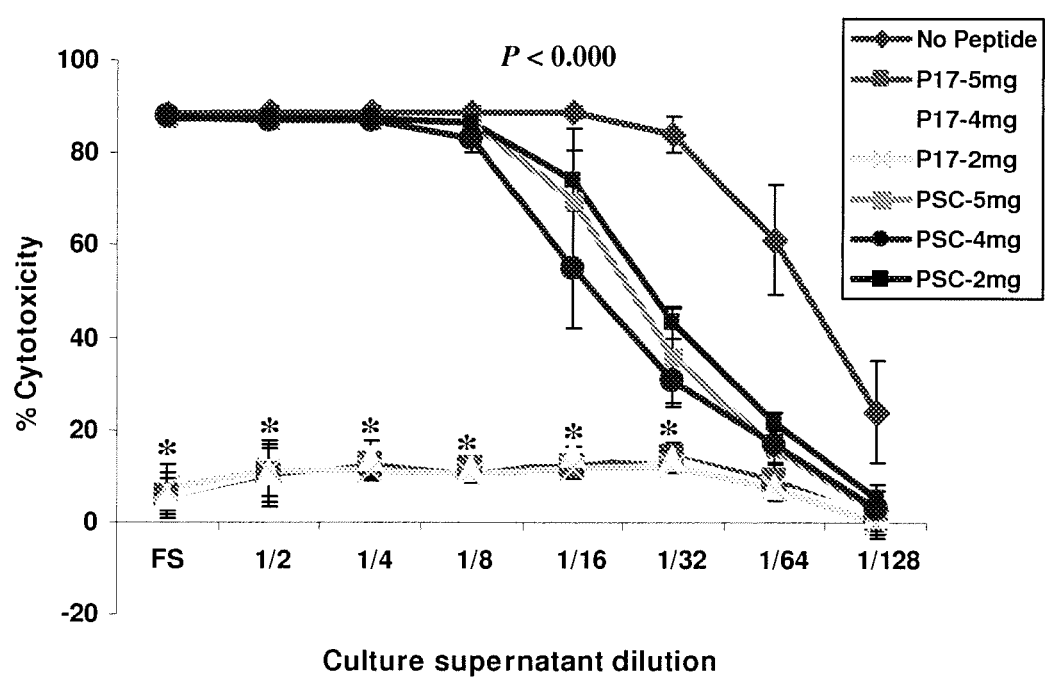
FIG. 9 shows, according to particular exemplary aspects, that co-incubation of peptide P17 with in vitro cultures of *M. haemolytica* abrogate leukotoxic activity. See working EXAMPLE 7 for details.
Figure 10:
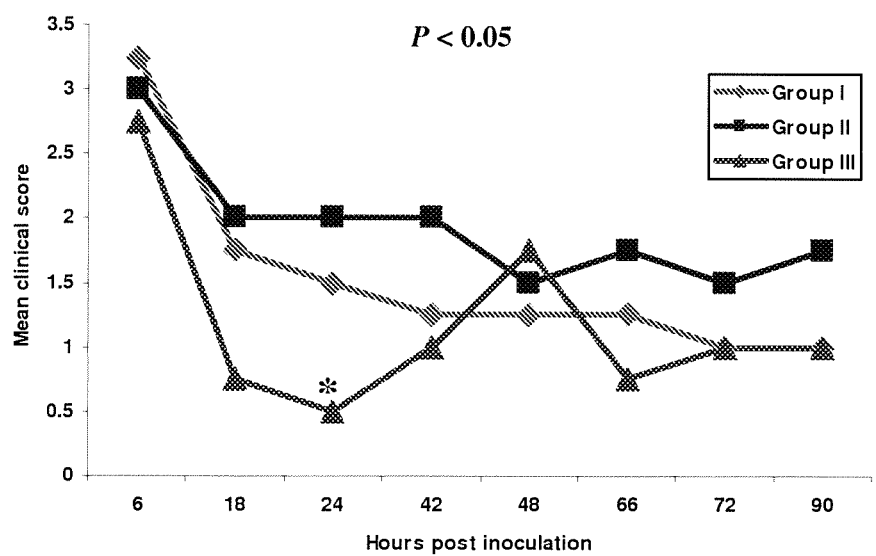
FIG. 10 shows mean clinical scores of calves inoculated with *M. haemolytica* only (Group I), *M. haemolytica* along with the irrelevant peptide PSC (Group II) and *M. haemolytica* along with the peptide P17 (Group III) at different time points post-inoculation. At 24 hours post-inoculation, the mean clinical score of Group III was statistically significantly lower than that of other groups (P<0.05). See working EXAMPLE 7 for details.

Before proceeding with the in vivo experiments, the inhibitory effect of the peptide P17 on the leukotoxic activity of in vitro cultures of *M. haemolytica* was determined. *M. haemolytica* cultures were incubated with 2, 4, or 5 mg of peptide P17 or the control peptide PSC, and the leukotoxic activity in the culture supernatant fluids was determined by the dye-reduction cytotoxicity assay. The supernatant fluids from *M. haemolytica* cultures incubated with the peptide P17 did not exhibit significant leukotoxic activity whereas those from cultures incubated with the control peptides had significant leukotoxic activity (FIG. 9). The difference in % cytotoxicity exhibited by the supernatant fluids from the cultures incubated with the peptide P17 and PSC was statistically significant (P<0.001). Inhibition of cytotoxicity did not decrease when the quantity of peptide P17 was reduced from 5 to 4 and 2 mg, indicating that the peptide P17 can inhibit the Lkt-induced cytolysis of target cells even at 2 mg (per $5 \times 10^9$ CFU of *M. haemolytica*).

Pre-Inoculation Status of Calves (Nasopharyngeal Flora and Anti-Lkt Antibodies).

The results of bacterial isolation are summarized in Table 4. Ten out of 12 calves carried *M. haemolytica* in their pharynx whereas only 4 calves carried it in the nasal cavity. None of the isolates belonged to serotype 1, the serotype of *M. haemolytica* used for inoculation. The unavailability of antisera specific for all known serotypes of *M. haemolytica* prevented us from identifying the precise serotype of these bacteria. *Pasteurella multocida* and *Bibersternia trehalosi* were isolated from two and three calves, respectively. All the calves used in the experiment had low titers of Lkt-neutralizing antibodies as revealed by the cytotoxicity inhibition assay. The titers ranged from 1/20 to 1/320.

TABLE 4

Bacteria isolated from calves pre-inoculation and at necropsy.

| Animal # | Region | *M. haemolytica* Before | *M. haemolytica* After | *P. multocida* Before | *P. multocida* After | *B. trehalosi* Before | *B. trehalosi* After |
|---|---|---|---|---|---|---|---|
| 16 | P | (+) | (+) | (−) | (−) | (−) | (−) |
|  | N | (−) | (+) | (−) | (−) | (−) | (−) |
| 21 | P | (+) | (+) | (−) | (−) | (−) | (−) |
|  | N | (−) | (+) | (−) | (−) | (−) | (−) |
| 25 | P | (+) | (+) | (−) | (−) | (−) | (−) |
|  | N | (−) | (−) | (−) | (+) | (−) | (−) |
| 26 | P | (−) | (−) | (−) | (−) | (−) | (−) |
|  | N | (−) | (−) | (−) | (+) | (−) | (−) |
| 29 | P | (+) | (+) | (−) | (−) | (−) | (−) |
|  | N | (+) | (−) | (−) | (+) | (−) | (−) |
| 36 | P | (+) | (+) | (−) | Past | (−) | (−) |
|  | N | (−) | (−) | (+) | (+) | (−) | (−) |
| 52 | P | (+) | (−) | (+) | (+) | (−) | (+) |
|  | N | (−) | (−) | (−) | (+) | (−) | (−) |
| 68 | P | (+) | (−) | (−) | (+) | (−) | (−) |
|  | N | (−) | (−) | (−) | (+) | (−) | (−) |
| 86 | P | (+) | (−) | (−) | (−) | (−) | (−) |
|  | N | (−) | (−) | (−) | (+) | (−) | (−) |
| 146 | P | (+) | (−) | (−) | (−) | (+) | (−) |
|  | N | (+) | (+) | (−) | (−) | (−) | (−) |
| 168 | P | (+) | (+) | (−) | (−) | (+) | (+) |
|  | N | (+) | (+) | (−) | (−) | (−) | (−) |
| 170 | P | (−) | (−) | (−) | (−) | (+) | (+) |
|  | N | (+) | (+) | (−) | (+) | (−) | (−) |

Before: before the challenge;
After: at necropsy;
P: Pharynx;
N: Nasal cavity;
(+): Present;
(−): Absent;
Past: *Pasteurella* species Clinical Disease Scores.

Physical examination of each calf was conducted immediately prior to experimental infection and 6, 18, 24, 42, 48, 66, 72, and 90 hours post-infection. All calves were clinically normal (clinical score=0) pre-inoculation. Within 6 hours of infection, all calves developed clinical symptoms of disease. Rectal temperature increased to 105-106° F. within 6 hours post-inoculation and returned to baseline 24 hours post-inoculation as previously reported by other workers (Corrigan et al., 2007). All calves in Groups I and II had nasal discharge throughout the study period, but the Group III calves had nasal discharge only up to 24 hours post-inoculation. The clinical scores for nasal discharge of Group III calves were statistically significantly different from those of Group I and II (P<0.05) of calves inoculated with peptide P17. The total observational disease scores for Group III calves (peptide P17) were lower than those for group I and II at all time points except 48 hours. This difference was statistically significant (P<0.05) at 24 hours post-inoculation.

Gross Lesions.

Figure 11A:
FIGS. 11A-11B shows, according to particular aspects, representative gross-(A) and histo-(B) pathology of the lungs of calves infected with *M. haemolytica* with or without peptides. See working EXAMPLE 7 for details.

All the calves presented gross pulmonary lesions consistent with fibrinonecrotic pneumonia characteristic of *M. haemolytica*-caused pneumonia. The pulmonary lesions in all calves were qualitatively similar but differed in severity and extent. Affected lung tissue exhibited consolidation, congestion, and prominent interlobular septae due to fibrin deposition. These lesions were mainly present in the right lung and to a limited extent in the left lung (FIG. 11A). The percent volume of the lungs exhibiting gross pneumonic lesions, as determined by morphometric techniques (Malazdrewich, et al., 2004) are shown in Table 5. The difference in the percent volume of lungs exhibiting gross pneumonic lesions among the three groups was not statistically significant (P=0.9).

Figure 11B:
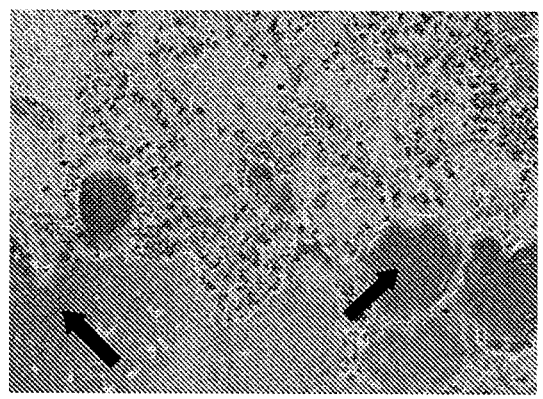

Histopathological examination of pulmonary tissues from the calves revealed that the lesions observed in the calves were characteristic of pneumonia caused by *M. haemolytica*. Interlobular septa were markedly widened by fibrin and fribrous tissue. Within lobules, discreet foci of parenchymal necrosis were outlined by dense bands of degenerate neutrophils, often with streaming nuclei ('oat cells'). Within necrotic foci, alveolar walls were lysed and alveolar spaces were filled with fibrin, red blood cells and nuclear debris. In some calves large colonies of coccobacilli were present within affected areas. Parenchyma adjacent to necrotic foci was either collapsed or filled with fibrin and macrophages (FIG. 11B).

TABLE 5

Gross pneumonic lesions expressed as a % of total lung volume

| Group | Animal # | Age (months) | Lesion (%) | Mean (%) |
|---|---|---|---|---|
| I | 25 | 4 | 16.62 | |
|  | 16 | 4 | 14.03 | 10.03 ± 2.85 |
|  | 52 | 6 | 3.07 | |
|  | 146 | 3 | 8.38 | |
| II | 29 | 4 | 24.57 | |
|  | 21 | 4 | 4.07 | 12.09 ± 4.39 |
|  | 68 | 6 | 10.70 | |
|  | 168 | 3 | 9.01 | |
| III | 36 | 4 | 15.67 | |
|  | 26 | 4 | 2.7 | 10.53 ± 3.02 |
|  | 86 | 6 | 13.22 | |
|  | 170 | 3 | 8.51 | |

Re-Isolation of *M. haemolytica* Serotype 1 from Pneumonic Lungs of Calves.

Pure cultures of bacteria (*M. haemolytica*) were recovered from the pneumonic lungs of all calves. All isolates were identified as *M. haemolytica* by PCR, and confirmed as serotype 1, by serotyping analysis. All heart blood cultures were negative for *M. haemolytica*, indicating that the infection was confined to the respiratory tract. *M. haemolytica* were isolated from pharynx and nasal cavity of most of the calves (Table 2). All the isolates from pharynx belonged to serotype 1 but the isolates from nasal cavity were not. Isolation of *M. haemolytica* from the lungs revealed that the calves in Group III carried approximately 100- to 1000-fold less organisms in the lungs than the calves in Group I and Group II (Table 6). This difference, expressed as CFU of *M. haemolytica* per g of lung tissue, was statistically significant (P<0.001).

TABLE 6

Number of *M. haemolytica* (CPU per gram of lung tissue) isolated from the lungs of calves at necropsy

| Group I | Group II | Group III |
|---|---|---|
| $2.38 \times 10^6$ | $1.89 \times 10^7$ | $5.29 \times 10^3$ |
| $1.50 \times 10^5$ | $6.73 \times 10^5$ | $4.92 \times 10^2$ |
| $2.68 \times 10^5$ | $6.50 \times 10^7$ | $5.70 \times 10^4$ |
| $2.9 \times 10^7$ | $1.87 \times 10^7$ | $8.00 \times 10^2$ |
| Mean $7.9 \pm 7.0 \times 10^6$ | $2.58 \pm 1.374 \times 10^7$ | $1.589 \pm 1.374 \times 10^4$ |

Example Discussion

*M. haemolytica* Lkt-induced cytolysis and degranulation of macrophages and PMNs is responsible for the acute inflammation and lung injury that is characteristic of pneumonia caused by this organism. According to certain embodiments, abrogation of Lkt-induced cytolysis prevents or mitigates the lung lesion. Applicants have shown that a peptide representing the amino acid sequence of Lkt-binding site on its receptor, CD18, effectively inhibits the Lkt-induced cytolysis of target cells (Shanthalingam and Srikumaran, 2009). Applicants have confirmed that this peptide analog of CD18 abrogates the leukotoxic activity of in vitro cultures of *M. haemolytica* (FIG. 9) which prompted us to test the efficacy of this peptide in a calf challenge model.

*M. haemolytica* serotype 1 was the obvious choice for this study since it is the serotype that predominantly causes pneumonia in cattle although other serotypes such as 2, 4 and 7 commonly inhabits the nasopharynx of healthy cattle (Frank and Smith 1983, Frank, 1988; Gonzalez and Maheswaran, 1993). All the pharyngeal isolates obtained from the calves pre-inoculation belonged to serotypes other than serotype 1 allowed us to track the inoculated *M. haemolytica* by serotyping. The presence of Lkt-neutralizing antibodies in the serum indicates that the calves had these antibodies in the epithelial lining fluid which, according to certain embodiments, had an effect on the bacterial clearance. The calves were matched for Lkt-neutralizing antibody titers. According to additional aspects, colostrum-deprived calves are used to eliminate any possible effects due to Lkt-neutralizing antibodies.

All the calves developed high rectal temperature within 6 hours of inoculation which dropped to normal levels in 24 hours. LPS represents 10 to 25% of the dry weight of *M. haemolytica* bacteria (Keiss et al., 1964) and it forms high-molecular-weight aggregates with Lkt (Li and Clinckenbeard, 1999). Since LPS stimulates alveolar macrophages to produce TNFα and interleukin-8, leading to inflammation, it is likely that some of the effects that we observed were LPS related. The total observational disease scores for Group III calves were lower than those for group I and II at all time points beyond 6 hours. This difference was statistically significant (P<0.05) at 24 hours post-inoculation. According to certain embodiments, the peptide is absorbed from the surface of the respiratory epithelium by 24 hours post-inoculation, which results in the loss of protective effect of the peptide. According to additional aspects, use of peptides absorbed to solid particles which slowly release the peptide provides for prolonging the protective effect of the peptides which mitigate the disease.

The peptide P17 strongly inhibited Lkt-induced cytolysis of bovine PMNs in in vitro assays. It is surprising that the gross pneumonic lesions in calves inoculated with this peptide and *M. haemolytica* (Group III) were no less than those in calves inoculated with the control peptide PSC and *M. haemolytica* (Group II), or *M. haemolytica* alone (Group I). According to particular aspects, the ability of the peptide to mitigate lung lesions could be enhanced by: (1) increasing the quantity of the peptide; (2) decreasing absorption of the peptide from the lung epithelial surface; or (3) protecting the peptide from proteolytic degradation. For example, by use of peptides adsorbed on solid particles which slowly release the peptide is likely to prolong the protective effect of the peptides which could be expected to mitigate the lung lesions (Freiberg and Zhu, 2004; Schroder and Stahl, 1984; Schroder, 1985). Although the lung lesions were similar in extent in all three groups, it is possible that the animals in Group III would have recovered from the disease if they were not euthanized at 90 hours post-inoculation, as we did in this study. This scenario is supported by the finding that the number of *M. haemolytica* recovered from the lungs of Group III animals was 100 to 1000 times less than that recovered from the lungs of animals in Group I and II (Table 6). The significantly lower number of bacteria isolated from the lungs of Group III animals is likely due to the presence of relatively larger number of functional phagocytes in the lungs which were protected from Lkt by the peptides. In contrast, the animals in Groups I and II would have had relatively smaller number of phagocytes in the lungs because of their cytolysis by Lkt.

Molecules such as proteins and peptides are often marginally stable and consequently could be easily damaged or degraded (Tibbetts et al., 2000). In vivo degradation when exposed to enzymes results in short biological half-lives (Tibetts, 2000). According to particular aspects, prolonging the presence of peptides in the lungs extends protection of the phagocytes from the Lkt, resulting in more effective clearance of bacteria from the lungs which in turn prevents or mitigates lung lesions.

In particular aspects, nanoparticle delivery systems are used to improve protein/peptide stability and provide sustained release. Adsorbing the peptides to solid particles such as dextran represents a method of prolonging the presence and activity of the peptides in the lungs. Dextran, under certain controlled conditions, aggregates into porous microspheres, forming crystallized dextran microspheres that can absorb/adsorb peptides, drugs and biologicals, protecting them against degradation and prolonging their release. Such dextran microspheres are available which are biodegradable, biocompatible, non-toxic, non-immunogenic and are removed from the body by normal physiological routes. These characteristics are uniquely advantageous for peptide delivery. According to particular aspects, crystallized dextran microspheres are used for the delivery of peptides and prolong the protective effects of the peptide.

References cited for Examples 1-6, and incorporated herein by reference for their relevant teachings as referred to herein:

1. Blobel, G. & Dobberstein, B. Transfer of proteins across membranes. I. Presence of proteolytically processed and non-processed nascent immunoglobulin light chains on membrane-bound ribosomes of murine myeloma. *J. cell. Biolo.* 67, 835-851 (1975).
2. von Heijne, G. The signal peptide. *J. Membrane Biol.* 115, 195-201 (1990).
3. Tuteja, R. Type I signal peptidase: An overview. *Arch. Biochem. Biophys.* 441, 107-111 (2005)
4. Deshpande, M. S., Ambagala, T. C., Ambagala, A. P. N., Kehrli, M. E. & Srikumaran, S. Bovine CD18 is necessary and sufficient to mediate *Mannheimia (Pasteurella) haemolytica* leukotoxin-induced cytolysis. *Infect. Immun.* 70, 5058-5064 (2002).
5. Dassanayake, R. P., Shanthalingam, S., Davis, W. C. & Srikumaran, S. *Mannheimia haemolytica* leukotoxin-induced cytolysis of ovine (*Ovis aries*) leukocytes is mediated by CD18, the β subunit of β$_2$-integrins. *Microb. Pathog.* 42, 167-173 (2007).
6. Liu, W., et al. *Mannheimia (Pasteurella) haemolytica* leukotoxin utilizes CD18 as its receptor on bighorn sheep leukocytes. *J. Wildl. Dis.* 43, 75-81 (2007)
7. Gopinath, R. S., Ambagala, T. C., Deshpande, M. S., Donis, R. O. & Srikumaran, S. *Mannheimia (Pasteurella) haemolytica* leukotoxin binding domain lies within amino acids 1 to 291 of bovine CD18. *Infect. Immun.* 73, 6179-6182 (2005).
8. Highlander, S. K. Molecular genetic analysis of virulence in *Mannheimia (Pasteurella) haemolytica. Front. Biosci.* 1, D1128-1150 (2001)
9. Petras, S. F. et al. Antigenic and virulence properties of *Pasteurella haemolytica* leukotoxin mutants. *Infect Immun.* 63, 1033-1039 (1995).
10. Tatum, F. M. et al. Construction of an isogenic leukotoxin deletion mutant of *Pasteurella haemolytica* serotype 1: characterization and virulence. *Microb. Pathog.* 24, 37-46 (1998).
11. Highlander, S. K., et al. Inactivation of *Pasteurella (Mannheimia) haemolytica* leukotoxin causes partial attenuation of virulence in a calf challenge model. *Infect. Immun.* 68, 3916-3922 (2000).
12. Dassanayake, R. P., et al. *Mannheimia haemolytica* serotype A1 exhibits differential pathogenicity in two related species *Ovis Canadensis* and *Ovis aries. Vet. Microbiol.* 133, 366-371 (2009).
13. Jeyaseelan, S., Sreevatsan, S. & Maheswaran, S. K. Role of *Mannheimia haemolytica* leukotoxin in the pathogenesis of bovine pneumonic pasteurellosis. *Anim. Health Res. Rev.* 3, 69-82 (2002).
14. Strathdee, C. A. & Lo, R. Y. Cloning, nucleotide sequence, and characterization of genes encoding the secretion function of the *Pasteurella haemolytica* leukotoxin determinant. *J. Bacteriol.* 171, 916-928 (1989).
15. Devenish, J. Rosendal, S. Johnson, R. & Hubler, S. Immunoserological comparison of 104-kilodalton proteins associated with hemolysis and cytolysis in *Actinobacillus pleuropneumoniae, Actinobacillus suis, Pasteurella haemolytica*, and *Escherichia coli. Infect. Immun.* 57, 3210-3213 (1989).
16. Kolodrubetz, D., Dailey, T., Ebersole, J. & Kraig, E. Cloning and expression of the leukotoxin gene from *Actinobacillus actinomycetemcomitans. Infect. Immun.* 57, 1465-1469 (1989).
17. Chang, Y. F., Renshaw, h. w., Martens, r. j. & Livingston, Jr. R. J. *Pasteurella haemolytica* leukotoxin: chemiluminescent responses of peripheral blood leukocytes from several different mammalian species to leukotoxin- and opsonin-treated living and killed *Pasteurella haemolytica* and *Staphylococcus aureus. Am. J. Vet. Res.* 47, 67-74 (1986).
18. Kaehler, K. L., Markham, R. J., Muscoplat, C. C. & Johnson D. W. Evidence of species specificity in the cytocidal effects of *Pasteurella haemolytica. Infect. Immun.* 30, 615-616 (1980).
19. Shewen, P. E., & Wilkie, B. N. Cytotoxin of *Pasteurella haemolytica* acting on bovine leukocytes. *Infect. Immun.* 35, 91-94 (1982).
20. Slocombe, R. F., Malark, J., Ingersoll, R., Derksen, F. J. & Robinson, N. E. Importance of neutrophils in the pathogenesis of acute pneumonic pasteurellosis in calves. *Am. J. Vet. Res.* 46, 2253-2258 (1985).
21. Stewart, R. S., Drisaldi, B. & Harris, D. A. A transmembrane form of the prion protein contains an uncleaved signal peptide and is retained in the endoplasmic reticulum. Mol. *Biol. Cell.* 12, 881-889 (2001)
22. von Heijne, G. Patterns of amino acids near signal-sequence cleavage sites. *Eur. J. Biochem.* 133, 17-21 (1983)
23. Rutz, C. et al. The corticotropin-releasing factor receptor type 2a contains an N-terminal pseudo signal peptide. *J. Biol. Chem.* 281, 24910-24921 (2006)
24. Dileepan, T., Kannan, M. S., Walcheck, B., Thumbikat, P. & Maheswaran, S. K. Mapping of the binding site for *Mannheimia haemolytica* leukotoxin within bovine CD18. *Infect. Immun.* 73, 5233-5237 (2005).
25. Dileepan, T., Kannan, M. S., Walcheck, B. & Maheswaran, S. K. Integrin-EGF-3 domain of bovine CD18 is critical for *Mannheimia haemolytica* leukotoxin species-specific susceptibility. *FEMS Microbiol.* 274, 67-72 (2007)
26. Klein, E., et al. Properties of the K562 cell line, derived from a patient with chronic myeloid leukemia. *Int. J. Cancer.* 18, 421-431 (1976)
27. Andersson, L. C., Nilsson, K. & Gahmberg, C. G. K562—a human erythroleukemic cell line. *Int. J. Cancer.* 23, 143-147 (1979)
28. Shuster, D. E., Bosworth, B. T. & Kehrli Jr, M. E. Sequence of the bovine CD18-encoding cDNA: comparison with the human and murine glycoproteins. *Gene.* 114, 267-271 (1992)

29. Gentry, M. J. & Srikumaran, S. Neutralizing monoclonal antibodies to *Pasteurella haemolytica* leukotoxin affinity-purify the toxin from crude culture supernatants. *Microb. Pathog.* 10, 411-417 (1991)
30. Ambagala, T. C., Ambagala, A. P. N. & Srikumaran. The leukotoxin of *Pasteurella haemolytica* binds to integrins on bovine leukocytes. *FEMS Microbiol. Lett.* 179, 161-167 (1999).

References cited for Example 7, and incorporated herein by reference for their relevant teachings as referred to herein:
1. Ambagala T C, Ambagala A P, Srikumaran S. 1999. The leukotoxin of *Pasteurella haemolytica* binds to beta(2) integrins on bovine leukocytes. FEMS Microbiol Lett 179:161-167.
2. Clinkenbeard K D, Upton M L. 1991. Lysis of bovine platelets by *Pasteurella haemolytica* leukotoxin. Am J Vet Res 52:453-57.
3. Confer A W, Panciera R J, Clinkenbeard K D, Mosier D A. 1990. Molecular aspects of virulence of *Pasteurella haemolytica*. Can J Vet Res 54:S48-52.
4. Coote J G. 1992. Structural and functional relationships among the RTX toxin determinants of Gram-negative bacteria. FEMS Microbiol Rev 88:137-62.
5. Corrigan M E, Drouillard J S, Spire M F, Mosier D A, Minton J E, Higgins J J, Loe E R, Depenbusch B E, Fox J T. 2007. Effects of melengestrol acetate on the inflammatory response in heifers challenged with *Mannheimia haemolytica*. J Anim Sci 85:1770-1779.
6. Dassanayake R P, Maheswaran S K, Srikumaran S. 2007a. Monomeric expression of bovine $\beta_2$-integrin subunits reveals their role in *Mannheimia haemolytica* leukotoxin-induced biological effects. Infect Immun 75:5004-5010.
7. Dassanayake R P, Shanthalingam S, Davis W C, Srikumaran S. 2007b. *Mannheimia haemolytica* leukotoxin-induced cytolysis of ovine (*Ovis aries*) leukocytes is mediated by CD18, the $\beta$ subunit of $\beta_2$-integrins. Microb Pathog 42:167-173.
8. Dassanayake R P, Shanthalingam S, Herndon C N, Lawrence P K, Frances C E, Potter K A, Foreyt W J, Clinkenbeard K D, Srikumaran S. 2009. *Mannheimia haemolytica* serotype A1 exhibits differential pathogenicity in two related species *Ovis Canadensis* and *Ovis aries*. Vet Microbiol 133:366-371.
9. Despande M S, Ambagala T C, Ambagala A P N, Kehrli Jr M E, Srikumaran S. 2002. Bovine CD18 is necessary and sufficient to mediate *Mannheimia (Pasteurella) haemolytica* leukotoxin-induced cytolysis. Infect Immun 70:5058-5068.
10. Frank G H, Smith P C. 1983. Prevalence of *Pasteurella haemolytica* in transported calves. Am J Vet Res 44:981-985.
11. Frank G H. 1989. Pasteurellosis of cattle. In: Adlam C, Rutter J M, Eds. *Pasteurella* and pasteurellosis. Academic Press 197-222.
12. Frank G H. 1988. When *Pasteurella haemolytica* colonizes the nasal passages of cattle. Vet Med 83:1060-1064.
13. Freiberg S, Zhu X X. 2004. Polymer microspheres for controlled drug release. Int J Pharm 282:1-18.
14. Gahmberg C G, Valmu L, Fagerholm S, Kotovuori P, Ihanus E, Tian L, Pessa-Morikawa T. 1998. Leukocyte integrins and inflammation. Cell mol life Sci 54:549-555.
15. Gentry M J, Srikumaran S. 1991. Neutralizing monoclonal antibodies to *Pasteurella haemolytica* leukotoxin affinity-purify the toxin from crude culture supernatants. *Microb Pathog* 10: 411-417.
16. Gonzalez C, Maheswaran S K. 1993. The role of induced virulence factors produced by *Pasteurella haemolytica* in the pathogenesis of bovine pneumonic pasteurellosis: review and hypothesis. British Vet J 149:183-193.
17. Gopinath R S, Ambagala T C, Deshpande M S, Donis R O, Srikumaran S. 2005. *Mannheimia (Pasteurella) haemolytica* leukotoxin binding domain lies within amino acids 1 to 291 of bovine CD18. Infect Immun 73:6179-6182.
18. Highlander S K, Fedorova M D, Dusek D M, Panciera R, Alvarez L E, Renehart C. 2000. Inactivation of *Pasteurella (Mannheimia) haemolytica* leukotoxin causes partial attenuation of virulence in a calf challenge model. Infect Immun 68:3916-3922.
19. Hochberg M C. 1989. NSAIDS: mechanisms and pathways of action. Hospital Practice. 24:185-190, 195, 198.
20. Jeyaseelan S, Hsuan S L, Kannan M S, Walcheck B, Wang J F, Kehrli Jr M E, Lally E T, Sieck G C, Maheswaran S K. 2000. Lymphocyte function-associated antigen 1 is a receptor for *Pasteurella haemolytica* leukotoxin in bovine leukocytes. Infect. Immun 68:72-79.
21. Jubb K V F, Kennedy P C. 1970. Pathology of domestic animals. $2^{nd}$ edn. New York. Academic Press.
22. Kaehler K H, Markham R F J, Muscoplat C C, Johnson D W. 1980. Evidence of cytocidal effects of *P. haemolytica* on bovine peripheral blood mononuclear leukocytes. Am J Vet Res. 41:1690-1693.
23. Keiss R E, Will D H, Collier J R. 1964. Skin toxicity and hemodynamic properties of endotoxin derived from *Pasteurella hemolytica*. Am J Vet Res 25:935-941.
24. Li J, Clinkenbeard K D. 1999. Lipopolysaccharide complexes with *Pasteurella haemolytica* leukotoxin. Infect Immun. 67:2920-2927.
25. Li J, Clinkenbeard K D, Ritchey J W. 1999. Bovine CD18 identified as a species specific receptor for *Pasteurella haemolytica* leukotoxin. Vet Microbiol 67:91-97.
26. Liu W, Brayton K A, Davis W C, Mansfield K, Lagerquist J, Foreyt W J, Srikumaran S. 2007. *Mannheimia (Pasteurella) haemolytica* leukotoxin utilizes CD18 as its receptor on bighorn sheep leukocytes. J Wildl Dis 43:75-81.
27. Maheswaran S K, Whiteley L O, Townsend E L, Ames T R, Weiss D J, Yoo H S, Gonzalez C, Kannan M S. 1992. Leukotoxin as a virulent factor of *Pasteurella haemolytica*. Proc Seventh World Buitric Congress. 3:199-01.
28. Malazdrewich C, Thumbikat P, Maheswaran S K. 2004. Protective effect of dexamethasone in experimental bovine pneumonic mannheimiosis. Microb Pathog 36:227-236.
29. Moiser D A, Confer A W, Panciera R J. 1989. The evolution of vaccines for bovine pneumonic pasteurellosis. Research in Vet Sci 47:1-10.
30. Noti J D, Johnson A K, Dillon J D. 2000. Structural and functional characterization of the leukocyte integrin gene CD11d. Essential role of Sp1 and Sp3. J boil Chem 275:8959-8969.
31. Petras S F, Chidambaram M, Illyes E F, Forshauer S, Weinstock G M, Reese C P. 1995. Antigenic and virulence properties of *Pasteurella haemolytica* leukotoxin mutants. Infect Immun 63:1033-1039.
32. Schroder U. 1985. Crystallized carbohydrate spheres for slow release and targeting. Methods Enzymol. 112:116-128.
33. Schroder U, Stahl A. 1984. Crystallized dextran nanospheres with entrapped antigen and their use as adjuvants. J Immunol Methods 70:127-132.
34. Shanthalingam S, Srikumaran S. 2009. Intact signal peptide of CD19, the $\beta$ subunit of $\beta_2$-integrins, renders ruminants susceptible to *Mannheimia haemolytica* leukotoxin. Pro Nat Acad Sci 106:15448-15453.
35. Shewan P E, Wilkie B N. 1982. Cytotoxin of *P. haemolytica* acting on bovine leukocytes. Infect Immun. 35:91-94.
36. Tatum F M, Briggs R E, Sreevatsan S S, Zehr E S, Whiteley L O, Ames T R, Maheswaran S K. 1998. Construction of an isogenic leukotoxin deletion mutant of *Pasteurella haemolytica* serotype 1: characterization and virulence. Microb Pathog 24:37-46.
37. Tibbetts S A, et al (1999) Peptides derived from ICAM-1 and LFA-1 modulates T cell adhesion and immune function in a mixed lymphocyte culture. *Transplantation* 68:685-692.
38. Tibbetts S A, Seetharama J D, Siahaan T J, Benedict S H, Chan M A. 2000. Linear and cyclic LFA-1 and ICAM-1 peptides inhibit T cell adhesion and function. Peptides 21:1161-1167.
39. Wang J F, Kieba I R, Korostoff J, Guo T L, Yamaguchi N, Rozmiarek H, Billings P C, Shenker B J, Lally E T. 1998. Molecular and biochemical mechanisms of *Pasteurella haemolytica* leukotoxin-induced cell death. Microb Pathog 25:317-331.
40. Watson G L, Slocombe R F, Robinson N E, and Sleight S D. 1995. Enzyme release by bovine neutrophils. Am J Vet Res 56:1055-1061.
41. Welch R A, Bauer M E, Kent A D, Leeds J A, Moayeri M, Regassa L B, Swenson D L. 1995. Battling against host pahagocytes: the wherefore of the RTX family of toxins. Infect Agents Dis 4:254-72.
42. Whiteley L O, Maheswaran S K, Weiss D J, Ames T R, Kannan M S. 1992. *Pasteurella haemolytica* A1 and bovine respiratory disease: pathogenesis. J Vet Inter Med 6:11-22.
43. Wilson S H. 1989. Why are meaningful field trials difficult to achieve for bovine respiratory disease vaccines? Can Vet J. 30:299-302.

The invention claimed is:

1. A genetically engineered ruminant animal having a genome comprising a nucleic acid sequence encoding a ruminant CD18 protein having a cleavable signal peptide with a helix-breaking amino acid residue at an amino acid positioned 5 residues upstream of the signal peptide cleavage site, wherein said nucleic acid sequence has been introduced by homozygous integration of the nucleic acid sequence into the endogenous CD18 gene thereby disrupting the expression of native CD18 having an intact signal peptide, wherein the mutant CD18 protein encoded by said nucleic acid sequence is expressed at least in the animal's leukocytes, and wherein the genetically engineered ruminant animal is resistant to, or less susceptible to, the effects of M. haemolytica, relative to a wild-type control animal.

2. The genetically engineered ruminant animal of claim 1, wherein said animal is a bovine animal.

3. The genetically engineered ruminant animal of claim 1, wherein the helix-breaking amino acid residue is selected from the group consisting of glycine, proline, and arginine.

4. A method of providing a genetically engineered ruminant animal, comprising introduction into the genome of a ruminant animal, a nucleic acid sequence encoding a ruminant CD18 protein having a cleavable signal peptide with a helix-breaking amino acid residue at amino acid positioned 5 residues upstream of the signal peptide cleavage site, wherein said nucleic acid sequence is introduced by homozygous integration of the nucleic acid sequence into the endogenous CD18 gene thereby disrupting the expression of native CD18 having an intact signal peptide, wherein the mutant CD18 protein encoded by said nucleic acid sequence is expressed at least in the animal's leukocytes, and wherein the genetically engineered ruminant animal is resistant to, or less susceptible to, the effects of M. haemolytica, relative to a wild-type control animal.

5. The method of claim 4, wherein said animal is a bovine animal.

6. The method of claim 4, wherein the helix-breaking amino acid residue is selected from the group consisting of glycine, proline, and arginine.

* * * * *

SEQUENCE LISTING

<160> NUMBER OF SEQ ID NOS: 75

<210> SEQ ID NO 1
<211> LENGTH: 2817
<212> TYPE: DNA
<213> ORGANISM: Bos taurus

<400> SEQUENCE: 1

| | | | | | |
|---|---|---|---|---|---|
| gtcttccag | atccgcgaag | caccagcctg | gtgaagagca | gagccgaagc | cctgccagt | 60 |
| ccagctggga | caccctgcc | gaggtctcca | gggcatccag | gggacatgct | gcgccagcgc | 120 |
| ccccagctgc | tgctcctagc | gggcctgctt | gccctccagt | ccgtcctgtc | caggagtgc | 180 |
| accaactaca | aggtcagcac | ctgccgggac | tgcatcgagt | cgggccccgg | ctgcgcctgg | 240 |
| tgccagaaac | tgaacttcac | agggcaaggg | gagcccgact | ccattcgctg | tgacacacga | 300 |
| gcggagctgc | tgtcaaaggg | ctgcccagct | gatgacatca | tggaacccaa | gagcctcgct | 360 |
| gagacccggg | acagccaggc | gggcagtcgg | aagcagctgt | cccacagga | agtgacgctc | 420 |
| tacctgagac | caggtcaggc | agttgcgttc | aacgtgacct | tccggagggc | caagggctac | 480 |
| cccatcgacc | tgtactacct | gatggacctc | tcctactcca | tggtggatga | cctcgtcaac | 540 |
| gtcaagaagc | tgggggggtga | cctgctccgg | gccctcaatg | gcatcaccga | gtcgggccgc | 600 |
| attggttcg | ggtccttcgt | ggacaagacg | gtgctcccct | tcgtcaacac | gcacccgag | 660 |
| aagctgcgga | acccctgccc | caacaaggag | aaggagtgcc | agcccccgtt | cgccttcagg | 720 |
| cacgtgttga | agctcactga | caactccaaa | cagttcgaga | cagaagtcgg | gaagcagctg | 780 |
| atctcgggga | acctggacgc | ccctgagggt | gggctggacg | ccatgatgca | ggtggccgcg | 840 |
| tgcccggagg | aaatcggctg | gcgcaatgtc | accaggctgc | tggtgttcgc | cacggacgat | 900 |
| gggttccact | ttgcgggcga | tggaaagctg | ggtgccatcc | tcacccccaa | tgacggccgc | 960 |
| tgccacctgg | aagacaacct | gtacaaaagc | agcaacgaat | ttgactaccc | atcggtgggc | 1020 |
| cagctggcac | acaaactggc | agaaagcaac | atccagccca | tctttgcagt | aaccaagaag | 1080 |
| atggtgaaaa | cgtacgagaa | gctgacagag | atcatcccca | gtctgcagt | cggggagctg | 1140 |
| tctgaagatt | ccaggaacgt | ggtggagctt | atcaagaatg | cctacaataa | actgtcctcc | 1200 |
| agagtcttcc | tggatcacag | caccctccct | gacaccctga | aagtcaccta | cgactccttc | 1260 |
| tgcagtaacg | ggaaatcgca | ggtggaccag | cccagagggg | actgcgacgg | cgtccagatc | 1320 |
| aacgtcccga | tcaccttcca | ggtgaaggtc | acagccaccg | agtgcatcca | gcagcagtcc | 1380 |

-continued

```
ttcaccatcc gggcgctggg cttcacggac acggtgaccg tgcgggtcct cccccagtgc    1440
gagtgccaat gccgggacgc cagcagggac ggcagcatct gcggcggcag aggctcgatg    1500
gagtgcggcg tctgcaggtg tgacgccggc tacatcggga agaactgcga gtgccagacg    1560
cagggccgga gcagccagga gctggagggc agctgccgca aggacaacag ctccatcatc    1620
tgctcggggc tggggggactg catctgcggg cagtgcgtgt gccacgag cgacgtgccc     1680
aacaagaaga tctacggcca gttctgcgag tgcgacaacg tcaactgcga acgctacgac    1740
ggccaagtct gcggggggcga aaagagggggg ctctgcttct gcggcacctg caggtgcgac   1800
gagcagtatg agggttcggc atgccagtgc ctcaagtcca ctcagggctg cctcaacttg    1860
gacggcgtcg agtgcagcgg ccgcggccga tgccgctgca atgtgtgcca gtgcgacccc    1920
ggctaccagc cgcccctgtg cagcgagtgc ccgggctgcc ccgtgccctg tgcgggcttc    1980
gccccctgca cagagtgcct gaagttcgac aagggcccct cgccaagaa ctgcagcgca     2040
gcgtgcgggc agacgaagct gctgtccagc ccggtgcccg gccgcaagtg caaggagcgc   2100
gactccgagg gctgctggat gacctacacc ctggtgcagc gcgacgggcg ggacagatac    2160
gacgtgcacg tggacgacat gctcgagtgt gtgaagggcc ccaacatcgc tgccatcgtg    2220
gggggcaccg tggggggcgt cgtgctcgtc ggcatcctcc tgctggtcat ctggaaggcc    2280
ctgacacacc tgagcgacct cagggagtac atcgctttg agaaggagaa gctcaagtcc    2340
cagtggaaca acgataaccc tctttttcaag agtgccacca cgacagtcat gaaccctaag    2400
tttgccgaga gttagggggtg cccggtgaag acaaggcctt ctgcaccacc cagatgggaa    2460
cacccccctct ccacgtcccc tccagcaggc tgaccgtgac cccgctgcct cgtggacgtg    2520
gctgacaact tcaccgttaa ccaaaaatgc actgcttttt ctgccccaga atgatgggcg    2580
tggccaggtt attctatggg ctcatggtaa gggccagcct accccttctg atatgaatga    2640
cttttgatag caagtcagag aaggaattgc ctacattttg tatggttaca cacaggtcct    2700
ttgtaaaaat tagtacagca gtctgatgaa gaattattta tgtgtgaact ctcagggta     2760
tgaagttaca tccccttggt tatgctgccc ccaatcaata aaaaaaaaaa aatcaat        2817
```

<210> SEQ ID NO 2
<211> LENGTH: 769
<212> TYPE: PRT
<213> ORGANISM: Bos taurus

<400> SEQUENCE: 2

```
Met Leu Arg Gln Arg Pro Gln Leu Leu Leu Ala Gly Leu Leu Ala
1               5                   10                  15

Leu Gln Ser Val Leu Ser Gln Glu Cys Thr Asn Tyr Lys Val Ser Thr
                20                  25                  30

Cys Arg Asp Cys Ile Glu Ser Gly Pro Gly Cys Ala Trp Cys Gln Lys
        35                  40                  45

Leu Asn Phe Thr Gly Gln Gly Glu Pro Asp Ser Ile Arg Cys Asp Thr
    50                  55                  60

Arg Ala Glu Leu Leu Ser Lys Gly Cys Pro Ala Asp Asp Ile Met Glu
65                  70                  75                  80

Pro Lys Ser Leu Ala Glu Thr Arg Asp Ser Gln Ala Gly Ser Arg Lys
                85                  90                  95

Gln Leu Ser Pro Gln Glu Val Thr Leu Tyr Leu Arg Pro Gly Gln Ala
                100                 105                 110

Val Ala Phe Asn Val Thr Phe Arg Arg Ala Lys Gly Tyr Pro Ile Asp
```

-continued

```
                115                 120                 125
Leu Tyr Tyr Leu Met Asp Leu Ser Tyr Ser Met Val Asp Asp Leu Val
130                 135                 140
Asn Val Lys Lys Leu Gly Gly Asp Leu Leu Arg Ala Leu Asn Gly Ile
145                 150                 155                 160
Thr Glu Ser Gly Arg Ile Gly Phe Gly Ser Phe Val Asp Lys Thr Val
                165                 170                 175
Leu Pro Phe Val Asn Thr His Pro Glu Lys Leu Arg Asn Pro Cys Pro
                180                 185                 190
Asn Lys Glu Lys Glu Cys Gln Pro Pro Phe Ala Phe Arg His Val Leu
                195                 200                 205
Lys Leu Thr Asp Asn Ser Lys Gln Phe Glu Thr Glu Val Gly Lys Gln
210                 215                 220
Leu Ile Ser Gly Asn Leu Asp Ala Pro Glu Gly Gly Leu Asp Ala Met
225                 230                 235                 240
Met Gln Val Ala Ala Cys Pro Glu Glu Ile Gly Trp Arg Asn Val Thr
                245                 250                 255
Arg Leu Leu Val Phe Ala Thr Asp Asp Gly Phe His Phe Ala Gly Asp
                260                 265                 270
Gly Lys Leu Gly Ala Ile Leu Thr Pro Asn Asp Gly Arg Cys His Leu
                275                 280                 285
Glu Asp Asn Leu Tyr Lys Ser Ser Asn Glu Phe Asp Tyr Pro Ser Val
                290                 295                 300
Gly Gln Leu Ala His Lys Leu Ala Glu Ser Asn Ile Gln Pro Ile Phe
305                 310                 315                 320
Ala Val Thr Lys Lys Met Val Lys Thr Tyr Glu Lys Leu Thr Glu Ile
                325                 330                 335
Ile Pro Lys Ser Ala Val Gly Glu Leu Ser Glu Asp Ser Arg Asn Val
                340                 345                 350
Val Glu Leu Ile Lys Asn Ala Tyr Asn Lys Leu Ser Ser Arg Val Phe
                355                 360                 365
Leu Asp His Ser Thr Leu Pro Asp Thr Leu Lys Val Thr Tyr Asp Ser
370                 375                 380
Phe Cys Ser Asn Gly Lys Ser Gln Val Asp Gln Pro Arg Gly Asp Cys
385                 390                 395                 400
Asp Gly Val Gln Ile Asn Val Pro Ile Thr Phe Gln Val Lys Val Thr
                405                 410                 415
Ala Thr Glu Cys Ile Gln Gln Ser Phe Thr Ile Arg Ala Leu Gly
                420                 425                 430
Phe Thr Asp Thr Val Thr Val Arg Val Leu Pro Gln Cys Glu Cys Gln
                435                 440                 445
Cys Arg Asp Ala Ser Arg Asp Gly Ser Ile Cys Gly Gly Arg Gly Ser
                450                 455                 460
Met Glu Cys Gly Val Cys Arg Cys Asp Ala Gly Tyr Ile Gly Lys Asn
465                 470                 475                 480
Cys Glu Cys Gln Thr Gln Gly Arg Ser Ser Gln Glu Leu Glu Gly Ser
                485                 490                 495
Cys Arg Lys Asp Asn Ser Ser Ile Ile Cys Ser Gly Leu Gly Asp Cys
                500                 505                 510
Ile Cys Gly Gln Cys Val Cys His Thr Ser Asp Val Pro Asn Lys Lys
                515                 520                 525
Ile Tyr Gly Gln Phe Cys Glu Cys Asp Asn Val Asn Cys Glu Arg Tyr
                530                 535                 540
```

Asp Gly Gln Val Cys Gly Gly Glu Lys Arg Gly Leu Cys Phe Cys Gly
545                 550                 555                 560

Thr Cys Arg Cys Asp Glu Gln Tyr Glu Gly Ser Ala Cys Gln Cys Leu
            565                 570                 575

Lys Ser Thr Gln Gly Cys Leu Asn Leu Asp Gly Val Glu Cys Ser Gly
        580                 585                 590

Arg Gly Arg Cys Arg Cys Asn Val Cys Gln Cys Asp Pro Gly Tyr Gln
    595                 600                 605

Pro Pro Leu Cys Ser Glu Cys Pro Gly Cys Pro Val Pro Cys Ala Gly
610                 615                 620

Phe Ala Pro Cys Thr Glu Cys Leu Lys Phe Asp Lys Gly Pro Phe Ala
625                 630                 635                 640

Lys Asn Cys Ser Ala Ala Cys Gly Gln Thr Lys Leu Leu Ser Ser Pro
            645                 650                 655

Val Pro Gly Arg Lys Cys Lys Glu Arg Asp Ser Glu Gly Cys Trp Met
        660                 665                 670

Thr Tyr Thr Leu Val Gln Arg Asp Gly Arg Asp Arg Tyr Asp Val His
    675                 680                 685

Val Asp Asp Met Leu Glu Cys Val Lys Gly Pro Asn Ile Ala Ala Ile
690                 695                 700

Val Gly Gly Thr Val Gly Gly Val Val Leu Val Gly Ile Leu Leu Leu
705                 710                 715                 720

Val Ile Trp Lys Ala Leu Thr His Leu Ser Asp Leu Arg Glu Tyr His
            725                 730                 735

Arg Phe Glu Lys Glu Lys Leu Lys Ser Gln Trp Asn Asn Asp Asn Pro
        740                 745                 750

Leu Phe Lys Ser Ala Thr Thr Thr Val Met Asn Pro Lys Phe Ala Glu
    755                 760                 765

Ser

<210> SEQ ID NO 3
<211> LENGTH: 2362
<212> TYPE: DNA
<213> ORGANISM: Bison bison

<400> SEQUENCE: 3
ggcatccagg ggacatgctg cgccagcgcc cccagctgct gctcctagcg ggcctgcttg     60
ccctccagtc cgtcctgtcc caggagtgca ccaagtacaa ggtcagcacc tgccgggact    120
gcatcgagtc gggccctggc tgcgcctggt gccagaaact gaacttcaca gggcaagggg    180
agcccgactc cattcgctgt gacacacgag cggagctgct gtcaaagggc tgcccagctg    240
atgacatcat ggaacccaag agcctcgctg agacctggac agccaggcg ggcagtcgga    300 agcagctgtc cccacaggaa gtgacgctct acctgagacc aggtcaggca gctgcgttca    360
gcgtgacctt ccagagggcc aagggctacc ccatcgacct gtactacctg atggaccctct   420 cctactccat ggtggatgac ctcgtcaatg tcaagaagct ggggggtgac ctgctccggg    480
ccctcaatgg catcaccgag tcgggccgca ttggtttcgg gtccttcgtg acaagacgg     540 tgctcccctt cgtcaacacg caccccgaga agctgcggaa ccctgcccc aacaaggaga     600 aggagtgcca gccccgttc gccttcaggc acgtgttgaa gctcactgac aactccaaac     660
agttcgagac agaagtcggg aagcagctga tctcggggaa cctggacgcc ctgaggtg      720 ggctggacgc catgatgcag gtggccgcgt gcccggagga atcggctgg cgcaatgtca     780

```
ccaggctgct ggtgttcgcc acggacgatg ggttccactt tgcgggcgat ggaaagctgg    840
gtgccatcct cacccccaat gacggccgct gccacctgga agacaacctg tacaaaagca    900
gcaacgaatt tgactaccca tcggtgggcc agctggcaca caaactggca gaaagcaaca    960
tccagcccat ctttgcagta accaagaaga tggtgaaaac gtacgagaag ctgacagaga   1020
tcatccccaa gtctgcagtc ggggagctgt ctgaagattc aagaacgtg gtggagctta    1080 tcaagaatgc ctacaataaa ctgtcctcca gagtcttcct ggatcacagc accctccctg   1140
acaccctgaa agtcacctac gactccttct gcagtaacgg gaaatcgcag gtggaccagc   1200
ccagagggga ctgcgacggc gtccagatca acgtcccgat caccttccag gtgaaggtca   1260
cagccaccga gtgcatccag cagcagtcct tcaccatccg ggcgctgggc ttcacggaca   1320
cggtgaccgt gcgggtcctc ccccagtgcg agtgccaatg ccgggacgcc agcagggacg   1380
gcagcatctg cggcggcaga ggctcgatgg agtgcggcgt ctgcaggtgt gacgccggct   1440
acatcgggaa gaactgcgag tgccagacgc agggccggag cagccaggag ctggagggca   1500
gctgccgcaa ggacaacagc tccatcatct gctcggggct gggggactgc atctgcgggc   1560
agtgcgtgtg ccacacgagc gacgtgccca acaagaagat ctacggccag ttctgcgagt   1620
gcgacaacgt caactgcgaa cgctacgacg gccaagtctg cggggggcgaa agagggggc   1680 tctgcttctg cggcacctgc aggtgcgacg agcagtatga gggttcggca tgccagtgcc   1740
tcaagtccac tcagggctgc ctcaacttgg acggcgtcga gtgcagcggc cgcggccgat   1800
gccgctgcaa tgtgtgccag tgcgaccccg gctaccagcc gcccctgtgc agcgagtgcc   1860
cgggctgccc cgtgccctgc gcgggcttcg ccccctgcac agagtgcctg aagttcgaca   1920 agggccccctt cgccaagaac tgcagcgcag cgtgcgggca gacgaagctg ctgtccagcc   1980
cggtgcccgg ccgcaagtgc aaggagcgcg actccgaggg ctgctggatg acctacaccc   2040
tggtgcagcg cgacgggcgg gacagatacg acgtgcacgt ggacgacatg ctcgagtgtg   2100
tgaagggccc caacatcgct gccatcgtgg ggggcaccgt ggggggcgtc gtgctcgtcg   2160
gcatcctcct gctggtcatc tggaaggccc tgacacacct gagcgacctc agggagtacc   2220
atcgcttcga aaggagaag ctcaagtccc agtggaacaa cgataaccct cttttcaaga   2280
gtgccaccac gacagtcatg aaccctaagt ttgccgagag ttagggggtgc ccggtgaaga   2340 caaggccttc tgcaccaccc ag                                            2362
```

<210> SEQ ID NO 4
<211> LENGTH: 769
<212> TYPE: PRT
<213> ORGANISM: Bison bison

<400> SEQUENCE: 4

Met Leu Arg Gln Arg Pro Gln Leu Leu Leu Ala Gly Leu Leu Ala
1               5                   10                  15

Leu Gln Ser Val Leu Ser Gln Glu Cys Thr Lys Tyr Lys Val Ser Thr
            20                  25                  30

Cys Arg Asp Cys Ile Glu Ser Gly Pro Gly Cys Ala Trp Cys Gln Lys
        35                  40                  45

Leu Asn Phe Thr Gly Gln Gly Glu Pro Asp Ser Ile Arg Cys Asp Thr
    50                  55                  60

Arg Ala Glu Leu Leu Ser Lys Gly Cys Pro Ala Asp Asp Ile Met Glu
65                  70                  75                  80

Pro Lys Ser Leu Ala Glu Thr Leu Asp Ser Gln Ala Gly Ser Arg Lys
                85                  90                  95

```
Gln Leu Ser Pro Gln Glu Val Thr Leu Tyr Leu Arg Pro Gly Gln Ala
            100                 105                 110

Ala Ala Phe Ser Val Thr Phe Gln Arg Ala Lys Gly Tyr Pro Ile Asp
        115                 120                 125

Leu Tyr Tyr Leu Met Asp Leu Ser Tyr Ser Met Val Asp Asp Leu Val
    130                 135                 140

Asn Val Lys Lys Leu Gly Gly Asp Leu Leu Arg Ala Leu Asn Gly Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Glu Lys Leu Arg Asn Pro Cys Pro
            180                 185                 190

Asn Lys Glu Lys Glu Cys Gln Pro Pro Phe Ala Phe Arg His Val Leu
        195                 200                 205

Lys Leu Thr Asp Asn Ser Lys Gln Phe Glu Thr Glu Val Gly Lys Gln
    210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
        275                 280                 285

Glu Asp Asn Leu Tyr Lys Ser Ser Asn Glu Phe Asp Tyr Pro Ser Val
    290                 295                 300

Gly Gln Leu Ala His Lys Leu Ala Glu Ser Asn Ile Gln Pro Ile Phe
305                 310                 315                 320

Ala Val Thr Lys Lys Met Val Lys Thr Tyr Glu Lys Leu Thr Glu Ile
                325                 330                 335

Ile Pro Lys Ser Ala Val Gly Glu Leu Ser Glu Asp Ser Lys Asn Val
            340                 345                 350

Val Glu Leu Ile Lys Asn Ala Tyr Asn Lys Leu Ser Ser Arg Val Phe
        355                 360                 365

Leu Asp His Ser Thr Leu Pro Asp Thr Leu Lys Val Thr Tyr Asp Ser
    370                 375                 380

Phe Cys Ser Asn Gly Lys Ser Gln Val Asp Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Gln Ser Phe Thr Ile Arg Ala Leu Gly
            420                 425                 430

Phe Thr Asp Thr Val Thr Val Arg Val Leu Pro Gln Cys Glu Cys Gln
        435                 440                 445

Cys Arg Asp Ala Ser Arg Asp Gly Ser Ile Cys Gly Arg Gly Ser
    450                 455                 460

Met Glu Cys Gly Val Cys Arg Cys Asp Ala Gly Tyr Ile Gly Lys Asn
465                 470                 475                 480

Cys Glu Cys Gln Thr Gln Gly Arg Ser Ser Gln Glu Leu Glu Gly Ser
                485                 490                 495

Cys Arg Lys Asp Asn Ser Ser Ile Ile Cys Ser Gly Leu Gly Asp Cys
            500                 505                 510
```

Ile Cys Gly Gln Cys Val Cys His Thr Ser Asp Val Pro Asn Lys Lys
515                 520                 525

Ile Tyr Gly Gln Phe Cys Glu Cys Asp Asn Val Asn Cys Glu Arg Tyr
530                 535                 540

Asp Gly Gln Val Cys Gly Gly Glu Lys Arg Gly Leu Cys Phe Cys Gly
545                 550                 555                 560

Thr Cys Arg Cys Asp Glu Gln Tyr Glu Gly Ser Ala Cys Gln Cys Leu
                565                 570                 575

Lys Ser Thr Gln Gly Cys Leu Asn Leu Asp Gly Val Glu Cys Ser Gly
                580                 585                 590

Arg Gly Arg Cys Arg Cys Asn Val Cys Gln Cys Asp Pro Gly Tyr Gln
                595                 600                 605

Pro Pro Leu Cys Ser Glu Cys Pro Gly Cys Pro Val Pro Cys Ala Gly
                610                 615                 620

Phe Ala Pro Cys Thr Glu Cys Leu Lys Phe Asp Lys Gly Pro Phe Ala
625                 630                 635                 640

Lys Asn Cys Ser Ala Ala Cys Gly Gln Thr Lys Leu Leu Ser Ser Pro
                645                 650                 655

Val Pro Gly Arg Lys Cys Lys Glu Arg Asp Ser Glu Gly Cys Trp Met
                660                 665                 670

Thr Tyr Thr Leu Val Gln Arg Asp Gly Arg Asp Arg Tyr Asp Val His
                675                 680                 685

Val Asp Asp Met Leu Glu Cys Val Lys Gly Pro Asn Ile Ala Ala Ile
                690                 695                 700

Val Gly Gly Thr Val Gly Gly Val Val Leu Val Gly Ile Leu Leu Leu
705                 710                 715                 720

Val Ile Trp Lys Ala Leu Thr His Leu Ser Asp Leu Arg Glu Tyr His
                725                 730                 735

Arg Phe Glu Lys Glu Lys Leu Lys Ser Gln Trp Asn Asn Asp Asn Pro
                740                 745                 750

Leu Phe Lys Ser Ala Thr Thr Thr Val Met Asn Pro Lys Phe Ala Glu
                755                 760                 765

Ser

<210> SEQ ID NO 5
<211> LENGTH: 2315
<212> TYPE: DNA
<213> ORGANISM: Bubalus bubalis

<400> SEQUENCE: 5
atgctgcgcc agcgccccca gctgctgttc ctatcgggcc tgctcgccct ccagtccgtc      60
ctgtcccagg agtgcaccaa gtacaaggtc agcacctgcc gggactgcat cgagtctggc     120
cccggctgcg cctggtgcca gaaactgaac ttcacagggc aaggggagcc tgactccctt     180
cgctgtgaca cacgggcgga gctgctgtca aagggctgcc agctgatga catcatggaa      240 cccaagagcc ttgctgagac ccgggacagc caggcggaca gacagaagca gctgtcccca     300
caggaagtga cgctctacct gagaccaggt caggcagctg cgttcaacgt gaccttccgg     360
agggccaagg ctaccccat cgacctgtac tacctgatgg acctctccta ctccatggtg      420
gacgacctca tcaacgtcaa gaagctgggg ggtgacctgc tccgggccct caacgacatc     480
accgagtcgg gccgcattgg tttcgggtcc ttcgtggaca agacggtgct cccattcgtc     540
aacacgcacc ccgagaagct gcggaacccc tgccccaaca aggagaagga gtgccagccc     600
ccgttcgcct tcaggcacgt gttgaagctc accgacaact ccaaacagtt cgagacagaa     660

-continued

```
gtcgggaagc agctgatctc ggggaacctg gacgccctg agggtgggct ggacgccatg      720
atgcaggtgg ctgcgtgccc ggaggaaatc ggctggcgca atgtcaccag gctgctggtg      780
tttgccacag acgatgggtt ccactttgcg ggcgatggaa agctgggtgc catcctcacc      840
cccaatgacg gccgctgcca cctggaagac aacctgtaca aaagcggcaa cgaatttgac      900
tacccatcgg tgggccagct ggcacacaaa ctggcagaaa gcaacatcca gcccatcttt      960
gcggtaacca agaagatggt gaaaacgtac gagaagctga cagagatcat ccccaagtct     1020
gcagtcgggg agctgtctga agattccaag aacgtggtgg agcttatcaa gaatgcctac     1080
aataaactgt cctccagagt cttcctggat cacagcaccc tccctgacac cctgaaagtc     1140
acctacgact ccttctgcag taacagggta tcgcaggtgg accagcccag aggggactgc     1200
gacggcgttc agatcaacgt cccgatcacc ttccaggtga aggtcacagc caccgagtgc     1260
atccagcagc agtccttcac catccgggcg ctgggcttca cggacacggt gaccgtgcgg     1320
gtcctccccc agtgcgagtg ccaatgccgg gacgccagca gggacggcag catctgcggc     1380
ggcagaggct cgatggagtg cggcgtctgc aagtgtgacg ccggctacat cgggaagaac     1440
tgcgagtgcc agacgcaggg ccggagcagc caggagctgg agggcagctg ccgcaaggac     1500
aatagctcca tcatctgctc ggggctgggg gactgtatct gcgggcagtg cgtgtgccac     1560
acgagcgacg tgcccaacaa gaagatctac ggccagttct gcgagtgcga caacgtcaac     1620
tgcgaacgct acgacggcca agtctgcggg ggcgaaaaga gggggctctg cttctgcggc     1680
acctgcaggt gcgacgagca gtatgagggt tcggcatgcc agtgcctcaa gtccactcag     1740
ggctgcctca acttggacgg cgtcgagtgc agcggccgcg gccgatgccg ctgcaatgtg     1800
tgccagtgcg accccggcta ccagccgccc ctgtgcagcg agtgcccggg ctgccccgtg     1860
ccctgtgcgg gcttcgcccc ctgcacagag tgcctgaagt tcgacaaggg ccccttcgcc     1920
aagaactgca gcgcagcgtg cgggcagacg aagctgctgt ccagcccggt gccggccgc      1980 aagtgcaagg agcgcgactc cgagggctgc tggatgacct acaccctggt gcagcgcgac     2040
gggcgggaca gatacgacgt gcacgtggac gacatgctcg agtgtgtgaa gggccccaac     2100
atcgctgcca tcgtgggggg caccgtgggg gcgtcgtgc tcgtcggcat cctcctgctg     2160
gtcatctgga aggccctgac acacctgagc gacctcaggg agtaccatcg ctttgagaag     2220
gagaagctca gtcccagtg gaacaacgat aaccctcttt tcaagagtgc caccacgaca     2280
gtcatgaacc ctaagtttgc cgagagttag gggtg                                2315
```

<210> SEQ ID NO 6
<211> LENGTH: 769
<212> TYPE: PRT
<213> ORGANISM: Bubalus bubalis

<400> SEQUENCE: 6

```
Met Leu Arg Gln Arg Pro Gln Leu Leu Phe Leu Ser Gly Leu Leu Ala
1               5                   10                  15

Leu Gln Ser Val Leu Ser Gln Glu Cys Thr Lys Tyr Lys Val Ser Thr
                20                  25                  30

Cys Arg Asp Cys Ile Glu Ser Gly Pro Gly Cys Ala Trp Cys Gln Lys
            35                  40                  45

Leu Asn Phe Thr Gly Gln Gly Glu Pro Asp Ser Leu Arg Cys Asp Thr
        50                  55                  60

Arg Ala Glu Leu Leu Ser Lys Gly Cys Pro Ala Asp Asp Ile Met Glu
65                  70                  75                  80
```

```
Pro Lys Ser Leu Ala Glu Thr Arg Asp Ser Gln Ala Asp Arg Gln Lys
                85                  90                  95
Gln Leu Ser Pro Gln Glu Val Thr Leu Tyr Leu Arg Pro Gly Gln Ala
            100                 105                 110
Ala Ala Phe Asn Val Thr Phe Arg Arg Ala Lys Gly Tyr Pro Ile Asp
        115                 120                 125
Leu Tyr Tyr Leu Met Asp Leu Ser Tyr Ser Met Val Asp Asp Leu Ile
    130                 135                 140
Asn Val Lys Lys Leu Gly Gly Asp Leu Leu Arg Ala Leu Asn Asp Ile
145                 150                 155                 160
Thr Glu Ser Gly Arg Ile Gly Phe Gly Ser Phe Val Asp Lys Thr Val
                165                 170                 175
Leu Pro Phe Val Asn Thr His Pro Glu Lys Leu Arg Asn Pro Cys Pro
            180                 185                 190
Asn Lys Glu Lys Glu Cys Gln Pro Pro Phe Ala Phe Arg His Val Leu
        195                 200                 205
Lys Leu Thr Asp Asn Ser Lys Gln Phe Glu Thr Glu Val Gly Lys Gln
    210                 215                 220
Leu Ile Ser Gly Asn Leu Asp Ala Pro Glu Gly Gly Leu Asp Ala Met
225                 230                 235                 240
Met Gln Val Ala Ala Cys Pro Glu Glu Ile Gly Trp Arg Asn Val Thr
                245                 250                 255
Arg Leu Leu Val Phe Ala Thr Asp Asp Gly Phe His Phe Ala Gly Asp
            260                 265                 270
Gly Lys Leu Gly Ala Ile Leu Thr Pro Asn Asp Gly Arg Cys His Leu
        275                 280                 285
Glu Asp Asn Leu Tyr Lys Ser Gly Asn Glu Phe Asp Tyr Pro Ser Val
    290                 295                 300
Gly Gln Leu Ala His Lys Leu Ala Glu Ser Asn Ile Gln Pro Ile Phe
305                 310                 315                 320
Ala Val Thr Lys Lys Met Val Lys Thr Tyr Glu Lys Leu Thr Glu Ile
                325                 330                 335
Ile Pro Lys Ser Ala Val Gly Glu Leu Ser Glu Asp Ser Lys Asn Val
            340                 345                 350
Val Glu Leu Ile Lys Asn Ala Tyr Asn Lys Leu Ser Ser Arg Val Phe
        355                 360                 365
Leu Asp His Ser Thr Leu Pro Asp Thr Leu Lys Val Thr Tyr Asp Ser
    370                 375                 380
Phe Cys Ser Asn Arg Val Ser Gln Val Asp Gln Pro Arg Gly Asp Cys
385                 390                 395                 400
Asp Gly Val Gln Ile Asn Val Pro Ile Thr Phe Gln Val Lys Val Thr
                405                 410                 415
Ala Thr Glu Cys Ile Gln Gln Ser Phe Thr Ile Arg Ala Leu Gly
            420                 425                 430
Phe Thr Asp Thr Val Thr Val Arg Val Leu Pro Gln Cys Glu Cys Gln
        435                 440                 445
Cys Arg Asp Ala Ser Arg Asp Gly Ser Ile Cys Gly Arg Gly Ser
    450                 455                 460
Met Glu Cys Gly Val Cys Lys Cys Asp Ala Gly Tyr Ile Gly Lys Asn
465                 470                 475                 480
Cys Glu Cys Gln Thr Gln Gly Arg Ser Ser Gln Glu Leu Glu Gly Ser
                485                 490                 495
```

```
Cys Arg Lys Asp Asn Ser Ser Ile Ile Cys Ser Gly Leu Gly Asp Cys
            500                 505                 510

Ile Cys Gly Gln Cys Val Cys His Thr Ser Asp Val Pro Asn Lys Lys
        515                 520                 525

Ile Tyr Gly Gln Phe Cys Glu Cys Asp Asn Val Asn Cys Glu Arg Tyr
    530                 535                 540

Asp Gly Gln Val Cys Gly Gly Glu Lys Arg Gly Leu Cys Phe Cys Gly
545                 550                 555                 560

Thr Cys Arg Cys Asp Glu Gln Tyr Glu Gly Ser Ala Cys Gln Cys Leu
            565                 570                 575

Lys Ser Thr Gln Gly Cys Leu Asn Leu Asp Gly Val Glu Cys Ser Gly
        580                 585                 590

Arg Gly Arg Cys Arg Cys Asn Val Cys Gln Cys Asp Pro Gly Tyr Gln
    595                 600                 605

Pro Pro Leu Cys Ser Glu Cys Pro Gly Cys Pro Val Pro Cys Ala Gly
610                 615                 620

Phe Ala Pro Cys Thr Glu Cys Leu Lys Phe Asp Lys Gly Pro Phe Ala
625                 630                 635                 640

Lys Asn Cys Ser Ala Ala Cys Gly Gln Thr Lys Leu Leu Ser Ser Pro
            645                 650                 655

Val Pro Gly Arg Lys Cys Lys Glu Arg Asp Ser Glu Gly Cys Trp Met
        660                 665                 670

Thr Tyr Thr Leu Val Gln Arg Asp Gly Arg Asp Arg Tyr Asp Val His
    675                 680                 685

Val Asp Asp Met Leu Glu Cys Val Lys Gly Pro Asn Ile Ala Ala Ile
690                 695                 700

Val Gly Thr Val Gly Gly Val Val Leu Val Gly Ile Leu Leu Leu
705                 710                 715                 720

Val Ile Trp Lys Ala Leu Thr His Leu Ser Asp Leu Arg Glu Tyr His
            725                 730                 735

Arg Phe Glu Lys Glu Lys Leu Lys Ser Gln Trp Asn Asn Asp Asn Pro
        740                 745                 750

Leu Phe Lys Ser Ala Thr Thr Thr Val Met Asn Pro Lys Phe Ala Glu
    755                 760                 765

Ser

<210> SEQ ID NO 7
<211> LENGTH: 2507
<212> TYPE: DNA
<213> ORGANISM: Capra hircus

<400> SEQUENCE: 7
cagcctggtg aagagcagag ccgaagcccc tgccagtcca gctgggacac ccctgccgtg      60
gtctccaggg catccagggg acatgctgcc ccagcgcccc cagctgctgc tcctagcagg     120
cctgctcgcc ctccagtctg tcctgtccca ggagtgcacc aagtacaaag tcagcacctg     180
ccgggactgc atcgagtcgg gccccggctg tgcctggtgc agaaactga acttcacagg     240 gcaaggggag cccgactcca ctcgctgtga tacacgggcg cagctgctgt caaagggctg     300
cccagctgat gacatcatgg aacccaagag cctcgctgag accggcagag ccaggcgggg     360
caaacagaag cagctgtccc agaggaagt gactctctac cttagaccag gtcaggcagc     420
tgcgttcaat gtgaccttcc agagggccaa gggctacccc atcgacctgt actatctgat     480
ggatctctcc tactccatgg tggacgacct cgccaacgtc aagaagctgg gggtgacct     540
```

| | | |
|---|---|---|
| gctccgggcc ctcaatgaca tcaccgagtc gggccgcatc gggttcgggt ccttcgtgga | 600 | |
| caagacagtg ctccccttcg tcaacacgca ccctgagaag ctgaggaacc cctgccccaa | 660 | |
| caaggagaag cagtgccagc cccgttcgc cttcaggcac gtgttgaagc tcaccgacaa | 720 | |
| ctccaaacag ttcgagacag aagtcgggaa gcagctgatc tcgggaact tggacgcccc | 780 | |
| tgagggtgga ctggacgcca tgatgcaagt ggccgcgtgc ccggaggaaa tcggctggcg | 840 | |
| caatgtcacc aggctgctgg tgttcgccac agatgatggg ttccactttg cgggcgatgg | 900 | |
| aaagctgggt gccatcctca ccccaacga cggccgctgc acctggaag acaacctgta | 960 | |
| caaaagcagc aacgaatttg actacccatc ggtgggccag ctggcacaca aactggcaga | 1020 | |
| aagcaacatc cagcccatct cgcggtaac caagaagatg gtgaaaacgt acgagaagct | 1080 | |
| gacagaaatc atccccaagt ctgcagtcgg ggagctgtct gaagattcca agaacgtggt | 1140 | |
| ggagcttatc aagagtgcct acaataaact gtcctccaga gtattcctgg atcacaacac | 1200 | |
| cctccctgac accctgaaag tcgcctacga ctccttctgc agtaacgggg tgtcacaggt | 1260 | |
| ggaccagccc agaggggact gtgacggcgt ccagatcaac gtcccgatca ccttccaggt | 1320 | |
| gaaggtcaca gccaccgagt gcatccagga gcagtccttc accatccggg cgctgggctt | 1380 | |
| cacggacacg gtgaccgtgc gggtccttcc ccagtgcgag tgccaatgcc gggacgccag | 1440 | |
| cagggaccgc agcgtctgcg gtggcagagg ctcgatggag tgcggcgtct gcaggtgcga | 1500 | |
| cgccggctac atcgggaaga actgcgagtg ccagacgcac ggccggagca gccaggagct | 1560 | |
| ggagggcagc tgccgcaagg acaacagctc catcatctgc tcggggctag gggactgcat | 1620 | |
| ctgcgggcag tgcgtgtgcc acacgagcga cgtgcccaac aagaagatct acggccagtt | 1680 | |
| ctgcgagtgc gacaacgtca actgcgagcg ctacgacggc caagtctgcg ggggcgagaa | 1740 | |
| gaggggctc tgcttctgcg gcacctgcag gtgcaacgag cagcatgagg gctcggcgtg | 1800 | |
| ccagtgcctc aagtccactc agggctgcct caacctggac ggcgtcgagt gcagcggccg | 1860 | |
| gggccgatgc cgctgcaacg tgtgccagtg cgaccccggc taccagccgc ccctgtgcat | 1920 | |
| cgactgcccg ggctgccccg tgcctgcgc tggcttcgcc ccctgcaccg agtgcctgaa | 1980 | |
| gttcgacaag ggcccccttcg ccaagaactg cagcgcagcg tgcgggcaga cgaagctgct | 2040 | |
| gtccagcccg gtgcccggcg ccgcaagtg caaggagcgc gactccgagg ctgctggat | 2100 | |
| gacctacacc ctggtgcagc gcgacggggcg gaacagatac gacgtgcacg tggacgacat | 2160 | |
| gctcgagtgt gtgaagggcc ccaacatcgc tgccatcgtg gggggcaccg tggggggagt | 2220 | |
| tgtgctcgtc ggcatcctcc tgctggtcat ctggaaggcc ctgacacacc tgagcgacct | 2280 | |
| cagggagtac atcgcttcg agaaggagaa gctcaagtcc cagtggaaca acgataaccc | 2340 | |
| tctttcaag agtgccacca cgacagtcat gaacccctaag tttgccgaga gttaggggtg | 2400 | |
| cctggtgaag acaaggcctt ctgccaccac cagacgggag cacgccctct cctcatcccc | 2460 | |
| tccagcaggc tgaccgtgac cttgctgctt agtggacgca gctgatg | 2507 | |

<210> SEQ ID NO 8
<211> LENGTH: 770
<212> TYPE: PRT
<213> ORGANISM: Capra hircus

<400> SEQUENCE: 8

Met Leu Pro Gln Arg Pro Gln Leu Leu Leu Leu Ala Gly Leu Leu Ala
1               5                   10                  15

Leu Gln Ser Val Leu Ser Gln Glu Cys Thr Lys Tyr Lys Val Ser Thr
            20                  25                  30

```
Cys Arg Asp Cys Ile Glu Ser Gly Pro Gly Cys Ala Trp Cys Gln Lys
         35                  40                  45

Leu Asn Phe Thr Gly Gln Gly Glu Pro Asp Ser Thr Arg Cys Asp Thr
 50                  55                  60

Arg Ala Gln Leu Leu Ser Lys Gly Cys Pro Ala Asp Asp Ile Met Glu
 65                  70                  75                  80

Pro Lys Ser Leu Ala Glu Thr Arg Gln Ser Gln Ala Gly Lys Gln Lys
                 85                  90                  95

Gln Leu Ser Pro Glu Glu Val Thr Leu Tyr Leu Arg Pro Gly Gln Ala
                100                 105                 110

Ala Ala Phe Asn Val Thr Phe Gln Arg Ala Lys Gly Tyr Pro Ile Asp
             115                 120                 125

Leu Tyr Tyr Leu Met Asp Leu Ser Tyr Ser Met Val Asp Asp Leu Ala
         130                 135                 140

Asn Val Lys Lys Leu Gly Gly Asp Leu Leu Arg Ala Leu Asn Asp Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Glu Lys Leu Arg Asn Pro Cys Pro
             180                 185                 190

Asn Lys Glu Lys Gln Cys Gln Pro Pro Phe Ala Phe Arg His Val Leu
         195                 200                 205

Lys Leu Thr Asp Asn Ser Lys Gln Phe Glu Thr Glu Val Gly Lys Gln
210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
             260                 265                 270

Gly Lys Leu Gly Ala Ile Leu Thr Pro Asn Asp Gly Arg Cys His Leu
         275                 280                 285

Glu Asp Asn Leu Tyr Lys Ser Ser Asn Glu Phe Asp Tyr Pro Ser Val
290                 295                 300

Gly Gln Leu Ala His Lys Leu Ala Glu Ser Asn Ile Gln Pro Ile Phe
305                 310                 315                 320

Ala Val Thr Lys Lys Met Val Lys Thr Tyr Glu Lys Leu Thr Glu Ile
                325                 330                 335

Ile Pro Lys Ser Ala Val Gly Glu Leu Ser Glu Asp Ser Lys Asn Val
             340                 345                 350

Val Glu Leu Ile Lys Ser Ala Tyr Asn Lys Leu Ser Ser Arg Val Phe
         355                 360                 365

Leu Asp His Asn Thr Leu Pro Asp Thr Leu Lys Val Ala Tyr Asp Ser
370                 375                 380

Phe Cys Ser Asn Gly Val Ser Gln Val Asp Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Glu Gln Ser Phe Thr Ile Arg Ala Leu Gly
             420                 425                 430

Phe Thr Asp Thr Val Thr Val Arg Val Leu Pro Gln Cys Glu Cys Gln
         435                 440                 445
```

```
Cys Arg Asp Ala Ser Arg Asp Arg Ser Val Cys Gly Arg Gly Ser
    450                 455                 460

Met Glu Cys Gly Val Cys Arg Cys Asp Ala Gly Tyr Ile Gly Lys Asn
465                 470                 475                 480

Cys Glu Cys Gln Thr His Gly Arg Ser Ser Gln Glu Leu Glu Gly Ser
                485                 490                 495

Cys Arg Lys Asp Asn Ser Ser Ile Ile Cys Ser Gly Leu Gly Asp Cys
                500                 505                 510

Ile Cys Gly Gln Cys Val Cys His Thr Ser Asp Val Pro Asn Lys Lys
                515                 520                 525

Ile Tyr Gly Gln Phe Cys Glu Cys Asp Asn Val Asn Cys Glu Arg Tyr
    530                 535                 540

Asp Gly Gln Val Cys Gly Gly Glu Lys Arg Gly Leu Cys Phe Cys Gly
545                 550                 555                 560

Thr Cys Arg Cys Asn Glu Gln His Glu Gly Ser Ala Cys Gln Cys Leu
                565                 570                 575

Lys Ser Thr Gln Gly Cys Leu Asn Leu Asp Gly Val Glu Cys Ser Gly
                580                 585                 590

Arg Gly Arg Cys Arg Cys Asn Val Cys Gln Cys Asp Pro Gly Tyr Gln
                595                 600                 605

Pro Pro Leu Cys Ile Asp Cys Pro Gly Cys Pro Val Pro Cys Ala Gly
    610                 615                 620

Phe Ala Pro Cys Thr Glu Cys Leu Lys Phe Asp Lys Gly Pro Phe Ala
625                 630                 635                 640

Lys Asn Cys Ser Ala Ala Cys Gly Gln Thr Lys Leu Leu Ser Ser Pro
                645                 650                 655

Val Pro Gly Gly Arg Cys Lys Glu Arg Asp Ser Glu Gly Cys Trp
                660                 665                 670

Met Thr Tyr Thr Leu Val Gln Arg Asp Gly Arg Asn Arg Tyr Asp Val
                675                 680                 685

His Val Asp Asp Met Leu Glu Cys Val Lys Gly Pro Asn Ile Ala Ala
    690                 695                 700

Ile Val Gly Gly Thr Val Gly Gly Val Val Leu Val Gly Ile Leu Leu
705                 710                 715                 720

Leu Val Ile Trp Lys Ala Leu Thr His Leu Ser Asp Leu Arg Glu Tyr
                725                 730                 735

His Arg Phe Glu Lys Glu Lys Leu Lys Ser Gln Trp Asn Asn Asp Asn
                740                 745                 750

Pro Leu Phe Lys Ser Ala Thr Thr Thr Val Met Asn Pro Lys Phe Ala
                755                 760                 765

Glu Ser
    770

<210> SEQ ID NO 9
<211> LENGTH: 2313
<212> TYPE: DNA
<213> ORGANISM: Ovis aries

<400> SEQUENCE: 9
atgctgcccc agcgccccca gctgctgctc ctagcgggcc tgctctccct ccagtccgtc     60
ctgtcccagg agtgcaccaa gtacaaagtc agcacctgcc gggactgcat cgagtcgggc    120
cccggctgtg cctggtgtca gaaactgaac ttcacagggc aagggagcc cgactccact    180 cgctgtgata cacgggcgca gctgctgtcg aagggctgcc cagctgatga catcatggaa    240
```

```
cccaagagcc tcgctgagac tcggcagagc caggcgggca acagaagca gctgtcccca    300
gaggaagtga ccctctacct gagaccaggt caggcagcag cgttcaacgt gaccttccag    360
agggccaagg gctaccccat cgacctgtac tatctgatgg atctctccta ctccatggtg    420
gacgacctcg ccaacgtcaa gaagctgggg ggtgacctgc tccgggccct caatgacatc    480
accgagtcag gccgcattgg tttcgggtcc ttcgtggaca gacggtgct cccttcgtc    540
aacacgcacc ccgagaagct gaggaacccc tgccccaaca aggagaagga gtgccagccg    600
ccgttcgcct tcaggcacgt gctgaagctc accgacaact ccaaacagtt cgagacagaa    660
gtcgggaagc agctgatctc ggggaacttg gacgcccctg agggtgggct ggacgccatg    720
atgcaagtgg ccgcgtgccc ggaggaaatt ggctggcgca atgtcaccag gctgctggtg    780
ttcgccacag acgatgggtt ccactttgcg ggcgatggaa agctgggtgc catcctcacc    840
cccaacgacg gccgctgcca cctggaagac aacctgtaca aaagcagcaa cgaatttgac    900
tacccatcgg tgggccagct ggcacacaaa ctggcagaaa gcaacatcca gcccatcttc    960
gcggtaacca agaagatggt gaaaacgtac gagaagctga cagaaatcat ccccaagtct   1020
gcagtcgggg agctgtctga agattccaag aacgtggtgg agcttatcaa gagtgcctac   1080
aataaactgt cctccagagt attcctggat acaacacccc tccctgacac cctgaaagtc   1140
gcctacgact ccttctgcag taacggggtg tcgcaggtgg accagcccag aggggactgc   1200
gacggcgtcc agatcaacgt cccgatcacc ttccaggtga aggtcacagc caccgagtgc   1260
atccaggagc agtccttcac catccggggcg ctgggcttca cggacacggt gaccgtgcgg   1320
gtccttcccc agtgcgagtg ccaatgccgg gaagccagca gggaccgcag cgtctgcggt   1380
ggcagaggct cgatggagtg cggcgtctgc aggtgcgacg ccggctacat cgggaagaac   1440
tgcgagtgcc agacgcacgg ccggagcagc caggagctgg agggcagctg ccgcaaggac   1500
aacagctcca tcatctgctc ggggctgggg gactgcatct gcgggcagtg cgtgtgccac   1560
acgagcgacg tgcccaacaa gaagatctac ggccagttct gcgagtgcga caacgtcaac   1620
tgcgagcgct acgacggcca agtctgcggg ggcgacaaga gggggctctg cttctgcggc   1680
acctgcaggt gcaacgacca gcatgagggc tcggcgtgcc agtgcctcaa gtccactcag   1740
ggctgcctca acctggacgg cgtcgagtgc agcggccgcg ccgatgccg ctgcaacgtg    1800
tgccagtgcg acccccggcta ccagccgccc ctgtgcatcg actgcccggg ctgccccgtg    1860
ccctgcgctg gcttcgcccc ctgcaccgag tgcctgaagt cgacaagggg tcccttcgcc    1920
aagaactgca gcgcagcgtg cgggcagacg aagctgctgt ccagcccggt gcccggcggc    1980
cgcaagtgca aggagcgtga ctccgagggc tgctggatga cctacaccct ggtgcagcgc    2040
gacgggcgga acagatacga cgtgcacgtg acgacatgc tcgagtgtgt gaagggcccc    2100
aacatcgctg ccatcgtggg gggcaccgtg ggggagttg tgctcgtcgg catcctcctg    2160
ctggccatct ggaaggccct gacacacctg agcgacctca gggagtacca tcgcttcgag    2220
aaggagaagc tcaagtccca gtggaacaac gataaccctc ttttcaagag tgccaccacg    2280
acagtcatga accctaagtt tgccgagagt tag                                2313
```

<210> SEQ ID NO 10
<211> LENGTH: 770
<212> TYPE: PRT
<213> ORGANISM: Ovis aries

<400> SEQUENCE: 10

Met Leu Pro Gln Arg Pro Gln Leu Leu Leu Leu Ala Gly Leu Leu Ser

-continued

```
1               5                   10                  15
Leu Gln Ser Val Leu Ser Gln Glu Cys Thr Lys Tyr Lys Val Ser Thr
            20                  25                  30
Cys Arg Asp Cys Ile Glu Ser Gly Pro Gly Cys Ala Trp Cys Gln Lys
            35                  40                  45
Leu Asn Phe Thr Gly Gln Gly Glu Pro Asp Ser Thr Arg Cys Asp Thr
50                  55                  60
Arg Ala Gln Leu Leu Ser Lys Gly Cys Pro Ala Asp Asp Ile Met Glu
65                  70                  75                  80
Pro Lys Ser Leu Ala Glu Thr Arg Gln Ser Gln Ala Gly Lys Gln Lys
                    85                  90                  95
Gln Leu Ser Pro Glu Glu Val Thr Leu Tyr Leu Arg Pro Gly Gln Ala
                100                 105                 110
Ala Ala Phe Asn Val Thr Phe Gln Arg Ala Lys Gly Tyr Pro Ile Asp
                115                 120                 125
Leu Tyr Tyr Leu Met Asp Leu Ser Tyr Ser Met Val Asp Asp Leu Ala
            130                 135                 140
Asn Val Lys Lys Leu Gly Gly Asp Leu Leu Arg Ala Leu Asn Asp Ile
145                 150                 155                 160
Thr Glu Ser Gly Arg Ile Gly Phe Gly Ser Phe Val Asp Lys Thr Val
                165                 170                 175
Leu Pro Phe Val Asn Thr His Pro Glu Lys Leu Arg Asn Pro Cys Pro
            180                 185                 190
Asn Lys Glu Lys Glu Cys Gln Pro Pro Phe Ala Phe Arg His Val Leu
                195                 200                 205
Lys Leu Thr Asp Asn Ser Lys Gln Phe Glu Thr Glu Val Gly Lys Gln
        210                 215                 220
Leu Ile Ser Gly Asn Leu Asp Ala Pro Glu Gly Gly Leu Asp Ala Met
225                 230                 235                 240
Met Gln Val Ala Ala Cys Pro Glu Glu Ile Gly Trp Arg Asn Val Thr
                245                 250                 255
Arg Leu Leu Val Phe Ala Thr Asp Asp Gly Phe His Phe Ala Gly Asp
            260                 265                 270
Gly Lys Leu Gly Ala Ile Leu Thr Pro Asn Asp Gly Arg Cys His Leu
        275                 280                 285
Glu Asp Asn Leu Tyr Lys Ser Ser Asn Glu Phe Asp Tyr Pro Ser Val
    290                 295                 300
Gly Gln Leu Ala His Lys Leu Ala Glu Ser Asn Ile Gln Pro Ile Phe
305                 310                 315                 320
Ala Val Thr Lys Lys Met Val Lys Thr Tyr Glu Lys Leu Thr Glu Ile
                325                 330                 335
Ile Pro Lys Ser Ala Val Gly Glu Leu Ser Glu Asp Ser Lys Asn Val
            340                 345                 350
Val Glu Leu Ile Lys Ser Ala Tyr Asn Lys Leu Ser Ser Arg Val Phe
        355                 360                 365
Leu Asp His Asn Thr Leu Pro Asp Thr Leu Lys Val Ala Tyr Asp Ser
    370                 375                 380
Phe Cys Ser Asn Gly Val Ser Gln Val Asp Gln Pro Arg Gly Asp Cys
385                 390                 395                 400
Asp Gly Val Gln Ile Asn Val Pro Ile Thr Phe Gln Val Lys Val Thr
                405                 410                 415
Ala Thr Glu Cys Ile Gln Glu Gln Ser Phe Thr Ile Arg Ala Leu Gly
            420                 425                 430
```

```
Phe Thr Asp Thr Val Thr Val Arg Val Leu Pro Gln Cys Glu Cys Gln
        435                 440                 445

Cys Arg Glu Ala Ser Arg Asp Arg Ser Val Cys Gly Arg Gly Ser
450                 455                 460

Met Glu Cys Gly Val Cys Arg Cys Asp Ala Gly Tyr Ile Gly Lys Asn
465                 470                 475                 480

Cys Glu Cys Gln Thr His Gly Arg Ser Gln Glu Leu Glu Gly Ser
                485                 490                 495

Cys Arg Lys Asp Asn Ser Ser Ile Ile Cys Ser Gly Leu Gly Asp Cys
                500                 505                 510

Ile Cys Gly Gln Cys Val Cys His Thr Ser Asp Val Pro Asn Lys Lys
                515                 520                 525

Ile Tyr Gly Gln Phe Cys Glu Cys Asp Asn Val Asn Cys Glu Arg Tyr
                530                 535                 540

Asp Gly Gln Val Cys Gly Gly Asp Lys Arg Gly Leu Cys Phe Cys Gly
545                 550                 555                 560

Thr Cys Arg Cys Asn Asp Gln His Glu Gly Ser Ala Cys Gln Cys Leu
                565                 570                 575

Lys Ser Thr Gln Gly Cys Leu Asn Leu Asp Gly Val Glu Cys Ser Gly
                580                 585                 590

Arg Gly Arg Cys Arg Cys Asn Val Cys Gln Cys Asp Pro Gly Tyr Gln
                595                 600                 605

Pro Pro Leu Cys Ile Asp Cys Pro Gly Cys Pro Val Pro Cys Ala Gly
                610                 615                 620

Phe Ala Pro Cys Thr Glu Cys Leu Lys Phe Asp Lys Gly Pro Phe Ala
625                 630                 635                 640

Lys Asn Cys Ser Ala Ala Cys Gly Gln Thr Lys Leu Leu Ser Ser Pro
                645                 650                 655

Val Pro Gly Gly Arg Lys Cys Lys Glu Arg Asp Ser Glu Gly Cys Trp
                660                 665                 670

Met Thr Tyr Thr Leu Val Gln Arg Asp Gly Arg Asn Arg Tyr Asp Val
                675                 680                 685

His Val Asp Asp Met Leu Glu Cys Val Lys Gly Pro Asn Ile Ala Ala
                690                 695                 700

Ile Val Gly Gly Thr Val Gly Gly Val Leu Val Gly Ile Leu Leu
705                 710                 715                 720

Leu Ala Ile Trp Lys Ala Leu Thr His Leu Ser Asp Leu Arg Glu Tyr
                725                 730                 735

His Arg Phe Glu Lys Glu Lys Leu Lys Ser Gln Trp Asn Asn Asp Asn
                740                 745                 750

Pro Leu Phe Lys Ser Ala Thr Thr Thr Val Met Asn Pro Lys Phe Ala
                755                 760                 765

Glu Ser
    770

<210> SEQ ID NO 11
<211> LENGTH: 2313
<212> TYPE: DNA
<213> ORGANISM: Ovis canadensis

<400> SEQUENCE: 11
atgctgcccc agcgccccca gctgctgctc ctagcgggcc tgctctccct ccagtccgtc      60
ctgtcccagg agtgcaccaa gtacaaggtc agcacctgcc gggactgcat cgagtcgggc     120
```

| | |
|---|---|
| cccagctgtg cctggtgcca gaaactgaac ttcacagggc aaggggagcc cgactccact | 180 |
| cgctgtgata caagggcgca gctgctgtcg aagggctgcc cagctgatga catcatggaa | 240 |
| cccaagagcc tcgctgagac ccggcagagc caggcgggca gacagaagca gctgtcccca | 300 |
| gaggaagtga ccctctacct gagaccaggt caggcagctg cgttcaacgt gaccttccag | 360 |
| agggccaagg gctaccccat cgacctgtac tatctgatgg atctctccta ctccatggtg | 420 |
| gacgacctcg ccaacgtcaa gaagctgggg ggtgacctgc tccgggccct caatgacatc | 480 |
| accgagtcgg gccgcattgg tttcgggtcc ttcgtggaca gacggtgct ccccttcgtc | 540 |
| aacacgcacc ccgagaagct gaggaacccc tgccccaaca aggagaagga gtgccagccg | 600 |
| ccgttcgcct tcaggcacgt gctgaagctc accgacaact ccaaacagtt cgagacagaa | 660 |
| gtcgggaagc agctgatctc ggggaacttg gacgcccctg agggtgggct ggacgccatg | 720 |
| atgcaagtgg ccgcgtgccc ggaggaaatt ggctggcgca atgtcaccag gctgctggtg | 780 |
| ttcgccacag acgatgggtt ccactttgcg ggcgatggaa agctgggtgc catcctcacc | 840 |
| cccaacgacg gccgctgcca cctggaagac aacctgtaca aaagcagcaa cgaatttgac | 900 |
| tacccatcgg tgggccagct ggcacacaaa ctggcagaaa gcaacatcca gcccatcttc | 960 |
| gcggtaacca agaagatggt gaaaacgtac gagaagctga cagaaatcat ccccaagtct | 1020 |
| gcagtcgggg agctgtctga agattccaag aacgtggtgg agcttatcaa gagtgcctac | 1080 |
| aataaactgt cctccagagt attcctggat cacaacaccc tccctgacac cctgaaagtc | 1140 |
| gcctacgact ccttctgcag taacagggtg tcacaggtgg accagcccag aggggactgt | 1200 |
| gacggcgtcc agatcaacgt cccgatcacc ttccaggtga aggtcacagc caccgagtgc | 1260 |
| atccaggagc agtccttcac catccgggcg ctgggcttca cggacacggt gaccgtgcgg | 1320 |
| gtccttcccc agtgcgagtg ccaatgccgg gaagccagca gggaccgcgg cgtctgcggt | 1380 |
| ggcagaggct cgatggagtg cggcgtctgc aggtgcgacg ccggctacat cgggaagaac | 1440 |
| tgcgagtgcc agacgcacgg ccggagcagc caggagctgg agggcagctg ccgcaaggac | 1500 |
| aacagctcca tcatctgctc ggggctgggg gactgcatct gcgggcagtg cgtgtgccac | 1560 |
| acgagcgacg tgcccaacaa gaagatctac ggccagttct gcgagtgcga caacgtcaac | 1620 |
| tgcgagcgct acgacggcca agtctgcggg ggcgacaaga gggggctctg cttctgcggc | 1680 |
| gcctgcaggt gcaacgacca gtatgagggc tcggcgtgcc agtgcctcaa gtccactcag | 1740 |
| ggctgcctca acctgaacgg cgtcgagtgc agcggccgcg gccgatgccg ctgcaacgtg | 1800 |
| tgccagtgcg accccggcta ccagccgccc tgtgcatcg actgcccggg ctgccccgtg | 1860 |
| ccctgcgctg gcttcgcccc ctgcaccgag tgcctgaagt tcgacaaggg tccccttcgcc | 1920 |
| aagaactgca gcgcagcgtg cgggcagacg aagctgctgt ccagcccggt gcccggcggc | 1980 |
| cgcaagtgca aggagcgtga ctccgagggc tgctggatga cctacaccct ggtgcagcgc | 2040 |
| gacgggcgga acagatacga cgtgcacgtg gacgacatgc tcgagtgtgt gaagggcccc | 2100 |
| aacatcgctg ccatcgtggg gggcaccgtg ggggagttgg tgctcgtcgg catcctcctg | 2160 |
| ctggccatct ggaaggccct gacacacctg agcgacctca gggagtacca tcgcttcgag | 2220 |
| aaggagaagc tcaagtccca gtggaacaac gataaccctc ttttcaagag tgccaccacg | 2280 |
| acagtcatga accctaagtt tgccgagagt tag | 2313 |

<210> SEQ ID NO 12
<211> LENGTH: 770
<212> TYPE: PRT
<213> ORGANISM: Ovis canadensis

<400> SEQUENCE: 12

```
Met Leu Pro Gln Arg Pro Gln Leu Leu Leu Ala Gly Leu Leu Ser
1               5                   10                  15

Leu Gln Ser Val Leu Ser Gln Glu Cys Thr Lys Tyr Lys Val Ser Thr
                20                  25                  30

Cys Arg Asp Cys Ile Glu Ser Gly Pro Ser Cys Ala Trp Cys Gln Lys
            35                  40                  45

Leu Asn Phe Thr Gly Gln Gly Glu Pro Asp Ser Thr Arg Cys Asp Thr
        50                  55                  60

Arg Ala Gln Leu Leu Ser Lys Gly Cys Pro Ala Asp Asp Ile Met Glu
65                  70                  75                  80

Pro Lys Ser Leu Ala Glu Thr Arg Gln Ser Gln Ala Gly Arg Gln Lys
                85                  90                  95

Gln Leu Ser Pro Glu Glu Val Thr Leu Tyr Leu Arg Pro Gly Gln Ala
            100                 105                 110

Ala Ala Phe Asn Val Thr Phe Gln Arg Ala Lys Gly Tyr Pro Ile Asp
        115                 120                 125

Leu Tyr Tyr Leu Met Asp Leu Ser Tyr Ser Met Val Asp Asp Leu Ala
130                 135                 140

Asn Val Lys Lys Leu Gly Gly Asp Leu Leu Arg Ala Leu Asn Asp Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Glu Lys Leu Arg Asn Pro Cys Pro
            180                 185                 190

Asn Lys Glu Lys Glu Cys Gln Pro Pro Phe Ala Phe Arg His Val Leu
        195                 200                 205

Lys Leu Thr Asp Asn Ser Lys Gln Phe Glu Thr Glu Val Gly Lys Gln
210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
        275                 280                 285

Glu Asp Asn Leu Tyr Lys Ser Ser Asn Glu Phe Asp Tyr Pro Ser Val
290                 295                 300

Gly Gln Leu Ala His Lys Leu Ala Glu Ser Asn Ile Gln Pro Ile Phe
305                 310                 315                 320

Ala Val Thr Lys Lys Met Val Lys Thr Tyr Glu Lys Leu Thr Glu Ile
                325                 330                 335

Ile Pro Lys Ser Ala Val Gly Glu Leu Ser Glu Asp Ser Lys Asn Val
            340                 345                 350

Val Glu Leu Ile Lys Ser Ala Tyr Asn Lys Leu Ser Ser Arg Val Phe
        355                 360                 365

Leu Asp His Asn Thr Leu Pro Asp Thr Leu Lys Val Ala Tyr Asp Ser
370                 375                 380

Phe Cys Ser Asn Arg Val Ser Gln Val Asp Gln Pro Arg Gly Asp Cys
385                 390                 395                 400

Asp Gly Val Gln Ile Asn Val Pro Ile Thr Phe Gln Val Lys Val Thr
```

```
                    405                 410                 415
Ala Thr Glu Cys Ile Gln Glu Gln Ser Phe Thr Ile Arg Ala Leu Gly
            420                 425                 430

Phe Thr Asp Thr Val Thr Val Arg Val Leu Pro Gln Cys Glu Cys Gln
        435                 440                 445

Cys Arg Glu Ala Ser Arg Arg Gly Val Cys Gly Arg Gly Ser
    450                 455                 460

Met Glu Cys Gly Val Cys Arg Cys Asp Ala Gly Tyr Ile Gly Lys Asn
465                 470                 475                 480

Cys Glu Cys Gln Thr His Gly Arg Ser Gln Glu Leu Glu Gly Ser
                485                 490                 495

Cys Arg Lys Asp Asn Ser Ser Ile Ile Cys Ser Gly Leu Gly Asp Cys
                500                 505                 510

Ile Cys Gly Gln Cys Val Cys His Thr Ser Asp Val Pro Asn Lys Lys
            515                 520                 525

Ile Tyr Gly Gln Phe Cys Glu Cys Asp Asn Val Asn Cys Glu Arg Tyr
        530                 535                 540

Asp Gly Gln Val Cys Gly Gly Asp Lys Arg Gly Leu Cys Phe Cys Gly
545                 550                 555                 560

Ala Cys Arg Cys Asn Asp Gln Tyr Glu Gly Ser Ala Cys Gln Cys Leu
                565                 570                 575

Lys Ser Thr Gln Gly Cys Leu Asn Leu Asn Gly Val Glu Cys Ser Gly
            580                 585                 590

Arg Gly Arg Cys Arg Cys Asn Val Cys Gln Cys Asp Pro Gly Tyr Gln
        595                 600                 605

Pro Pro Leu Cys Ile Asp Cys Pro Gly Cys Pro Val Pro Cys Ala Gly
        610                 615                 620

Phe Ala Pro Cys Thr Glu Cys Leu Lys Phe Asp Lys Gly Pro Phe Ala
625                 630                 635                 640

Lys Asn Cys Ser Ala Ala Cys Gly Gln Thr Lys Leu Leu Ser Ser Pro
                645                 650                 655

Val Pro Gly Gly Arg Lys Cys Lys Glu Arg Asp Ser Glu Gly Cys Trp
            660                 665                 670

Met Thr Tyr Thr Leu Val Gln Arg Asp Gly Arg Asn Arg Tyr Asp Val
        675                 680                 685

His Val Asp Asp Met Leu Glu Cys Val Lys Gly Pro Asn Ile Ala Ala
        690                 695                 700

Ile Val Gly Gly Thr Val Gly Gly Val Val Leu Val Gly Ile Leu Leu
705                 710                 715                 720

Leu Ala Ile Trp Lys Ala Leu Thr His Leu Ser Asp Leu Arg Glu Tyr
                725                 730                 735

His Arg Phe Glu Lys Glu Lys Leu Lys Ser Gln Trp Asn Asn Asp Asn
            740                 745                 750

Pro Leu Phe Lys Ser Ala Thr Thr Thr Val Met Asn Pro Lys Phe Ala
        755                 760                 765

Glu Ser
    770

<210> SEQ ID NO 13
<211> LENGTH: 2310
<212> TYPE: DNA
<213> ORGANISM: Odocoileus hemionus

<400> SEQUENCE: 13
```

```
atgctgcgcc agcgccccca gctgctgctc ctagcaggcc tgctagccct ccagtctgtc    60
cggtcccagg agtgcaccaa atacaaggtc agcacctgcc gggactgcat cgagtcgggc   120
cccggctgtg cctggtgcca agctgaact tcacagggc aaggggagcc cgactccgct    180
cgctgtgaca cacgggcgca gctgctgtcc aagggctgtg ccactgatga catcatggaa   240
cccaggagcc tcgctgagac ccaggagagc caggcaggca gacagaagca gctgtcccca   300
caggaagtga cgctctacct gagaccaggt caggcagctg cgttcaacgt gactttccgg   360
agggccaaag gatacccat cgacctgtac tacctgatgg atctctccta ctccatggtg   420
gacgacctcg tcaacgtcaa gaagctgggg ggtgacctgc tccgggccct caacggcatc   480
actgagtcgg gccgcatcgg tttcgggtcc ttcgtggaca gacggtgct cccctttgtc    540
aacacgcacc ccgagaagct gcggaacccc tgccccaaca aggagaagca gtgccagccc   600
ccgttcgcct tcaggcacgt gctgaagctc accaacaact ccaaacagtt cgagacagaa   660
gtcgggaagc agctgatctc gggaaacctg gacgccccg agggagggct ggacgccatg   720
atgcaggtgg ccgtgtgccc ggaggaaatc ggctggcgca atgtcaccag gctgctggtg   780
tttgccacgg atgatggctt ccactttgcg ggcgatggaa agctgggtgc catcctcacc   840
cccaacgacg gccgctgcca cctggaagac aacctgtaca aaagcagcaa tgaatttgac   900
tacccatcgg tgggccagct ggcacacaaa ctggcagaaa gcaacatcca gcccatcttt   960
gcggtaacca agaagatggt gaaaacgtac gagaagctga cggagatcat ccccaagtct  1020
gcagtcgggg agctgtctga agactccagg aacgtggtgg agcttatcaa gagtgcctac  1080
aacaaactgt cctccagagt cttcctggat cacaacaccc tccctgacac cctgaaagtc  1140
acctacgact ccttctgcag taacggggtg tcgaaggtgg accagcccag aggggactgc  1200
gacggcgtcc agatcaacgt cccgatcacc ttcaggtga aggtcacagc caccgagtgc  1260
atccaggagc agtccttcac catccgggcc ctgggcttta cggacacggt gaccgtgcgg  1320
gtcctccccc agtgcgagtg ccaatgccgg gacgcgagca gggaccgcag cgtctgcggt  1380
ggcagaggct cgatggagtg cggcgtctgc aggtgcgacg ccggctacat cgggaagaac  1440
tgcgagtgcc agacgcaggg ccggagcagc aggagctgg agggcagctg ccgcaaggac  1500
aacagctcca tcatctgctc ggggctgggg gactgcatct gcgggcagtg cgtgtgccac  1560
acgagcgacg ttcccaacaa gaagatctac ggccagttct gcgagtgcga caacgtcaac  1620
tgcgagcgct acgacggcca agtctgcggg ggcgacaaga gggggctctg cttctgcggc  1680
acctgcaggt gccaggacca gtacgagggc tcggcgtgcc agtgcctcaa gtccacgcag  1740
ggctgcctca acctgaacgg cgtcgagtgc agcggccgcg gccggtgccg ctgcaacgtg  1800
tgccagtgcg acccccggcta ccagccgccc tgtgcaaag agtgcccggg ctgccccgcg  1860
ccctgcgccg gctttgcctc ctgcaccgag tgcctgaagt cgacaagggg ccccttcgcc  1920
aagaactgca gcgcagcttg cggggagacg aagctgctgt ccagcccgcc gcccggccgc  1980
aagtgcaagg agcgcgactc cgagggctgc tggatgacct acaccctggt gcagcgcgac  2040
gggcgggaca gatacgacgt gcacgtgaac gacacgcgcg agtgtgtaaa gggccccaac  2100
atcgctgcca ttgtgggggg caccgtgcg ggagttgtgc ttgtcggcat cctcctgctg  2160
gtcatctgga aggccctgac acacctgagc gacctcaggg agtaccatcg cttcgagaag  2220
gagaagctca gtcccagtg gaacaacgat aaccctcttt tcaagagtgc caccacgaca  2280
gtcatgaacc ctaagtttgc cgagagttag                                   2310
```

```
<210> SEQ ID NO 14
<211> LENGTH: 769
<212> TYPE: PRT
<213> ORGANISM: Odocoileus hemionus

<400> SEQUENCE: 14

Met Leu Arg Gln Arg Pro Gln Leu Leu Leu Ala Gly Leu Leu Ala
1               5                   10                  15

Leu Gln Ser Val Arg Ser Gln Glu Cys Thr Lys Tyr Lys Val Ser Thr
                20                  25                  30

Cys Arg Asp Cys Ile Glu Ser Gly Pro Gly Cys Ala Trp Cys Gln Lys
            35                  40                  45

Leu Asn Phe Thr Gly Gln Gly Glu Pro Asp Ser Ala Arg Cys Asp Thr
50                  55                  60

Arg Ala Gln Leu Leu Ser Lys Gly Cys Ala Thr Asp Asp Ile Met Glu
65                  70                  75                  80

Pro Arg Ser Leu Ala Glu Thr Gln Glu Ser Gln Ala Gly Arg Gln Lys
                85                  90                  95

Gln Leu Ser Pro Gln Glu Val Thr Leu Tyr Leu Arg Pro Gly Gln Ala
                100                 105                 110

Ala Ala Phe Asn Val Thr Phe Arg Arg Ala Lys Gly Tyr Pro Ile Asp
            115                 120                 125

Leu Tyr Tyr Leu Met Asp Leu Ser Tyr Ser Met Val Asp Asp Leu Val
130                 135                 140

Asn Val Lys Lys Leu Gly Gly Asp Leu Leu Arg Ala Leu Asn Gly Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Glu Lys Leu Arg Asn Pro Cys Pro
            180                 185                 190

Asn Lys Glu Lys Gln Cys Gln Pro Pro Phe Ala Phe Arg His Val Leu
            195                 200                 205

Lys Leu Thr Asn Asn Ser Lys Gln Phe Glu Thr Glu Val Gly Lys Gln
210                 215                 220

Leu Ile Ser Gly Asn Leu Asp Ala Pro Glu Gly Gly Leu Asp Ala Met
225                 230                 235                 240

Met Gln Val Ala Val Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
            275                 280                 285

Glu Asp Asn Leu Tyr Lys Ser Ser Asn Glu Phe Asp Tyr Pro Ser Val
290                 295                 300

Gly Gln Leu Ala His Lys Leu Ala Glu Ser Asn Ile Gln Pro Ile Phe
305                 310                 315                 320

Ala Val Thr Lys Lys Met Val Lys Thr Tyr Glu Lys Leu Thr Glu Ile
                325                 330                 335

Ile Pro Lys Ser Ala Val Gly Glu Leu Ser Glu Asp Ser Arg Asn Val
            340                 345                 350

Val Glu Leu Ile Lys Ser Ala Tyr Asn Lys Leu Ser Ser Arg Val Phe
            355                 360                 365

Leu Asp His Asn Thr Leu Pro Asp Thr Leu Lys Val Thr Tyr Asp Ser
        370                 375                 380
```

Phe Cys Ser Asn Gly Val Ser Lys Val Asp Gln Pro Arg Gly Asp Cys
385                 390                 395                 400

Asp Gly Val Gln Ile Asn Val Pro Ile Thr Phe Gln Val Lys Val Thr
            405                 410                 415

Ala Thr Glu Cys Ile Gln Glu Gln Ser Phe Thr Ile Arg Ala Leu Gly
        420                 425                 430

Phe Thr Asp Thr Val Thr Val Arg Val Leu Pro Gln Cys Glu Cys Gln
    435                 440                 445

Cys Arg Asp Ala Ser Arg Asp Arg Ser Val Cys Gly Arg Gly Ser
    450                 455                 460

Met Glu Cys Gly Val Cys Arg Cys Asp Ala Gly Tyr Ile Gly Lys Asn
465                 470                 475                 480

Cys Glu Cys Gln Thr Gln Gly Arg Ser Gln Glu Leu Glu Gly Ser
            485                 490                 495

Cys Arg Lys Asp Asn Ser Ser Ile Ile Cys Ser Gly Leu Gly Asp Cys
                500                 505                 510

Ile Cys Gly Gln Cys Val Cys His Thr Ser Asp Val Pro Asn Lys Lys
    515                 520                 525

Ile Tyr Gly Gln Phe Cys Glu Cys Asp Asn Val Asn Cys Glu Arg Tyr
    530                 535                 540

Asp Gly Gln Val Cys Gly Gly Asp Lys Arg Gly Leu Cys Phe Cys Gly
545                 550                 555                 560

Thr Cys Arg Cys Gln Asp Gln Tyr Glu Gly Ser Ala Cys Gln Cys Leu
                565                 570                 575

Lys Ser Thr Gln Gly Cys Leu Asn Leu Asn Gly Val Glu Cys Ser Gly
            580                 585                 590

Arg Gly Arg Cys Arg Cys Asn Val Cys Gln Cys Asp Pro Gly Tyr Gln
            595                 600                 605

Pro Pro Leu Cys Lys Glu Cys Pro Gly Cys Pro Ala Pro Cys Ala Gly
        610                 615                 620

Phe Ala Ser Cys Thr Glu Cys Leu Lys Phe Asp Lys Gly Pro Phe Ala
625                 630                 635                 640

Lys Asn Cys Ser Ala Ala Cys Gly Glu Thr Lys Leu Leu Ser Ser Pro
            645                 650                 655

Pro Pro Gly Arg Lys Cys Lys Glu Arg Asp Ser Glu Gly Cys Trp Met
            660                 665                 670

Thr Tyr Thr Leu Val Gln Arg Asp Gly Arg Asp Arg Tyr Asp Val His
            675                 680                 685

Val Asn Asp Thr Arg Glu Cys Val Lys Gly Pro Asn Ile Ala Ala Ile
        690                 695                 700

Val Gly Gly Thr Val Ala Gly Val Val Leu Val Gly Ile Leu Leu Leu
705                 710                 715                 720

Val Ile Trp Lys Ala Leu Thr His Leu Ser Asp Leu Arg Glu Tyr His
                725                 730                 735

Arg Phe Glu Lys Glu Lys Leu Lys Ser Gln Trp Asn Asn Asp Asn Pro
            740                 745                 750

Leu Phe Lys Ser Ala Thr Thr Thr Val Met Asn Pro Lys Phe Ala Glu
            755                 760                 765

Ser

<210> SEQ ID NO 15
<211> LENGTH: 2824
<212> TYPE: DNA
<213> ORGANISM: Cervus elaphus

<400> SEQUENCE: 15

```
aagcaccagc ctggtgaaga gcagagccga agccctgcc agtccagccg ggacgtccct    60
gccgaggtct ccagggcatc cagtgggaca tgctgcgcca gcgccccag ctgctgctcc   120
tagcgggcct gctagccctc cagtctgtcc agtcccagga gtgcaccaag tacaaggtca   180
gcacctgccg ggactgcatc gagtcgggcc ccggctgtgc ctggtgccag aagctgaact   240
tcacagggca aggggagccc gactccgctc gctgtgacac acgggcgcag ctgctgtcaa   300
agggctgtgc cgctgatgac atcatggatc caggagcct cgctgagacc cgggagagcc   360
aggcgggcag acagaagcag aagcagctgt ccccacagga agtgacgctc tacctgagac   420
caggtcaggc agctgcgttt aacgtgactt ccagagggc caagggctac cccatcgacc   480
tgtactacct gatggacctc tcctactcca tggtggatga cctcgtcaac gtcaagaagc   540
tggggggtga cctgctccgg gccctcaacg acatcaccga gtcgggccgc atcggttttcg   600
ggtccttcgt ggacaagacg gtgctccctt cgtcaacac gcaccccgag aagctgcgga   660
accctgccc caacaaggag aagcagtgcc agccccgtt cgccttcagg cacgtgctga   720
agctcaccga caactccaaa cagttcgaga cagaagtcgg gaagcagctg atctcgggga   780
acctggacgc ccccgaggga gggctggacg ccatgatgca ggtggccgcg tgcccggagg   840
aaatcggctg gcgcaatgtc accaggttgc tggtgtttgc cacgatgat ggcttccact   900
ttgcgggcga tggaaagctg ggtgccatcc tcaccccccaa cgacggccgc tgccacctgg   960
aagacaacct gtacaaaagc agcaacgaat ttgactaccc atcggtgggc cagctggcac  1020
acaaactggc agaaagcaac atccagccca tctttgcggt aaccaagaag atggtgaaaa  1080
cgtacgagaa gctgacggag atcatcccca gtctgcagt cggggagctg tctgaagatt  1140
ccaagaacgt ggtggagctt atcaagagtg cctacaataa actgtcctcc agagtcttcc  1200
tggatcacaa caccctccct gacaccctga agtccaccta cgactccttc tgcagtaaag  1260
gggtgtcgaa ggtggaccag cccagagggg actgcgacgg cgtccagatc aacgtcccga  1320
tcaccttcca ggtgaaggtc acagccaccg agtgcatcca ggaacagtcc ttcaccatcc  1380
gggcgctggg ctttacggac acggtgaccg tgcgggtcct ccccagtgc gagtgccaat  1440
gccgggacgc gagcagggac cgcagcgtct gcggtggcag aggttcgatg gagtgcggcg  1500
tctgcaggtg cgacgccggc tacatcggga agaactgcga gtgccagacg cagggccgga  1560
gcagccagga gctggagggc agctgccgca aggacaacag ctccatcatc tgctcggggc  1620
tgggggactg catctgcggg cagtgcgtgt gccacacgag cgacgtgccc aacaagaaga  1680
tctacggcca gttctgcgag tgtgacaacg tcaactgcga acgctacgac ggccaagtct  1740
gcggggggcga caagagggg ctctgcttct gcggcacctg caggtgccag gaccagtacg  1800
agggctcggc gtgccagtgc ctcaagtcca cgcagggctg cctcaacctg aacggcgtcg  1860
agtgcagcgg ccgcggccgg tgccgctgca acgtgtgcca gtgcgacccc ggctaccagc  1920
cgccctgtg cttagagtgc cccggctgcc ccgcaccctg cgccggcttt gccccctgca  1980
ccgagtgcct gaagttcaag ggccccttcg ccaagaactg cagcgcagcg tgcgggagaa  2040
cgaagctgct gtccaacccg ctgccgccc gcaagtgcaa ggagcgcgac tcggagggct  2100
gctggatgac ctacaccctg tgcagcgcg acgggcggga cagatacgac gtgcacgtga  2160
acgacacgcg cgagtgtgtg aagggcccca acatcgcggc cattgtgggg gcaccgtgg  2220
ggggagttgt gctggttggc atcctcctgc tggtcatctg gaaggccctg acacacctga  2280
```

```
gcgacctcag ggagtaccat cgcttcgaga aggagaagct caagtcccag tggaacaatg    2340
ataaccctct tttcaagagt gccaccacga cagtcatgaa ccctaagttt gccgagagtt    2400
aggggtgcct ggtgaagaca aggccttctg caccacccag atgggaccac gccctctcca    2460
cgtcccctcc agcaggccga ccgtgaccct gctgccttgt ggacgtggct gatgatgctt    2520
gacaactcca ctgttaacca aaatgcact gcttttcctg ccccagaatg atgggcgtga     2580
ccaaatgatc ctatgggctc atggtaaggg ccagcctccc ccttgatgtc aataactttt    2640
gctagcaagt cagaggagga attgcctaca ttttgtacgg ttacacacca gtcctttgta    2700
aaaattagca cagcagtctg atgaagaatt atttatatgt gaacttctca gggtatgaag    2760
ttatatcccc ttggttatgc tgccccccaa tcaataaaaa aaatcaagaa aaaaaaaaa     2820 aaaa                                                                2824
```

<210> SEQ ID NO 16
<211> LENGTH: 770
<212> TYPE: PRT
<213> ORGANISM: Cervus elaphus

<400> SEQUENCE: 16

```
Met Leu Arg Gln Arg Pro Gln Leu Leu Leu Ala Gly Leu Leu Ala
1               5                   10                  15

Leu Gln Ser Val Gln Ser Gln Glu Cys Thr Lys Tyr Lys Val Ser Thr
            20                  25                  30

Cys Arg Asp Cys Ile Glu Ser Gly Pro Gly Cys Ala Trp Cys Gln Lys
        35                  40                  45

Leu Asn Phe Thr Gly Gln Gly Glu Pro Asp Ser Ala Arg Cys Asp Thr
    50                  55                  60

Arg Ala Gln Leu Leu Ser Lys Gly Cys Ala Ala Asp Asp Ile Met Asp
65                  70                  75                  80

Pro Arg Ser Leu Ala Glu Thr Arg Glu Ser Gln Ala Gly Arg Gln Lys
                85                  90                  95

Gln Lys Gln Leu Ser Pro Gln Glu Val Thr Leu Tyr Leu Arg Pro Gly
            100                 105                 110

Gln Ala Ala Ala Phe Asn Val Thr Phe Gln Arg Ala Lys Gly Tyr Pro
        115                 120                 125

Ile Asp Leu Tyr Tyr Leu Met Asp Leu Ser Tyr Ser Met Val Asp Asp
    130                 135                 140

Leu Val Asn Val Lys Lys Leu Gly Gly Asp Leu Leu Arg Ala Leu Asn
145                 150                 155                 160

Asp Ile Thr Glu Ser Gly Arg Ile Gly Phe Gly Ser Phe Val Asp Lys
                165                 170                 175

Thr Val Leu Pro Phe Val Asn Thr His Pro Glu Lys Leu Arg Asn Pro
            180                 185                 190

Cys Pro Asn Lys Glu Lys Gln Cys Gln Pro Pro Phe Ala Phe Arg His
        195                 200                 205

Val Leu Lys Leu Thr Asp Asn Ser Lys Gln Phe Glu Thr Glu Val Gly
    210                 215                 220

Lys Gln Leu Ile Ser Gly Asn Leu Asp Ala Pro Glu Gly Gly Leu Asp
225                 230                 235                 240

Ala Met Met Gln Val Ala Ala Cys Pro Glu Glu Ile Gly Trp Arg Asn
                245                 250                 255

Val Thr Arg Leu Leu Val Phe Ala Thr Asp Asp Gly Phe His Phe Ala
            260                 265                 270
```

```
Gly Asp Gly Lys Leu Gly Ala Ile Leu Thr Pro Asn Asp Gly Arg Cys
            275                 280                 285

His Leu Glu Asp Asn Leu Tyr Lys Ser Ser Asn Glu Phe Asp Tyr Pro
        290                 295                 300

Ser Val Gly Gln Leu Ala His Lys Leu Ala Glu Ser Asn Ile Gln Pro
305                 310                 315                 320

Ile Phe Ala Val Thr Lys Lys Met Val Lys Thr Tyr Glu Lys Leu Thr
                325                 330                 335

Glu Ile Ile Pro Lys Ser Ala Val Gly Glu Leu Ser Glu Asp Ser Lys
            340                 345                 350

Asn Val Val Glu Leu Ile Lys Ser Ala Tyr Asn Lys Leu Ser Ser Arg
        355                 360                 365

Val Phe Leu Asp His Asn Thr Leu Pro Asp Thr Leu Lys Val Thr Tyr
370                 375                 380

Asp Ser Phe Cys Ser Lys Gly Val Ser Lys Val Asp Gln Pro Arg Gly
385                 390                 395                 400

Asp Cys Asp Gly Val Gln Ile Asn Val Pro Ile Thr Phe Gln Val Lys
                405                 410                 415

Val Thr Ala Thr Glu Cys Ile Gln Glu Gln Ser Phe Thr Ile Arg Ala
            420                 425                 430

Leu Gly Phe Thr Asp Thr Val Thr Val Arg Val Leu Pro Gln Cys Glu
        435                 440                 445

Cys Gln Cys Arg Asp Ala Ser Arg Asp Arg Ser Val Cys Gly Gly Arg
    450                 455                 460

Gly Ser Met Glu Cys Gly Val Cys Arg Cys Asp Ala Gly Tyr Ile Gly
465                 470                 475                 480

Lys Asn Cys Glu Cys Gln Thr Gln Gly Arg Ser Ser Gln Glu Leu Glu
                485                 490                 495

Gly Ser Cys Arg Lys Asp Asn Ser Ser Ile Ile Cys Ser Gly Leu Gly
            500                 505                 510

Asp Cys Ile Cys Gly Gln Cys Val Cys His Thr Ser Asp Val Pro Asn
        515                 520                 525

Lys Lys Ile Tyr Gly Gln Phe Cys Glu Cys Asp Asn Val Asn Cys Glu
530                 535                 540

Arg Tyr Asp Gly Gln Val Cys Gly Gly Asp Lys Arg Gly Leu Cys Phe
545                 550                 555                 560

Cys Gly Thr Cys Arg Cys Gln Asp Gln Tyr Glu Gly Ser Ala Cys Gln
                565                 570                 575

Cys Leu Lys Ser Thr Gln Gly Cys Leu Asn Leu Asn Gly Val Glu Cys
            580                 585                 590

Ser Gly Arg Gly Arg Cys Arg Cys Asn Val Cys Gln Cys Asp Pro Gly
        595                 600                 605

Tyr Gln Pro Pro Leu Cys Leu Glu Cys Pro Gly Cys Pro Ala Pro Cys
610                 615                 620

Ala Gly Phe Ala Pro Cys Thr Glu Cys Leu Lys Phe Lys Gly Pro Phe
625                 630                 635                 640

Ala Lys Asn Cys Ser Ala Ala Cys Gly Glu Thr Lys Leu Leu Ser Asn
                645                 650                 655

Pro Leu Pro Gly Arg Lys Cys Lys Glu Arg Asp Ser Glu Gly Cys Trp
            660                 665                 670

Met Thr Tyr Thr Leu Val Gln Arg Asp Gly Arg Asp Arg Tyr Asp Val
        675                 680                 685

His Val Asn Asp Thr Arg Glu Cys Val Lys Gly Pro Asn Ile Ala Ala
```

```
                   690                 695                 700
Ile Val Gly Gly Thr Val Gly Val Val Leu Val Gly Ile Leu Leu
705                 710                 715                 720

Leu Val Ile Trp Lys Ala Leu Thr His Leu Ser Asp Leu Arg Glu Tyr
                725                 730                 735

His Arg Phe Glu Lys Glu Lys Leu Lys Ser Gln Trp Asn Asn Asp Asn
            740                 745                 750

Pro Leu Phe Lys Ser Ala Thr Thr Thr Val Met Asn Pro Lys Phe Ala
        755                 760                 765

Glu Ser
    770

<210> SEQ ID NO 17
<211> LENGTH: 2977
<212> TYPE: DNA
<213> ORGANISM: Homo sapiens

<400> SEQUENCE: 17
```

| | | | | | |
|---|---|---|---|---|---|
| gggccgctct | ctgacatcag | agctgctgta | gagcggagag | gggcaggggt | gaagggccac | 60 |
| ggtggtgcaa | cccaccactt | cctccaagga | ggagctgaga | ggaacaggaa | gtgtcaggac | 120 |
| tttacgaccc | gcgcctccag | ctgaggtttc | tagacgtgac | ccagggcaga | ctggtagcaa | 180 |
| agccccacg | cccagccagg | agcaccgccg | aggactccag | cacaccgagg | acatgctgg | 240 |
| gcctgcgccc | cccactgctc | gccctggtgg | ggctgctctc | cctcgggtgc | gtcctctctc | 300 |
| aggagtgcac | gaagttcaag | gtcagcagct | gccgggaatg | catcgagtcg | ggcccggct | 360 |
| gcacctggtg | ccagaagctg | aacttcacag | ggccggggga | tcctgactcc | attcgctgcg | 420 |
| acacccggcc | acagctgctc | atgagggggct | gtgcggctga | cgacatcatg | accccacaa | 480 |
| gcctcgctga | aacccaggaa | gaccacaatg | ggggccagaa | gcagctgtcc | ccacaaaaag | 540 |
| tgacgcttta | cctgcgacca | ggccaggcag | cagcgttcaa | cgtgaccttc | cggcgggcca | 600 |
| agggctaccc | catcgacctg | tactatctga | tggacctctc | ctactccatg | cttgatgacc | 660 |
| tcaggaatgt | caagaagcta | ggtggcgacc | tgctccgggc | cctcaacgag | atcaccgagt | 720 |
| ccggccgcat | tggcttcggg | tccttcgtgg | acaagaccgt | gctgccgttc | gtgaacacgc | 780 |
| accctgataa | gctgcgaaac | ccatgccccca | acaaggagaa | agagtgccag | ccccgtttg | 840 |
| ccttcaggca | cgtgctgaag | ctgaccaaca | actccaacca | gtttcagacc | gaggtcggga | 900 |
| agcagctgat | ttccggaaac | ctggatgcac | ccgagggtgg | gctggacgcc | atgatgcagg | 960 |
| tcgccgcctg | cccggaggaa | atcggctggc | gcaacgtcac | gcggctgctg | gtgtttgcca | 1020 |
| ctgatgacgg | cttccattc | gcgggcgacg | ggaagctggg | cgccatcctg | accccaacg | 1080 |
| acggccgctg | tcacctggag | gacaacttgt | acaagaggag | caacgaattc | gactacccat | 1140 |
| cggtgggcca | gctggcgcac | aagctggctg | aaaacaacat | ccagccatc | ttcgcggtga | 1200 |
| ccagtaggat | ggtgaagacc | tacgagaaac | tcaccgagat | catccccaag | tcagccgtgg | 1260 |
| gggagctgtc | tgaggactcc | agcaatgtgg | tccaactcat | taagaatgct | tacaataaac | 1320 |
| tctcctccag | ggtcttcctg | gatcacaacg | ccctccccga | caccctgaaa | gtcacctacg | 1380 |
| actccttctg | cagcaatgga | gtgacgcaca | ggaaccagcc | cagaggtgac | tgtgatggcg | 1440 |
| tgcagatcaa | tgtccgatc | accttccagg | tgaaggtcac | ggccacagag | tgcatccagg | 1500 |
| agcagtcgtt | tgtcatccgg | gcgctgggct | tcacggacat | agtgaccgtg | caggttcttc | 1560 |
| cccagtgtga | gtgccggtgc | cgggaccaga | gcagagaccg | cagcctctgc | catggcaagg | 1620 |

```
gcttcttgga gtgcggcatc tgcaggtgtg acactggcta cattgggaaa aactgtgagt   1680
gccagacaca gggccggagc agccaggagc tggaaggaag ctgccggaag acaacaact    1740 ccatcatctg ctcagggctg ggggactgtg tctgcgggca gtgcctgtgc cacaccagcg   1800
acgtccccgg caagctgata tacgggcagt actgcgagtg tgacaccatc aactgtgagc   1860
gctacaacgg ccaggtctgc ggcggcccgg ggagggggct ctgcttctgc gggaagtgcc   1920
gctgccaccc gggctttgag ggctcagcgt gccagtgcga gaggaccact gagggctgcc   1980
tgaacccgcg gcgtgttgag tgtagtggtc gtggccggtg ccgctgcaac gtatgcgagt   2040
gccattcagg ctaccagctg cctctgtgcc aggagtgccc cggctgcccc tcaccctgtg   2100
gcaagtacat ctcctgcgcc gagtgcctga agttcgaaaa gggccccttt gggaagaact   2160
gcagcgcggc gtgtccgggc ctgcagctgt cgaacaaccc cgtgaagggc aggacctgca   2220
aggagaggga ctcagagggc tgctgggtgg cctacacgct ggagcagcag gacgggatgg   2280
accgctacct catctatgtg gatgagagcc gagagtgtgt ggcaggcccc aacatcgccg   2340
ccatcgtcgg gggcaccgtg gcaggcatcg tgctgatcgg cattctcctg ctggtcatct   2400
ggaaggctct gatccacctg agcgacctcc gggagtacag gcgctttgag aaggagaagc   2460
tcaagtccca gtggaacaat gataatcccc ttttcaagag cgccaccacg acggtcatga   2520
accccaagtt tgctgagagt taggagcact tggtgaagac aaggccgtca ggacccacca   2580
tgtctgcccc atcacgcggc cgagacatgg cttgccacac ctcttgagga tgtcaccaat   2640
taaccagaaa tccagttatt ttccgccctc aaaatgacag ccatggccgg ccgggtgctt   2700
ctgggggctc gtcgggggga cagctccact ctgactggca cagtctttgc atggagactt   2760
gaggagggag ggcttgaggt tggtgaggtt aggtgcgtgt ttcctgtgca agtcaggaca   2820
tcagtctgat taaggtggt gccaatttat ttacatttaa acttgtcagg gtataaaatg   2880
acatcccatt aattatattg ttaatcaatc acgtgtatag aaaaaaaata aaacttcaat   2940
acaggctgtc catggaaaaa aaaaaaaaaa aaaaaaa                            2977
```

<210> SEQ ID NO 18
<211> LENGTH: 769
<212> TYPE: PRT
<213> ORGANISM: Homo sapiens

<400> SEQUENCE: 18

```
Met Leu Gly Leu Arg Pro Pro Leu Leu Ala Leu Val Gly Leu Leu Ser
1               5                   10                  15

Leu Gly Cys Val Leu Ser Gln Glu Cys Thr Lys Phe Lys Val Ser Ser
                20                  25                  30

Cys Arg Glu Cys Ile Glu Ser Gly Pro Gly Cys Thr Trp Cys Gln Lys
            35                  40                  45

Leu Asn Phe Thr Gly Pro Gly Asp Pro Asp Ser Ile Arg Cys Asp Thr
        50                  55                  60

Arg Pro Gln Leu Leu Met Arg Gly Cys Ala Ala Asp Asp Ile Met Asp
65                  70                  75                  80

Pro Thr Ser Leu Ala Glu Thr Gln Glu Asp His Asn Gly Gly Gln Lys
                85                  90                  95

Gln Leu Ser Pro Gln Lys Val Thr Leu Tyr Leu Arg Pro Gly Gln Ala
                100                 105                 110

Ala Ala Phe Asn Val Thr Phe Arg Arg Ala Lys Gly Tyr Pro Ile Asp
            115                 120                 125

Leu Tyr Tyr Leu Met Asp Leu Ser Tyr Ser Met Leu Asp Asp Leu Arg
```

```
        130                 135                 140
Asn Val Lys Lys Leu Gly Gly Asp Leu Leu Arg Ala Leu Asn Glu Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Asp Lys Leu Arg Asn Pro Cys Pro
                180                 185                 190

Asn Lys Glu Lys Glu Cys Gln Pro Pro Phe Ala Phe Arg His Val Leu
            195                 200                 205

Lys Leu Thr Asn Asn Ser Asn Gln Phe Gln Thr Glu Val Gly Lys Gln
        210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
                260                 265                 270

Gly Lys Leu Gly Ala Ile Leu Thr Pro Asn Asp Gly Arg Cys His Leu
            275                 280                 285

Glu Asp Asn Leu Tyr Lys Arg Ser Asn Glu Phe Asp Tyr Pro Ser Val
        290                 295                 300

Gly Gln Leu Ala His Lys Leu Ala Glu Asn Asn Ile Gln Pro Ile Phe
305                 310                 315                 320

Ala Val Thr Ser Arg Met Val Lys Thr Tyr Glu Lys Leu Thr Glu Ile
                325                 330                 335

Ile Pro Lys Ser Ala Val Gly Glu Leu Ser Glu Asp Ser Ser Asn Val
                340                 345                 350

Val Gln Leu Ile Lys Asn Ala Tyr Asn Lys Leu Ser Ser Arg Val Phe
            355                 360                 365

Leu Asp His Asn Ala Leu Pro Asp Thr Leu Lys Val Thr Tyr Asp Ser
        370                 375                 380

Phe Cys Ser Asn Gly Val Thr His Arg Asn Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Glu Gln Ser Phe Val Ile Arg Ala Leu Gly
                420                 425                 430

Phe Thr Asp Ile Val Thr Val Gln Val Leu Pro Gln Cys Glu Cys Arg
            435                 440                 445

Cys Arg Asp Gln Ser Arg Asp Arg Ser Leu Cys His Gly Lys Gly Phe
        450                 455                 460

Leu Glu Cys Gly Ile Cys Arg Cys Asp Thr Gly Tyr Ile Gly Lys Asn
465                 470                 475                 480

Cys Glu Cys Gln Thr Gln Gly Arg Ser Ser Gln Glu Leu Glu Gly Ser
                485                 490                 495

Cys Arg Lys Asp Asn Asn Ser Ile Ile Cys Ser Gly Leu Gly Asp Cys
                500                 505                 510

Val Cys Gly Gln Cys Leu Cys His Thr Ser Asp Val Pro Gly Lys Leu
            515                 520                 525

Ile Tyr Gly Gln Tyr Cys Glu Cys Asp Thr Ile Asn Cys Glu Arg Tyr
        530                 535                 540

Asn Gly Gln Val Cys Gly Gly Pro Gly Arg Gly Leu Cys Phe Cys Gly
545                 550                 555                 560
```

Lys Cys Arg Cys His Pro Gly Phe Glu Gly Ser Ala Cys Gln Cys Glu
            565                 570                 575

Arg Thr Thr Glu Gly Cys Leu Asn Pro Arg Arg Val Glu Cys Ser Gly
        580                 585                 590

Arg Gly Arg Cys Arg Cys Asn Val Cys Glu Cys His Ser Gly Tyr Gln
    595                 600                 605

Leu Pro Leu Cys Gln Glu Cys Pro Gly Cys Pro Ser Pro Cys Gly Lys
    610                 615                 620

Tyr Ile Ser Cys Ala Glu Cys Leu Lys Phe Glu Lys Gly Pro Phe Gly
625                 630                 635                 640

Lys Asn Cys Ser Ala Ala Cys Pro Gly Leu Gln Leu Ser Asn Asn Pro
            645                 650                 655

Val Lys Gly Arg Thr Cys Lys Glu Arg Asp Ser Glu Gly Cys Trp Val
        660                 665                 670

Ala Tyr Thr Leu Glu Gln Gln Asp Gly Met Asp Arg Tyr Leu Ile Tyr
    675                 680                 685

Val Asp Glu Ser Arg Glu Cys Val Ala Gly Pro Asn Ile Ala Ala Ile
    690                 695                 700

Val Gly Gly Thr Val Ala Gly Ile Val Leu Ile Gly Ile Leu Leu Leu
705                 710                 715                 720

Val Ile Trp Lys Ala Leu Ile His Leu Ser Asp Leu Arg Glu Tyr Arg
            725                 730                 735

Arg Phe Glu Lys Glu Lys Leu Lys Ser Gln Trp Asn Asn Asp Asn Pro
        740                 745                 750

Leu Phe Lys Ser Ala Thr Thr Thr Val Met Asn Pro Lys Phe Ala Glu
    755                 760                 765

Ser

<210> SEQ ID NO 19
<211> LENGTH: 2828
<212> TYPE: DNA
<213> ORGANISM: Mus musculus

<400> SEQUENCE: 19
cgaggcccct ggcaagaagt aggcaaagac atctccagtc agattctcgg agtggaggct    60
tcctgggact gagaggggga catgctgggc ccacactcac tgctgcttgc cctagctgga   120
ctgttcttcc tgggatctgc tgtgtcccag gaatgcacca agtacaaagt cagcagttgc   180
cgggactgta tccagtcggg gcctggctgt tcctggtgcc agaagctgaa cttcactgga   240
ccaggagaac ctgactcctt gcgctgtgac acacgggcac agctgctgct gaagggttgt   300
ccagccgatg atatcatgga ccccaggagc atcgctaatc ctgagttcga ccaacggggg   360
caacggaaac agctatctcc acaaaaagtg acacttact tgcgaccagg acaggctgcc   420
gcattcaatg tgacttttcg gcgggccaag ggatacccca ttgatctgta ctacctcatg   480
gatctctcct actccatgct tgatgacctc aacaacgtca gaagctgggc ggggacttg   540 ctgcaggccc tcaacgagat caccgagtct ggccgcatcg ctttgggtc gtttgtggac   600 aagacggtgc tgccttttgt taacacccat cctgagaagc tgaggaaccc atgtcccaac   660
aaggagaagg cctgccagcc cccatttgcc tttcggcacg tgctcaagtt aaccgacaac   720
tccaaccagt ttcagacaga ggtcggcaag caactgattt ccggaaacct ggacgcccct   780
gagggtgggc tggatgccat aatgcaagtt gctgcatgtc cggaggaaat tggctggcgc   840
aatgtcacga ggctgctggt gtttgccaca gacgatggct ccactttgc tggtgatggc   900

```
aaactgggtg ccatcctgac ccccaatgat ggccgctgcc acctggagga taacatgtac    960
aagaggagca atgagttcga ctacccatcc gtgggtcagc tggcacacaa actttccgag   1020
agcaacatcc agcccatctt tgcggtgaca aagaagatgg tgaaaacgta tgagaaactc   1080
acggagatca tccccaagtc agcagtgggg gaactgtctg acgactccag caacgtggtg   1140
cagctcatca agaatgccta ctataaactc tcctctagag tcttcctgga ccacagcacc   1200
ctcccggaca ccctgaaagt cacctatgac tccttctgca gtaatggagc atcgagtata   1260
ggcaaatccc gtggggactg tgatggcgta cagatcaaca acccggtcac cttccaggta   1320
aaggtcatgg cttccgagtg tatccaggag cagtcctttg tcatccgggc actgggtttc   1380
actgatacag tgaccgtgca ggtccgtccc cagtgtgagt gtcagtgccg ggaccagagt   1440
cgggagcaga gtctctgtgg aggcaaggga gtcatggagt gtggtatctg caggtgtgag   1500
tctggctaca ttgggaaaaa ctgtgagtgc cagactcagg gtcggagcag ccaggagctg   1560
gagagaaact gtcggaagga caatagttcc atcgtgtgct cagggcttgg ggactgcatc   1620
tgtgggcagt gtgtatgcca taccagtgac gtccccaaca aagagatctt tgggcaatac   1680
tgcgagtgtg acaatgtcaa ctgtgagaga tataacagcc aagtctgcgg tggctcagat   1740
cggggttcct gcaactgtgg caaatgtagt tgcaagcccg ttacgaggg ctcggcctgc   1800 cagtgtcaga ggtccaccac gggctgtctg aatgcacggc tggtagagtg cagtggccgt   1860
ggccactgcc aatgcaacag gtgcatatgt gacgaaggct accagccacc gatgtgtgag   1920
gattgtccca gctgtggctc gcactgcagg gacaaccaca cctcttgtgc cgagtgcctg   1980
aagtttgata agggcccttt tgagaagaac tgtagtgttc agtgtgctgg tatgacgctg   2040
cagactatcc ctttgaagaa aaagccctgc aaggagaggg actcggaagg ctgttggata   2100
acttacactt tgcagcagaa ggacggaagg aacatttaca catccatgt ggaggacagt   2160 ctagagtgtg tgaagggccc caatgtggct gccatcgtag ggggcaccgt ggtaggtgtc   2220
gtactgattg gtgtcctcct cctggtcatc tggaaggccc tgacccacct gactgacctc   2280
agggagtaca gccgctttga aaggagaaaa ctcaagtccc aatggaacaa tgacaacccc   2340
ctcttcaaga gtgctacgac aacggtcatg aaccccaagt ttgctgaaag ctagagcatg   2400
agttatcata atcaagcaga tgtgaccccc tcagaccacg cctcctcccc tctgcaaaca   2460
caacgtggct tacagctcac cccagtgctg ccaaggatcc aaaagcctgc tcggtttctt   2520
tccgccatta tatcaagtct gccagggttt ccagggactt gtcttccgac ctgcacaatc   2580
ttgccgcaga gccctaagaa ttgtcccgag tcccaagagg ttccacccac attttcttgc   2640
ataaaggaag acagcagtct cagtaaaggt ggccccaact tatttatatt taaacttgtc   2700
agagtataaa actcctatta tattgttaac atcccatctg ttgtattata tgtgagtata   2760
aaaactatat ccaacgtatt atttcataat catgtatgaa aaataataaa gcttccatcc   2820
atgctgtc                                                           2828

<210> SEQ ID NO 20
<211> LENGTH: 770
<212> TYPE: PRT
<213> ORGANISM: Mus musculus

<400> SEQUENCE: 20

Met Leu Gly Pro His Ser Leu Leu Leu Ala Leu Ala Gly Leu Phe Phe
1               5                   10                  15

Leu Gly Ser Ala Val Ser Gln Glu Cys Thr Lys Tyr Lys Val Ser Ser
```

```
                 20                  25                  30
Cys Arg Asp Cys Ile Gln Ser Gly Pro Gly Cys Ser Trp Cys Gln Lys
             35                  40                  45
Leu Asn Phe Thr Gly Pro Gly Glu Pro Asp Ser Leu Arg Cys Asp Thr
 50                  55                  60
Arg Ala Gln Leu Leu Leu Lys Gly Cys Pro Ala Asp Asp Ile Met Asp
 65                  70                  75                  80
Pro Arg Ser Ile Ala Asn Pro Glu Phe Asp Gln Arg Gly Gln Arg Lys
                 85                  90                  95
Gln Leu Ser Pro Gln Lys Val Thr Leu Tyr Leu Arg Pro Gly Gln Ala
            100                 105                 110
Ala Ala Phe Asn Val Thr Phe Arg Arg Ala Lys Gly Tyr Pro Ile Asp
            115                 120                 125
Leu Tyr Tyr Leu Met Asp Leu Ser Tyr Ser Met Leu Asp Asp Leu Asn
            130                 135                 140
Asn Val Lys Lys Leu Gly Gly Asp Leu Leu Gln Ala Leu Asn Glu Ile
145                 150                 155                 160
Thr Glu Ser Gly Arg Ile Gly Phe Gly Ser Phe Val Asp Lys Thr Val
                165                 170                 175
Leu Pro Phe Val Asn Thr His Pro Glu Lys Leu Arg Asn Pro Cys Pro
            180                 185                 190
Asn Lys Glu Lys Ala Cys Gln Pro Pro Phe Ala Phe Arg His Val Leu
            195                 200                 205
Lys Leu Thr Asp Asn Ser Asn Gln Phe Gln Thr Glu Val Gly Lys Gln
210                 215                 220
Leu Ile Ser Gly Asn Leu Asp Ala Pro Glu Gly Gly Leu Asp Ala Ile
225                 230                 235                 240
Met Gln Val Ala Ala Cys Pro Glu Glu Ile Gly Trp Arg Asn Val Thr
                245                 250                 255
Arg Leu Leu Val Phe Ala Thr Asp Asp Gly Phe His Phe Ala Gly Asp
            260                 265                 270
Gly Lys Leu Gly Ala Ile Leu Thr Pro Asn Asp Gly Arg Cys His Leu
            275                 280                 285
Glu Asp Asn Met Tyr Lys Arg Ser Asn Glu Phe Asp Tyr Pro Ser Val
            290                 295                 300
Gly Gln Leu Ala His Lys Leu Ser Glu Ser Asn Ile Gln Pro Ile Phe
305                 310                 315                 320
Ala Val Thr Lys Lys Met Val Lys Thr Tyr Glu Lys Leu Thr Glu Ile
                325                 330                 335
Ile Pro Lys Ser Ala Val Gly Glu Leu Ser Asp Asp Ser Ser Asn Val
            340                 345                 350
Val Gln Leu Ile Lys Asn Ala Tyr Tyr Lys Leu Ser Ser Arg Val Phe
            355                 360                 365
Leu Asp His Ser Thr Leu Pro Asp Thr Leu Lys Val Thr Tyr Asp Ser
            370                 375                 380
Phe Cys Ser Asn Gly Ala Ser Ser Ile Gly Lys Ser Arg Gly Asp Cys
385                 390                 395                 400
Asp Gly Val Gln Ile Asn Asn Pro Val Thr Phe Gln Val Lys Val Met
                405                 410                 415
Ala Ser Glu Cys Ile Gln Glu Gln Ser Phe Val Ile Arg Ala Leu Gly
            420                 425                 430
Phe Thr Asp Thr Val Thr Val Gln Val Arg Pro Gln Cys Glu Cys Gln
            435                 440                 445
```

Cys Arg Asp Gln Ser Arg Glu Gln Ser Leu Cys Gly Gly Lys Gly Val
        450                 455                 460

Met Glu Cys Gly Ile Cys Arg Cys Glu Ser Gly Tyr Ile Gly Lys Asn
465                 470                 475                 480

Cys Glu Cys Gln Thr Gln Gly Arg Ser Ser Gln Glu Leu Glu Arg Asn
                485                 490                 495

Cys Arg Lys Asp Asn Ser Ser Ile Val Cys Ser Gly Leu Gly Asp Cys
                500                 505                 510

Ile Cys Gly Gln Cys Val Cys His Thr Ser Asp Val Pro Asn Lys Glu
            515                 520                 525

Ile Phe Gly Gln Tyr Cys Glu Cys Asp Asn Val Asn Cys Glu Arg Tyr
530                 535                 540

Asn Ser Gln Val Cys Gly Gly Ser Asp Arg Gly Ser Cys Asn Cys Gly
545                 550                 555                 560

Lys Cys Ser Cys Lys Pro Gly Tyr Glu Gly Ser Ala Cys Gln Cys Gln
                565                 570                 575

Arg Ser Thr Thr Gly Cys Leu Asn Ala Arg Leu Val Glu Cys Ser Gly
                580                 585                 590

Arg Gly His Cys Gln Cys Asn Arg Cys Ile Cys Asp Glu Gly Tyr Gln
            595                 600                 605

Pro Pro Met Cys Glu Asp Cys Pro Ser Cys Gly Ser His Cys Arg Asp
610                 615                 620

Asn His Thr Ser Cys Ala Glu Cys Leu Lys Phe Asp Lys Gly Pro Phe
625                 630                 635                 640

Glu Lys Asn Cys Ser Val Gln Cys Ala Gly Met Thr Leu Gln Thr Ile
                645                 650                 655

Pro Leu Lys Lys Lys Pro Cys Lys Glu Arg Asp Ser Glu Gly Cys Trp
                660                 665                 670

Ile Thr Tyr Thr Leu Gln Gln Lys Asp Gly Arg Asn Ile Tyr Asn Ile
            675                 680                 685

His Val Glu Asp Ser Leu Glu Cys Val Lys Gly Pro Asn Val Ala Ala
690                 695                 700

Ile Val Gly Gly Thr Val Val Gly Val Val Leu Ile Gly Val Leu Leu
705                 710                 715                 720

Leu Val Ile Trp Lys Ala Leu Thr His Leu Thr Asp Leu Arg Glu Tyr
                725                 730                 735

Arg Arg Phe Glu Lys Glu Lys Leu Lys Ser Gln Trp Asn Asn Asp Asn
                740                 745                 750

Pro Leu Phe Lys Ser Ala Thr Thr Thr Val Met Asn Pro Lys Phe Ala
            755                 760                 765

Glu Ser
    770

<210> SEQ ID NO 21
<211> LENGTH: 3161
<212> TYPE: DNA
<213> ORGANISM: Rattus norvegicus

<400> SEQUENCE: 21
caccaccaca gagccagctg gtgagaagca ggcagagaca tctccagtca gtcagattca      60
cggattggag gcttcctggg accaagaggg gtacttgacc acctgagcca gccccccac     120 atccctccct gaggtagctg agtgacatct gtgctggccc tctctgatcc tcgtaccctg     180
tggcagcaag cctgcaagga ggaactcctt gggtgatcag cctggagtca tctggcccct     240

```
ctctccacag gacatgctgg gcccacacac actgctactc atcctagctg gactactctt      300
cctgggatct gccctgtccg aggaatgcac caagtacaaa gtcagcaact gccgggactg      360
tatccagtcg gggcctggct gctcgtggtg ccagaagctg aacttcaccg gaccagggga      420
gcctgactcc ttgcgctgtg acacgcgggc acagctgctc tcaagggtt gcccagccga       480
tgatataatg gaccccaaga gctttgctga tctccacccc caatatcagg tgcaacggag      540
tcaactgtct ccacaaaaag tgacccttaa cttgcgacca gggcaggctg ctgcattcaa      600
tgtgactttc cgacgggcca agggctaccc cattgatctg tactacctca tggacctctc      660
ctactctatg ctcgatgacc tgaacaatgt caagaagttg ggtggtgatt tgctgcaggc      720
cctcaacgag atcacagagt ccggccgcat cggcttcggg tccttcgtgg acaagacggt      780
gctgcctttt gtcaacaccc atcccgaaaa gctgaggaac ccatgcccca caaggagaa       840
agcctgccag cctccgtttg cctttcgcca cgtgctcaag ctaaccgaca actccaacca      900
gtttcagaca gaggtcggca agcaactgat ttccggaaac ctggacgccc tgagggcgg      960
gctggatgcc ataatgcaag tggctgcctg tccggaggaa attggctggc gcaatgtcac     1020
gaggctgctg gtgtttgcca cagacgacgg cttccacttt gccggtgatg ggaaactggg     1080
tgccatcctg accccaacg atggccgctg ccacctggag gataacatgt acaagaggag      1140
caatgagttc gactaccgt cagtgggcca gctggcccac aaactttccg agagcaacat      1200
ccagcccatc tttgcagtga caaagaagat ggtgaaaacc tatgagaaac tgacagagat     1260
tatccccaag tcagcggtgg gcgagctgtc tgacgattcc agtaacgtag tccagcttat     1320
caagaaagcc tactacaaac tctcctctag agtcttcctg gaccacacca ccatcccgga     1380
caccctgaaa gtcacctatg actccttctg taataacaga gtatcgagta taggcaaatc     1440
ccgaggggac tgtgacggtg tgcagatcaa caacccggtc accttccagg taaaggtcac     1500
ggcttcggag tgtatccagg agcagtcctt tgtcatccgg gcgctgggct tcaccgacac     1560
agtgacggta caggtccatc cccagtgcga gtgccagtgc cgggaccaga gtcggatgag     1620
gaatctctgt ggaggcaagg gagtcatgga gtgtggcatc tgcaggtgtg agtctggcta     1680
cattgggaaa aactgtgagt gtcagacgca gggccggagc agccaggagc tggaggggaa     1740
ctgccggaag gacaatagtt ccattgtgtg ctcggggctg ggggactgca tctgcgggca     1800
gtgcgtgtgc cacacgagtg acatccccaa caaagtgatc tttgggcaat actgcgagtg     1860
tgacaacttc aactgtgaga gatatgatgg ccaagtctgc ggtggcctaa agagaggctc     1920
ctgctcctgt ggccagtgta attgcaagga gggtttcgag ggttctgctt gccagtgtca     1980
gaggtctacc acgggctgtc tgaacgcacg gctggtggag tgcagtggcc gtggccggtg     2040
ccaatgcaac agatgcatct gtgagaaagg ttaccagcca cctctgtgtg aagagtgtcc     2100
cggctgcccc ttgccctgca gcacctacgt cttctgtgcc gagtgcctga atttgataa      2160
gggcccctt cagaagaatt gtagtgttca gtgtgccaat gtgacgctgc agactgtccc     2220
tttcaagaaa aagccctgca aggagaggga ctcggagggc tgctggataa cctacacttt     2280
gcagcagaag gacggaaacg cttacaacat ccatgtggac gacgatcgag agtgtgtgaa     2340
aggccccaac gtggctgcca tcatagggg cactgtggcc ggcgttgtac tgattggtgt     2400
cctcctcctg gtcatctgga aggctcttac ccacctgact gacctcaatg aatacagacg     2460
ctttgagaag gagaaactca gtcccagtg gaacaacgac aaccccctct tcaagagcgc     2520
cacgacaacg gtcatgaacc ctaagtttgc tgagagctag agaaggagtc agaggagacc     2580
```

-continued

```
cctccagacc atgcctcctc ccctctgcaa atagaatgta gcttacagct agccccagtg    2640
ctgccaagga tccaaaagcc tactttgttt ctttccgcca ttatatcaag gctgccaggg    2700
tttccacaga ctcatcttcc gacctataca atcttgccac agagcctgca gattgttccg    2760
gagtcccaag aggttccaca cacgttttcg tgcataaagg gaagacaggg gtctcagtaa    2820
aggtggcccc agcttattta tatttaaact tgttagcgta taaaactact attatattgt    2880
taacatcctg tccgttgtat tatatgtgag tgtaaaacta tatcccacat atatcagaat    2940
catgtgtgta aaataataaa agcttccatt cagggctgca gagatggctc agtggttaag    3000
agcactgact gctcttccag aggtcctgag ttcaattccc agcatccaca tggtggctca    3060
caaccatctg taatgggatc tgatgccctt gtctggtgtg gctgaagata gcaacagtgt    3120
actcacatac ataaaataaa taaagccttt taataaaaaa a                        3161
```

<210> SEQ ID NO 22
<211> LENGTH: 768
<212> TYPE: PRT
<213> ORGANISM: Rattus norvegicus

<400> SEQUENCE: 22

```
Met Leu Gly Pro His Thr Leu Leu Ile Leu Ala Gly Leu Leu Phe
1               5                   10                  15

Leu Gly Ser Ala Leu Ser Glu Glu Cys Thr Lys Tyr Lys Val Ser Asn
            20                  25                  30

Cys Arg Asp Cys Ile Gln Ser Gly Pro Gly Cys Ser Trp Cys Gln Lys
        35                  40                  45

Leu Asn Phe Thr Gly Pro Gly Glu Pro Asp Ser Leu Arg Cys Asp Thr
    50                  55                  60

Arg Ala Gln Leu Leu Lys Gly Cys Pro Ala Asp Asp Ile Met Asp
65                  70                  75                  80

Pro Lys Ser Phe Ala Asp Leu His Pro Gln Tyr Gln Val Gln Arg Ser
                85                  90                  95

Gln Leu Ser Pro Gln Lys Val Thr Leu Asn Leu Arg Pro Gly Gln Ala
            100                 105                 110

Ala Ala Phe Asn Val Thr Phe Arg Arg Ala Lys Gly Tyr Pro Ile Asp
        115                 120                 125

Leu Tyr Tyr Leu Met Asp Leu Ser Tyr Ser Met Leu Asp Asp Leu Asn
    130                 135                 140

Asn Val Lys Lys Leu Gly Gly Asp Leu Leu Gln Ala Leu Asn Glu Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Glu Lys Leu Arg Asn Pro Cys Pro
            180                 185                 190

Asn Lys Glu Lys Ala Cys Gln Pro Pro Phe Ala Phe Arg His Val Leu
        195                 200                 205

Lys Leu Thr Asp Asn Ser Asn Gln Phe Gln Thr Glu Val Gly Lys Gln
    210                 215                 220

Leu Ile Ser Gly Asn Leu Asp Ala Pro Glu Gly Gly Leu Asp Ala Ile
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270
```

-continued

```
Gly Lys Leu Gly Ala Ile Leu Thr Pro Asn Asp Gly Arg Cys His Leu
            275                 280                 285
Glu Asp Asn Met Tyr Lys Arg Ser Asn Glu Phe Asp Tyr Pro Ser Val
        290                 295                 300
Gly Gln Leu Ala His Lys Leu Ser Glu Ser Asn Ile Gln Pro Ile Phe
305                 310                 315                 320
Ala Val Thr Lys Lys Met Val Lys Thr Tyr Glu Lys Leu Thr Glu Ile
                325                 330                 335
Ile Pro Lys Ser Ala Val Gly Glu Leu Ser Asp Ser Ser Asn Val
            340                 345                 350
Val Gln Leu Ile Lys Lys Ala Tyr Tyr Lys Leu Ser Ser Arg Val Phe
        355                 360                 365
Leu Asp His Thr Thr Ile Pro Asp Thr Leu Lys Val Thr Tyr Asp Ser
    370                 375                 380
Phe Cys Asn Asn Arg Val Ser Ser Ile Gly Lys Ser Arg Gly Asp Cys
385                 390                 395                 400
Asp Gly Val Gln Ile Asn Asn Pro Val Thr Phe Gln Val Lys Val Thr
                405                 410                 415
Ala Ser Glu Cys Ile Gln Glu Gln Ser Phe Val Ile Arg Ala Leu Gly
            420                 425                 430
Phe Thr Asp Thr Val Thr Val Gln Val His Pro Gln Cys Glu Cys Gln
        435                 440                 445
Cys Arg Asp Gln Ser Arg Met Arg Asn Leu Cys Gly Lys Gly Val
    450                 455                 460
Met Glu Cys Gly Ile Cys Arg Cys Glu Ser Gly Tyr Ile Gly Lys Asn
465                 470                 475                 480
Cys Glu Cys Gln Thr Gln Gly Arg Ser Ser Gln Glu Leu Glu Gly Asn
                485                 490                 495
Cys Arg Lys Asp Asn Ser Ser Ile Val Cys Ser Gly Leu Gly Asp Cys
            500                 505                 510
Ile Cys Gly Gln Cys Val Cys His Thr Ser Asp Ile Pro Asn Lys Val
        515                 520                 525
Ile Phe Gly Gln Tyr Cys Glu Cys Asp Asn Phe Asn Cys Glu Arg Tyr
    530                 535                 540
Asp Gly Gln Val Cys Gly Gly Leu Lys Arg Gly Ser Cys Ser Cys Gly
545                 550                 555                 560
Gln Cys Asn Cys Lys Glu Gly Phe Glu Gly Ser Ala Cys Gln Cys Gln
                565                 570                 575
Arg Ser Thr Thr Gly Cys Leu Asn Ala Arg Leu Val Glu Cys Ser Gly
            580                 585                 590
Arg Gly Arg Cys Gln Cys Asn Arg Cys Ile Cys Glu Lys Gly Tyr Gln
        595                 600                 605
Pro Pro Leu Cys Glu Glu Cys Pro Gly Cys Pro Leu Pro Cys Ser Thr
    610                 615                 620
Tyr Val Phe Cys Ala Glu Cys Leu Lys Phe Asp Lys Gly Pro Phe Gln
625                 630                 635                 640
Lys Asn Cys Ser Val Gln Cys Ala Asn Val Thr Leu Gln Thr Val Pro
                645                 650                 655
Phe Lys Lys Lys Pro Cys Lys Glu Arg Asp Ser Glu Gly Cys Trp Ile
            660                 665                 670
Thr Tyr Thr Leu Gln Gln Lys Asp Gly Asn Ala Tyr Asn Ile His Val
        675                 680                 685
Asp Asp Asp Arg Glu Cys Val Lys Gly Pro Asn Val Ala Ala Ile Ile
```

```
                690            695            700
Gly Gly Thr Val Ala Gly Val Val Leu Ile Gly Val Leu Leu Leu Val
705                 710                 715                 720

Ile Trp Lys Ala Leu Thr His Leu Thr Asp Leu Asn Glu Tyr Arg Arg
            725                 730                 735

Phe Glu Lys Glu Lys Leu Lys Ser Gln Trp Asn Asn Asp Asn Pro Leu
                740                 745                 750

Phe Lys Ser Ala Thr Thr Thr Val Met Asn Pro Lys Phe Ala Glu Ser
            755                 760                 765

<210> SEQ ID NO 23
<211> LENGTH: 2929
<212> TYPE: DNA
<213> ORGANISM: Sus scrofa

<400> SEQUENCE: 23
```

| | | | | | |
|---|---|---|---|---|---|
| ggccttcgcc | agcagggcct | ctgcgggcgg | gtgtcttccc | agacgcgcac | gagacccagc | 60 |
| ctgccaaagg | gtggaactga | agcccccag | cccagccggg | accccctgcg | gaggtctcca | 120 |
| ggacatcaag | caggacatgc | tgtgccggtg | ctccccgctg | ctcctcctgg | tgggcctgct | 180 |
| cacccctccgg | tccgccctct | cccaggagtg | tgccaagtac | aaggtcagca | cctgccggga | 240 |
| ctgcattgag | tcgggacccg | gctgtgcctg | gtgccagaag | ctgaacttct | ctgggcaagg | 300 |
| ggagcccgac | tccgtccgct | gtgacacgcg | ggagcagctg | cttgcaaagg | ctgtgtcgc | 360 |
| ggatgacatc | gtggatccca | ggagcctggc | cgagacccag | aggaccagg | caggggcca | 420 |
| gaagcagctg | tccccacaga | aagtgacact | ctacctgaga | ccaggtcagg | cggccacgtt | 480 |
| caacgtgacc | ttccggcgcg | ccaagggcta | ccccatcgac | ctgtactacc | tgatggacct | 540 |
| gtcctactcc | atgctcgacg | acctcatcaa | cgtgaagaag | ctggggggcg | acctgctcag | 600 |
| ggctctcaac | gagatcaccg | agtctggccg | catcggcttt | gggtcttttcg | tggacaagac | 660 |
| ggtgcttccc | ttcgtcaaca | cgcacccga | gaagctgcgg | aacccctgcc | caacaaaga | 720 |
| gaaggagtgc | caggccccgt | tcgccttccg | acacgtgctc | aagctcacgg | acaactccaa | 780 |
| ccagttccag | acgaggtcg | ggaagcagct | gatctcgggg | aacctggacg | ccccgaggg | 840 |
| cgggctggat | gccatgatgc | aggtggccgc | gtgcccggag | gagatcggct | ggcgcaacgt | 900 |
| caccaggctg | ctggtgttcg | ccacggacga | tggcttccac | tttgcgggcg | acgggaagct | 960 |
| gggcgccatc | ctgacccca | atgacggccg | ctgccacctg | gaagacaact | tatacaaaag | 1020 |
| cagcaatgaa | ttcgactacc | catcagtggg | acagctggca | cacaaactgg | ccgaaagcaa | 1080 |
| catccagccc | atctttgccg | tgaccaagaa | aatggtgaaa | acgtatgaga | agctcacaga | 1140 |
| catcatcccc | aagtccgccg | tcggggagct | gtcggaggat | tccagcaacg | tcctggagct | 1200 |
| cattaagaac | gcctacaata | aactgtcctc | cagagtgttt | ttggatcaca | acgccctccc | 1260 |
| tgacaccctg | aaggtcacgt | acgactcctt | ctgcagcaac | ggggtgtcgc | aggtgaacca | 1320 |
| gcccagaggg | gactgcgacg | gcgtccagat | caacgtcccg | atcaccttcc | aggtgaaggt | 1380 |
| caccgcctcc | gagtgcatcc | aggagcagtc | gttcgtcatc | cgggcgctgg | gcttcaccga | 1440 |
| cacggtgacc | gtgcgggtgc | tccccagtg | tgagtgccgc | tgcggggaca | gcagcaagga | 1500 |
| gcgcacgctc | tgcggcaaca | agggctccat | ggagtgcggg | gtctgcaggt | gcgatgccgg | 1560 |
| ctacatcggg | aagcactgcg | agtgccagac | gcagggccgg | agcagccagg | agctggaagg | 1620 |
| aagctgccgc | aaggacaaca | gctccatcat | ctgctcgggg | ctgggcgact | gcatctgcgg | 1680 |
| gcagtgcgtg | tgccacacga | gcgacgtgcc | caacaagaag | atttacggcc | agttctgcga | 1740 |

-continued

```
gtgtgacaac atgaactgcg agcgcttcga tggccaagtc tgcggggggcg agaagcgggg    1800
cctctgcttc tgcagcacct gcaggtgcca agaaggtttc gagggctcgg cgtgccagtg    1860
cctcaagtcc acgcagggct gcctcaacct gcagggcgtc gagtgcagcg ccgcggccg     1920
gtgccgctgc aacgtgtgcc agtgtgactt tggctaccag ccgcccctgt gcaccgactg    1980
ccccagctgc caggtgccct gcgccgcta cgccaaatgc gccgagtgcc tgaagttcga    2040
caccggcccc ttcgccaaaa actgcagcgc ggagtgcggg accactaagc tgctgcccag    2100
ccggatgtcg ggccgcaagt gcaatgagcg ggactccgag ggctgctgga tgacctactt    2160
cctggtgcag cgcgacggcc gggacaacta cgacctgcac gtggaggaga cgcgcgagtg    2220
tgtgaaaggc cccaacatcg ccgccatcgt ggggggcacc gtgggggag tcgtgctcgt     2280
gggcatcttc ctgctggtca tctggaaggt cctgacccac ctgagtgacc tcagggagta    2340
caagcgcttc gagaaggaga agctcaagtc ccagtggaac aacgataacc ccttttcaa     2400
gagcgccacc acgacagtta tgaaccccaa gtttgctgag cgctaggggt gcttggtgaa    2460
gacaaggtct tctgctccgt ccagacgggg ccgcctcccc tccggcaggc tgaccgtgac    2520
cctgtctggc ggacccagct gacgtccccc caccccgac cccctcaaca tcagctgaaa     2580
acctgctctt ttccctgcgc cccaaatgac ggatctgttc agatgcttca atggactcat    2640
cggaagggac aatctcccgc ttctgagagg tgtgacttct ggtagccact tgaaaaagga    2700
ctcgcttgtg tctcgtaagg tcagacacct gtcttccttt gtaaaaatta gcacagcagt    2760
cagatggatg gagattccga tttatttata tgtgaactta tagggaatag aattgcattc    2820
ctgtgattat gctgtttcca atcatgtgca cggaaaaaaa tcgaataaat ctgcagaggc    2880
tcgctggggg ctgggctctg cgccccatct cagctgtgcc cacactccc                2929
```

<210> SEQ ID NO 24
<211> LENGTH: 769
<212> TYPE: PRT
<213> ORGANISM: Sus scrofa

<400> SEQUENCE: 24

```
Met Leu Cys Arg Cys Ser Pro Leu Leu Leu Val Gly Leu Leu Thr
1               5                   10                  15

Leu Arg Ser Ala Leu Ser Gln Glu Cys Ala Lys Tyr Lys Val Ser Thr
            20                  25                  30

Cys Arg Asp Cys Ile Glu Ser Gly Pro Gly Cys Ala Trp Cys Gln Lys
        35                  40                  45

Leu Asn Phe Ser Gly Gln Gly Glu Pro Asp Ser Val Arg Cys Asp Thr
    50                  55                  60

Arg Glu Gln Leu Leu Ala Lys Gly Cys Val Ala Asp Asp Ile Val Asp
65                  70                  75                  80

Pro Arg Ser Leu Ala Glu Thr Gln Glu Asp Gln Ala Gly Gly Gln Lys
                85                  90                  95

Gln Leu Ser Pro Gln Lys Val Thr Leu Tyr Leu Arg Pro Gly Gln Ala
            100                 105                 110

Ala Thr Phe Asn Val Thr Phe Arg Arg Ala Lys Gly Tyr Pro Ile Asp
        115                 120                 125

Leu Tyr Tyr Leu Met Asp Leu Ser Tyr Ser Met Leu Asp Asp Leu Ile
    130                 135                 140

Asn Val Lys Lys Leu Gly Gly Asp Leu Leu Arg Ala Leu Asn Glu Ile
145                 150                 155                 160
```

Thr Glu Ser Gly Arg Ile Gly Phe Gly Ser Phe Val Asp Lys Thr Val
                165                 170                 175

Leu Pro Phe Val Asn Thr His Pro Glu Lys Leu Arg Asn Pro Cys Pro
            180                 185                 190

Asn Lys Glu Lys Glu Cys Gln Ala Pro Phe Ala Phe Arg His Val Leu
        195                 200                 205

Lys Leu Thr Asp Asn Ser Asn Gln Phe Gln Thr Glu Val Gly Lys Gln
    210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
            245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
        275                 280                 285

Glu Asp Asn Leu Tyr Lys Ser Ser Asn Glu Phe Asp Tyr Pro Ser Val
    290                 295                 300

Gly Gln Leu Ala His Lys Leu Ala Glu Ser Asn Ile Gln Pro Ile Phe
305                 310                 315                 320

Ala Val Thr Lys Lys Met Val Lys Thr Tyr Glu Lys Leu Thr Asp Ile
            325                 330                 335

Ile Pro Lys Ser Ala Val Gly Glu Leu Ser Glu Asp Ser Ser Asn Val
            340                 345                 350

Leu Glu Leu Ile Lys Asn Ala Tyr Asn Lys Leu Ser Ser Arg Val Phe
        355                 360                 365

Leu Asp His Asn Ala Leu Pro Asp Thr Leu Lys Val Thr Tyr Asp Ser
    370                 375                 380

Phe Cys Ser Asn Gly Val Ser Gln Val Asn Gln Pro Arg Gly Asp Cys
385                 390                 395                 400

Asp Gly Val Gln Ile Asn Val Pro Ile Thr Phe Gln Val Lys Val Thr
            405                 410                 415

Ala Ser Glu Cys Ile Gln Glu Gln Ser Phe Val Ile Arg Ala Leu Gly
            420                 425                 430

Phe Thr Asp Thr Val Thr Val Arg Val Leu Pro Gln Cys Glu Cys Arg
        435                 440                 445

Cys Gly Asp Ser Ser Lys Glu Arg Thr Leu Cys Gly Asn Lys Gly Ser
    450                 455                 460

Met Glu Cys Gly Val Cys Arg Cys Asp Ala Gly Tyr Ile Gly Lys His
465                 470                 475                 480

Cys Glu Cys Gln Thr Gln Gly Arg Ser Ser Gln Glu Leu Glu Gly Ser
            485                 490                 495

Cys Arg Lys Asp Asn Ser Ser Ile Ile Cys Ser Gly Leu Gly Asp Cys
            500                 505                 510

Ile Cys Gly Gln Cys Val Cys His Thr Ser Asp Val Pro Asn Lys Lys
        515                 520                 525

Ile Tyr Gly Gln Phe Cys Glu Cys Asp Asn Met Asn Cys Glu Arg Phe
    530                 535                 540

Asp Gly Gln Val Cys Gly Gly Glu Lys Arg Gly Leu Cys Phe Cys Ser
545                 550                 555                 560

Thr Cys Arg Cys Gln Glu Gly Phe Glu Gly Ser Ala Cys Gln Cys Leu
            565                 570                 575

Lys Ser Thr Gln Gly Cys Leu Asn Leu Gln Gly Val Glu Cys Ser Gly

```
             580             585              590
Arg Gly Arg Cys Arg Cys Asn Val Cys Gln Cys Asp Phe Gly Tyr Gln
            595              600              605

Pro Pro Leu Cys Thr Asp Cys Pro Ser Cys Gln Val Pro Cys Ala Arg
            610              615              620

Tyr Ala Lys Cys Ala Glu Cys Leu Lys Phe Asp Thr Gly Pro Phe Ala
625              630              635              640

Lys Asn Cys Ser Ala Glu Cys Gly Thr Thr Lys Leu Leu Pro Ser Arg
                 645              650              655

Met Ser Gly Arg Lys Cys Asn Glu Arg Asp Ser Glu Gly Cys Trp Met
            660              665              670

Thr Tyr Phe Leu Val Gln Arg Asp Gly Arg Asp Asn Tyr Asp Leu His
            675              680              685

Val Glu Glu Thr Arg Glu Cys Val Lys Gly Pro Asn Ile Ala Ala Ile
            690              695              700

Val Gly Gly Thr Val Gly Gly Val Val Leu Val Gly Ile Phe Leu Leu
705              710              715              720

Val Ile Trp Lys Val Leu Thr His Leu Ser Asp Leu Arg Glu Tyr Lys
                 725              730              735

Arg Phe Glu Lys Glu Lys Leu Lys Ser Gln Trp Asn Asn Asp Asn Pro
            740              745              750

Leu Phe Lys Ser Ala Thr Thr Thr Val Met Asn Pro Lys Phe Ala Glu
            755              760              765

Arg

<210> SEQ ID NO 25
<211> LENGTH: 2365
<212> TYPE: DNA
<213> ORGANISM: Pan troglodytes

<400> SEQUENCE: 25
ccaggagcac cgccgaggac tccagagcac caagggacat gctgggcctg cgcccccac      60 tgctcgccct ggtggggctg ctctccctcg ggtgcgtcct ctctcaggag tgcacgaagt     120
tcaaggtcag cagctgccgg gaatgcatcg agtcggggcc cggctgcacc tggtgccaga    180
agctgaactt cacagggccg ggggatcctg actccattcg ctgcgacacc cggccacagc    240
tgctcatgag gggctgtgcg gctgacgaca tcatggaccc caagagcctc gctgaaaccc    300
aggaagacca caatgggggc cagaagcagc tgtccccaca aaagtgacg ctttacctgc     360 gaccaggcca ggcagcagcg ttcaacgtga ccttccggcg ggccaagggc taccccatcg    420
acctgtacta cctgatggac ctctcctact ccatgcttga tgacctcagg aatgtcaaga    480
agctgggggg cgacctgcta cgggccctca cgagatcac cgagtccggc cgcattggct     540
tcgggtcctt cgtggacaag accgtgctgc cgttcgtgaa cacgcaccct gataagctgc    600
gaaacccatg cccaacaag gagaaggagt gccagccccc gtttgccttc aggcacgtgc     660
tgaagctgac caacaactcc agccagtttc agaccgaggt cgggaagcag ctgatttccg    720
gaaacctgga cgcacccgag ggtgggctgg atgccatgat gcaggtcgcc gcctgcccgg    780
aggaaatcgg ctggcgcaac gtcacgcggc tgctggtgtt tgccaccgat gacggcttcc    840
atttcgcggg cgacgggaag ctgggcgcca tcctgacccc caacgacggc cgctgtcacc    900
tggaggacaa cttgtacaag aggagcaacg aattcgacta cccatcggtg ggccagctgg    960
cgcacaagct ggctgaaaac aacatccagc ccatcttcgc ggtgaccagt aggatggtga   1020
```

| | | |
|---|---|---|
| agacctacga gaaactcacc gagatcatcc ccaagtcagc cgtgggggag ctgtctgagg | 1080 |
| actccagcaa tgtggtccat ctcattaaga atgcttacaa taaactctcc tccagggtct | 1140 |
| tcctggatca caacgccctc cccgacaccc tgaaagtcac ctatgactcc ttctgcagca | 1200 |
| atggagtgac gcacaggaac cagcccgag gtgactgtga tggcgtgcag atcaatgtcc | 1260 |
| cgatcacctt ccaggtgaag gtcacggcca cagagtgtat ccaggagcag tcatttgtca | 1320 |
| tccgggcgct gggcttcacg gacatagtga ccgtgcgggt ccttccccag tgcgagtgcc | 1380 |
| ggtgccggga ccagagcaga gaccgcagcc tctgccatgg caagggcttc ttggagtgcg | 1440 |
| gcatctgcag gtgtgacact ggctacattg ggaaaaactg tgagtgccag acacagggcc | 1500 |
| ggagcagcca ggagctggaa ggaagctgcc ggaaggacaa caactccatc atctgctcag | 1560 |
| ggctggggga ctgtgtctgc gggcagtgcc tgtgccacac cagcgacgtc cccggcaagc | 1620 |
| tgatatacgg gcagtactgc gagtgtgaca ccatcaactg tgagcgctac aacggccagg | 1680 |
| tctgcggtgg cccggggagg gggctctgct tctgcgggaa gtgccgctgc cacccgggct | 1740 |
| ttgagggctc agcgtgccag tgcgagagga ccaccgaggg ctgcctgaac ccgcggcgtg | 1800 |
| ttgagtgcag tggccgtggc cggtgccgct gcaacgtatg tgagtgccat tcaggctacc | 1860 |
| agctgcctct gtgccaggag tgccccggct gcccctcacc ctgtggcaag tacatctcct | 1920 |
| gtgccgagtg cctgaagttc gaaaagggcc cctttgggaa gaactgcagc gcggcgtgtc | 1980 |
| cgggcctgca gctgtcgaac aacccgtga agggcaggac ctgcaaggag agggactcag | 2040 |
| agggctgctg ggtggcctac acgctggagc agcaggacgg gatggaccgc tacctcatct | 2100 |
| atgtggatga gagccgagag tgcgtggcag gccccaacat cgctgccatt gtcgggggca | 2160 |
| ccgtggcagg catcgtgctg atcggcatcc tcctgctggt catctggaag gctctgatcc | 2220 |
| acctgagcga cctccgggag tacaggcgct ttgagaagga gaagctcaag tcccagtgga | 2280 |
| acaatgataa tccccttttc aagagcgcca ccacgacggt catgaaccct aagtttgctg | 2340 |
| agagttagga gcacttggtg aagac | 2365 |

<210> SEQ ID NO 26
<211> LENGTH: 769
<212> TYPE: PRT
<213> ORGANISM: Pan troglodytes

<400> SEQUENCE: 26

```
Met Leu Gly Leu Arg Pro Pro Leu Leu Ala Leu Val Gly Leu Leu Ser
1               5                   10                  15

Leu Gly Cys Val Leu Ser Gln Glu Cys Thr Lys Phe Lys Val Ser Ser
                20                  25                  30

Cys Arg Glu Cys Ile Glu Ser Gly Pro Gly Cys Thr Trp Cys Gln Lys
            35                  40                  45

Leu Asn Phe Thr Gly Pro Gly Asp Pro Asp Ser Ile Arg Cys Asp Thr
        50                  55                  60

Arg Pro Gln Leu Leu Met Arg Gly Cys Ala Ala Asp Asp Ile Met Asp
65                  70                  75                  80

Pro Lys Ser Leu Ala Glu Thr Gln Glu Asp His Asn Gly Gly Gln Lys
                85                  90                  95

Gln Leu Ser Pro Gln Lys Val Thr Leu Tyr Leu Arg Pro Gly Gln Ala
                100                 105                 110

Ala Ala Phe Asn Val Thr Phe Arg Arg Ala Lys Gly Tyr Pro Ile Asp
            115                 120                 125

Leu Tyr Tyr Leu Met Asp Leu Ser Tyr Ser Met Leu Asp Asp Leu Arg
```

```
            130             135             140
Asn Val Lys Lys Leu Gly Gly Asp Leu Leu Arg Ala Leu Asn Glu Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Asp Lys Leu Arg Asn Pro Cys Pro
            180                 185                 190

Asn Lys Glu Lys Glu Cys Gln Pro Pro Phe Ala Phe Arg His Val Leu
            195                 200                 205

Lys Leu Thr Asn Asn Ser Ser Gln Phe Gln Thr Glu Val Gly Lys Gln
            210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
            275                 280                 285

Glu Asp Asn Leu Tyr Lys Arg Ser Asn Glu Phe Asp Tyr Pro Ser Val
290                 295                 300

Gly Gln Leu Ala His Lys Leu Ala Glu Asn Asn Ile Gln Pro Ile Phe
305                 310                 315                 320

Ala Val Thr Ser Arg Met Val Lys Thr Tyr Glu Lys Leu Thr Glu Ile
                325                 330                 335

Ile Pro Lys Ser Ala Val Gly Glu Leu Ser Glu Asp Ser Ser Asn Val
            340                 345                 350

Val His Leu Ile Lys Asn Ala Tyr Asn Lys Leu Ser Ser Arg Val Phe
            355                 360                 365

Leu Asp His Asn Ala Leu Pro Asp Thr Leu Lys Val Thr Tyr Asp Ser
            370                 375                 380

Phe Cys Ser Asn Gly Val Thr His Arg Asn Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Glu Gln Ser Phe Val Ile Arg Ala Leu Gly
            420                 425                 430

Phe Thr Asp Ile Val Thr Val Arg Val Leu Pro Gln Cys Glu Cys Arg
            435                 440                 445

Cys Arg Asp Gln Ser Arg Asp Arg Ser Leu Cys His Gly Lys Gly Phe
            450                 455                 460

Leu Glu Cys Gly Ile Cys Arg Cys Asp Thr Gly Tyr Ile Gly Lys Asn
465                 470                 475                 480

Cys Glu Cys Gln Thr Gln Gly Arg Ser Ser Gln Glu Leu Glu Gly Ser
                485                 490                 495

Cys Arg Lys Asp Asn Asn Ser Ile Ile Cys Ser Gly Leu Gly Asp Cys
            500                 505                 510

Val Cys Gly Gln Cys Leu Cys His Thr Ser Asp Val Pro Gly Lys Leu
            515                 520                 525

Ile Tyr Gly Gln Tyr Cys Glu Cys Asp Thr Ile Asn Cys Glu Arg Tyr
            530                 535                 540

Asn Gly Gln Val Cys Gly Gly Pro Gly Arg Gly Leu Cys Phe Cys Gly
545                 550                 555                 560
```

```
Lys Cys Arg Cys His Pro Gly Phe Glu Gly Ser Ala Cys Gln Cys Glu
                565                 570                 575
Arg Thr Thr Glu Gly Cys Leu Asn Pro Arg Arg Val Glu Cys Ser Gly
            580                 585                 590
Arg Gly Arg Cys Arg Cys Asn Val Cys Glu Cys His Ser Gly Tyr Gln
        595                 600                 605
Leu Pro Leu Cys Gln Glu Cys Pro Gly Cys Pro Ser Pro Cys Gly Lys
    610                 615                 620
Tyr Ile Ser Cys Ala Glu Cys Leu Lys Phe Glu Lys Gly Pro Phe Gly
625                 630                 635                 640
Lys Asn Cys Ser Ala Ala Cys Pro Gly Leu Gln Leu Ser Asn Asn Pro
                645                 650                 655
Val Lys Gly Arg Thr Cys Lys Glu Arg Asp Ser Glu Gly Cys Trp Val
            660                 665                 670
Ala Tyr Thr Leu Glu Gln Gln Asp Gly Met Asp Arg Tyr Leu Ile Tyr
        675                 680                 685
Val Asp Glu Ser Arg Glu Cys Val Ala Gly Pro Asn Ile Ala Ala Ile
    690                 695                 700
Val Gly Gly Thr Val Ala Gly Ile Val Leu Ile Gly Ile Leu Leu Leu
705                 710                 715                 720
Val Ile Trp Lys Ala Leu Ile His Leu Ser Asp Leu Arg Glu Tyr Arg
                725                 730                 735
Arg Phe Glu Lys Glu Lys Leu Lys Ser Gln Trp Asn Asn Asp Asn Pro
            740                 745                 750
Leu Phe Lys Ser Ala Thr Thr Thr Val Met Asn Pro Lys Phe Ala Glu
        755                 760                 765
Ser

<210> SEQ ID NO 27
<211> LENGTH: 75
<212> TYPE: DNA
<213> ORGANISM: Artificial Sequence
<220> FEATURE:
<223> OTHER INFORMATION: DNA sequence that encodes the wildtype 25 aa
      peptide

<400> SEQUENCE: 27
atgctgcgcc agcgccccca gctgctgctc ctagcgggcc tgcttgccct ccagtccgtc      60
ctgtcccagg agtgc                                                        75

<210> SEQ ID NO 28
<211> LENGTH: 25
<212> TYPE: PRT
<213> ORGANISM: Artificial Sequence
<220> FEATURE:
<223> OTHER INFORMATION: 25 mer peptide of the signal sequence from CD18
      cattle/bison protein

<400> SEQUENCE: 28

Met Leu Arg Gln Arg Pro Gln Leu Leu Leu Leu Ala Gly Leu Leu Ala
1               5                   10                  15
Leu Gln Ser Val Leu Ser Gln Glu Cys
            20                  25

<210> SEQ ID NO 29
<211> LENGTH: 75
<212> TYPE: DNA
<213> ORGANISM: Artificial Sequence
```

```
<220> FEATURE:
<223> OTHER INFORMATION: peptide containing CD18 signal sequence water
      buffalo

<400> SEQUENCE: 29
atgctgcgcc agcgccccca gctgctgttc ctatcgggcc tgctcgccct ccagtccgtc    60
ctgtcccagg agtgc                                                      75

<210> SEQ ID NO 30
<211> LENGTH: 25
<212> TYPE: PRT
<213> ORGANISM: Artificial Sequence
<220> FEATURE:
<223> OTHER INFORMATION: peptide containing the CD18 signal sequence
      from water buffalo protein

<400> SEQUENCE: 30

Met Leu Arg Gln Arg Pro Gln Leu Leu Phe Leu Ser Gly Leu Leu Ala
1               5                   10                  15

Leu Gln Ser Val Leu Ser Gln Glu Cys
            20                  25

<210> SEQ ID NO 31
<211> LENGTH: 75
<212> TYPE: DNA
<213> ORGANISM: Artificial Sequence
<220> FEATURE:
<223> OTHER INFORMATION: peptide of CD18 signal sequence from goat mRNA

<400> SEQUENCE: 31
atgctgcccc agcgccccca gctgctgctc ctagcaggcc tgctcgccct ccagtctgtc    60
ctgtcccagg agtgc                                                      75

<210> SEQ ID NO 32
<211> LENGTH: 25
<212> TYPE: PRT
<213> ORGANISM: Artificial Sequence
<220> FEATURE:
<223> OTHER INFORMATION: peptide containing CD18 signal sequence goat
      protein

<400> SEQUENCE: 32

Met Leu Pro Gln Arg Pro Gln Leu Leu Leu Leu Ala Gly Leu Leu Ala
1               5                   10                  15

Leu Gln Ser Val Leu Ser Gln Glu Cys
            20                  25

<210> SEQ ID NO 33
<211> LENGTH: 75
<212> TYPE: DNA
<213> ORGANISM: Artificial Sequence
<220> FEATURE:
<223> OTHER INFORMATION: peptide of CD18 signal sequence sheep mRNA

<400> SEQUENCE: 33
atgctgcccc agcgccccca gctgctgctc ctagcgggcc tgctctccct ccagtccgtc    60
ctgtcccagg agtgc                                                      75

<210> SEQ ID NO 34
<211> LENGTH: 25
<212> TYPE: PRT
<213> ORGANISM: Artificial Sequence
<220> FEATURE:
<223> OTHER INFORMATION: peptide containing CD18 signal sequence sheep
``` protein

<400> SEQUENCE: 34

Met Leu Pro Gln Arg Pro Gln Leu Leu Leu Ala Gly Leu Leu Ser
1               5                   10                  15

Leu Gln Ser Val Leu Ser Gln Glu Cys
            20                  25

<210> SEQ ID NO 35
<211> LENGTH: 75
<212> TYPE: DNA
<213> ORGANISM: Artificial Sequence
<220> FEATURE:
<223> OTHER INFORMATION: peptide containing CD 18 signal sequence deer m

<400> SEQUENCE: 35
atgctgcgcc agcgccccca gctgctgctc ctagcaggcc tgctagccct ccagtctgtc     60
cggtcccagg agtgc                                                      75

<210> SEQ ID NO 36
<211> LENGTH: 25
<212> TYPE: PRT
<213> ORGANISM: Artificial Sequence
<220> FEATURE:
<223> OTHER INFORMATION: peptide of CD18 signal peptide deer protein

<400> SEQUENCE: 36

Met Leu Arg Gln Arg Pro Gln Leu Leu Leu Ala Gly Leu Leu Ala
1               5                   10                  15

Leu Gln Ser Val Arg Ser Gln Glu Cys
            20                  25

<210> SEQ ID NO 37
<211> LENGTH: 75
<212> TYPE: DNA
<213> ORGANISM: Artificial Sequence
<220> FEATURE:
<223> OTHER INFORMATION: peptide containing CD18 signal sequence elk
      mRNA sequence

<400> SEQUENCE: 37
atgctgcgcc agcgccccca gctgctgctc ctagcgggcc tgctagccct ccagtctgtc     60
cagtcccagg agtgc                                                      75

<210> SEQ ID NO 38
<211> LENGTH: 25
<212> TYPE: PRT
<213> ORGANISM: Artificial Sequence
<220> FEATURE:
<223> OTHER INFORMATION: peptide containing CD18 signal sequence elk
      protein

<400> SEQUENCE: 38

Met Leu Arg Gln Arg Pro Gln Leu Leu Leu Ala Gly Leu Leu Ala
1               5                   10                  15

Leu Gln Ser Val Gln Ser Gln Glu Cys
            20                  25

<210> SEQ ID NO 39
<211> LENGTH: 75
<212> TYPE: DNA
<213> ORGANISM: Artificial Sequence
<220> FEATURE:
<223> OTHER INFORMATION: peptide containing CD18 signal sequence human/chimp mRNA

<400> SEQUENCE: 39
atgctgggcc tgcgcccccc actgctcgcc ctggtggggc tgctctccct cgggtgcgtc    60
ctctctcagg agtgc                                                     75

<210> SEQ ID NO 40
<211> LENGTH: 25
<212> TYPE: PRT
<213> ORGANISM: Artificial Sequence
<220> FEATURE:
<223> OTHER INFORMATION: peptide contains CD18 signal sequence
      human/chimp protein

<400> SEQUENCE: 40

Met Leu Gly Leu Arg Pro Pro Leu Leu Ala Leu Val Gly Leu Leu Ser
1               5                   10                  15
Leu Gly Cys Val Leu Ser Gln Glu Cys
            20                  25

<210> SEQ ID NO 41
<211> LENGTH: 75
<212> TYPE: DNA
<213> ORGANISM: Artificial Sequence
<220> FEATURE:
<223> OTHER INFORMATION: peptide of CD18 signal sequence mouse protein

<400> SEQUENCE: 41
atgctgggcc cacactcact gctgcttgcc ctagctggac tgttcttcct gggatctgct    60
gtgtcccagg aatgc                                                     75

<210> SEQ ID NO 42
<211> LENGTH: 25
<212> TYPE: PRT
<213> ORGANISM: Artificial Sequence
<220> FEATURE:
<223> OTHER INFORMATION: peptide containing CD18 signal sequence mouse
      protein

<400> SEQUENCE: 42

Met Leu Gly Pro His Ser Leu Leu Leu Ala Leu Ala Gly Leu Phe Phe
1               5                   10                  15
Leu Gly Ser Ala Val Ser Gln Glu Cys
            20                  25

<210> SEQ ID NO 43
<211> LENGTH: 75
<212> TYPE: DNA
<213> ORGANISM: Artificial Sequence
<220> FEATURE:
<223> OTHER INFORMATION: peptide containing CD18 signal sequence rat
      mRNA

<400> SEQUENCE: 43
atgctgggcc cacacacact gctactcatc ctagctggac tactcttcct gggatctgcc    60
ctgtccgagg aatgc                                                     75

<210> SEQ ID NO 44
<211> LENGTH: 25
<212> TYPE: PRT
<213> ORGANISM: Artificial Sequence
<220> FEATURE:
<223> OTHER INFORMATION: peptide containing CD18 signal sequence rat
      protein

<400> SEQUENCE: 44

Met Leu Gly Pro His Thr Leu Leu Leu Ile Leu Ala Gly Leu Leu Phe
1               5                   10                  15

Leu Gly Ser Ala Leu Ser Glu Glu Cys
            20                  25

<210> SEQ ID NO 45
<211> LENGTH: 75
<212> TYPE: DNA
<213> ORGANISM: Artificial Sequence
<220> FEATURE:
<223> OTHER INFORMATION: peptide containing CD18 signal sequence pig
      mRNA

<400> SEQUENCE: 45
atgctgtgcc ggtgctcccc gctgctcctc ctggtgggcc tgctcaccct ccggtccgcc    60
ctctcccagg agtgt                                                     75

<210> SEQ ID NO 46
<211> LENGTH: 25
<212> TYPE: PRT
<213> ORGANISM: Artificial Sequence
<220> FEATURE:
<223> OTHER INFORMATION: peptide containing CD18 signal sequence pig
      protein

<400> SEQUENCE: 46

Met Leu Cys Arg Cys Ser Pro Leu Leu Leu Val Gly Leu Leu Thr
1               5                   10                  15

Leu Arg Ser Ala Leu Ser Gln Glu Cys
            20                  25

<210> SEQ ID NO 47
<211> LENGTH: 75
<212> TYPE: DNA
<213> ORGANISM: Artificial Sequence
<220> FEATURE:
<223> OTHER INFORMATION: mutated peptide of CD18 signal sequence from
      human/chimp mRNA

<400> SEQUENCE: 47
atgctgggcc tgcgcccccc actgctcgcc ctggtggggc tgctctccct ccagtgcgtc    60
ctctctcagg agtgc                                                     75

<210> SEQ ID NO 48
<211> LENGTH: 25
<212> TYPE: PRT
<213> ORGANISM: Artificial Sequence
<220> FEATURE:
<223> OTHER INFORMATION: mutated peptide of CD18 signal sequence from
      human/chimp protein

<400> SEQUENCE: 48

Met Leu Gly Leu Arg Pro Pro Leu Leu Ala Leu Val Gly Leu Leu Ser
1               5                   10                  15

Leu Gln Cys Val Leu Ser Gln Glu Cys
            20                  25

<210> SEQ ID NO 49
<211> LENGTH: 75
<212> TYPE: DNA
<213> ORGANISM: Artificial Sequence
<220> FEATURE:

<223> OTHER INFORMATION: mutated peptide of CD18 signal sequence from
     mouse mRNA

<400> SEQUENCE: 49
atgctgggcc cacactcact gctgcttgcc ctagctggac tgttcttcct gcaatctgct    60
gtgtcccagg aatgc    75

<210> SEQ ID NO 50
<211> LENGTH: 25
<212> TYPE: PRT
<213> ORGANISM: Artificial Sequence
<220> FEATURE:
<223> OTHER INFORMATION: mutated peptide of CD18 signal sequence from
     mouse protein

<400> SEQUENCE: 50

Met Leu Gly Pro His Ser Leu Leu Leu Ala Leu Ala Gly Leu Phe Phe
1               5                   10                  15

Leu Gln Ser Ala Val Ser Gln Glu Cys
            20                  25

<210> SEQ ID NO 51
<211> LENGTH: 75
<212> TYPE: DNA
<213> ORGANISM: Artificial Sequence
<220> FEATURE:
<223> OTHER INFORMATION: mutated peptide of CD18 signal sequence rat
     mRNA

<400> SEQUENCE: 51
atgctgggcc cacacacact gctactcatc ctagctggac tactcttcct gcaatctgcc    60
ctgtccgagg aatgc    75

<210> SEQ ID NO 52
<211> LENGTH: 25
<212> TYPE: PRT
<213> ORGANISM: Artificial Sequence
<220> FEATURE:
<223> OTHER INFORMATION: mutated peptide of CD18 signal sequence from
     rat protein

<400> SEQUENCE: 52

Met Leu Gly Pro His Thr Leu Leu Leu Ile Leu Ala Gly Leu Leu Phe
1               5                   10                  15

Leu Gln Ser Ala Leu Ser Glu Glu Cys
            20                  25

<210> SEQ ID NO 53
<211> LENGTH: 75
<212> TYPE: DNA
<213> ORGANISM: Artificial Sequence
<220> FEATURE:
<223> OTHER INFORMATION: mutated peptide of CD18 sig seq pig mRNA

<400> SEQUENCE: 53
atgctgtgcc ggtgctcccc gctgctcctc ctggtgggcc tgctcaccct ccaatccgcc    60
ctctcccagg agtgt    75

<210> SEQ ID NO 54
<211> LENGTH: 25
<212> TYPE: PRT
<213> ORGANISM: Artificial Sequence
<220> FEATURE:
<223> OTHER INFORMATION: mutated peptide of CD18 signal sequence from pig protein

<400> SEQUENCE: 54

Met Leu Cys Arg Cys Ser Pro Leu Leu Leu Val Gly Leu Leu Thr
1               5                   10                  15

Leu Gln Ser Ala Leu Ser Gln Glu Cys
            20                  25

<210> SEQ ID NO 55
<211> LENGTH: 2817
<212> TYPE: DNA
<213> ORGANISM: Artificial Sequence
<220> FEATURE:
<223> OTHER INFORMATION: mutated CD18 protein cow mRNA

<400> SEQUENCE: 55

| | | | | | |
|---|---|---|---|---|---|
| gtcttcccag | atccgcgaag | caccagcctg | gtgaagagca | gagccgaagc | cctgccagt | 60 |
| ccagctggga | cacccctgcc | gaggtctcca | gggcatccag | gggacatgct | gcgccagcgc | 120 |
| ccccagctgc | tgctcctagc | gggcctgctt | gccctcgggt | ccgtcctgtc | ccaggagtgc | 180 |
| accaactaca | aggtcagcac | ctgccgggac | tgcatcgagt | cgggccccgg | ctgcgcctgg | 240 |
| tgccagaaac | tgaacttcac | agggcaaggg | gagcccgact | ccattcgctg | tgacacacga | 300 |
| gcggagctgc | tgtcaaaggg | ctgcccagct | gatgacatca | tggaacccaa | gagcctcgct | 360 |
| gagacccggg | acagccaggc | gggcagtcgg | aagcagctgt | ccccacagga | agtgacgctc | 420 |
| tacctgagac | aggtcaggc | agttgcgttc | aacgtgacct | tccggagggc | caagggctac | 480 |
| cccatcgacc | tgtactacct | gatggacctc | tcctactcca | tggtggatga | cctcgtcaac | 540 |
| gtcaagaagc | tgggggggtga | cctgctccgg | gccctcaatg | gcatcaccga | gtcgggccgc | 600 |
| attggtttcg | ggtccttcgt | ggacaagacg | gtgctcccct | tcgtcaacac | gcaccccgag | 660 |
| aagctgcgga | acccctgccc | caacaaggag | aaggagtgcc | agccccgtt | cgccttcagg | 720 |
| cacgtgttga | agctcactga | caactccaaa | cagttcgaga | cagaagtcgg | gaagcagctg | 780 |
| atctcgggga | acctggacgc | ccctgagggt | gggctggacg | ccatgatgca | ggtggccgcg | 840 |
| tgccccgagg | aaatcggctg | gcgcaatgtc | accaggctgc | tggtgttcgc | cacggacgat | 900 |
| gggttccact | tgcgggcga | tggaaagctg | ggtgccatcc | tcaccccaa | tgacggccgc | 960 |
| tgccacctgg | aagacaacct | gtacaaaagc | agcaacgaat | ttgactaccc | atcggtgggc | 1020 |
| cagctggcac | acaaactggc | agaaagcaac | atccagccca | tctttgcagt | aaccaagaag | 1080 |
| atggtgaaaa | cgtacgagaa | gctgacgag | atcatcccca | gtctgcagt | cggggagctg | 1140 |
| tctgaagatt | ccaggaacgt | ggtggagctt | atcaagaatg | cctacaataa | actgtcctcc | 1200 |
| agagtcttcc | tggatcacag | caccctccct | gacaccctga | agtcaccta | cgactccttc | 1260 |
| tgcagtaacg | ggaaatcgca | ggtggaccag | cccagagggg | actgcgacgg | cgtccagatc | 1320 |
| aacgtcccga | tcaccttcca | ggtgaaggtc | acagccaccg | agtgcatcca | gcagcagtcc | 1380 |
| ttcaccatcc | gggcgctggg | cttcacggac | acggtgaccg | tgcgggtcct | cccccagtgc | 1440 |
| gagtgccaat | gccgggacgc | cagcagggac | ggcagcatct | gcggcggcag | aggctcgatg | 1500 |
| gagtgcggcg | tctgcaggtg | tgacgccggc | tacatcggga | agaactgcga | gtgccagacg | 1560 |
| cagggccgga | gcagccagga | gctggagggc | agctgccgca | aggacaacag | ctccatcatc | 1620 |
| tgctcggggc | tggggactg | catctgcggg | cagtgcgtgt | gccacacgag | cgacgtgccc | 1680 |
| aacaagaaga | tctacggcca | gttctgcgag | tgcgacaacg | tcaactgcga | acgctacgac | 1740 |
| ggccaagtct | gcggggggcga | aaagaggggg | ctctgcttct | gcggcacctg | caggtgcgac | 1800 |

```
gagcagtatg agggttcggc atgccagtgc ctcaagtcca ctcagggctg cctcaacttg    1860
gacggcgtcg agtgcagcgg ccgcggccga tgccgctgca atgtgtgcca gtgcgacccc    1920
ggctaccagc cgcccctgtg cagcgagtgc ccgggctgcc ccgtgccctg tgcgggcttc    1980 gcccctgca cagagtgcct gaagttcgac aagggcccct cgccaagaa ctgcagcgca     2040 gcgtgcgggc agacgaagct gctgtccagc ccggtgcccg ccgcaagtg caaggagcgc    2100 gactccgagg gctgctggat gacctacacc ctggtgcagc gcgacgggcg ggacagatac    2160
gacgtgcacg tggacgacat gctcgagtgt gtgaagggcc ccaacatcgc tgccatcgtg    2220
gggggcaccg tgggggcgt cgtgctcgtc ggcatcctcc tgctggtcat ctggaaggcc    2280
ctgacacacc tgagcgacct cagggagtac atcgctttg agaaggagaa gctcaagtcc    2340
cagtggaaca cgataaccc tcttttcaag agtgccacca cgacagtcat gaaccctaag    2400
tttgccgaga gttaggggtg cccggtgaag acaaggcctt ctgcaccacc cagatgggaa    2460
caccccctct ccacgtcccc tccagcaggc tgaccgtgac cccgctgcct cgtggacgtg    2520
gctgacaact tcaccgttaa ccaaaaatgc actgcttttt ctgccccaga atgatgggcg    2580
tggccaggtt attctatggg ctcatggtaa gggccagcct acccccttctg atatgaatga    2640 cttttgatag caagtcagag aaggaattgc ctacattttg tatggttaca cacaggtcct    2700
ttgtaaaaat tagtacagca gtctgatgaa gaattattta tgtgtgaact tctcagggta    2760
tgaagttaca tccccttggt tatgctgccc ccaatcaata aaaaaaaaa aatcaat       2817
```

<210> SEQ ID NO 56
<211> LENGTH: 2315
<212> TYPE: DNA
<213> ORGANISM: Artificial Sequence
<220> FEATURE:
<223> OTHER INFORMATION: mutated CD18 protein water buffalo mRNA

<400> SEQUENCE: 56

```
atgctgcgcc agcgcccca gctgctgttc ctatcgggcc tgctcgccct cgggtccgtc      60
ctgtcccagg agtgcaccaa gtacaaggtc agcacctgcc gggactgcat cgagtctggc    120
cccggctgcg cctggtgcca gaaactgaac ttcacagggc aagggggagcc tgactccctt    180 cgctgtgaca cacggcgga gctgctgtca aagggctgcc cagctgatga catcatggaa    240
cccaagagcc ttgctgagac ccgggacagc caggcggaca gacagaagca gctgtcccca    300
caggaagtga cgctctacct gagaccaggt caggcagctg cgttcaacgt gaccttccgg    360
agggccaagg gctacccat cgacctgtac tacctgatgg acctctccta ctccatggtg    420
gacgacctca tcaacgtcaa gaagctgggg ggtgacctgc tccgggccct caacgacatc    480
accgagtcgg gccgcattgg tttcgggtcc ttcgtggaca gacggtgct cccattcgtc    540 aacacgcacc ccgagaagct gcggaacccc tgccccaaca aggagaagga gtgccagccc    600
ccgttcgcct tcaggcacgt gttgaagctc accgacaact ccaaacagtt cgagacagaa    660
gtcgggaagc agctgatctc ggggaacctg gacgcccctg agggtgggct ggacgccatg    720
atgcaggtgg ctgcgtgccc ggaggaaatc ggctggcgca atgtcaccag gctgctggtg    780
tttgccacag acgatgggtt ccactttgcg ggcgatggaa agctgggtgc catcctcacc    840
cccaatgacg gccgctgcca cctggaagac aacctgtaca aaagcggcaa cgaatttgac    900
tacccatcgg tggccagct ggcacacaaa ctggcagaaa gcaacatcca gcccatctttt    960 gcggtaacca agaagatggt gaaaacgtac gagaagctga cagagatcat ccccaagtct   1020
```

```
gcagtcgggg agctgtctga agattccaag aacgtggtgg agcttatcaa gaatgcctac    1080
aataaactgt cctccagagt cttcctggat cacagcaccc tccctgacac cctgaaagtc    1140
acctacgact ccttctgcag taacagggta tcgcaggtgg accagcccag aggggactgc    1200
gacggcgttc agatcaacgt cccgatcacc ttccaggtga aggtcacagc accgagtgc     1260 atccagcagc agtccttcac catccgggcg ctgggcttca cggacacggt gaccgtgcgg    1320
gtcctccccc agtgcgagtg ccaatgccgg gacgccagca gggacggcag catctgcggc    1380
ggcagaggct cgatggagtg cggcgtctgc aagtgtgacg ccggctacat cgggaagaac    1440
tgcgagtgcc agacgcaggg ccggagcagc caggagctgg agggcagctg ccgcaaggac    1500
aatagctcca tcatctgctc ggggctgggg gactgtatct gcgggcagtg cgtgtgccac    1560
acgagcgacg tgcccaacaa gaagatctac ggccagttct gcgagtgcga caacgtcaac    1620
tgcgaacgct acgacggcca gtctgcgggg gcgaaaaga gggggctctg cttctgcggc      1680
acctgcaggt gcgacgagca gtatgagggt tcggcatgcc agtgcctcaa gtccactcag    1740
ggctgcctca acttggacgg cgtcgagtgc agcggccgcg gccgatgccg ctgcaatgtg    1800
tgccagtgcg accccggcta ccagccgccc ctgtgcagcg agtgcccggg ctgccccgtg    1860
ccctgtgcgg gcttcgcccc ctgcacagag tgcctgaagt cgacaagggg cccttcgcc      1920 aagaactgca gcgcagcgtg cgggcagacg aagctgctgt ccagcccggt gccggccgc      1980 aagtgcaagg agcgcgactc cgagggctgc tggatgacct acaccctggt gcagcgcgac    2040
gggcgggaca gatacgacgt gcacgtggac gacatgctcg agtgtgtgaa gggccccaac    2100
atcgctgcca tcgtgggggg caccgtgggg ggcgtcgtgc tcgtcggcat cctcctgctg    2160
gtcatctgga aggccctgac acacctgagc gacctcaggg agtaccatcg ctttgagaag    2220
gagaagctca gtcccagtg gaacaacgat aaccctcttt tcaagagtgc caccacgaca    2280
gtcatgaacc ctaagtttgc cgagagttag ggtg                                 2315
```

<210> SEQ ID NO 57
<211> LENGTH: 769
<212> TYPE: PRT
<213> ORGANISM: Artificial Sequence
<220> FEATURE:
<223> OTHER INFORMATION: mutated CD18 protein water buffalo protein

<400> SEQUENCE: 57

```
Met Leu Arg Gln Arg Pro Gln Leu Leu Phe Leu Ser Gly Leu Leu Ala
1               5                   10                  15

Leu Gly Ser Val Leu Ser Gln Glu Cys Thr Lys Tyr Lys Val Ser Thr
                20                  25                  30

Cys Arg Asp Cys Ile Glu Ser Gly Pro Gly Cys Ala Trp Cys Gln Lys
            35                  40                  45

Leu Asn Phe Thr Gly Gln Gly Glu Pro Asp Ser Leu Arg Cys Asp Thr
        50                  55                  60

Arg Ala Glu Leu Leu Ser Lys Gly Cys Pro Ala Asp Asp Ile Met Glu
65                  70                  75                  80

Pro Lys Ser Leu Ala Glu Thr Arg Asp Ser Gln Ala Asp Arg Gln Lys
                85                  90                  95

Gln Leu Ser Pro Gln Glu Val Thr Leu Tyr Leu Arg Pro Gly Gln Ala
                100                 105                 110

Ala Ala Phe Asn Val Thr Phe Arg Arg Ala Lys Gly Tyr Pro Ile Asp
            115                 120                 125

Leu Tyr Tyr Leu Met Asp Leu Ser Tyr Ser Met Val Asp Asp Leu Ile
```

```
              130                 135                 140

Asn Val Lys Lys Leu Gly Gly Asp Leu Leu Arg Ala Leu Asn Asp Ile
145                 150                 155                 160

Thr Glu Ser Gly Arg Ile Gly Phe Gly Ser Phe Val Asp Lys Thr Val
                    165                 170                 175

Leu Pro Phe Val Asn Thr His Pro Glu Lys Leu Arg Asn Pro Cys Pro
                180                 185                 190

Asn Lys Glu Lys Glu Cys Gln Pro Pro Phe Ala Phe Arg His Val Leu
            195                 200                 205

Lys Leu Thr Asp Asn Ser Lys Gln Phe Glu Thr Glu Val Gly Lys Gln
        210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                    245                 250                 255

Arg Leu Leu Val Phe Ala Thr Asp Asp Gly Phe His Phe Ala Gly Asp
                260                 265                 270

Gly Lys Leu Gly Ala Ile Leu Thr Pro Asn Asp Gly Arg Cys His Leu
            275                 280                 285

Glu Asp Asn Leu Tyr Lys Ser Gly Asn Glu Phe Asp Tyr Pro Ser Val
        290                 295                 300

Gly Gln Leu Ala His Lys Leu Ala Glu Ser Asn Ile Gln Pro Ile Phe
305                 310                 315                 320

Ala Val Thr Lys Lys Met Val Lys Thr Tyr Glu Lys Leu Thr Glu Ile
                    325                 330                 335

Ile Pro Lys Ser Ala Val Gly Glu Leu Ser Glu Asp Ser Lys Asn Val
                340                 345                 350

Val Glu Leu Ile Lys Asn Ala Tyr Asn Lys Leu Ser Ser Arg Val Phe
            355                 360                 365

Leu Asp His Ser Thr Leu Pro Asp Thr Leu Lys Val Thr Tyr Asp Ser
        370                 375                 380

Phe Cys Ser Asn Arg Val Ser Gln Val Asp Gln Pro Arg Gly Asp Cys
385                 390                 395                 400

Asp Gly Val Gln Ile Asn Val Pro Ile Thr Phe Gln Val Lys Val Thr
                    405                 410                 415

Ala Thr Glu Cys Ile Gln Gln Ser Phe Thr Ile Arg Ala Leu Gly
                420                 425                 430

Phe Thr Asp Thr Val Thr Val Arg Val Leu Pro Gln Cys Glu Cys Gln
            435                 440                 445

Cys Arg Asp Ala Ser Arg Asp Gly Ser Ile Cys Gly Arg Gly Ser
        450                 455                 460

Met Glu Cys Gly Val Cys Lys Cys Asp Ala Gly Tyr Ile Gly Lys Asn
465                 470                 475                 480

Cys Glu Cys Gln Thr Gln Gly Arg Ser Ser Gln Glu Leu Glu Gly Ser
                    485                 490                 495

Cys Arg Lys Asp Asn Ser Ser Ile Ile Cys Ser Gly Leu Gly Asp Cys
                500                 505                 510

Ile Cys Gly Gln Cys Val Cys His Thr Ser Asp Val Pro Asn Lys Lys
            515                 520                 525

Ile Tyr Gly Gln Phe Cys Glu Cys Asp Asn Val Asn Cys Glu Arg Tyr
        530                 535                 540

Asp Gly Gln Val Cys Gly Gly Glu Lys Arg Gly Leu Cys Phe Cys Gly
545                 550                 555                 560
```

```
Thr Cys Arg Cys Asp Glu Gln Tyr Glu Gly Ser Ala Cys Gln Cys Leu
                565                 570                 575

Lys Ser Thr Gln Gly Cys Leu Asn Leu Asp Gly Val Glu Cys Ser Gly
            580                 585                 590

Arg Gly Arg Cys Arg Cys Asn Val Cys Gln Cys Asp Pro Gly Tyr Gln
        595                 600                 605

Pro Pro Leu Cys Ser Glu Cys Pro Gly Cys Pro Val Pro Cys Ala Gly
    610                 615                 620

Phe Ala Pro Cys Thr Glu Cys Leu Lys Phe Asp Lys Gly Pro Phe Ala
625                 630                 635                 640

Lys Asn Cys Ser Ala Ala Cys Gly Gln Thr Lys Leu Leu Ser Ser Pro
                645                 650                 655

Val Pro Gly Arg Lys Cys Lys Glu Arg Asp Ser Glu Gly Cys Trp Met
            660                 665                 670

Thr Tyr Thr Leu Val Gln Arg Asp Gly Arg Asp Arg Tyr Asp Val His
        675                 680                 685

Val Asp Asp Met Leu Glu Cys Val Lys Gly Pro Asn Ile Ala Ala Ile
    690                 695                 700

Val Gly Gly Thr Val Gly Gly Val Val Leu Val Gly Ile Leu Leu Leu
705                 710                 715                 720

Val Ile Trp Lys Ala Leu Thr His Leu Ser Asp Leu Arg Glu Tyr His
                725                 730                 735

Arg Phe Glu Lys Glu Lys Leu Lys Ser Gln Trp Asn Asn Asp Asn Pro
            740                 745                 750

Leu Phe Lys Ser Ala Thr Thr Thr Val Met Asn Pro Lys Phe Ala Glu
        755                 760                 765

Ser

<210> SEQ ID NO 58
<211> LENGTH: 769
<212> TYPE: PRT
<213> ORGANISM: Artificial Sequence
<220> FEATURE:
<223> OTHER INFORMATION: mutated CD18 protein cattle protein

<400> SEQUENCE: 58

Met Leu Arg Gln Arg Pro Gln Leu Leu Leu Leu Ala Gly Leu Leu Ala
1               5                   10                  15

Leu Gln Ser Val Leu Ser Gln Glu Cys Thr Asn Tyr Lys Val Ser Thr
            20                  25                  30

Cys Arg Asp Cys Ile Glu Ser Gly Pro Gly Cys Ala Trp Cys Gln Lys
        35                  40                  45

Leu Asn Phe Thr Gly Gln Gly Glu Pro Asp Ser Ile Arg Cys Asp Thr
    50                  55                  60

Arg Ala Glu Leu Leu Ser Lys Gly Cys Pro Ala Asp Asp Ile Met Glu
65                  70                  75                  80

Pro Lys Ser Leu Ala Glu Thr Arg Asp Ser Gln Ala Gly Ser Arg Lys
                85                  90                  95

Gln Leu Ser Pro Gln Glu Val Thr Leu Tyr Leu Arg Pro Gly Gln Ala
            100                 105                 110

Val Ala Phe Asn Val Thr Phe Arg Arg Ala Lys Gly Tyr Pro Ile Asp
        115                 120                 125

Leu Tyr Tyr Leu Met Asp Leu Ser Tyr Ser Met Val Asp Asp Leu Val
    130                 135                 140
```

-continued

Asn Val Lys Lys Leu Gly Gly Asp Leu Leu Arg Ala Leu Asn Gly Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Glu Lys Leu Arg Asn Pro Cys Pro
            180                 185                 190

Asn Lys Glu Lys Glu Cys Gln Pro Pro Phe Ala Phe Arg His Val Leu
        195                 200                 205

Lys Leu Thr Asp Asn Ser Lys Gln Phe Glu Thr Glu Val Gly Lys Gln
    210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
                260                 265                 270

Gly Lys Leu Gly Ala Ile Leu Thr Pro Asn Asp Gly Arg Cys His Leu
            275                 280                 285

Glu Asp Asn Leu Tyr Lys Ser Ser Asn Glu Phe Asp Tyr Pro Ser Val
290                 295                 300

Gly Gln Leu Ala His Lys Leu Ala Glu Ser Asn Ile Gln Pro Ile Phe
305                 310                 315                 320

Ala Val Thr Lys Lys Met Val Lys Thr Tyr Glu Lys Leu Thr Glu Ile
                325                 330                 335

Ile Pro Lys Ser Ala Val Gly Glu Leu Ser Glu Asp Ser Arg Asn Val
            340                 345                 350

Val Glu Leu Ile Lys Asn Ala Tyr Asn Lys Leu Ser Ser Arg Val Phe
        355                 360                 365

Leu Asp His Ser Thr Leu Pro Asp Thr Leu Lys Val Thr Tyr Asp Ser
370                 375                 380

Phe Cys Ser Asn Gly Lys Ser Gln Val Asp Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Gln Ser Phe Thr Ile Arg Ala Leu Gly
            420                 425                 430

Phe Thr Asp Thr Val Thr Val Arg Val Leu Pro Gln Cys Glu Cys Gln
        435                 440                 445

Cys Arg Asp Ala Ser Arg Asp Gly Ser Ile Cys Gly Gly Arg Gly Ser
450                 455                 460

Met Glu Cys Gly Val Cys Arg Cys Asp Ala Gly Tyr Ile Gly Lys Asn
465                 470                 475                 480

Cys Glu Cys Gln Thr Gln Gly Arg Ser Ser Gln Glu Leu Glu Gly Ser
                485                 490                 495

Cys Arg Lys Asp Asn Ser Ser Ile Ile Cys Ser Gly Leu Gly Asp Cys
            500                 505                 510

Ile Cys Gly Gln Cys Val Cys His Thr Ser Asp Val Pro Asn Lys Lys
        515                 520                 525

Ile Tyr Gly Gln Phe Cys Glu Cys Asp Asn Val Asn Cys Glu Arg Tyr
    530                 535                 540

Asp Gly Gln Val Cys Gly Gly Glu Lys Arg Gly Leu Cys Phe Cys Gly
545                 550                 555                 560

Thr Cys Arg Cys Asp Glu Gln Tyr Glu Gly Ser Ala Cys Gln Cys Leu

```
                565                 570                 575
Lys Ser Thr Gln Gly Cys Leu Asn Leu Asp Gly Val Glu Cys Ser Gly
            580                 585                 590
Arg Gly Arg Cys Arg Cys Asn Val Cys Gln Cys Asp Pro Gly Tyr Gln
        595                 600                 605
Pro Pro Leu Cys Ser Glu Cys Pro Gly Cys Pro Val Pro Cys Ala Gly
    610                 615                 620
Phe Ala Pro Cys Thr Glu Cys Leu Lys Phe Asp Lys Gly Pro Phe Ala
625                 630                 635                 640
Lys Asn Cys Ser Ala Ala Cys Gly Gln Thr Lys Leu Leu Ser Ser Pro
                645                 650                 655
Val Pro Gly Arg Lys Cys Lys Glu Arg Asp Ser Glu Gly Cys Trp Met
            660                 665                 670
Thr Tyr Thr Leu Val Gln Arg Asp Gly Arg Asp Arg Tyr Asp Val His
        675                 680                 685
Val Asp Asp Met Leu Glu Cys Val Lys Gly Pro Asn Ile Ala Ala Ile
    690                 695                 700
Val Gly Gly Thr Val Gly Gly Val Val Leu Val Gly Ile Leu Leu Leu
705                 710                 715                 720
Val Ile Trp Lys Ala Leu Thr His Leu Ser Asp Leu Arg Glu Tyr His
                725                 730                 735
Arg Phe Glu Lys Glu Lys Leu Lys Ser Gln Trp Asn Asn Asp Asn Pro
            740                 745                 750
Leu Phe Lys Ser Ala Thr Thr Thr Val Met Asn Pro Lys Phe Ala Glu
        755                 760                 765
Ser

<210> SEQ ID NO 59
<211> LENGTH: 2362
<212> TYPE: DNA
<213> ORGANISM: Artificial Sequence
<220> FEATURE:
<223> OTHER INFORMATION: mutated CD18 protein bison mR

<400> SEQUENCE: 59
ggcatccagg ggacatgctg cgccagcgcc cccagctgct gctcctagcg ggcctgcttg      60
ccctcgggtc cgtcctgtcc caggagtgca ccaagtacaa ggtcagcacc tgccgggact     120
gcatcgagtc gggccctggc tgcgcctggt gccagaaact gaacttcaca gggcaagggg     180
agcccgactc cattcgctgt gacacacgag cggagctgct gtcaaagggc tgcccagctg     240
atgacatcat ggaacccaag agcctcgctg agaccctgga cagccaggcg ggcagtcgga     300
agcagctgtc cccacaggaa gtgacgctct acctgagacc aggtcaggca gctgcgttca     360
gcgtgacctt ccagagggcc aagggctacc ccatcgacct gtactacctg atggacctct     420
cctactccat ggtggatgac ctcgtcaatg tcaagaagct ggggggtgac ctgctccggg     480
ccctcaatgg catcaccgag tcgggccgca ttggtttcgg gtccttcgtg acaagacgg      540
tgctccccct cgtcaacacg caccccgaga gctgcggaa ccctgcccc aacaaggaga      600
aggagtgcca gccccgttc gccttcaggc acgtgttgaa gctcactgac aactccaaac      660
agttcgagac agaagtcggg aagcagctga tctcggggaa cctggacgcc ctgagggtg      720
ggctggacgc catgatgcag gtggccgcgt gccggaagga aatcggctgg cgcaatgtca     780
ccaggctgct ggtgttcgcc acggacgatg ggttccactt tgcgggcgat ggaaagctgg     840
gtgccatcct cacccccaat gacggccgct gccacctgga agacaacctg tacaaaagca     900
```

```
gcaacgaatt tgactaccca tcggtgggcc agctggcaca caaactggca gaaagcaaca    960
tccagcccat ctttgcagta accaagaaga tggtgaaaac gtacgagaag ctgacagaga   1020
tcatccccaa gtctgcagtc ggggagctgt ctgaagattc aagaacgtg gtggagctta   1080
tcaagaatgc ctacaataaa ctgtcctcca gagtcttcct ggatcacagc accctccctg   1140
acaccctgaa agtcacctac gactccttct gcagtaacgg gaaatcgcag gtggaccagc   1200
ccagagggga ctgcgacggc gtccagatca acgtcccgat caccttccag gtgaaggtca   1260
cagccaccga gtgcatccag cagcagtcct tcaccatccg ggcgctgggc ttcacggaca   1320
cggtgaccgt gcgggtcctc ccccagtgcg agtgccaatg ccgggacgcc agcagggacg   1380
gcagcatctg cggcggcaga ggctcgatgg agtgcggcgt ctgcaggtgt gacgccggct   1440
acatcgggaa gaactgcgag tgccagacgc agggccggag cagccaggag ctggagggca   1500
gctgccgcaa ggacaacagc tccatcatct gctcggggct gggggactgc atctgcgggc   1560
agtgcgtgtg ccacacgagc gacgtgccca acaagaagat ctacggccag ttctgcgagt   1620
gcgacaacgt caactgcgaa cgctacgacg gccaagtctg cggggggcgaa agagggggc   1680
tctgcttctg cggcacctgc aggtgcgacg agcagtatga gggttcggca tgccagtgcc   1740
tcaagtccac tcagggctgc ctcaacttgg acggcgtcga gtgcagcggc cgcggccgat   1800
gccgctgcaa tgtgtgccag tgcgaccccg gctaccagcc gccctgtgc agcgagtgcc   1860
cgggctgccc cgtgccctgc gcgggcttcg ccccctgcac agagtgcctg aagttcgaca   1920
agggcccctt cgccaagaac tgcagcgcag cgtgcgggca gacgaagctg ctgtccagcc   1980
cggtgcccgg ccgcaagtgc aaggagcgcg actccgaggg ctgctggatg acctacaccc   2040
tggtgcagcg cgacgggcgg gacagatacg acgtgcacgt ggacgacatg ctcgagtgtg   2100
tgaagggccc caacatcgct gccatcgtgg ggggcaccgt ggggggcgtc gtgctcgtcg   2160
gcatcctcct gctggtcatc tggaaggccc tgacacacct gagcgacctc agggagtacc   2220
atcgcttcga gaaggagaag ctcaagtccc agtggaacaa cgataaccct cttttcaaga   2280
gtgccaccac gacagtcatg aaccctaagt ttgccgagag ttaggggtgc ccggtgaaga   2340
caaggccttc tgcaccaccc ag                                            2362
```

<210> SEQ ID NO 60
<211> LENGTH: 769
<212> TYPE: PRT
<213> ORGANISM: Artificial Sequence
<220> FEATURE:
<223> OTHER INFORMATION: mutated CD18 protein bison protein

<400> SEQUENCE: 60

```
Met Leu Arg Gln Arg Pro Gln Leu Leu Leu Ala Gly Leu Leu Ala
1               5                   10                  15

Leu Gly Ser Val Leu Ser Gln Glu Cys Thr Lys Tyr Lys Val Ser Thr
            20                  25                  30

Cys Arg Asp Cys Ile Glu Ser Gly Pro Gly Cys Ala Trp Cys Gln Lys
        35                  40                  45

Leu Asn Phe Thr Gly Gln Gly Glu Pro Asp Ser Ile Arg Cys Asp Thr
    50                  55                  60

Arg Ala Glu Leu Leu Ser Lys Gly Cys Pro Ala Asp Asp Ile Met Glu
65                  70                  75                  80

Pro Lys Ser Leu Ala Glu Thr Leu Asp Ser Gln Ala Gly Ser Arg Lys
                85                  90                  95
```

```
Gln Leu Ser Pro Gln Glu Val Thr Leu Tyr Leu Arg Pro Gly Gln Ala
                100                 105                 110
Ala Ala Phe Ser Val Thr Phe Gln Arg Ala Lys Gly Tyr Pro Ile Asp
            115                 120                 125
Leu Tyr Tyr Leu Met Asp Leu Ser Tyr Ser Met Val Asp Asp Leu Val
        130                 135                 140
Asn Val Lys Lys Leu Gly Gly Asp Leu Leu Arg Ala Leu Asn Gly Ile
145                 150                 155                 160
Thr Glu Ser Gly Arg Ile Gly Phe Gly Ser Phe Val Asp Lys Thr Val
                165                 170                 175
Leu Pro Phe Val Asn Thr His Pro Glu Lys Leu Arg Asn Pro Cys Pro
            180                 185                 190
Asn Lys Glu Lys Glu Cys Gln Pro Pro Phe Ala Phe Arg His Val Leu
        195                 200                 205
Lys Leu Thr Asp Asn Ser Lys Gln Phe Glu Thr Glu Val Gly Lys Gln
210                 215                 220
Leu Ile Ser Gly Asn Leu Asp Ala Pro Glu Gly Gly Leu Asp Ala Met
225                 230                 235                 240
Met Gln Val Ala Ala Cys Pro Glu Glu Ile Gly Trp Arg Asn Val Thr
                245                 250                 255
Arg Leu Leu Val Phe Ala Thr Asp Asp Gly Phe His Phe Ala Gly Asp
            260                 265                 270
Gly Lys Leu Gly Ala Ile Leu Thr Pro Asn Asp Gly Arg Cys His Leu
        275                 280                 285
Glu Asp Asn Leu Tyr Lys Ser Ser Asn Glu Phe Asp Tyr Pro Ser Val
290                 295                 300
Gly Gln Leu Ala His Lys Leu Ala Glu Ser Asn Ile Gln Pro Ile Phe
305                 310                 315                 320
Ala Val Thr Lys Lys Met Val Lys Thr Tyr Glu Lys Leu Thr Glu Ile
                325                 330                 335
Ile Pro Lys Ser Ala Val Gly Glu Leu Ser Glu Asp Ser Lys Asn Val
            340                 345                 350
Val Glu Leu Ile Lys Asn Ala Tyr Asn Lys Leu Ser Ser Arg Val Phe
        355                 360                 365
Leu Asp His Ser Thr Leu Pro Asp Thr Leu Lys Val Thr Tyr Asp Ser
370                 375                 380
Phe Cys Ser Asn Gly Lys Ser Gln Val Asp Gln Pro Arg Gly Asp Cys
385                 390                 395                 400
Asp Gly Val Gln Ile Asn Val Pro Ile Thr Phe Gln Val Lys Val Thr
                405                 410                 415
Ala Thr Glu Cys Ile Gln Gln Gln Ser Phe Thr Ile Arg Ala Leu Gly
            420                 425                 430
Phe Thr Asp Thr Val Thr Val Arg Val Leu Pro Gln Cys Glu Cys Gln
        435                 440                 445
Cys Arg Asp Ala Ser Arg Asp Gly Ser Ile Cys Gly Gly Arg Gly Ser
450                 455                 460
Met Glu Cys Gly Val Cys Arg Cys Asp Ala Gly Tyr Ile Gly Lys Asn
465                 470                 475                 480
Cys Glu Cys Gln Thr Gln Gly Arg Ser Ser Gln Glu Leu Glu Gly Ser
                485                 490                 495
Cys Arg Lys Asp Asn Ser Ser Ile Ile Cys Ser Gly Leu Gly Asp Cys
            500                 505                 510
Ile Cys Gly Gln Cys Val Cys His Thr Ser Asp Val Pro Asn Lys Lys
```

```
                515                 520                 525
Ile Tyr Gly Gln Phe Cys Glu Cys Asp Asn Val Asn Cys Glu Arg Tyr
    530                 535                 540

Asp Gly Gln Val Cys Gly Gly Glu Lys Arg Gly Leu Cys Phe Cys Gly
545                 550                 555                 560

Thr Cys Arg Cys Asp Glu Gln Tyr Glu Gly Ser Ala Cys Gln Cys Leu
            565                 570                 575

Lys Ser Thr Gln Gly Cys Leu Asn Leu Asp Gly Val Glu Cys Ser Gly
        580                 585                 590

Arg Gly Arg Cys Arg Cys Asn Val Cys Gln Cys Asp Pro Gly Tyr Gln
    595                 600                 605

Pro Pro Leu Cys Ser Glu Cys Pro Gly Cys Pro Val Pro Cys Ala Gly
610                 615                 620

Phe Ala Pro Cys Thr Glu Cys Leu Lys Phe Asp Lys Gly Pro Phe Ala
625                 630                 635                 640

Lys Asn Cys Ser Ala Ala Cys Gly Gln Thr Lys Leu Leu Ser Ser Pro
            645                 650                 655

Val Pro Gly Arg Lys Cys Lys Glu Arg Asp Ser Glu Gly Cys Trp Met
        660                 665                 670

Thr Tyr Thr Leu Val Gln Arg Asp Gly Arg Asp Arg Tyr Asp Val His
    675                 680                 685

Val Asp Asp Met Leu Glu Cys Val Lys Gly Pro Asn Ile Ala Ala Ile
690                 695                 700

Val Gly Gly Thr Val Gly Gly Val Val Leu Val Gly Ile Leu Leu Leu
705                 710                 715                 720

Val Ile Trp Lys Ala Leu Thr His Leu Ser Asp Leu Arg Glu Tyr His
            725                 730                 735

Arg Phe Glu Lys Glu Lys Leu Lys Ser Gln Trp Asn Asn Asp Asn Pro
        740                 745                 750

Leu Phe Lys Ser Ala Thr Thr Thr Val Met Asn Pro Lys Phe Ala Glu
    755                 760                 765

Ser

<210> SEQ ID NO 61
<211> LENGTH: 2507
<212> TYPE: DNA
<213> ORGANISM: Artificial Sequence
<220> FEATURE:
<223> OTHER INFORMATION: mutated CD18 protein goat mRNA (Q-->G)

<400> SEQUENCE: 61
cagcctggtg aagagcagag ccgaagcccc tgccagtcca gctgggacac ccctgccgtg      60
gtctccaggg catccagggg acatgctgcc ccagcgcccc cagctgctgc tcctagcagg     120
cctgctcgcc ctcgggtctg tcctgtccca ggagtgcacc aagtacaaag tcagcacctg     180
ccgggactgc atcgagtcgg gccccggctg tgcctggtgc cagaaactga acttcacagg     240
gcaaggggag cccgactcca ctcgctgtga tacacgggcg cagctgctgt caaagggctg     300
cccagctgat gacatcatgg aacccaagag cctcgctgag acccggcaga gccaggcggg     360
caaacagaag cagctgtccc agaggaagt gactctctac cttagaccag gtcaggcagc     420
tgcgttcaat gtgaccttcc agagggccaa gggctacccc atcgacctgt actatctgat     480
ggatctctcc tactccatgg tggacgacct cgccaacgtc aagaagctgg ggggtgacct     540
gctccgggcc ctcaatgaca tcaccgagtc gggccgcatc gggttcgggt ccttcgtgga     600
```

```
caagacagtg ctccccttcg tcaacacgca ccctgagaag ctgaggaacc cctgccccaa    660
caaggagaag cagtgccagc ccccgttcgc cttcaggcac gtgttgaagc tcaccgacaa    720
ctccaaacag ttcgagacag aagtcgggaa gcagctgatc tcggggaact ggacgcccc     780
tgagggtgga ctggacgcca tgatgcaagt ggccgcgtgc ccgaggaaa tcggctggcg     840
caatgtcacc aggctgctgg tgttcgccac agatgatggg ttccactttg cgggcgatgg    900
aaagctgggt gccatcctca cccccaacga cggccgctgc cacctggaag acaacctgta    960
caaaagcagc aacgaatttg actacccatc ggtgggccag ctggcacaca aactggcaga   1020
aagcaacatc cagcccatct cgcggtaac caagaagatg gtgaaaacgt acgagaagct    1080
gacagaaatc atccccaagt ctgcagtcgg ggagctgtct gaagattcca gaacgtggt    1140
ggagcttatc aagagtgcct acaataaact gtcctccaga gtattcctgg atcacaacac   1200
cctccctgac accctgaaag tcgcctacga ctccttctgc agtaacgggg tgtcacaggt   1260
ggaccagccc agaggggact gtgacggcgt ccagatcaac gtcccgatca ccttccaggt   1320
gaaggtcaca gccaccgagt gcatccagga gcagtccttc accatccggg cgctgggctt   1380
cacggacacg gtgaccgtgc gggtccttcc ccagtgcgag tgccaatgcc gggacgccag   1440
cagggaccgc agcgtctgcg gtggcagagg ctcgatggag tgcggcgtct gcaggtgcga   1500
cgccggctac atcgggaaga actgcgagtg ccagacgcac ggccggagca gccaggagct   1560
ggagggcagc tgccgcaagg acaacagctc catcatctgc tcggggctag ggactgcat    1620
ctgcgggcag tgcgtgtgcc acacgagcga cgtgcccaac aagaagatct acggccagtt   1680
ctgcgagtgc gacaacgtca actgcgagcg ctacgacggc caagtctgcg ggggcgagaa   1740
gaggggggctc tgcttctgcg gcacctgcag gtgcaacgag cagcatgagg gctcggcgtg   1800
ccagtgcctc aagtccactc agggctgcct caacctggac ggcgtcgagt gcagcggccg   1860
gggccgatgc cgctgcaacg tgtgccagtg cgaccccggc taccagccgc ccctgtgcat   1920
cgactgcccg ggctgccccg tgccctgcgc tggcttcgcc ccctgcaccg agtgcctgaa   1980
gttcgacaag ggccccttcg ccaagaactg cagcgcagcg tgcgggcaga cgaagctgct   2040
gtccagcccg gtgcccggcg gccgcaagtg caaggagcgc gactccgagg gctgctggat   2100
gacctacacc ctggtgcagc gcgacgggcg gaacagatac gacgtgcacg tggacgacat   2160
gctcgagtgt gtgaagggcc caacatcgc tgccatcgtg gggggcaccg tgggggagt    2220
tgtgctcgtc ggcatcctcc tgctggtcat ctggaaggcc ctgacacacc tgagcgacct   2280
cagggagtac catcgcttcg agaaggagaa gctcaagtcc cagtggaaca acgataaccc   2340
tcttttcaag agtgccacca cgacagtcat gaaccctaag tttgccgaga gttaggggtg   2400
cctggtgaag acaaggcctt ctgcaccacc cagacgggag cacgccctct cctcatcccc   2460
tccagcaggc tgaccgtgac cttgctgctt agtggacgca gctgatg                 2507
```

<210> SEQ ID NO 62
<211> LENGTH: 770
<212> TYPE: PRT
<213> ORGANISM: Artificial Sequence
<220> FEATURE:
<223> OTHER INFORMATION: mutated CD18 protein goat protein (Q-->G)

<400> SEQUENCE: 62

Met Leu Pro Gln Arg Pro Gln Leu Leu Leu Leu Ala Gly Leu Leu Ala
1               5                   10                  15

Leu Gly Ser Val Leu Ser Gln Glu Cys Thr Lys Tyr Lys Val Ser Thr
            20                  25                  30

-continued

Cys Arg Asp Cys Ile Glu Ser Gly Pro Gly Cys Ala Trp Cys Gln Lys
        35                  40                  45

Leu Asn Phe Thr Gly Gln Gly Glu Pro Asp Ser Thr Arg Cys Asp Thr
 50                  55                  60

Arg Ala Gln Leu Leu Ser Lys Gly Cys Pro Ala Asp Asp Ile Met Glu
 65                  70                  75                  80

Pro Lys Ser Leu Ala Glu Thr Arg Gln Ser Gln Ala Gly Lys Gln Lys
                 85                  90                  95

Gln Leu Ser Pro Glu Glu Val Thr Leu Tyr Leu Arg Pro Gly Gln Ala
                100                 105                 110

Ala Ala Phe Asn Val Thr Phe Gln Arg Ala Lys Gly Tyr Pro Ile Asp
                115                 120                 125

Leu Tyr Tyr Leu Met Asp Leu Ser Tyr Ser Met Val Asp Asp Leu Ala
                130                 135                 140

Asn Val Lys Lys Leu Gly Gly Asp Leu Leu Arg Ala Leu Asn Asp Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Glu Lys Leu Arg Asn Pro Cys Pro
                180                 185                 190

Asn Lys Glu Lys Gln Cys Gln Pro Pro Phe Ala Phe Arg His Val Leu
                195                 200                 205

Lys Leu Thr Asp Asn Ser Lys Gln Phe Glu Thr Glu Val Gly Lys Gln
210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
                260                 265                 270

Gly Lys Leu Gly Ala Ile Leu Thr Pro Asn Asp Gly Arg Cys His Leu
                275                 280                 285

Glu Asp Asn Leu Tyr Lys Ser Ser Asn Glu Phe Asp Tyr Pro Ser Val
                290                 295                 300

Gly Gln Leu Ala His Lys Leu Ala Glu Ser Asn Ile Gln Pro Ile Phe
305                 310                 315                 320

Ala Val Thr Lys Lys Met Val Lys Thr Tyr Glu Lys Leu Thr Glu Ile
                325                 330                 335

Ile Pro Lys Ser Ala Val Gly Glu Leu Ser Glu Asp Ser Lys Asn Val
                340                 345                 350

Val Glu Leu Ile Lys Ser Ala Tyr Asn Lys Leu Ser Ser Arg Val Phe
                355                 360                 365

Leu Asp His Asn Thr Leu Pro Asp Thr Leu Lys Val Ala Tyr Asp Ser
                370                 375                 380

Phe Cys Ser Asn Gly Val Ser Gln Val Asp Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Glu Gln Ser Phe Thr Ile Arg Ala Leu Gly
                420                 425                 430

Phe Thr Asp Thr Val Thr Val Arg Val Leu Pro Gln Cys Glu Cys Gln
                435                 440                 445

```
Cys Arg Asp Ala Ser Arg Asp Arg Ser Val Cys Gly Arg Gly Ser
    450                 455                 460

Met Glu Cys Gly Val Cys Arg Cys Asp Ala Gly Tyr Ile Gly Lys Asn
465                 470                 475                 480

Cys Glu Cys Gln Thr His Gly Arg Ser Gln Glu Leu Gly Ser
                485                 490                 495

Cys Arg Lys Asp Asn Ser Ser Ile Ile Cys Ser Gly Leu Gly Asp Cys
                500                 505                 510

Ile Cys Gly Gln Cys Val Cys His Thr Ser Asp Val Pro Asn Lys Lys
                515                 520                 525

Ile Tyr Gly Gln Phe Cys Glu Cys Asp Asn Val Asn Cys Glu Arg Tyr
                530                 535                 540

Asp Gly Gln Val Cys Gly Gly Glu Lys Arg Gly Leu Cys Phe Cys Gly
545                 550                 555                 560

Thr Cys Arg Cys Asn Glu Gln His Glu Gly Ser Ala Cys Gln Cys Leu
                565                 570                 575

Lys Ser Thr Gln Gly Cys Leu Asn Leu Asp Gly Val Glu Cys Ser Gly
                580                 585                 590

Arg Gly Arg Cys Arg Cys Asn Val Cys Gln Cys Asp Pro Gly Tyr Gln
                595                 600                 605

Pro Pro Leu Cys Ile Asp Cys Pro Gly Cys Pro Val Pro Cys Ala Gly
                610                 615                 620

Phe Ala Pro Cys Thr Glu Cys Leu Lys Phe Asp Lys Gly Pro Phe Ala
625                 630                 635                 640

Lys Asn Cys Ser Ala Ala Cys Gly Gln Thr Lys Leu Leu Ser Ser Pro
                645                 650                 655

Val Pro Gly Gly Arg Lys Cys Lys Glu Arg Asp Ser Glu Gly Cys Trp
                660                 665                 670

Met Thr Tyr Thr Leu Val Gln Arg Asp Gly Arg Asn Arg Tyr Asp Val
                675                 680                 685

His Val Asp Asp Met Leu Glu Cys Val Lys Gly Pro Asn Ile Ala Ala
                690                 695                 700

Ile Val Gly Gly Thr Val Gly Gly Val Val Leu Val Gly Ile Leu Leu
705                 710                 715                 720

Leu Val Ile Trp Lys Ala Leu Thr His Leu Ser Asp Leu Arg Glu Tyr
                725                 730                 735

His Arg Phe Glu Lys Glu Lys Leu Lys Ser Gln Trp Asn Asn Asp Asn
                740                 745                 750

Pro Leu Phe Lys Ser Ala Thr Thr Thr Val Met Asn Pro Lys Phe Ala
                755                 760                 765

Glu Ser
    770

<210> SEQ ID NO 63
<211> LENGTH: 2313
<212> TYPE: DNA
<213> ORGANISM: Artificial Sequence
<220> FEATURE:
<223> OTHER INFORMATION: mutated CD18 protein domestic sheep mRNA
      (Q-->G)

<400> SEQUENCE: 63
atgctgcccc agcgccccca gctgctgctc ctagcgggcc tgctctccct cgggtccgtc      60
ctgtcccagg agtgcaccaa gtacaaagtc agcacctgcc gggactgcat cgagtcgggc     120
cccggctgtg cctggtgtca gaaactgaac ttcacagggc aaggggagcc cgactccact     180
```

```
cgctgtgata cacgggcgca gctgctgtcg aagggctgcc cagctgatga catcatggaa    240
cccaagagcc tcgctgagac tcggcagagc caggcgggca aacagaagca gctgtcccca    300
gaggaagtga ccctctacct gagaccaggt caggcagcag cgttcaacgt gaccttccag    360
agggccaagg gctaccccat cgacctgtac tatctgatgg atctctccta ctccatggtg    420
gacgacctcg ccaacgtcaa gaagctgggg ggtgacctgc tccgggccct caatgacatc    480
accgagtcag gccgcattgg tttcgggtcc ttcgtggaca agacggtgct ccccttcgtc    540
aacacgcacc ccgagaagct gaggaacccc tgccccaaca aggagaagga gtgccagccg    600
ccgttcgcct tcaggcacgt gctgaagctc accgacaact ccaaacagtt cgagacagaa    660
gtcgggaagc agctgatctc ggggaacttg gacgcccctg agggtgggct ggacgccatg    720
atgcaagtgg ccgcgtgccc ggaggaaatt ggctggcgca atgtcaccag gctgctggtg    780
ttcgccacag acgatgggtt ccactttgcg ggcgatggaa agctgggtgc catcctcacc    840
cccaacgacg ccgctgcca cctggaagac aacctgtaca aaagcagcaa cgaatttgac    900
tacccatcgg tgggccagct ggcacacaaa ctggcagaaa gcaacatcca gcccatcttc    960
gcggtaacca agaagatggt gaaaacgtac gagaagctga cagaaatcat ccccaagtct    1020
gcagtcgggg agctgtctga agattccaag aacgtggtgg agcttatcaa gagtgcctac    1080
aataaactgt cctccagagt attcctggat cacaacaccc tccctgacac cctgaaagtc    1140
gcctacgact ccttctgcag taacggggtg tcgcaggtgg accagcccag aggggactgc    1200
gacggcgtcc agatcaacgt cccgatcacc ttccaggtga aggtcacagc caccgagtgc    1260
atccaggagc agtccttcac catccgggcg ctgggcttca cggacacggt gaccgtgcgg    1320
gtccttcccc agtgcgagtg ccaatgccgg gaagccagca gggaccgcag cgtctgcggt    1380
ggcagaggct cgatggagtg cggcgtctgc aggtgcgacg ccggctacat cgggaagaac    1440
tgcgagtgcc agacgcacgg ccggagcagc caggagctgg agggcagctg ccgcaaggac    1500
aacagctcca tcatctgctc ggggctgggg gactgcatct gcgggcagtg cgtgtgccac    1560
acgagcgacg tgcccaacaa gaagatctac ggccagttct gcgagtgcga caacgtcaac    1620
tgcgagcgct acgacggcca agtctgcggg gcgacaaga ggggctctg cttctgcggc    1680 acctgcaggt gcaacgacca gcatgagggc tcggcgtgcc agtgcctcaa gtccactcag    1740
ggctgcctca acctggacgg cgtcgagtgc agcggccgcg gccgatgccg ctgcaacgtg    1800
tgccagtgcg accccggcta ccagccgccc ctgtgcatcg actgcccggg ctgccccgtg    1860
ccctgcgctg gcttcgcccc ctgcaccgag tgcctgaagt cgacaagggg tcccttcgcc    1920
aagaactgca gcgcagcgtg cgggcagacg aagctgctgt ccagcccggt gcccggcggc    1980
cgcaagtgca aggagcgtga ctccgagggc tgctggatga cctacaccct ggtgcagcgc    2040
gacgggcgga acagatacga cgtgcacgtg gacgacatgc tcgagtgtgt gaagggcccc    2100
aacatcgctg ccatcgtggg gggcaccgtg gggagttg tgctcgtcgg catcctcctg    2160
ctggccatct ggaaggccct gacacacctg agcgacctca gggagtacca tcgcttcgag    2220
aaggagaagc tcaagtccca gtggaacaac gataaccctc ttttcaagag tgccaccacg    2280
acagtcatga cccctaagtt tgccgagagt tag                               2313
```

<210> SEQ ID NO 64
<211> LENGTH: 770
<212> TYPE: PRT
<213> ORGANISM: Artificial Sequence
<220> FEATURE:

<223> OTHER INFORMATION: mutated CD18 protein domestic sheep protein (Q-->G)

<400> SEQUENCE: 64

```
Met Leu Pro Gln Arg Pro Gln Leu Leu Leu Ala Gly Leu Leu Ser
1               5                   10                  15

Leu Gly Ser Val Leu Ser Gln Glu Cys Thr Lys Tyr Lys Val Ser Thr
                20                  25                  30

Cys Arg Asp Cys Ile Glu Ser Gly Pro Gly Cys Ala Trp Cys Gln Lys
            35                  40                  45

Leu Asn Phe Thr Gly Gln Gly Glu Pro Asp Ser Thr Arg Cys Asp Thr
50                  55                  60

Arg Ala Gln Leu Leu Ser Lys Gly Cys Pro Ala Asp Asp Ile Met Glu
65                  70                  75                  80

Pro Lys Ser Leu Ala Glu Thr Arg Gln Ser Gln Ala Gly Lys Gln Lys
                85                  90                  95

Gln Leu Ser Pro Glu Glu Val Thr Leu Tyr Leu Arg Pro Gly Gln Ala
            100                 105                 110

Ala Ala Phe Asn Val Thr Phe Gln Arg Ala Lys Gly Tyr Pro Ile Asp
        115                 120                 125

Leu Tyr Tyr Leu Met Asp Leu Ser Tyr Ser Met Val Asp Asp Leu Ala
130                 135                 140

Asn Val Lys Lys Leu Gly Gly Asp Leu Leu Arg Ala Leu Asn Asp Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Glu Lys Leu Arg Asn Pro Cys Pro
            180                 185                 190

Asn Lys Glu Lys Glu Cys Gln Pro Pro Phe Ala Phe Arg His Val Leu
        195                 200                 205

Lys Leu Thr Asp Asn Ser Lys Gln Phe Glu Thr Glu Val Gly Lys Gln
210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
        275                 280                 285

Glu Asp Asn Leu Tyr Lys Ser Ser Asn Glu Phe Asp Tyr Pro Ser Val
290                 295                 300

Gly Gln Leu Ala His Lys Leu Ala Glu Ser Asn Ile Gln Pro Ile Phe
305                 310                 315                 320

Ala Val Thr Lys Lys Met Val Lys Thr Tyr Glu Lys Leu Thr Glu Ile
                325                 330                 335

Ile Pro Lys Ser Ala Val Gly Glu Leu Ser Glu Asp Ser Lys Asn Val
            340                 345                 350

Val Glu Leu Ile Lys Ser Ala Tyr Asn Lys Leu Ser Ser Arg Val Phe
        355                 360                 365

Leu Asp His Asn Thr Leu Pro Asp Thr Leu Lys Val Ala Tyr Asp Ser
370                 375                 380

Phe Cys Ser Asn Gly Val Ser Gln Val Asp Gln Pro Arg Gly Asp Cys
385                 390                 395                 400
```

Asp Gly Val Gln Ile Asn Val Pro Ile Thr Phe Gln Val Lys Val Thr
            405                 410                 415

Ala Thr Glu Cys Ile Gln Glu Gln Ser Phe Thr Ile Arg Ala Leu Gly
        420                 425                 430

Phe Thr Asp Thr Val Thr Val Arg Val Leu Pro Gln Cys Glu Cys Gln
    435                 440                 445

Cys Arg Glu Ala Ser Arg Asp Arg Ser Val Cys Gly Arg Gly Gly Ser
450                 455                 460

Met Glu Cys Gly Val Cys Arg Cys Asp Ala Gly Tyr Ile Gly Lys Asn
465                 470                 475                 480

Cys Glu Cys Gln Thr His Gly Arg Ser Ser Gln Glu Leu Glu Gly Ser
                485                 490                 495

Cys Arg Lys Asp Asn Ser Ser Ile Ile Cys Ser Gly Leu Gly Asp Cys
            500                 505                 510

Ile Cys Gly Gln Cys Val Cys His Thr Ser Asp Val Pro Asn Lys Lys
        515                 520                 525

Ile Tyr Gly Gln Phe Cys Glu Cys Asp Asn Val Asn Cys Glu Arg Tyr
    530                 535                 540

Asp Gly Gln Val Cys Gly Gly Asp Lys Arg Gly Leu Cys Phe Cys Gly
545                 550                 555                 560

Thr Cys Arg Cys Asn Asp Gln His Glu Gly Ser Ala Cys Gln Cys Leu
                565                 570                 575

Lys Ser Thr Gln Gly Cys Leu Asn Leu Asp Gly Val Glu Cys Ser Gly
            580                 585                 590

Arg Gly Arg Cys Arg Cys Asn Val Cys Gln Cys Asp Pro Gly Tyr Gln
        595                 600                 605

Pro Pro Leu Cys Ile Asp Cys Pro Gly Cys Pro Val Pro Cys Ala Gly
    610                 615                 620

Phe Ala Pro Cys Thr Glu Cys Leu Lys Phe Asp Lys Gly Pro Phe Ala
625                 630                 635                 640

Lys Asn Cys Ser Ala Ala Cys Gly Gln Thr Lys Leu Leu Ser Ser Pro
                645                 650                 655

Val Pro Gly Gly Arg Lys Cys Lys Glu Arg Asp Ser Glu Gly Cys Trp
            660                 665                 670

Met Thr Tyr Thr Leu Val Gln Arg Asp Gly Arg Asn Arg Tyr Asp Val
        675                 680                 685

His Val Asp Asp Met Leu Glu Cys Val Lys Gly Pro Asn Ile Ala Ala
    690                 695                 700

Ile Val Gly Gly Thr Val Gly Gly Val Val Leu Val Gly Ile Leu Leu
705                 710                 715                 720

Leu Ala Ile Trp Lys Ala Leu Thr His Leu Ser Asp Leu Arg Glu Tyr
                725                 730                 735

His Arg Phe Glu Lys Glu Lys Leu Lys Ser Gln Trp Asn Asn Asp Asn
            740                 745                 750

Pro Leu Phe Lys Ser Ala Thr Thr Thr Val Met Asn Pro Lys Phe Ala
        755                 760                 765

Glu Ser
    770

<210> SEQ ID NO 65
<211> LENGTH: 2313
<212> TYPE: DNA
<213> ORGANISM: Artificial Sequence
<220> FEATURE:

-continued

<223> OTHER INFORMATION: mutated CD18 protein wild sheep mRNA (Q-->G)

<400> SEQUENCE: 65
atgctgcccc agcgccccca gctgctgctc ctagcgggcc tgctctccct cgggtccgtc 60
ctgtcccagg agtgcaccaa gtacaaggtc agcacctgcc gggactgcat cgagtcgggc 120
cccagctgtg cctggtgcca gaaactgaac ttcacagggc aaggggagcc cgactccact 180
cgctgtgata caagggcgca gctgctgtcg aagggctgcc cagctgatga catcatggaa 240
cccaagagcc tcgctgagac ccggcagagc caggcgggca gacagaagca gctgtcccca 300
gaggaagtga ccctctacct gagaccaggt caggcagctg cgttcaacgt gaccttccag 360
agggccaagg gctaccccat cgacctgtac tatctgatgg atctctccta ctccatggtg 420
gacgacctcg ccaacgtcaa gaagctgggg ggtgacctgc tccgggccct caatgacatc 480
accgagtcgg gccgcattgg tttcgggtcc ttcgtggaca agacggtgct ccccttcgtc 540
aacacgcacc ccgagaagct gaggaacccc tgccccaaca aggagaagga gtgccagccg 600
ccgttcgcct tcaggcacgt gctgaagctc accgacaact ccaaacagtt cgagacagaa 660
gtcgggaagc agctgatctc ggggaacttg gacgcccctg agggtgggct ggacgccatg 720
atgcaagtgg ccgcgtgccc ggaggaaatt ggctggcgca atgtcaccag gctgctggtg 780
ttcgccacag acgatgggtt ccactttgcg ggcgatggaa agctgggtgc catcctcacc 840
cccaacgacg gccgctgcca cctggaagac aacctgtaca aaagcagcaa cgaatttgac 900
tacccatcgg tgggccagct ggcacacaaa ctggcagaaa gcaacatcca gcccatcttc 960
gcggtaacca agaagatggt gaaaacgtac gagaagctga cagaaatcat ccccaagtct 1020
gcagtcgggg agctgtctga agattccaag aacgtggtgg agcttatcaa gagtgcctac 1080
aataaactgt cctccagagt attcctggat cacaacaccc tccctgacac cctgaaagtc 1140
gcctacgact ccttctgcag taacagggtg tcacaggtgg accagcccag aggggactgt 1200
gacggcgtcc agatcaacgt cccgatcacc ttccaggtga aggtcacagc caccgagtgc 1260
atccaggagc agtccttcac catccgggcg ctgggcttca cggacacggt gaccgtgcgg 1320
gtccttcccc agtgcgagtg ccaatgccgg gaagccagca gggaccgcgg cgtctgcggt 1380
ggcagaggct cgatggagtg cggcgtctgc aggtgcgacg ccggctacat cgggaagaac 1440
tgcgagtgcc agacgcacgg ccggagcagc caggagctgg agggcagctg ccgcaaggac 1500
aacagctcca tcatctgctc ggggctgggg gactgcatct gcgggcagtg cgtgtgccac 1560
acgagcgacg tgcccaacaa gaagatctac ggccagttct gcgagtgcga caacgtcaac 1620
tgcgagcgct acgacggcca agtctgcggg ggcgacaaga gggggctctg cttctgcggc 1680
gcctgcaggt gcaacgacca gtatgagggc tcggcgtgcc agtgcctcaa gtccactcag 1740
ggctgcctca acctgaacgg cgtcgagtgc agcggccgcg gccgatgccg ctgcaacgtg 1800
tgccagtgcg accccggcta ccagccgccc ctgtgcatcg actgcccggg ctgccccgtg 1860
ccctgcgctg gcttcgcccc ctgcaccgag tgcctgaagt tcgacaaggg tcccttcgcc 1920
aagaactgca gcgcagcgtg cgggcagacg aagctgctgt ccagcccggt gcccggcggc 1980
cgcaagtgca aggagcgtga ctccgagggc tgctggatga cctacaccct ggtgcagcgc 2040
gacgggcgga acagatacga cgtgcacgtg gacgacatgc tcgagtgtgt gaagggcccc 2100
aacatcgctg ccatcgtggg gggcaccgtg gggggagttg tgctcgtcgg catcctcctg 2160
ctggccatct ggaaggccct gacacacctg agcgacctca gggagtacca tcgcttcgag 2220
aaggagaagc tcaagtccca gtggaacaac gataaccctc ttttcaagag tgccaccacg 2280
acagtcatga accctaagtt tgccgagagt tag 2313

<210> SEQ ID NO 66
<211> LENGTH: 770
<212> TYPE: PRT
<213> ORGANISM: Artificial Sequence
<220> FEATURE:
<223> OTHER INFORMATION: mutated CD18 protein wild sheep protein (Q-->G)

<400> SEQUENCE: 66

```
Met Leu Pro Gln Arg Pro Gln Leu Leu Leu Ala Gly Leu Leu Ser
1               5                   10                  15

Leu Gly Ser Val Leu Ser Gln Glu Cys Thr Lys Tyr Lys Val Ser Thr
            20                  25                  30

Cys Arg Asp Cys Ile Glu Ser Gly Pro Ser Cys Ala Trp Cys Gln Lys
        35                  40                  45

Leu Asn Phe Thr Gly Gln Gly Glu Pro Asp Ser Thr Arg Cys Asp Thr
50                  55                  60

Arg Ala Gln Leu Leu Ser Lys Gly Cys Pro Ala Asp Asp Ile Met Glu
65                  70                  75                  80

Pro Lys Ser Leu Ala Glu Thr Arg Gln Ser Gln Ala Gly Arg Gln Lys
                85                  90                  95

Gln Leu Ser Pro Glu Glu Val Thr Leu Tyr Leu Arg Pro Gly Gln Ala
            100                 105                 110

Ala Ala Phe Asn Val Thr Phe Gln Arg Ala Lys Gly Tyr Pro Ile Asp
        115                 120                 125

Leu Tyr Tyr Leu Met Asp Leu Ser Tyr Ser Met Val Asp Asp Leu Ala
130                 135                 140

Asn Val Lys Lys Leu Gly Gly Asp Leu Leu Arg Ala Leu Asn Asp Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Glu Lys Leu Arg Asn Pro Cys Pro
            180                 185                 190

Asn Lys Glu Lys Glu Cys Gln Pro Pro Phe Ala Phe Arg His Val Leu
        195                 200                 205

Lys Leu Thr Asp Asn Ser Lys Gln Phe Glu Thr Glu Val Gly Lys Gln
210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
        275                 280                 285

Glu Asp Asn Leu Tyr Lys Ser Ser Asn Glu Phe Asp Tyr Pro Ser Val
290                 295                 300

Gly Gln Leu Ala His Lys Leu Ala Glu Ser Asn Ile Gln Pro Ile Phe
305                 310                 315                 320

Ala Val Thr Lys Lys Met Val Lys Thr Tyr Glu Lys Leu Thr Glu Ile
                325                 330                 335

Ile Pro Lys Ser Ala Val Gly Glu Leu Ser Glu Asp Ser Lys Asn Val
            340                 345                 350
```

```
Val Glu Leu Ile Lys Ser Ala Tyr Asn Lys Leu Ser Ser Arg Val Phe
            355                 360                 365

Leu Asp His Asn Thr Leu Pro Asp Thr Leu Lys Val Ala Tyr Asp Ser
370                 375                 380

Phe Cys Ser Asn Arg Val Ser Gln Val Asp Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Glu Gln Ser Phe Thr Ile Arg Ala Leu Gly
            420                 425                 430

Phe Thr Asp Thr Val Thr Val Arg Val Leu Pro Gln Cys Glu Cys Gln
        435                 440                 445

Cys Arg Glu Ala Ser Arg Asp Arg Gly Val Cys Gly Arg Gly Ser
450                 455                 460

Met Glu Cys Gly Val Cys Arg Cys Asp Ala Gly Tyr Ile Gly Lys Asn
465                 470                 475                 480

Cys Glu Cys Gln Thr His Gly Arg Ser Ser Gln Glu Leu Glu Gly Ser
                485                 490                 495

Cys Arg Lys Asp Asn Ser Ser Ile Ile Cys Ser Gly Leu Gly Asp Cys
            500                 505                 510

Ile Cys Gly Gln Cys Val Cys His Thr Ser Asp Val Pro Asn Lys Lys
        515                 520                 525

Ile Tyr Gly Gln Phe Cys Glu Cys Asp Asn Val Asn Cys Glu Arg Tyr
    530                 535                 540

Asp Gly Gln Val Cys Gly Gly Asp Lys Arg Gly Leu Cys Phe Cys Gly
545                 550                 555                 560

Ala Cys Arg Cys Asn Asp Gln Tyr Glu Gly Ser Ala Cys Gln Cys Leu
                565                 570                 575

Lys Ser Thr Gln Gly Cys Leu Asn Leu Asn Gly Val Glu Cys Ser Gly
            580                 585                 590

Arg Gly Arg Cys Arg Cys Asn Val Cys Gln Cys Asp Pro Gly Tyr Gln
        595                 600                 605

Pro Pro Leu Cys Ile Asp Cys Pro Gly Cys Pro Val Pro Cys Ala Gly
    610                 615                 620

Phe Ala Pro Cys Thr Glu Cys Leu Lys Phe Asp Lys Gly Pro Phe Ala
625                 630                 635                 640

Lys Asn Cys Ser Ala Ala Cys Gly Gln Thr Lys Leu Leu Ser Ser Pro
                645                 650                 655

Val Pro Gly Gly Arg Lys Cys Lys Glu Arg Asp Ser Glu Gly Cys Trp
            660                 665                 670

Met Thr Tyr Thr Leu Val Gln Arg Asp Gly Arg Asn Arg Tyr Asp Val
        675                 680                 685

His Val Asp Asp Met Leu Glu Cys Val Lys Gly Pro Asn Ile Ala Ala
    690                 695                 700

Ile Val Gly Gly Thr Val Gly Gly Val Val Leu Val Gly Ile Leu Leu
705                 710                 715                 720

Leu Ala Ile Trp Lys Ala Leu Thr His Leu Ser Asp Leu Arg Glu Tyr
                725                 730                 735

His Arg Phe Glu Lys Glu Lys Leu Lys Ser Gln Trp Asn Asn Asp Asn
            740                 745                 750

Pro Leu Phe Lys Ser Ala Thr Thr Thr Val Met Asn Pro Lys Phe Ala
        755                 760                 765

Glu Ser
```

770

<210> SEQ ID NO 67
<211> LENGTH: 2310
<212> TYPE: DNA
<213> ORGANISM: Artificial Sequence
<220> FEATURE:
<223> OTHER INFORMATION: mutated CD18 protein deer mRNA (q-->g)

<400> SEQUENCE: 67

```
atgctgcgcc agcgccccca gctgctgctc ctagcaggcc tgctagccct cgggtctgtc        60
cggtcccagg agtgcaccaa atacaaggtc agcacctgcc gggactgcat cgagtcgggc       120
cccggctgtg cctggtgcca gaagctgaac ttcacagggc aaggggagcc cgactccgct       180
cgctgtgaca cacgggcgca gctgctgtcc aagggctgtg ccactgatga catcatggaa       240
cccaggagcc tcgctgagac ccaggagagc caggcaggca cagaagca gctgtcccca         300 caggaagtga cgctctacct gagaccaggt caggcagctg cgttcaacgt gactttccgg       360
agggccaaag ataccccat cgacctgtac tacctgatgg atctctccta ctccatggtg        420
gacgacctcg tcaacgtcaa gaagctgggg ggtgacctgc tccgggccct caacggcatc       480
actgagtcgg ccgcatcgg tttcgggtcc ttcgtggaca agacggtgct cccctttgtc        540
aacacgcacc ccgagaagct gcggaacccc tgccccaaca aggagaagca gtgccagccc       600
ccgttcgcct tcaggcacgt gctgaagctc accaacaact ccaaacagtt cgagacagaa       660
gtcgggaagc agctgatctc gggaaacctg gacgccccg agggagggct ggacgccatg       720
atgcaggtgg ccgtgtgccc ggaggaaatc ggctggcgca atgtcaccag gctgctggtg       780
tttgccacgg atgatggctt ccactttgcg ggcgatggaa agctgggtgc catcctcacc       840
cccaacgacg gccgctgcca cctggaagac aacctgtaca aaagcagcaa tgaatttgac       900
tacccatcgg tgggccagct ggcacacaaa ctggcagaaa gcaacatcca gcccatcttt       960
gcggtaacca agaagatggt gaaaacgtac gagaagctga cggagatcat ccccaagtct      1020
gcagtcgggg agctgtctga agactccagg aacgtggtgg agcttatcaa gagtgcctac      1080
aacaaactgt cctccagagt cttcctggat cacaacaccc tccctgacac cctgaaagtc      1140
acctacgact ccttctgcag taacggggtg tcgaaggtgg accagcccag aggggactgc      1200
gacggcgtcc agatcaacgt cccgatcacc ttccaggtga aggtcacagc caccgagtgc      1260
atccaggagc agtccttcac catccgggcc ctgggctttta cggacacggt gaccgtgcgg      1320
gtcctccccc agtgcgagtg ccaatgccgg gacgcgagca gggaccgcag cgtctgcggt      1380
ggcagaggct cgatggagtg cggcgtctgc aggtgcgacg ccggctacat cgggaagaac      1440
tgcgagtgcc agacgcaggg ccggagcagc aggagctggg agggcagctg ccgcaaggac      1500
aacagctcca tcatctgctc ggggctgggg gactgcatct gcgggcagtg cgtgtgccac      1560
acgagcgacg ttcccaacaa gaagatctac ggccagttct gcgagtgcga caacgtcaac      1620
tgcgagcgct acgacggcca agtctgcggg gcgacaagag gggctctg cttctgcggc        1680 acctgcaggt gccaggacca gtacgagggc tcggcgtgcc agtgcctcaa gtccacgcag      1740
ggctgcctca acctgaacgg cgtcgagtgc agcggccgcg ccggtgccg ctgcaacgtg       1800 tgccagtgcg accccggcta ccagccgccc ctgtgcaaag agtgcccggg ctgccccgcg      1860
ccctgcgccg gctttgcctc ctgcaccgag tgcctgaagt cgacaagggg cccttcgcc       1920 aagaactgca gcgcagcttg cggggagacg aagctgctgt ccagcccgcc gcccggccgc      1980
aagtgcaagg agcgcgactc cgagggctgc tggatgacct acacctggt gcagcgcgac      2040
```

-continued

```
gggcgggaca gatacgacgt gcacgtgaac gacacgcgcg agtgtgtaaa gggccccaac    2100
atcgctgcca ttgtgggggg caccgtggcg ggagttgtgc ttgtcggcat cctcctgctg    2160
gtcatctgga aggccctgac acacctgagc gacctcaggg agtaccatcg cttcgagaag    2220
gagaagctca agtcccagtg gaacaacgat aaccctcttt tcaagagtgc caccacgaca    2280
gtcatgaacc ctaagtttgc cgagagttag                                     2310
```

<210> SEQ ID NO 68
<211> LENGTH: 769
<212> TYPE: PRT
<213> ORGANISM: Artificial Sequence
<220> FEATURE:
<223> OTHER INFORMATION: mutated CD18 protein deer protein (Q-->G)

<400> SEQUENCE: 68

```
Met Leu Arg Gln Arg Pro Gln Leu Leu Leu Ala Gly Leu Leu Ala
1               5                   10                  15

Leu Gly Ser Val Arg Ser Gln Glu Cys Thr Lys Tyr Lys Val Ser Thr
            20                  25                  30

Cys Arg Asp Cys Ile Glu Ser Gly Pro Gly Cys Ala Trp Cys Gln Lys
        35                  40                  45

Leu Asn Phe Thr Gly Gln Gly Glu Pro Asp Ser Ala Arg Cys Asp Thr
    50                  55                  60

Arg Ala Gln Leu Leu Ser Lys Gly Cys Ala Thr Asp Asp Ile Met Glu
65                  70                  75                  80

Pro Arg Ser Leu Ala Glu Thr Gln Glu Ser Gln Ala Gly Arg Gln Lys
                85                  90                  95

Gln Leu Ser Pro Gln Glu Val Thr Leu Tyr Leu Arg Pro Gly Gln Ala
            100                 105                 110

Ala Ala Phe Asn Val Thr Phe Arg Arg Ala Lys Gly Tyr Pro Ile Asp
        115                 120                 125

Leu Tyr Tyr Leu Met Asp Leu Ser Tyr Ser Met Val Asp Asp Leu Val
    130                 135                 140

Asn Val Lys Lys Leu Gly Gly Asp Leu Leu Arg Ala Leu Asn Gly Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Glu Lys Leu Arg Asn Pro Cys Pro
            180                 185                 190

Asn Lys Glu Lys Gln Cys Gln Pro Pro Phe Ala Phe Arg His Val Leu
        195                 200                 205

Lys Leu Thr Asn Asn Ser Lys Gln Phe Glu Thr Glu Val Gly Lys Gln
    210                 215                 220

Leu Ile Ser Gly Asn Leu Asp Ala Pro Glu Gly Gly Leu Asp Ala Met
225                 230                 235                 240

Met Gln Val Ala Val Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
        275                 280                 285

Glu Asp Asn Leu Tyr Lys Ser Ser Asn Glu Phe Asp Tyr Pro Ser Val
    290                 295                 300

Gly Gln Leu Ala His Lys Leu Ala Glu Ser Asn Ile Gln Pro Ile Phe
```

-continued

```
            305                 310                 315                 320
Ala Val Thr Lys Lys Met Val Lys Thr Tyr Glu Lys Leu Thr Glu Ile
                    325                 330                 335
Ile Pro Lys Ser Ala Val Gly Glu Leu Ser Glu Asp Ser Arg Asn Val
                    340                 345                 350
Val Glu Leu Ile Lys Ser Ala Tyr Asn Lys Leu Ser Ser Arg Val Phe
                    355                 360                 365
Leu Asp His Asn Thr Leu Pro Asp Thr Leu Lys Val Thr Tyr Asp Ser
                    370                 375                 380
Phe Cys Ser Asn Gly Val Ser Lys Val Asp Gln Pro Arg Gly Asp Cys
385                 390                 395                 400
Asp Gly Val Gln Ile Asn Val Pro Ile Thr Phe Gln Val Lys Val Thr
                    405                 410                 415
Ala Thr Glu Cys Ile Gln Glu Gln Ser Phe Thr Ile Arg Ala Leu Gly
                    420                 425                 430
Phe Thr Asp Thr Val Thr Val Arg Val Leu Pro Gln Cys Glu Cys Gln
                    435                 440                 445
Cys Arg Asp Ala Ser Arg Asp Arg Ser Val Cys Gly Arg Gly Ser
                    450                 455                 460
Met Glu Cys Gly Val Cys Arg Cys Asp Ala Gly Tyr Ile Gly Lys Asn
465                 470                 475                 480
Cys Glu Cys Gln Thr Gln Gly Arg Ser Ser Gln Glu Leu Glu Gly Ser
                    485                 490                 495
Cys Arg Lys Asp Asn Ser Ser Ile Ile Cys Ser Gly Leu Gly Asp Cys
                    500                 505                 510
Ile Cys Gly Gln Cys Val Cys His Thr Ser Asp Val Pro Asn Lys Lys
                    515                 520                 525
Ile Tyr Gly Gln Phe Cys Glu Cys Asp Asn Val Asn Cys Glu Arg Tyr
                    530                 535                 540
Asp Gly Gln Val Cys Gly Gly Asp Lys Arg Gly Leu Cys Phe Cys Gly
545                 550                 555                 560
Thr Cys Arg Cys Gln Asp Gln Tyr Glu Gly Ser Ala Cys Gln Cys Leu
                    565                 570                 575
Lys Ser Thr Gln Gly Cys Leu Asn Leu Asn Gly Val Glu Cys Ser Gly
                    580                 585                 590
Arg Gly Arg Cys Arg Cys Asn Val Cys Gln Cys Asp Pro Gly Tyr Gln
                    595                 600                 605
Pro Pro Leu Cys Lys Glu Cys Pro Gly Cys Pro Ala Pro Cys Ala Gly
610                 615                 620
Phe Ala Ser Cys Thr Glu Cys Leu Lys Phe Asp Lys Gly Pro Phe Ala
625                 630                 635                 640
Lys Asn Cys Ser Ala Ala Cys Gly Glu Thr Lys Leu Leu Ser Ser Pro
                    645                 650                 655
Pro Pro Gly Arg Lys Cys Lys Glu Arg Asp Ser Glu Gly Cys Trp Met
                    660                 665                 670
Thr Tyr Thr Leu Val Gln Arg Asp Gly Arg Asp Arg Tyr Asp Val His
                    675                 680                 685
Val Asn Asp Thr Arg Glu Cys Val Lys Gly Pro Asn Ile Ala Ala Ile
                    690                 695                 700
Val Gly Gly Thr Val Ala Gly Val Val Leu Val Gly Ile Leu Leu Leu
705                 710                 715                 720
Val Ile Trp Lys Ala Leu Thr His Leu Ser Asp Leu Arg Glu Tyr His
                    725                 730                 735
```

Arg Phe Glu Lys Glu Lys Leu Lys Ser Gln Trp Asn Asn Asp Asn Pro
            740                 745                 750

Leu Phe Lys Ser Ala Thr Thr Thr Val Met Asn Pro Lys Phe Ala Glu
            755                 760                 765

Ser

<210> SEQ ID NO 69
<211> LENGTH: 2824
<212> TYPE: DNA
<213> ORGANISM: Artificial Sequence
<220> FEATURE:
<223> OTHER INFORMATION: mutated CD18 protein elk mRNA (q-->g)

<400> SEQUENCE: 69

| | | | | |
|---|---|---|---|---|
| aagcaccagc | ctggtgaaga | gcagagccga | agcccctgcc | agtccagccg | ggacgtccct | 60 |
| gccgaggtct | ccagggcatc | cagtgggaca | tgctgcgcca | gcgcccccag | ctgctgctcc | 120 |
| tagcgggcct | gctagccctc | gggtctgtcc | agtcccagga | gtgcaccaag | tacaaggtca | 180 |
| gcacctgccg | ggactgcatc | gagtcgggcc | ccggctgtgc | ctggtgccag | aagctgaact | 240 |
| tcacagggca | aggggagccc | gactccgctc | gctgtgacac | acgggcgcag | ctgctgtcaa | 300 |
| agggctgtgc | cgctgatgac | atcatggatc | ccaggagcct | cgctgagacc | cgggagagcc | 360 |
| aggcgggcag | acagaagcag | aagcagctgt | ccccacagga | agtgacgctc | tacctgagac | 420 |
| caggtcaggc | agctgcgttt | aacgtgactt | tccagagggc | aagggctac | cccatcgacc | 480 |
| tgtactacct | gatggacctc | tcctactcca | tggtggatga | cctcgtcaac | gtcaagaagc | 540 |
| tgggggggtga | cctgctccgg | gccctcaacg | acatcaccga | gtcggccgc | atcggttcg | 600 |
| ggtccttcgt | ggacaagacg | gtgctcccct | tcgtcaacac | gcaccccgag | aagctgcgga | 660 |
| accccctgccc | caacaaggag | aagcagtgcc | agccccgtt | cgccttcagg | cacgtgctga | 720 |
| agctcaccga | caactccaaa | cagttcgaga | cagaagtcgg | gaagcagctg | atctcgggga | 780 |
| acctggacgc | ccccgaggga | gggctggacg | ccatgatgca | ggtggccgcg | tgcccggagg | 840 |
| aaatcggctg | gcgcaatgtc | accaggttgc | tggtgtttgc | cacggatgat | ggcttccact | 900 |
| ttgcggggcga | tggaaagctg | ggtgccatcc | tcacccccaa | cgacggccgc | tgccacctgg | 960 |
| aagacaacct | gtacaaaagc | agcaacgaat | ttgactaccc | atcggtgggc | cagctggcac | 1020 |
| acaaactggc | agaaagcaac | atccagccca | tctttgcggt | aaccaagaag | atggtgaaaa | 1080 |
| cgtacgagaa | gctgacggag | atcatcccca | gtctgcagt | cggggagctg | tctgaagatt | 1140 |
| ccaagaacgt | ggtggagctt | atcaagagtg | cctacaataa | actgtcctcc | agagtcttcc | 1200 |
| tggatcacaa | caccctccct | gacaccctga | agtcaccta | cgactccttc | tgcagtaaag | 1260 |
| gggtgtcgaa | ggtggaccag | cccagagggg | actgcgacgg | cgtccagatc | aacgtcccga | 1320 |
| tcaccttcca | ggtgaaggtc | acagccaccg | agtgcatcca | ggaacagtcc | ttcaccatcc | 1380 |
| gggcgctggg | ctttacggac | acggtgaccg | tgcgggtcct | cccccagtgc | gagtgccaat | 1440 |
| gccgggacgc | gagcagggac | cgcagcgtct | gcggtggcag | aggttcgatg | gagtgcggcg | 1500 |
| tctgcaggtg | cgacgccggc | tacatcggga | agaactgcga | gtgccagacg | cagggccgga | 1560 |
| gcagccagga | gctggagggc | agctgccgca | aggacaacaa | ctccatcatc | tgctcggggc | 1620 |
| tgggggactg | catctgcggg | cagtgcgtgt | gccacacgag | cgacgtgccc | aacaagaaga | 1680 |
| tctacgccca | gttctgcgag | tgtgacaacg | tcaactgcga | acgctacgac | ggccaagtct | 1740 |
| gcggggggcga | caagaggggg | ctctgcttct | gcggcacctg | caggtgccag | gaccagtacg | 1800 |

```
agggctcggc gtgccagtgc ctcaagtcca cgcagggctg cctcaacctg aacggcgtcg   1860
agtgcagcgg ccgcggccgg tgccgctgca acgtgtgcca gtgcgacccc ggctaccagc   1920 cgccctgtg cttagagtgc cccggctgcc ccgcaccctg cgccggcttt gccccctgca    1980
ccgagtgcct gaagttcaag ggccccttcg ccaagaactg cagcgcagcg tgcggggaga   2040
cgaagctgct gtccaacccg ctgccggcc gcaagtgcaa ggagcgcgac tcggagggct    2100
gctggatgac ctacacctg gtgcagcgcg acgggcggga cagatacgac gtgcacgtga    2160
acgacacgcg cgagtgtgtg aagggcccca acatcgcggc cattgtgggg ggcaccgtgg   2220
ggggagttgt gctggttggc atcctcctgc tggtcatctg gaaggccctg acacacctga   2280
gcgacctcag ggagtaccat cgcttcgaga aggagaagct caagtcccag tggaacaatg   2340
ataaccctct tttcaagagt gccaccacga cagtcatgaa ccctaagttt gccgagagtt   2400
aggggtgcct ggtgaagaca aggccttctg caccacccag atgggaccac gccctctcca   2460
cgtcccctcc agcaggccga ccgtgaccct gctgccttgt ggacgtggct gatgatgctt   2520
gacaactcca ctgttaacca aaaatgcact gcttttcctg ccccagaatg atgggcgtga   2580
ccaaatgatc ctatgggctc atggtaaggg ccagcctccc ccttgatgtc aataactttt   2640
gctagcaagt cagaggagga attgcctaca ttttgtacgg ttacacacca gtcctttgta   2700
aaaattagca cagcagtctg atgaagaatt atttatatgt gaacttctca gggtatgaag   2760
ttatatcccc ttggttatgc tgcccccaa tcaataaaaa aaatcaagaa aaaaaaaaa    2820 aaaa                                                                 2824
```

<210> SEQ ID NO 70
<211> LENGTH: 770
<212> TYPE: PRT
<213> ORGANISM: Artificial Sequence
<220> FEATURE:
<223> OTHER INFORMATION: mutated CD18 protein elk protein (Q-->G)

<400> SEQUENCE: 70

```
Met Leu Arg Gln Arg Pro Gln Leu Leu Leu Ala Gly Leu Leu Ala
1               5                   10                  15

Leu Gly Ser Val Gln Ser Gln Glu Cys Thr Lys Tyr Lys Val Ser Thr
            20                  25                  30

Cys Arg Asp Cys Ile Glu Ser Gly Pro Gly Cys Ala Trp Cys Gln Lys
        35                  40                  45

Leu Asn Phe Thr Gly Gln Gly Glu Pro Asp Ser Ala Arg Cys Asp Thr
    50                  55                  60

Arg Ala Gln Leu Leu Ser Lys Gly Cys Ala Ala Asp Asp Ile Met Asp
65                  70                  75                  80

Pro Arg Ser Leu Ala Glu Thr Arg Glu Ser Gln Ala Gly Arg Gln Lys
                85                  90                  95

Gln Lys Gln Leu Ser Pro Gln Glu Val Thr Leu Tyr Leu Arg Pro Gly
            100                 105                 110

Gln Ala Ala Ala Phe Asn Val Thr Phe Gln Arg Ala Lys Gly Tyr Pro
        115                 120                 125

Ile Asp Leu Tyr Tyr Leu Met Asp Leu Ser Tyr Ser Met Val Asp Asp
    130                 135                 140

Leu Val Asn Val Lys Lys Leu Gly Gly Asp Leu Leu Arg Ala Leu Asn
145                 150                 155                 160

Asp Ile Thr Glu Ser Gly Arg Ile Gly Phe Gly Ser Phe Val Asp Lys
                165                 170                 175
```

-continued

```
Thr Val Leu Pro Phe Val Asn Thr His Pro Glu Lys Leu Arg Asn Pro
            180                 185                 190

Cys Pro Asn Lys Glu Lys Gln Cys Gln Pro Pro Phe Ala Phe Arg His
        195                 200                 205

Val Leu Lys Leu Thr Asp Asn Ser Lys Gln Phe Glu Thr Glu Val Gly
    210                 215                 220

Lys Gln Leu Ile Ser Gly Asn Leu Asp Ala Pro Glu Gly Gly Leu Asp
225                 230                 235                 240

Ala Met Met Gln Val Ala Ala Cys Pro Glu Glu Ile Gly Trp Arg Asn
                245                 250                 255

Val Thr Arg Leu Leu Val Phe Ala Thr Asp Asp Gly Phe His Phe Ala
            260                 265                 270

Gly Asp Gly Lys Leu Gly Ala Ile Leu Thr Pro Asn Asp Gly Arg Cys
        275                 280                 285

His Leu Glu Asp Asn Leu Tyr Lys Ser Ser Asn Glu Phe Asp Tyr Pro
    290                 295                 300

Ser Val Gly Gln Leu Ala His Lys Leu Ala Glu Ser Asn Ile Gln Pro
305                 310                 315                 320

Ile Phe Ala Val Thr Lys Lys Met Val Lys Thr Tyr Glu Lys Leu Thr
                325                 330                 335

Glu Ile Ile Pro Lys Ser Ala Val Gly Glu Leu Ser Glu Asp Ser Lys
            340                 345                 350

Asn Val Glu Leu Ile Lys Ser Ala Tyr Asn Lys Leu Ser Ser Arg
        355                 360                 365

Val Phe Leu Asp His Asn Thr Leu Pro Asp Thr Leu Lys Val Thr Tyr
    370                 375                 380

Asp Ser Phe Cys Ser Lys Gly Val Ser Lys Val Asp Gln Pro Arg Gly
385                 390                 395                 400

Asp Cys Asp Gly Val Gln Ile Asn Val Pro Ile Thr Phe Gln Val Lys
                405                 410                 415

Val Thr Ala Thr Glu Cys Ile Gln Glu Gln Ser Phe Thr Ile Arg Ala
            420                 425                 430

Leu Gly Phe Thr Asp Thr Val Thr Val Arg Val Leu Pro Gln Cys Glu
        435                 440                 445

Cys Gln Cys Arg Asp Ala Ser Arg Asp Arg Ser Val Cys Gly Gly Arg
    450                 455                 460

Gly Ser Met Glu Cys Gly Val Cys Arg Cys Asp Ala Gly Tyr Ile Gly
465                 470                 475                 480

Lys Asn Cys Glu Cys Gln Thr Gln Gly Arg Ser Ser Gln Glu Leu Glu
                485                 490                 495

Gly Ser Cys Arg Lys Asp Asn Ser Ser Ile Ile Cys Ser Gly Leu Gly
            500                 505                 510

Asp Cys Ile Cys Gly Gln Cys Val Cys His Thr Ser Asp Val Pro Asn
        515                 520                 525

Lys Lys Ile Tyr Gly Gln Phe Cys Glu Cys Asp Asn Val Asn Cys Glu
    530                 535                 540

Arg Tyr Asp Gly Gln Val Cys Gly Gly Asp Lys Arg Gly Leu Cys Phe
545                 550                 555                 560

Cys Gly Thr Cys Arg Cys Gln Asp Gln Tyr Glu Gly Ser Ala Cys Gln
                565                 570                 575

Cys Leu Lys Ser Thr Gln Gly Cys Leu Asn Leu Asn Gly Val Glu Cys
            580                 585                 590

Ser Gly Arg Gly Arg Cys Arg Cys Asn Val Cys Gln Cys Asp Pro Gly
```

```
                    595                 600                 605
Tyr Gln Pro Pro Leu Cys Leu Glu Cys Pro Gly Cys Pro Ala Pro Cys
            610                 615                 620

Ala Gly Phe Ala Pro Cys Thr Glu Cys Leu Lys Phe Lys Gly Pro Phe
625                 630                 635                 640

Ala Lys Asn Cys Ser Ala Ala Cys Gly Glu Thr Lys Leu Leu Ser Asn
                645                 650                 655

Pro Leu Pro Gly Arg Lys Cys Lys Glu Arg Asp Ser Glu Gly Cys Trp
            660                 665                 670

Met Thr Tyr Thr Leu Val Gln Arg Asp Gly Arg Asp Arg Tyr Asp Val
        675                 680                 685

His Val Asn Asp Thr Arg Glu Cys Val Lys Gly Pro Asn Ile Ala Ala
    690                 695                 700

Ile Val Gly Gly Thr Val Gly Gly Val Val Leu Val Gly Ile Leu Leu
705                 710                 715                 720

Leu Val Ile Trp Lys Ala Leu Thr His Leu Ser Asp Leu Arg Glu Tyr
                725                 730                 735

His Arg Phe Glu Lys Glu Lys Leu Lys Ser Gln Trp Asn Asn Asp Asn
            740                 745                 750

Pro Leu Phe Lys Ser Ala Thr Thr Thr Val Met Asn Pro Lys Phe Ala
        755                 760                 765

Glu Ser
    770

<210> SEQ ID NO 71
<211> LENGTH: 13
<212> TYPE: PRT
<213> ORGANISM: Bos taurus

<400> SEQUENCE: 71

Arg Pro Gln Leu Leu Leu Leu Ala Gly Leu Leu Ala Leu
1               5                   10

<210> SEQ ID NO 72
<211> LENGTH: 13
<212> TYPE: PRT
<213> ORGANISM: Artificial Sequence
<220> FEATURE:
<223> OTHER INFORMATION: randomly scrambled sequence of CD18 bovine
      Amino Acids 5-17

<400> SEQUENCE: 72

Leu Arg Ala Leu Leu Pro Leu Gln Leu Leu Ala Gly Leu
1               5                   10

<210> SEQ ID NO 73
<211> LENGTH: 21
<212> TYPE: DNA
<213> ORGANISM: Artificial Sequence
<220> FEATURE:
<223> OTHER INFORMATION: M. haemolytica forward primer to examine
      representative colonies

<400> SEQUENCE: 73
agaggccaat ctgcaaacct c                                           21

<210> SEQ ID NO 74
<211> LENGTH: 20
<212> TYPE: DNA
<213> ORGANISM: Artificial Sequence
<220> FEATURE:
```

-continued

```
<223> OTHER INFORMATION: M. haemolytica forward primer to examine
      representative colonies

<400> SEQUENCE: 74
gttcgtattg cccaacgccg                                          20

<210> SEQ ID NO 75
<211> LENGTH: 8
<212> TYPE: PRT
<213> ORGANISM: Artificial Sequence
<220> FEATURE:
<223> OTHER INFORMATION: FLAG epitope

<400> SEQUENCE: 75

Asp Tyr Lys Asp Asp Asp Asp Lys
1               5
```